US008748614B2

(12) United States Patent
Plettenburg et al.

(10) Patent No.: US 8,748,614 B2
(45) Date of Patent: Jun. 10, 2014

(54) SUBSTITUTED ISOQUINOLINE AND ISOQUINOLINONE DERIVATIVES

(75) Inventors: Oliver Plettenburg, Frankfurt am Main (DE); Armin Hofmeister, Frankfurt am Main (DE); Jochen Goerlitzer, Frankfurt am Main (DE); Matthias Löhn, Frankfurt am Main (DE)

(73) Assignee: Sanofi, Paris (FR)

( * ) Notice: Subject to any disclaimer, the term of this patent is extended or adjusted under 35 U.S.C. 154(b) by 715 days.

(21) Appl. No.: 12/487,455

(22) Filed: Jun. 18, 2009

(65) Prior Publication Data

US 2010/0105650 A1 Apr. 29, 2010

Related U.S. Application Data

(63) Continuation of application No. PCT/EP2007/011165, filed on Dec. 19, 2007.

(30) Foreign Application Priority Data

Dec. 27, 2006 (EP) .................................... 06026896

(51) Int. Cl.
*A61K 31/535* (2006.01)
*C07D 217/00* (2006.01)

(52) U.S. Cl.
USPC ........................................ 546/139; 514/235.2

(58) Field of Classification Search
None
See application file for complete search history.

(56) References Cited

U.S. PATENT DOCUMENTS

| | | | | |
|---|---|---|---|---|
| 5,480,883 | A | 1/1996 | Spada et al. | |
| 6,903,107 | B1 | 6/2005 | Timmers et al. | |
| 7,217,722 | B2 | 5/2007 | Takami et al. | |
| 7,618,985 | B2 * | 11/2009 | Ray | 514/309 |
| 2003/0220368 | A1 | 11/2003 | Ozaki et al. | |
| 2004/0138286 | A1 | 7/2004 | Imazaki et al. | |
| 2006/0079556 | A1 | 4/2006 | Sher et al. | |
| 2007/0060595 | A1 | 3/2007 | Yoshizawa et al. | |
| 2008/0045566 | A1 | 2/2008 | Ray et al. | |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087629 | 4/1996 |
| WO | 199202476 | 2/1992 |
| WO | 9706802 | 2/1997 |
| WO | 9723214 | 7/1997 |
| WO | WO 98/06433 | 2/1998 |
| WO | 9911642 | 3/1999 |
| WO | 0024718 | 5/2000 |
| WO | WO 0024718 A1 * | 5/2000 |
| WO | 200073299 | 12/2000 |
| WO | WO 01/39726 | 6/2001 |
| WO | 0153288 | 7/2001 |
| WO | 0156988 | 8/2001 |
| WO | 0164656 | 9/2001 |
| WO | WO 01/64238 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | WO 03/053330 | 7/2003 |
| WO | 2004113297 | 12/2004 |
| WO | WO 2004/106325 | 12/2004 |
| WO | 200535933 | 2/2005 |
| WO | 2005035516 | 4/2005 |
| WO | WO 2005/030130 | 4/2005 |
| WO | WO 2005/030791 | 4/2005 |
| WO | 2005054202 | 6/2005 |
| WO | 2005074535 | 8/2005 |
| WO | 2005087226 | 9/2005 |
| WO | 2005095362 | 10/2005 |
| WO | 2007012421 A1 | 2/2007 |
| WO | 2007012422 A1 | 2/2007 |
| WO | 2007039563 A1 | 4/2007 |
| WO | WO 2007/065916 | 6/2007 |
| WO | 2008020081 A1 | 2/2008 |

(Continued)

OTHER PUBLICATIONS

Silverman, R., "The Organic Chemistry of Drug Design and Drug Action," 2004, Elsevier, pp. 29-32.*

(Continued)

*Primary Examiner* — Heidi Reese

(74) *Attorney, Agent, or Firm* — Scully, Scott, Murphy & Presser, P.C.

(57) ABSTRACT

The invention relates to 6-substituted isoquinoline and isochinolone derivatives of the formula (I)

(I)

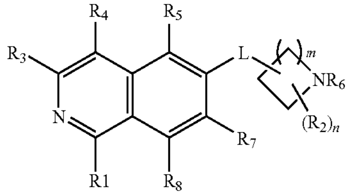

useful for the treatment and/or prevention of diseases associated with Rho-kinase and/or Rho-kinase mediated phosphorylation of myosin light chain phosphatase, and compositions containing such compounds.

45 Claims, No Drawings

(56) References Cited

FOREIGN PATENT DOCUMENTS

| | | | |
|---|---|---|---|
| WO | WO 2008/020081 | | 2/2008 |
| WO | 2008077555 | A2 | 7/2008 |
| WO | 2008077556 | A1 | 7/2008 |

OTHER PUBLICATIONS

Alvarez, M. et al., "Product Class 5: Isoquinolines" Science of Synthesis (2005) pp. 661-838, vol. 15.
Alvarez, M. et al., "Product Class 6: Isoquinolines" Science of Synthesis (2005) pp. 839-90, vol. 15.
Remington's Pharmaceutical Sciences 17th Edition (1985), p. 1418.
Forzato, C. et al., "Baker's yeast reduction of 4-hetero-2-(2-nitroethyl)cyclohexanones" Tetrahedron: Asymmetry (1997) pp. 1811-1820, vol. 8.
U.S. Appl. No. 12/970,376, filed Dec. 16, 2010, Inventor: Plettenburg, et al, entitled: "6-Substituted Isoquinolines and Isoquinolinones".
U.S. Appl. No. 13/000,754, filed Apr. 20, 2011, Inventor: Plettenburg et al., entitled: "Substituted Isoquinolines and Isoquinolinones as Rho Kinase Inhibitors".
U.S. Appl. No. 13/000,202, filed Dec. 20, 2010, Inventor: Plettenburg et al., entitled: "Bi- and Polycyclic Substituted Isoquinoline and Isoquinolinone Derivatives".
Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.
Takami, A. et al., "Design and Synthesis of Rho Kinase Inhibitors (I)" Bioorganic & Medicinal Chemistry (2004) pp. 2115-2137, vol. 12.
Iwakubo, M. et al., "Design and Synthesis of Rho Kinase Inhibitors (III)" Bioorganic & Medicinal Chemistry (2007) pp. 1022-1033, vol. 15.
Iwakubo, M. et al., "Design and Synthesis of Rho Kinase Inhibitors (II)" Bioorganic & Medicinal Chemistry (2007) pp. 350-364, vol. 15.
Tamura, M. et al., "Development of Specific Rho-Kinase Inhibitors and Their Clinical Application" Biochimicia et Biophysica Acta (2005) pp. 245-252, vol. 1754.
Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.
Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.
Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.
Caron, S. et al., "The Synthesis of a Selective PDE4/INFα Inhibitor" Organic Process Research and Development (2001) pp. 587-592, vol. 5.
U.S. Appl. No. 11/961,193, filed Dec. 20, 2007, Plettenburg, et al.
U.S. Appl. No. 12/019,866, filed Jan. 25, 2008, Plettenburg, et al.
U.S. Appl. No. 12/019,799, filed Jan. 25, 2008, Plettenburg, et al.
U.S. Appl. No. 12/487,479, filed Jun. 18, 2009, Plettenburg, et al.
U.S. Appl. No. 12/487,403, filed Jun. 18, 2009, Plettenburg, et al.
U.S. Appl. No. 12/487,525, filed Jun. 18, 2009, Plettenburg, et al.
U.S. Appl. No. 12/487,386, filed Jun. 18, 2009, Plettenburg, et al.
U.S. Appl. No. 12/487,409, filed Jun. 18, 2009, Plettenburg, et al.
U.S. Appl. No. 12/487,503, filed Jun. 18, 2009, Plettenburg, et al.
Yoshii, A., et al., Relaxation of Contracted Rabbit Tracheal and Human Broncial Smooth Muscle by Y-27632 Through Inhibition of Ca2+ Sensitization, Am. J. Resp. Cell Mol. Biol., vol. 20, pp. 1190-1200, (1999).
Zhou, Y., et al., Nonsteroidal Anti-Inflammatory Drugs Can Lower Amyloidogenic AB42 by Inhibiting Rho, Science, vol. 302, pp. 1215-1217, (2003).
Al, S., et. al., Rho-Rho Kinase is Involved in Smooth Muscle Cell Migration Through Myosin Light Chain Phosphorylation-Dependent and Independent Pathways, Atherosclerosis, vol. 155, pp. 321-327, (2001).
Amano, M., et al., Formation of Actin Stress Fibers and Focal Adhesions Enhanced by Rho-Kinase, Science, vol. 275, pp. 1308-1311, (1997).
Bauer, M., et al., Dichotomous Regulation of Myosin Phosphorylation and Shape Change by Rho-Kinase and Calcium in Intact Human Platelets, Blood, vol. 94, No. 5, (1999), pp. 1665-1672.
Chellaiah, M., et. al.,, Rho-Dependent Rho Kinase Activation Increases CD44 Surface Expression and Bone Resorption in Osteoclasts, The Journal of Biological Chemistry. vol. 278, No. 31, (2003), pp. 29086-29097.
Chitaley, K., et. al., Antagonism of Rho-Kinase Stimualates Rat Penile Erection Via a Nitric Oxide-independent Pathway, Nature Medicine, vol. 7, No. 1, (2001), pp. 119-122.
Demiryurek, S., et. al., Effects of Fasudil, a Rho-Kinase inhibitor, On Myocardial Preconditioning in Anesthetized Rats, European Journal of Pharmacology, vol. 527, (2005), pp. 129-140.
Fukumoto, Y., et. al., Acute Vasodilator Effects of a Rho-Kinase inhibitor, Fasudil, in Pateients With Severe Pulmonary Hypertension, Heart, (2005), vol. 91, pp. 391-392.
Furukawa, N., et. al., Role of Rho-Kinase in Regulation of Insulin Action and Glucose Homeostasis, Cell Metabolism, vol. 2, pp. 119-129, (2005).
Gingras, D., et. al., Tyrosine Phosphorylation of the Vascular Endothelial-Growth-Factor Receptor-2 (VEGFR-2) is Modulated by Rho Proteins, Biochem. J., (2000), vol. 348, pp. 273-280.
Gokina, N. I., et. al., Effects of Rho Kinase Inhibition on Cerebral Artery Myogenic Tone and Reactivity, J. Appl. Physiol. vol. 98, pp. 1940-1948, (2005).
Hara, M., et. al., Protein Kinase Inhibition by Fasudil Hydrochloride Promotes Neurological Recovery After Spinal Cord Injury in Rats, J Neurosurg. (Spine 1), vol. 93, pp. 94-101, (2000).
Hattori, T., et. al., Long-Term inhibition of Rho-Kinase Suppresses Left Ventricular Remodeling After Myocardial Infarction in Mice, Circulation, (2004), vol. 109, pp. 2234-2239.
Okada, H., et. al., Synthesis and Antitumor Activities of Prodrugs of Benzoylphenylureas, Chem. Pharm. Bull (1994), pp. 57-61, vol. 42, No. 1.
Hitomi, A., et. al., Hemorheological Abnormalities in Experimental Cerebral Ischemia and Effects of Protein Kinase Inhibitor on Blood Fluidity, Life Sciences, vol. 67, (2000), pp. 1929-1939.
Honjo, M., et. al., Effects of Rho-Associated Protein Kinase inhibitors Y-27632 on Intraocular Pressure and Outflow Facility, Investigative Ophthalmology & Visual Science, (2001), vol. 42, No. 1, pp. 137-144.
Inoue, M., et. al., Initiation of Neuropathic Pain Requires Lysophospatidic Acid Receptor Signaling, Nature Medicine, vol. 10, No. 7, pp. 712-718, (2004).
Itoh, et. al., An Essential Part for Rho-Associated Kinase in the Transcellular Invasion of Tumor Cells, Nature Medicine, vol. 5, No. 2, pp. 221-225, (1999).
Kawaguchi, A., et al., The Effect of a Rho Kinase Inhibitor Y-27632 on Superoxide Production, Aggregation and Adhesion in Human Polymorphonuclear Leukocytes, European Journal of Pharmacology, vol. 403, (2000), pp. 203-208.
Kim, I., et. al., Thin and Thick Filament Regulation of Contractility in Experimental Cerebral Vasospasm. Neurosurgery, vol. 46, No. 2, (2000), pp. 440-447.
Kimura, K., et al., Regulation of the Associaton of Adducin With Actin Filaments by Rho-Associated Kinase (Rho-Kinase) and Myosin Phosphatase, The Journal of Biological Chemistry, vol. 273, No. 10, pp. 5542-5548, (1998).
Kishi, T., et. al., Rho-Kinase Inhibitor Improves Increased Vascular Resistance and Impared Vasodilation of the Forearm in Patients With Heart Failure, Circulation, (2005), vol. 111, pp. 2741-2747.
Klages, B., et al., Activation of G12/G13 Results in Shape Change and Rho/Rho-Kinase-Mediated Myosin Light Chain Phosphorylation in Mouse Platelets, The Journal of Cell Biology, vol. 144, No. 4, (1999), pp. 745-754.

(56) References Cited

OTHER PUBLICATIONS

Lin, T., et. ai., Rho-ROCK-LIMK-Cofilin Pathway Regulates Shear Stress Activation of Sterol Regulatory Element Binding Proteins, Circulation Research, (2003). vol. 92, pp. 1296-1304.
Maruoka, S., et. al., Elastase Anti-Elastase Imbalance in the Pathogenesis of COPD, Nippon Rinsho, (1999), vol. 57, pp. 1982-1987.
Masumoto, A. et. al., Suppression of Coronary Artery Spasm by the Rho-Kinase Inhibitor Fasudii in Patients With Vasospastic Angina, Circulation, (2002), vol. 105, pp. 1545-1547.
Nakahara, T., et. al., Y-27632 Potentiates Relaxant Effects of B2-Adrenoceptor Agonists in Bovine Tracheal Smooth Muscle, European Journal of Pharmacology, vol. 389, (2000), pp. 103-106.
Negoro, N., et. al., The Kinase Inhibitor Fasudil (HA-1077) Reduces Intimal Hyperplasia through Inhibiting Migration and Enhancing Cell Loss of Vascular Smooth Muscle Cells, Biochemical and Biophysical Research Communications, vol. 262, pp. 211-215, (1999).
Noma, K., et. al., Physiological Role of ROCKS in the Cardiovascular System, Am. J. Physiol. Cell Physiol., vol. 290, pp. C661-C668, (2006).
Pacaud, P., et. al., Rho Proteins and Vascular Diseases, Archives Des Maladies Du CCeur Et Des Vaisseaux vol. 98, pp. 249-254, (2005).
Pommereau, A., et al., Two Simple and Generic Antibody-Independent Kinase Assays: Comparison of a Bioluminescent and a Microfluidic Assay Format, J. Biomol. Screen, (2004), vol. 9, pp. 409-416.
Retzer, M., et. al., Lysophosphatidic Acid-Induced Platelet Shape Change Proceeds Via Rho/Rho Kinase-Mediated Myosin Light-Chain and Moesin Phosphorylation, Cellular Signalling, vol. 12, pp. 645-648, (2000).
Retzer, M., et al., Mildly Oxidised Low Density Lipoprotein Induces Platelet Shape Change Via Rho-Kinase-Dependent Phosphorylation of Myosin Light Chain and Moesin, FEBS Letters, vol. 460 pp. 70-74, (2000).
Sandu, O. A., et. al., Diabetes in the Goto-Kakizaki Rat Is Accompanied by Impaired Insulin-Mediated Myosin-Bound Phosphatase Activation and Vascular Smooth Muscle Cell Relaxation, Diabetes, vol. 49, (2000), pp. 2178-2189.
Sato, M., et. al., Involvement of Rho-Kinase-Mediated Phosphorylation of Myosin Light Chain in Enhancement of Cereberal Vasospasm, Circulation Research, (2000), vol. 87, pp. 195-200.
Satoh, S.-i., et. al., Pharmacological Profile of Hydroxy Fasudil as a Selective Rho Kinase Inhitor on Ischemic Brain Damage, Life Sciences, vol. 69, (2001), pp. 1441-1453.
Seasholtz, T. M., et. al., Rho and Rho Kinase Mediate Thrombin-Stimulated Vascular Smooth Muscle Cell DNA Synthesis and Migration , Circulation Research, (1999), vol. 84, pp. 1186-1193.
Setoguchi, H., et. al., Leukotriene C4 Enhances the Contraction of Porcine Tracheal Smooth Muscle Through the Activation of Y-27632, a Rho Kinase Inhibitor, Sensitive Pathway, British Journal of Pharmacology, (2001), vol. 132, pp. 111-118.
Shimokawa, H.. et. al., Anti-Anginal Effect of Fasudil, a Rho-Kinase Inhibitor, in Patients With Stable Effort Angina: A Multicenter Study, Journal of Cardiovascular Pharmacology, (2002), vol. 40, pp. 751-761.
Somlyo, A. V., et. al., Rho-Kinase Inhibitor Retards Migration and in Vivo Dissemination of Human Prostate Cancer Cells, Biochemical and Biophysical Research Communications, vol. 269, pp. 652-659, (2000).
Steioff, K., et al., Long Term Rho-Kinase Inhibition Amellorates Endothelial Dysfunciton in LDL-Receptor Deficient Mice, European Journal of Pharmacology, vol. 512, (2005), pp. 247-249.
Tatsumi, S., et al., Involvement of Rho-Kinase in Inflammatory and Neuropathic Pain Through Phosphoryiation of Myristoylated Alainine-Rich C-Kinase Substrate (MARCKS), Neuroscience, vol. 131, pp. 491-498, (2005).
Totsukawa, G., et. al., Distinct Roles of ROCK (Rho-Kinase) and MLCK in Spatial Regulation of MLC Phosphorylation for Assembly of Stress Fibers and Focal Adhesions in 3T3 Fibroblasts. The Journal of Cell Biology, vol. 150, No. 4, pp. 797-806, (2000).
Uchida, S., et. al., The Suppression of Small GTPase Rho Signal Transduction Pathway Inhibits Angiogenesis in Vitro and in Vivo, Biochemical and Biophysical Research Communications, vol. 269, pp. 633-640, (2000).
Uehata, M., et. al., Calcium Sensitization of Smooth Muscle Mediated by a Rho-Associated Protein Kinase in Hypertension, Nature, vol. 389, pp. 990-994, (1997).
Vicente-Manzanares, M., et. al., A Role For The Rho-p160 Rho Coiled-Coil Kinase Axis in the Chemokine Stromal Cell-Derived Factor-1a-Induced Lymphocyte Actomyosin and Microtubular Organizatoin and Chemotaxis, The Journal of Immunology, (2002), vol. 168, pp. 400-410.
Vicente-Manzanares, M., et. al., The RhoA Effector MDia is Induced During T Cell Activation and Regulates Actin Polymerization and Cell Migration in T Lymphocytes, The Journal of Immunology, (2003), vol. 171, pp. 1023-1034.
Wakino, S., et al., Rho/Rho Kinase as a Potential Target for the Treatement of Renal Disease, Drug News Perspective, (2005), vol. 18, pp. 639-643.
Yamakawa, T., et al., Involvement of Rho-Kinase in Angiotensin Il-Induced Hypertrophy of Rat Vascular Smooth Muscle Cells, Hypertension, (2000), vol. 35, pp. 313-318.
Tamamoto, Y., et al., The Protein Kinase Inhibitor Fasudil Protects Against Ischemic Myocardial Injury Induced by Endothelin-1 in the Rabbit, Journal of Cardiovascular Pharmacology, vol. 35, pp. 203-211, (2000).
Yoshida, Y., et al., Studies of Anti-*Helicobacter pylori* Agents. Part 1: Benzyloxyisoquinoline Derivatives, Bioorg. & Med. Chem., vol. 7 (1999), pp. 2647-2666.
Curran, T.T., et al., “The Preparation of Optically Active 2-Cyclopentan-1,4-Diol Derivatives from Furfurl Alcohol”, Tetrahedron, pp. 1983-2004, vol. 53(6), Feb. 10, 1997.

* cited by examiner

SUBSTITUTED ISOQUINOLINE AND ISOQUINOLINONE DERIVATIVES

FIELD OF THE INVENTION

The present invention relates to novel isoquinoline and isoquinolinone derivatives as described in the claims, their preparation and their use in the treatment and/or prevention of diseases related to the inhibition of Rho-kinase and/or of Rho-kinase mediated phosphorylation of myosin light chain phosphatase.

BACKGROUND OF THE INVENTION

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-8), bronchial smooth muscle contraction (Yoshii et al. Am. J. Resp. Cell Mol. Biol. 20, 1190-1200), asthma (Setoguchi et al. Br J Pharmacol. 2001, 132, 111-8; Nakahara, et al. Eur J 2000, 389, 103) and chronic obstructive pulmonary disease (COPD, Maruoka, Nippon Rinsho, 1999, 57, 1982-7), hypertension, pulmonary hypertension (Fukumoto et al. Heart, 91, 391-2, 2005, Mukai et al. Nature 1997, 389, 990-4) and ocular hypertension and regulation of intraoccular pressure (Honjo et al. Invest. Opthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-47, Shimokawa et al. JCP, 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-43), myocardial infarction (Demiryurek et al. Eur J Pharmacol. 2005, 527, 129-40, Hattori et al. Circulation, 2004, 109, 2234-9), cardiac hypertrophy and failure (Yamakawa, et al. Hypertension 2000, 35, 313-318, Liao et al. Am J Physiol Cell Physiol. 2006, 290, C661-8, Kishi et al. Circ 2005, 111, 2741-2747), coronary heart disease, artherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu, et al. Diabetes 2000, 49, 2178, Maeda et al. Cell Metab. 2005, 2, 119-29), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Nara, et al. JNeurosurg 2000, 93, 94), cerebral ischemia (Uehata, et al. Nature 1997, 389, 990; Satoh et al. Life Sci. 2001, 69, 1441-53; Hitomi, et al. Life Sci 2000, 67, 1929; Yamamoto, et al. J Cardiovasc Pharmacol. 2000, 35, 203-11), cerebral vasospasm (Sato, et al. Circ Res 2000, 87, 195; Kim, et al. Neurosurgery 2000, 46, 440), pain, e.g. neuropathic pain (Tatsumi, et al. Neuroscience 2005, 131, 491, Inoue, et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh, et al. Nature Medicine 1999, 5, 221; Somlyo, et al. Res Commun 2000, 269, 652), angiogenesis (Uchida, et al. Biochem Biophys Res 2000, 269, 633-40; Gingras, et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa, et al. FEBS Lett. 2000, 466, 70-74; Bauer et al. Blood 1999, 94, 1665-1672, Klages, et al. J Cell Biol 1999, 144, 745; Retzer, et al. Cell Signal 2000, 12, 645) and leukocyte aggregation (Kawaguchi, et al. Eur J Pharmacol. 2000, 403:203-8; Sanchez-Madrid, et al. J Immunol. 2003, 171:1023-34, Sanchez-Madrid, et al. J Immunol. 2002, 168:400-10), and bone resorption (Chellaiah, et al. J Biol Chem. 2003, 278:29086-97). Na/H exchange transport system activation (Kawaguchi, et al. Eur J Pharmacol. 2000, 403:203-8), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a $-(CH_2)_{1-6}-O-(CH_2)_{0-6}-$, a $-(CH_2)_{0-6}-S-(CH_2)_{0-6}-$ or a $-(CH_2)_{0-6}-$linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes $-O-(C_0-C_{10})$ alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[($C_1$-$C_6$)alkylene)]$_{0-1}$-Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori.*

U.S. Pat. No. 5,480,883 generically discloses as EGF and/or PDGF receptor inhibitors useful for inhibiting cell proliferation compounds of the formula "Ar I—X—Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}R^{52}$, wherein $R^{51}$ and $R^{52}$ may be hydrogen, ($C_1$-$C_6$)alkyl etc.; or $R^{43}$ is a group $R^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}R^{52}$, wherein $R^{51}$ and $R^{52}$ may be hydrogen, ($C_1$-$C_6$)alkyl etc.; or $R^{43}$ is a group $R^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 03/053330 (Ube) generically describes isoquinolone derivatives of the formula

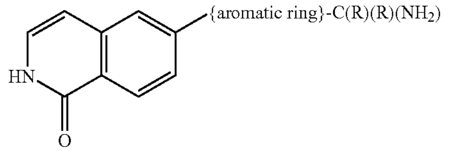

as Rho-kinase inhibitors.

SUMMARY OF THE INVENTION

An embodiment of the present invention is a compound of the formula (I)

(I)

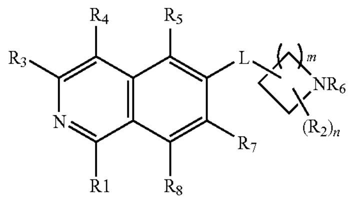

wherein $R_1$ is H, OH or $NH_2$;

$R_2$ is hydrogen, halogen or ($C_1$-$C_6$)alkyl;

$R_3$ is
H,
halogen,
($C_1$-$C_6$)alkyl,
($C_1$-$C_6$)alkylene-R',
OH,
O—R",
$NH_2$,
NHR",
NR"R" or
NH—C(O)—R", $R_4$ is
H,
halogen,
hydroxy,
CN,
($C_1$-$C_6$)alkyl,
R',
($C_1$-$C_6$)alkylene-R;

$R_5$ is
H,
halogen,
CN,
$NO_2$,
($C_1$-$C_6$)alkyl,
($C_2$-$C_6$)alkenyl,
R',
($C_1$-$C_6$)alkylene-($C_6$-$C_{10}$)aryl,
($C_2$-$C_6$)alkenylene-($C_6$-$C_{10}$)aryl,
($C_1$-$C_6$)alkylene-($C_5$-$C_{10}$)heterocyclyl,
CH(OH)—($C_1$-$C_6$)alkyl,
$NH_2$,
NH—R',
NH—$SO_2$H,
NH—$SO_2$—($C_1$-$C_6$)alkyl,
NH—$SO_2$—R',
NH—C(O)—($C_1$-$C_6$)alkyl,
NH—C(O)—R',
C(O)N[($C_1$-$C_6$)alkyl]$_2$,
C(O)OH, or
C(O)O—($C_1$-$C_6$)alkyl;

$R_6$ is
H,
R',
($C_1$-$C_8$)alkyl,
($C_1$-$C_6$)alkylene-R',
($C_1$-$C_6$)alkylene-O—($C_1$-$C_6$)alkyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)$NH_2$,
($C_1$-$C_6$)alkylene-C(O)NH—R',
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)N[R']$_2$;
($C_1$-$C_6$)alkylene-C(O)O—($C_1$-$C_6$)alkyl,
C(O)O—($C_1$-$C_6$)alkyl,
C(O)OR'
C(O)($C_1$-$C_6$)alkyl,
C(O)R',
C(O)NH—($C_1$-$C_6$)alkyl,
C(O)NHR',
C(O)N[($C_1$-$C_6$)alkyl]R'
C(O)N[($C_1$-$C_6$)alkyl]$_2$, C(O)—($C_1$-$C_6$)alkylene-R', or
C(O)O($C_1$-$C_6$)alkylene-R';
$R_7$ is
H,
halogen,
CN,
$NO_2$,
($C_1$-$C_6$)alkyl,
O—($C_1$-$C_6$)alkyl,
($C_2$-$C_6$)alkenyl,
R',
($C_2$-$C_6$)alkenylene-($C_6$-$C_{10}$)aryl,
($C_1$-$C_6$)alkylene-R',
CH(OH)—($C_1$-$C_6$)alkyl,
$NH_2$,
NH—R',
NH—$SO_2$H,
NH—$SO_2$—($C_1$-$C_6$)alkyl,
NH—$SO_2$—R',
$SO_2$—$NH_2$,
$SO_2$—NHR',
NH—C(O)—($C_1$-$C_6$)alkyl,
NH—C(O)—R',
C(O)N[($C_1$-$C_6$)alkyl]$_2$,
C(O)OH, or
C(O)O—($C_1$-$C_6$)alkyl;
$R_8$ is H, halogen or ($C_1$-$C_6$)alkyl;
n is 1, 2, 3 or 4;
m is 1, 2, 3, 4 or 5; and
L is S($CH_2$)$_p$, S(O)($CH_2$)$_p$, $SO_2$($CH_2$)$_p$, NH($CH_2$)$_p$, N($C_1$-$C_6$)alkyl-($CH_2$)$_p$; N($C_3$-$C_6$)cycloalkyl-($CH_2$)$_p$, N[CO($C_1$-$C_6$)alkyl]-($CH_2$)$_p$ or N[($C_1$-$C_3$)alkylene-R']—($CH_2$)$_p$;
p is 0, 1, 2, 3, or 4;
R' is
($C_3$-$C_8$)cycloalkyl,
($C_5$-$C_{10}$)heterocyclyl,
($C_6$-$C_{10}$)aryl; and
R" is
($C_3$-$C_8$)cycloalkyl,
($C_5$-$C_{10}$)heterocyclyl,
($C_6$-$C_{10}$)aryl,
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R', or
($C_1$-$C_6$)alkylene-$NR_xR_y$; and
$R_x$ and $R_y$ are independently of each other
($C_1$-$C_6$)alkyl,
($C_5$-$C_{10}$)heterocyclyl,
($C_6$-$C_{10}$)aryl,
($C_1$-$C_4$)alkylene-($C_5$-$C_{10}$)heterocyclyl,
($C_1$-$C_4$)alkylene-($C_6$-$C_{10}$)aryl,
($C_1$-$C_4$)alkylene-NH($C_1$-$C_6$)alkyl,
($C_1$-$C_4$)alkylene-N[($C_1$-$C_6$)alkyl]$_2$,
($C_1$-$C_4$)alkylene-N[($C_6$-$C_{10}$)aryl]$_2$, or
($C_1$-$C_4$)alkylene-N[($C_5$-$C_{10}$)heterocyclyl]$_2$;

wherein in residues $R_4$, $R_5$, $R_6$, $R_7$ and $R_8$ as alkyl, alkylene or cycloalkyl can optionally be substituted one or more times by OH, $OCH_3$, COOH, $COOCH_3$, $NH_2$, $NHCH_3$, N($CH_3$)$_2$, $CONH_2$, $CONHCH_3$ or CON($CH_3$)$_2$;

wherein in residues $R_2$ to $R_8$ as alkyl or alkylene can optionally be substituted one or more times by halogen;

wherein in residues $R_3$ to $R_8$ as ($C_6$-$C_{10}$)aryl and ($C_5$-$C_{10}$)heterocyclyl are unsubstituted or substituted one or more times by a suitable group independently selected from halogen, OH, $NO_2$, $N_3$, CN, C(O)—($C_1$-$C_6$)alkyl, C(O)—($C_1$-$C_6$)aryl, COOH, COO($C_1$-$C_6$)alkyl, $CONH_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-OH, ($C_1$-$C_6$)alkylene-$NH_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, $PO_3H_2$, $SO_3H$, $SO_2$—$NH_2$, $SO_2$NH($C_1$-$C_6$)alkyl, $SO_2$N[($C_1$-$C_6$)alkyl]$_2$, S—($C_1$-$C_6$)alkyl, SO—($C_1$-$C_6$)alkyl, $SO_2$—($C_1$-$C_6$)alkyl, $SO_2$—N═CH—N[($C_1$-$C_6$)alkyl]$_2$, C(NH)($NH_2$), $NH_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—$SO_2$—($C_1$-$C_6$)alkyl, NH—$SO_2$—($C_6$-$C_{10}$)aryl, NH—$SO_2$-($C_5$-$C_{10}$)heterocyclyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl], ($C_6$-$C_{10}$)aryl, ($C_1$-$C_6$)alkylene-($C_6$-$C_{10}$)aryl, O—($C_6$-$C_{10}$)aryl, O—($C_1$-$C_6$)alkylene-($C_6$-$C_{10}$)aryl, ($C_5$-$C_{10}$)heterocyclyl, ($C_1$-$C_6$)alkylene-($C_5$-$C_{10}$)heterocyclyl, and O—($C_1$-$C_6$)alkylene-($C_5$-$C_{10}$)heterocyclyl, wherein the ($C_6$-$C_{10}$)aryl or ($C_5$-$C_{10}$)heterocyclyl in the substituent may be substituted one to three times by a group independently selected from halogen, OH, $NO_2$, CN, O—($C_1$-$C_6$)alkyl, ($C_1$-$C_6$)alkyl, $NH_2$, NH($C_1$-$C_6$)alkyl, N[($C_1$-$C_6$)alkyl]$_2$, $SO_2CH_3$, COOH, C(O)O—($C_1$-$C_6$)alkyl, $CONH_2$, ($C_1$-$C_6$)alkylene-O—($C_1$-$C_6$)alkyl, ($C_1$-$C_6$)alkylene-O—($C_6$-$C_{10}$)aryl, or O—($C_1$-$C_6$)alkylene-($C_6$-$C_{10}$)aryl; or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to; and wherein aryl substituent of ($C_6$-$C_{10}$)aryl and ($C_5$-$C_{10}$)heterocyclyl substituent groups may not be further substituted by an aryl or heterocyclyl containing group; or stereoisomeric form thereof and/or tautomeric form thereof and/or pharmaceutically acceptable salt thereof.

DETAILED DESCRIPTION OF THE INVENTION

Definitions

The terms ($C_1$-$C_2$)alkyl, ($C_1$-$C_4$)alkyl, ($C_1$-$C_6$)alkyl, ($C_1$-$C_8$)alkyl and the corresponding alkylene substituents are understood as a hydrocarbon residue which can be linear, i.e. straight-chain, or branched and has 1, 2, 3, 4, 5, 6, 7 or 8 carbon atoms, respectively. This also applies if an alkyl group occurs as a substituent on another group, for example in an alkoxy group (O-alkyl), S-alkyl or a —O—($C_1$-$C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may—if not otherwise stated—be halogenated once or more, e.g. alkyl groups may be fluorinated, e.g. perfluorinated. Examples of halogenated alkyl groups are $CF_3$ and $CH_2CF_3$, $OCF_3$, $SCF_3$, or —O—($CF_2$)$_2$—O—.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Alkynyl are, for example, ethynyl, 1-propynyl, 2-propynyl (=propargyl) or 2-butynyl.

Halogen means fluoro, chloro, bromo or iodo.

($C_3$-$C_8$)cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A $(C_6-C_{10})$aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

A $(C_5-C_{10})$heterocyclyl group means a mono- or bicyclic ring system in which one or more carbon atoms can be replaced by one or more heteroatoms such as, for example 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. $(C_5-C_{10})$heterocyclyl groups may be (1) aromatic [=heteroaryl groups] or (2) saturated or (3) mixed aromatic/saturated.

Suitable $(C_5-C_{10})$heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadiazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_5-C_{10})$heterocyclyl residues can occur on free carbon atoms or on nitrogen atoms.

Preferred examples of $(C_5-C_{10})$heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl.

$(C_6-C_{10})$aryl and $(C_5-C_{10})$heterocyclyl groups are unsubstituted or, if not stated otherwise, substituted one or more times, preferably one to three times, by suitable groups independently selected from halogen, OH, $NO_2$, $N_3$, CN, C(O)—$(C_1-C_6)$alkyl, C(O)—$(C_1-C_6)$aryl, COOH, COO$(C_1-C_6)$alkyl, $CONH_2$, CONH$(C_1-C_6)$alkyl, CON$[(C_1-C_6)$alkyl$]_2$, $(C_3-C_8)$cycloalkyl, $(C_1-C_6)$alkyl, $(C_1-C_6)$alkylene-OH, $(C_1-C_6)$alkylene-$NH_2$, $(C_1-C_6)$alkylene-NH$(C_1-C_6)$alkyl, $(C_1-C_6)$alkylene-N$[(C_1-C_6)$alkyl$]_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2NH(C_1-C_6)$alkyl, $SO_2N[(C_1-C_6)$alkyl$]_2$, S—$(C_1-C_6)$alkyl; SO—$(C_1-C_6)$alkyl, $SO_2$—$(C_1-C_6)$alkyl, $SO_2$—N═CH—N$[(C_1-C_6)$alkyl$]_2$, C(NH)($NH_2$), $NH_2$, NH—$(C_1-C_6)$alkyl, N$[(C_1-C_6)$alkyl$]_2$, NH—C(O)—$(C_1-C_6)$alkyl, NH—C(O)O—$(C_1-C_6)$alkyl, NH—$SO_2$—$(C_1-C_6)$alkyl, NH—$SO_2$—$(C_6-C_{10})$aryl, NH—$SO_2$-$(C_5-C_{10})$heterocyclyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heterocyclyl, $(C_1-C_6)$alkylene-$(C_5-C_{10})$heterocyclyl, O—$(C_1-C_6)$alkylene-$(C_5-C_{10})$heterocyclyl, wherein the $(C_6-C_{10})$aryl or $(C_5-C_{10})$heterocyclyl may be substituted one to 3 times by a group independently selected from halogen, OH, $NO_2$, CN, O—$(C_1-C_6)$alkyl, $(C_1-C_6)$alkyl, $NH_2$, NH$(C_1-C_6)$alkyl, N$[(C_1-C_6)$alkyl$]_2$, $SO_2CH_3$, COOH, C(O)O—$(C_1-C_6)$alkyl, $CONH_2$, $(C_1-C_6)$alkylene-O—$(C_1-C_6)$alkyl, $(C_1-C_6)$alkylene-O—$(C_6-C_{10})$aryl, O—$(C_1-C_6)$alkylene-$(C_6-C_{10})$aryl; or wherein $(C_6-C_{10})$aryl is vicinally substituted by a O—$(C_1-C_4)$alkylene-O group whereby a 5-8-membered ring is formed together with the carbon atoms the oxygen atoms are attached to. Aryl or heterocyclyl substituents of $(C_6-C_{10})$aryl and $(C_5-C_{10})$heterocyclyl groups may not be further substituted by an aryl or heterocyclyl containing group.

Preferred substituents for $(C_6-C_{10})$aryl groups are $(C_1-C_4)$alkyl, O—$(C_1-C_4)$alkyl, O-phenyl, phenyl, C(O)O—$(C_1-C_6)$alkyl, C(O)OH, C(O)—$(C_1-C_4)$alkyl, halogen, $NO_2$, $SO_2NH_2$, CN, $SO_2$—$(C_1-C_4)$alkyl, $SO_2$—N═CH—N$[(C_1-C_6)$alkyl$]_2$, NH—$SO_2$—$(C_1-C_4)$alkyl, $NH_2$, NH—C(O)—$(C_1-C_4)$alkyl, $(C_3-C_8)$cycloalkyl, $(C_1-C_4)$alkyl-OH, C(O)N$[(C_1-C_4)$alkyl$]_2$, CONH$(C_1-C_6)$alkyl, C(O)$NH_2$, N$[(C_1-C_4)$alkyl$]_2$, $(C_1-C_4)$alkylene-$(C_6-C_{10})$aryl, wherein the $(C_6-C_{10})$aryl may be further substituted one to three times, preferably once, by $(C_1-C_4)$alkyl, $(C_1-C_4)$alkylene-O—$(C_1-C_6)$alkyl, $(C_6-C_{10})$aryl O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_6-C_{10})$aryl are halogen, CN, phenyl, O-phenyl, NH—C(O)-$(C_1-C_4)$alkyl especially NH—C(O)—$CH_3$, C(O)—$(C_1-C_4)$alkyl especially C(O)—$CH_3$, $(C_1-C_4)$alkyl especially $CH_3$ or $CF_3$, O—$(C_1-C_4)$alkyl especially O—$CH_3$, $SO_2$—$NH_2$, $SO_2$—$(C_1-C_4)$alkyl especially $SO_2$—$CH_3$ or $SO_2$—$CF_3$ or $SO_2$—N═CH—N$[(C_1-C_4)$alkyl$]_2$ especially $SO_2$—N═CH—N$[(CH3)_2$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

Preferred substituents for $(C_5-C_{10})$heterocyclyl groups are $(C_1-C_4)$alkyl, O—$(C_1-C_4)$alkyl, $(C_1-C_4)$alkylene-phenyl, halogen, $(C_1-C_4)$alkylene-O—$(C_1-C_4)$alkyl, $(C_5-C_{10})$heterocyclyl, $(C_1-C_4)$alkylene-N$[(C_1-C_4)$alkyl$]_2$, or $(C_6-C_{10})$aryl, wherein the $(C_6-C_{10})$aryl may be further substituted by $(C_1-C_4)$alkyl, O—$(C_1-C_6)$alkyl, halogen, $(C_1-C_4)$alkylene-O—$(C_1-C_6)$alkyl, O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_5-C_{10})$heterocyclyl groups are $(C_1-C_4)$alkyl, halogen or phenyl, wherein the phenyl may be further substituted one to three times, preferably once, by halogen, $(C_1-C_4)$alkyl or O—$(C_1-C_4)$alkyl.

The general and preferred substituents of $(C_6-C_{10})$aryl and $(C_5-C_{10})$heterocyclyl groups may be combined with the general and preferred definitions of $R_1$, $R_2$, $R_3$, $R_4$, $R_5$, $R_6$, $R_7$, $R_8$, n, m, L and p as described above.

Embodiments

In one embodiment of the present invention $R_1$ is H, the compound is thus characterized by the formula (II)

(II)

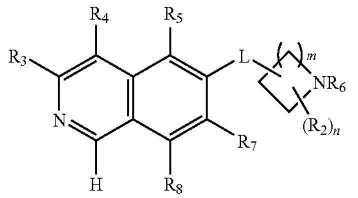

In another embodiment $R_1$ is OH, the compound is thus characterized by the formula (III)

(III)

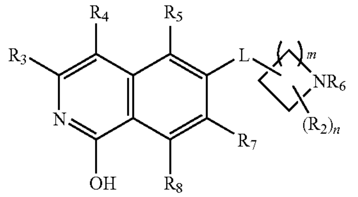

The compound of formula (III) has a tautomeric form of the formula (III')

(III')

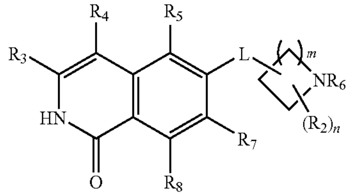

The tautomeric form is also an embodiment of the present invention. In a further embodiment $R_1$ is $NH_2$ and the compound has the formula (IV)

(IV)

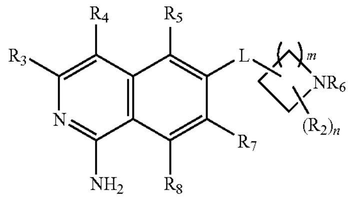

$R_1$ is preferably H or OH.

$R_3$ is preferably H, halogen, $(C_1-C_4)$alkylene-R', O—R" or NHR". More preferred, $R_3$ is H or NHR". Most preferred, $R_3$ is H, NH—$(C_5-C_6)$heterocyclyl or NH-phenyl, especially preferred are H, NH—$(C_5-C_6)$heteroaryl containing one or more N atoms or NH-phenyl. Most especially preferred, $R_3$ is H. Examples of $R_3$ substituents are

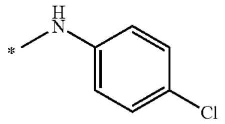

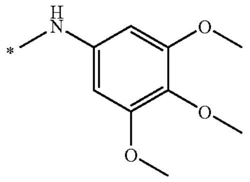

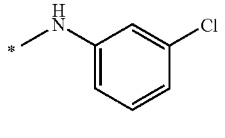

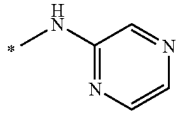

Preferably, $R_4$ is H, halogen or $(C_1-C_6)$alkyl. More preferred, $R_4$ is H, halogen or $(C_1-C_4)$alkyl. Most preferred, $R_4$ is H.

Preferably, $R_5$ is H, halogen, CN, $(C_1-C_6)$alkyl, $(C_2-C_6)$alkenyl, R', NH—$(C_6-C_{10})$aryl or $(C_1-C_6)$alkylene-R'. More preferably, $R_5$ is H, halogen, $(C_1-C_6)$alkyl, $(C_2-C_6)$alkenyl, R', NH—$(C_6-C_{10})$aryl or $(C_1-C_6)$alkylene-R'. Most preferably, $R_5$ is H, halogen, $(C_1-C_6)$alkyl, $(C_2-C_6)$alkenyl, $(C_6-C_{10})$aryl, NH—$(C_6-C_{10})$aryl, $(C_1-C_2)$alkyl-$(C_6-C_{10})$aryl or $(C_5-C_{10})$heteroaryl. Especially preferred, $R_5$ is H, halogen, phenyl, $(C_1-C_6)$alkyl, $(C_2-C_6)$alkenyl, $(C_6-C_{10})$aryl or $(C_5-C_6)$heteroaryl. Most especially preferred $R_5$ is H, halogen, methyl, ethyl, vinyl, phenyl, thienyl or pyridyl.

Examples of $R_5$ are hydrogen, fluoro, chloro, bromo, iodo, methyl, ethyl, vinyl, phenyl, thienyl or pyridyl, nitrile, nitro, (p-methoxy)-phenyl, N-aniline, benzyl, 2-propenyl, s-butenyl, cyclopropyl, tetrazol, amino, 4-methoxy-aniline or N-acetyl, preferably hydrogen, fluoro, chloro, bromo, iodo, methyl, ethyl, vinyl, phenyl, thienyl or pyridyl More preferred, $R_5$ is H, halogen, methyl, or ethyl, most preferred $R_5$ is H.

Preferably, $R_6$ is H, $(C_1-C_6)$alkyl, R', $(C_1-C_4)$alkylene-$(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_6)$alkylene-O—$(C_1-C_6)$alkyl, $(C_1-C_4)$alkylene-C(O)—$(C_5-C_{10})$heterocyclyl, $(C_1-C_4)$alkylene-C(O)—$(C_6-C_{10})$aryl, $(C_1-C_6)$alkylene-C(O)N$[(C_1-C_6)alkyl]_2$, $(C_1-C_6)$alkylene-C(O)NH—$(C_1-C_6)$alkyl, $(C_1-C_6)$alkylene-C(O)O—$(C_1-C_6)$alkyl, C(O)O—$(C_1-C_6)$alkyl, C(O)$(C_1-C_6)$alkyl, C(O)R', C(O)NH—$(C_1-C_6)$alkyl, C(O)N$[(C_1-C_6)alkyl]_2$, or C(O)$(C_1-C_6)$alkylene-R'.

In a further preferred embodiment $R_6$ is H, $(C_1-C_6)$alkyl, $(C_5-C_{10})$heterocyclyl, $(C_3-C_8)$cycloalkyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)N$[(C_1-C_6)alkyl]_2$, $(C_1-C_6)$alkylene-C(O)NH—$(C_1-C_6)$alkyl, $(C_1-C_6)$alkylene-C(O)O—$(C_1-C_6)$alkyl, C(O)O—$(C_1-C_6)$alkyl, C(O)$(C_1-C_6)$alkyl, C(O)—$(C_5-C_{10})$heterocyclyl, C(O)$(C_3-C_8)$cycloalkyl, C(O)NH—$(C_1-C_6)$alkyl, C(O)N$[(C_1-C_6)alkyl]_2$, C(O)$(C_1-C_6)$alkylene-$(C_3-C_8)$cycloalkyl, C(O)$(C_1-C_6)$alkylene-$C_5-C_{10})$heterocyclyl, or C(O)$(C_1-C_6)$alkylene-$(C_6-C_{10})$aryl.

In a further more preferred embodiment $R_6$ is H, $(C_1-C_6)$alkyl, $(C_3-C_8)$cycloalkyl, $(C_5-C_{10})$heterocyclyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)NH—$(C_1-C_6)$alkyl, $(C_1-C_6)$alkylene-C(O)N$[(C_1-C_6)alkyl]_2$, C(O)

O—($C_1$-$C_6$)alkyl, C(O)($C_1$-$C_6$)alkyl, C(O)($C_3$-$C_8$) cycloalkyl, C(O)—($C_5$-$C_{10}$)heterocyclyl, C(O)NH—($C_1$-$C_6$)alkyl, C(O)N[($C_1$-$C_6$)alkyl]$_2$, C(O)($C_1$-$C_6$)alkylene-($C_3$-$C_8$)cycloalkyl, C(O)($C_1$-$C_6$)alkylene-($C_5$-$C_{10}$)heterocyclyl, or C(O)($C_1$-$C_6$)alkylene-($C_6$-$C_{10}$)aryl.

In an more preferred embodiment $R_6$ is H, ($C_1$-$C_6$)alkyl, ($C_3$-$C_8$)cycloalkyl, ($C_6$-$C_{10}$)aryl, ($C_1$-$C_4$)alkylene-($C_3$-$C_8$) cycloalkyl, ($C_1$-$C_4$)alkylene-($C_5$-$C_{10}$)heterocyclyl, ($C_1$-$C_4$) alkylene-($C_6$-$C_{10}$)aryl, ($C_1$-$C_4$)alkylene-O—($C_1$-$C_4$)alkyl, C(O)($C_1$-$C_6$)alkyl, C(O)($C_3$-$C_8$)cycloalkyl, C(O)—($C_5$-$C_{10}$) heterocyclyl, C(O)($C_1$-$C_4$)alkylene-($C_5$-$C_{10}$)heterocyclyl, or C(O)($C_1$-$C_4$)alkylene-($C_6$-$C_{10}$)aryl.

In an even more preferred embodiment $R_6$ is

H, ($C_1$-$C_6$)alkyl, ($C_3$-$C_8$)cycloalkyl;

($C_1$-$C_4$)alkylene-($C_3$-$C_8$)cycloalkyl;

($C_1$-$C_4$)alkylene-($C_5$-$C_{10}$)heterocyclyl wherein heterocyclyl is unsubstituted or substituted one or more times, preferably one or two times, by ($C_1$-$C_4$)alkyl;

($C_1$-$C_4$)alkylene-($C_6$-$C_{10}$)aryl wherein aryl is unsubstituted or substituted one or more times, preferably one to three times, by halogen, ($C_1$-$C_4$)alkyl especially $CH_3$ or $CF_3$, O—($C_1$-$C_4$)alkyl especially $OCH_3$, $SO_2$—($C_1$-$C_4$)alkyl especially $S(O)_2CH_3$ or $SO_2CF_3$, or $SO_2$—N═CH—N[($C_1$-$C_6$)alkyl]$_2$ especially $SO_2$—N═CH—N($CH_3$)$_2$.

Especially preferred $R_6$ is H, ($C_1$-$C_6$)alkyl or ($C_3$-$C_8$)cycloalkyl. In an even more especially preferred embodiment $R_6$ is H, preferably unsubstituted ($C_1$-$C_6$)alkyl or preferably unsubstituted ($C_3$-$C_8$)cycloalkyl. Most preferred $R_6$ is H.

As examples for these embodiments, R6 is hydrogen, methyl, ethyl, propyl, isopropyl, 3-methyl-butyl, 2-methyl-propyl, 1-ethyl-propyl, butyl, pentyl, 3,3,3-trifluoropropyl, 4,4,4-trifluorobutyl or a substituent selected from the group consisting of

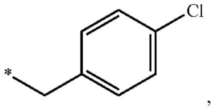 , 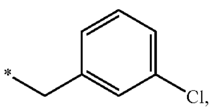 ,

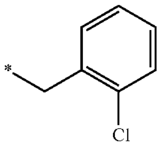 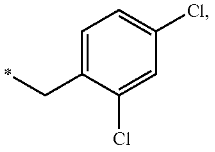

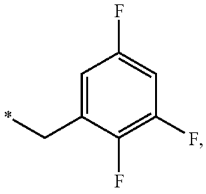 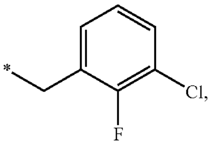

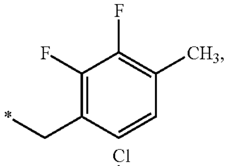 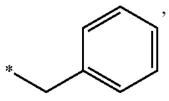 ,

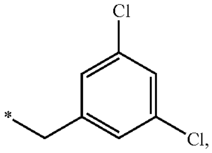 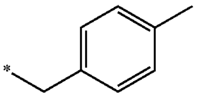 ,

-continued

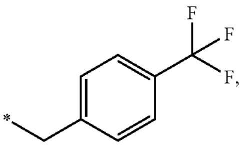 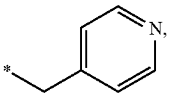

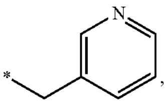 , 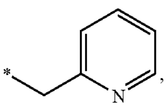

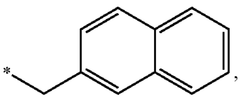 , 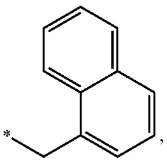

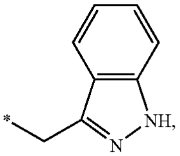 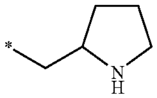 , 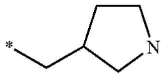

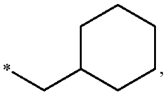 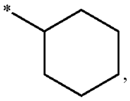 , 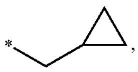

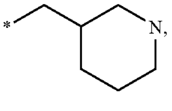 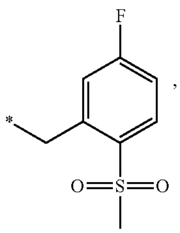 ,

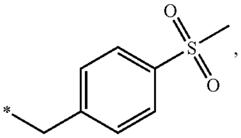 , 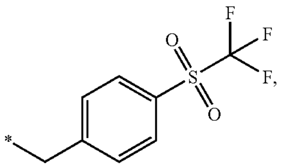

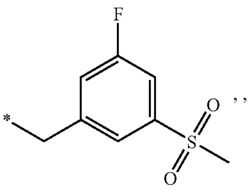 , , 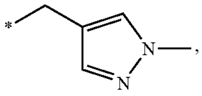

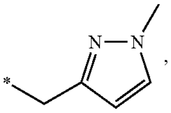 , 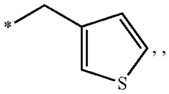 , ,

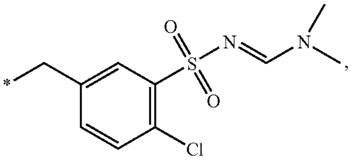

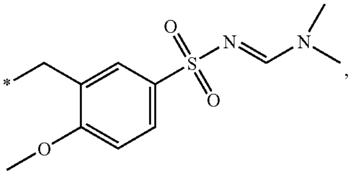 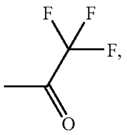

-continued

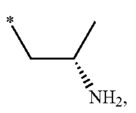,

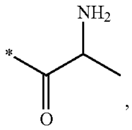,

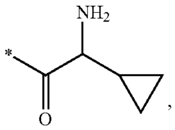,

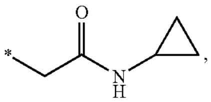,

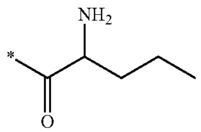

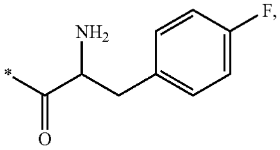, or

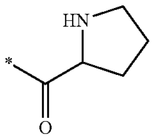

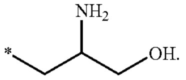.

The asterisk (*) denotes where the bond is connected to the N-atom of the ring.

Preferably, $R_7$ is H, halogen, CN, $(C_1$-$C_6)$alkyl, O—$(C_1$-$C_6)$alkyl, $(C_2$-$C_6)$alkenyl, R' or $(C_1$-$C_6)$alkylene-$(C_3$-$C_8)$cycloalkyl. More preferred, $R_7$ is H, halogen, CN, $(C_1$-$C_4)$alkyl, O—$(C_1$-$C_4)$alkyl, $(C_2$-$C_4)$alkenyl, phenyl, cyclopropyl or $(C_5$-$C_6)$heteroaryl. Most preferably, $R_7$ is H, fluoro, chloro, bromo, methyl, ethyl, methoxy, propyl, phenyl, nitrile, cyclopropyl, thienyl or vinyl, most especially preferred $R_7$ is H, fluoro, chloro, bromo, methyl, propyl or methoxy. Most preferred $R_7$ is H.

$R_8$ is preferably H, halogen or $(C_1$-$C_4)$alkyl. More preferred, $R_8$ is H, Cl, F, methyl or ethyl. Most preferred $R_8$ is H.

Preferably, $R_2$ is H, halogen or $(C_1$-$C_4)$alkyl. Preferably, $R_2$ is H or $(C_1$-$C_2)$alkyl. More preferred, $R_2$ is H, methyl or ethyl. Most preferred $R_2$ is H. $R_2$ may be bound to any carbon atom of the ring including the position where the linker group L is bound.

Preferably, n is 1, 2 or 3. More preferred, n is 1 or 2. Most preferred n is 1.

Preferably m is 2, 3 or 4. More preferred m is 3.

The linker group L may be bound to the ring in any position via a ring carbon atom. In a preferred embodiment, m is 3 and L is attached to the 4-position of the piperidine ring

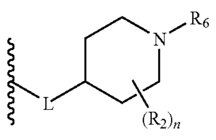

or L is attached to the 3-position of the piperidine ring

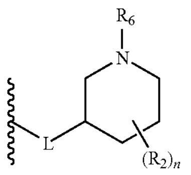

in all their stereochemical forms.

In an especially preferred embodiment, L is attached to the 4-position of the piperidine ring.

In a further embodiment of L, L is $S(CH_2)p$, $S(O)(CH_2)p$ or $SO_2(CH_2)p$, In another embodiment L is $NH(CH_2)p$, $N(C_1$-

$C_6)$alkyl-$(CH_2)p$, $N(C_3$-$C_6)$cycloalkyl-$(CH_2)p$ $N[CO(C_1$-$C_6)$ alkyl]-$(CH_2)p$, $N[(C_1$-$C_3)$alkylene-aryl]-$(CH_2)p$ or $N[(C_1$-$C_3)$alkylene-$(C_5$-$C_6)$heterocyclyl]-$(CH_2)p$ with $NH(CH_2)p$, $N(C_1$-$C_6)$alkyl-$(CH_2)p$ being more preferred. A preferred $N(C_1$-$C_6)$alkyl is $N(C_1$-$C_4)$alkyl, more preferably $NCH_3$ or $NCH_2CH_3$ with $NCH_3$ being more preferred. Even more preferred L is $S(CH_2)p$ or $NH(CH_2)p$. Most preferred L is S or NH.

Preferably p is 0, 1, 2, or 3, more preferred 0 or 1, with 0 being most preferred.

More preferably, m is 3 and L is S or NH and is attached to the 4-position of the piperidine ring.

In residues $R_2$ to $R_8$ an alkyl or alkylene can optionally be substituted one or more times by halogen. Preferably alkyl or alkylene is substituted one to three times by halogen selected from chloro or bromo but may be substituted by fluoro once or more, e.g. being perfluorinated. Preferably halogen is Fluor. More preferred an alkyl or alkylene is not halogenated.

In residues $R_4$, $R_5$, $R_6$, $R_7$ and $R_8$ alkyl, alkylene or cycloalkyl can optionally be substituted one or more times by a group selected independently from OH, $OCH_3$, COOH, $COOCH_3$, $NH_2$, $NHCH_3$, $N(CH_3)_2$, $CONH_2$, $CONHCH_3$ or $CON(CH_3)_2$.

If substituted, the number of substituents is preferably between 1, 2, 3 or 4, more preferably 1 or 2 with 1 being even more preferred. Preferably an alkylene or cycloalkyl is not substituted. More preferably an alkyl, alkylene or cycloalkyl is not substituted. Preferably in $R_4$, $R_5$, $R_7$ and $R_8$ an alkyl, alkylene or cycloalkyl is not substituted. More preferred, in $R_4$, $R_5$, $R_6$, $R_7$ and $R_8$ an alkyl, alkylene or cycloalkyl is not substituted.

In preferred embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

The term "*—" in the exemplified substituents vide supra marks the point where the substituent is attached, which means, for example, for a $R_3$ substituent

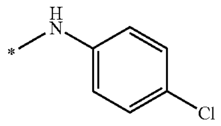

and m is 3 and R1 is H a compound of the formula

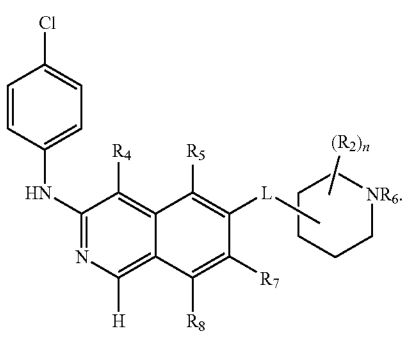

A preferred embodiment is a compound of the formula (I) wherein $R_1$ is H, OH or $NH_2$;

$R_2$ is hydrogen, halogen, or $(C_1-C_6)$alkyl;

$R_3$ is H, halogen, $(C_1-C_4)$alkylene-R', O—R'' or NHR'';

$R_4$ is H, halogen or $(C_1-C_6)$alkyl;

$R_5$ is H, $(C_1-C_6)$alkyl, halogen, CN, $(C_2-C_6)$alkenyl, $(C_6-C_{10})$aryl, NH—$(C_6-C_{10})$aryl, $(C_1-C_6)$alkylene-$(C_6-C_{10})$aryl, $(C_5-C_{10})$heterocyclyl or $(C_1-C_6)$alkylene-$(C_5-C_{10})$heterocyclyl;

$R_6$ is H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH$[R']_2$, $(C_1-C_6)$alkylene-C(O)$NH_2$, $(C_1-C_6)$alkylene-C(O)NH—R', $(C_1-C_6)$alkylene-C(O)N$[(C_1-C_4)alkyl]_2$, C(O)$(C_1-C_4)$alkyl or $(C_1-C_6)$alkylene-C(O)N$[R']_2$, C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N$[(C_1-C_6)alkyl]_2$, C(O)$(C_1-C_6)$alkylene-$C_3-C_8$)cycloalkyl, C(O)$(C_1-C_6)$alkylene-$C_5-C_{10}$)heterocyclyl or C(O)$(C_1-C_6)$alkylene-$(C_6-C_{10})$aryl.

$R_7$ is H, halogen, CN, $(C_1-C_6)$alkyl, O—$(C_1-C_6)$alkyl, $(C_2-C_6)$alkenyl or R';

$R_8$ is H, halogen or $(C_1-C_6)$alkyl;

m is 2, 3 or 4 n is 1, 2 or 3,

L is S$(CH_2)$p, NH$(CH_2)$p or N$(C_1-C_6)$alkyl-$(CH_2)$p, and p is 0, 1 or 2;

or stereoisomeric form thereof and/or tautomeric form thereof and/or pharmaceutically acceptable salt thereof.

A further preferred embodiment is a compound of the formula (I) wherein $R_1$ is H or OH;

$R_2$ is H or $(C_1-C_4)$alkyl;

$R_3$ is H, halogen or NHR'', wherein R'' is defined as above;

$R_4$ is H, halogen or $(C_1-C_4)$alkyl;

$R_5$ is H, $(C_1-C_6)$alkyl, halogen, $(C_2-C_4)$alkenyl, $(C_6-C_{10})$aryl, $(C_1-C_6)$alkylene-$(C_6-C_{10})$aryl or $(C_5-C_{10})$heterocyclyl;

$R_6$ is H, $(C_3-C_8)$cycloalkyl, $(C_1-C_8)$alkyl, $(C_1-C_6)$alkylene-O—$(C_1-C_6)$alkyl, $(C_1-C_3)$alkylene-R', C(O)O—$(C_1-C_6)$alkyl, C(O)$(C_1-C_6)$alkyl, C(O)$(C_3-C_8)$cycloalkyl, C(O)—$(C_5-C_{10})$heterocyclyl, C(O)NH—$(C_1-C_6)$alkyl, C(O)N$[(C_1-C_6)alkyl]_2$, C(O)$(C_1-C_3)$alkylene-$(C_3-C_8)$cycloalkyl, C(O)$(C_1-C_3)$alkylene-$(C_5-C_{10})$heterocyclyl, or C(O)$(C_1-C_3)$alkylene-$(C_6-C_{10})$aryl;

$R_7$ is H, halogen, CN, $(C_1-C_6)$alkyl, O—$(C_1-C_6)$alkyl, $(C_2-C_6)$alkenyl or R';

$R_8$ is H, halogen or $(C_1-C_6)$alkyl;

m is 2, 3 or 4;

n is 1, 2 or 3;

L is S$(CH_2)$p or NH$(CH_2)$p, and p is 0 or 1;

or stereoisomeric form thereof and/or tautomeric form thereof and/or pharmaceutically acceptable salt thereof.

An especially preferred embodiment is a compound of the formula (I) wherein $R_1$ is H or OH;

$R_2$ is H, $(C_1-C_4)$alkyl;

$R_3$ is H, NH—$(C_5-C_6)$heteroaryl or NH-phenyl;

$R_4$ is H, halogen or $(C_1-C_4)$alkyl;

$R_5$ is H, $(C_1-C_4)$alkyl, halogen, $(C_2-C_4)$alkenyl, $(C_6-C_{10})$aryl, $(C_1-C_2)$alkyl-$(C_6-C_{10})$aryl or $(C_5-C_6)$heteroaryl;

$R_6$ is H, $(C_3-C_8)$cycloalkyl, $(C_1-C_8)$alkyl, $(C_1-C_3)$alkylene-R'; C(O)$(C_1-C_6)$alkyl, C(O)$(C_3-C_8)$cycloalkyl, C(O)—$(C_5-C_{10})$heterocyclyl, C(O)$(C_1-C_3)$alkylene-$(C_5-C_{10})$heterocyclyl, or C(O)$(C_1-C_3)$alkylene-$(C_6-C_{10})$aryl.

$R_7$ is H, halogen, CN, $(C_1-C_4)$alkyl, O—$(C_1-C_4)$alkyl, $(C_2-C_4)$alkenyl, phenyl, cyclopropyl, $(C_5-C_6)$heteroaryl;

$R_8$ is H, halogen or $(C_1-C_4)$alkyl;

m is 3 n is 1; and

L is S or NH;

or stereoisomeric form thereof and/or tautomeric form thereof and/or pharmaceutically acceptable salt thereof.

In an embodiment the present invention relates to a compound independently selected from the group consisting of 38. 6-(Piperidin-4-ylamino)-2H-isoquinolin-1-one, 39. 7-Chloro-6-(piperidin-4-ylamino)-2H-isoquinolin-1-one, 40. 6-(Methyl-piperidin-4-yl-amino)-2H-isoquinolin-1-one, 41 6-(Ethyl-piperidin-4-yl-amino)-2H-isoquinolin-1-one, 42 6-(Propyl-piperidin-4-yl-amino)-2H-isoquinolin-1-one, 46 6-(Azepan-4-ylamino)-2H-isoquinolin-1-one, 48 [(R)-1-(5-Fluoro-2-methanesulfonyl-benzyl)-piperidin-3-yl]-isoquinolin-6-yl-amine, 49 6-((S)-1-Benzyl-pyrrolidin-3-ylamino)-2H-isoquinolin-1-one, 50 6-(1-Ethyl-piperidin-3-ylamino)-2H-isoquinolin-1-one, 51 6-[(Piperidin-3-ylmethyl)-amino]-2H-isoquinolin-1-one, 52 6-(Azetidin-3-ylamino)-2H-isoquinolin-1-one, 53 6-[(Pyrrolidin-2-ylmethyl)-amino]-2H-isoquinolin-1-one, 54 6-(1-Benzyl-piperidin-4-ylamino)-2H-isoquinolin-1-one, 55 6-((R)-1-Benzyl-pyrrolidin-3-ylamino)-2H-isoquinolin-1-one, 61 Isoquinolin-6-yl-(S)-pyrrolidin-3-yl-amine 192 6-[(R)-1-(2,3,5-Trifluoro-benzyl)-piperidin-3-ylamino]-2H-isoquinolin-1-one, 193 6-[(R)-1-(3-Chloro-2-fluoro-benzyl)-piperidin-3-ylamino]-2H-isoquinolin-1-one, 194 6-[(R)-1-(2,3-Difluoro-4-methyl-benzyl)-piperidin-3-ylamino]-2H-isoquinolin-1-one, 195 6-((R)-1-Propyl-piperidin-3-ylamino)-2H-isoquinolin-1-one, 196 6-((R)-1-Butyl-piperidin-3-ylamino)-2H-isoquinolin-1-one, 197 6-((R)-1-Isobutyl-piperidin-3-ylamino)-2H-isoquinolin-1-one, 198 6-((R)-1-Cyclopropylmethyl-piperidin-3-ylamino)-2H-isoquinolin-1-one, 199 6-[(R)-1-(3-Methyl-butyl)-piperidin-3-ylamino]-2H-isoquinolin-1-one, 200 6-[(R)-1-(3,3,3-Trifluoro-propyl)-piperidin-3-ylamino]-2H-isoquinolin-1-one, 201 6-((R)-1-Cyclohexylmethyl-piperidin-3-ylamino)-2H-isoquinolin-1-one, 202 6-((R)-1-Cyclohexyl-piperidin-3-ylamino)-2H-isoquinolin-1-one, 203 6-[(R)-1-(4-Chloro-benzyl)-piperidin-3-ylamino]-2H-isoquinolin-1-one, 204 6-[(R)-1-(3-Chloro-benzyl)-piperidin-3-ylamino]-2H-isoquinolin-1-one, 205 6-[(R)-1-(2-Chloro-benzyl)-piperidin-3-ylamino]-2H-isoquinolin-1-one, 206 6-[(R)-1-(2,4-Dichloro-benzyl)-piperidin-3-ylamino]-2H-isoquinolin-1-one, 207 6-((R)-1-Benzyl-piperidin-3-ylamino)-2H-isoquinolin-1-one, 208 6-[(R)-1-(3,5-Dichloro-benzyl)-piperidin-3-ylamino]-2H-isoquinolin-1-one, 209 2-Chloro-N-[1-dimethylamino-meth-(E)-ylidene]-5-[(R)-3-(1-oxo-1,2-dihydro-isoquinolin-6-ylamino)-piperidin-1-ylmethyl]-benzenesulfonamide, 210 N-[1-Dimethylamino-meth-(E)-ylidene]-4-methoxy-3-[(R)-3-(1-oxo-1,2-dihydro-isoquinolin-6-ylamino)-piperidin-1-ylmethyl]-benzenesulfonamide, 211 6-[(R)-1-(4-Methyl-benzyl)-piperidin-3-ylamino]-2H-isoquinolin-1-one,
212 6-[(R)-1-(4-Trifluoromethyl-benzyl)-piperidin-3-ylamino]-2H-isoquinolin-1-one,
213 6-((R)-1-Pyridin-4-ylmethyl-piperidin-3-ylamino)-2H-isoquinolin-1-one,
214 6-((R)-1-Pyridin-3-ylmethyl-piperidin-3-ylamino)-2H-isoquinolin-1-one,
215 6-((R)-1-Pyridin-2-ylmethyl-piperidin-3-ylamino)-2H-isoquinolin-1-one,
216 6-[(R)-1-(4-Methanesulfonyl-benzyl)-piperidin-3-ylamino]-2H-isoquinolin-1-one,
217 6-[(R)-1-(5-Fluoro-2-methanesulfonyl-benzyl)-piperidin-3-ylamino]-2H-isoquinolin-1-one,
218 6-((R)-1-Naphthalen-2-ylmethyl-piperidin-3-ylamino)-2H-isoquinolin-1-one,
219 6-[(S)-1-(2,3,5-Trifluoro-benzyl)-pyrrolidin-3-ylamino]-2H-isoquinolin-1-one,
220 6-[(S)-1-(3-Chloro-2-fluoro-benzyl)-pyrrolidin-3-ylamino]-2H-isoquinolin-1-one,
221 6-[(S)-1-(2,3-Difluoro-4-methyl-benzyl)-pyrrolidin-3-ylamino]-2H-isoquinolin-1-one,
222 6-((S)-1-Butyl-pyrrolidin-3-ylamino)-2H-isoquinolin-1-one,
223 6-((S)-1-Isopropyl-pyrrolidin-3-ylamino)-2H-isoquinolin-1-one,
224 6-[(S)-1-(1-Ethyl-propyl)-pyrrolidin-3-ylamino]-2H-isoquinolin-1-one,
225 6-((S)-1-Isobutyl-pyrrolidin-3-ylamino)-2H-isoquinolin-1-one,
226 6-((S)-1-Cyclopropylmethyl-pyrrolidin-3-ylamino)-2H-isoquinolin-1-one,
227 6-[(S)-1-(3-Methyl-butyl)-pyrrolidin-3-ylamino]-2H-isoquinolin-1-one,
228 6-((S)-1-Cyclohexylmethyl-pyrrolidin-3-ylamino)-2H-isoquinolin-1-one,
229 6-((S)-1-Cyclohexyl-pyrrolidin-3-ylamino)-2H-isoquinolin-1-one,
230 6-[(S)-1-(4-Chloro-benzyl)-pyrrolidin-3-ylamino]-2H-isoquinolin-1-one,
231 6-[(S)-1-(3-Chloro-benzyl)-pyrrolidin-3-ylamino]-2H-isoquinolin-1-one,
232 6-[(S)-1-(2-Chloro-benzyl)-pyrrolidin-3-ylamino]-2H-isoquinolin-1-one,
233 6-[(S)-1-(2,4-Dichloro-benzyl)-pyrrolidin-3-ylamino]-2H-isoquinolin-1-one,
234 6-[(S)-1-(3,5-Dichloro-benzyl)-pyrrolidin-3-ylamino]-2H-isoquinolin-1-one,
235 2-Chloro-N-[1-dimethylamino-meth-(E)-ylidene]-5-[(S)-3-(1-oxo-1,2-dihydro-isoquinolin-6-ylamino)-pyrrolidin-1-ylmethyl]-benzenesulfonamide,
236 6-[(S)-1-(4-Methyl-benzyl)-pyrrolidin-3-ylamino]-2H-isoquinolin-1-one,
237 6-[(S)-1-(4-Trifluoromethyl-benzyl)-pyrrolidin-3-ylamino]-2H-isoquinolin-1-one,
238 6-((S)-1-Pyridin-4-ylmethyl-pyrrolidin-3-ylamino)-2H-isoquinolin-1-one,
239 6-((S)-1-Pyridin-3-ylmethyl-pyrrolidin-3-ylamino)-2H-isoquinolin-1-one,
240 6-((S)-1-Pyridin-2-ylmethyl-pyrrolidin-3-ylamino)-2H-isoquinolin-1-one,
241 6-[(S)-1-(4-Methanesulfonyl-benzyl)-pyrrolidin-3-ylamino]-2H-isoquinolin-1-one,
242 6-[(S)-1-(5-Fluoro-2-methanesulfonyl-benzyl)-pyrrolidin-3-ylamino]-2H-isoquinolin-1-one,
243 6-((S)-1-Naphthalen-2-ylmethyl-pyrrolidin-3-ylamino)-2H-isoquinolin-1-one,
244 6-((S)-1-Naphthalen-1-ylmethyl-pyrrolidin-3-ylamino)-2H-isoquinolin-1-one,
245 6-((S)-1-Pyrrolidin-3-ylmethyl-pyrrolidin-3-ylamino)-2H-isoquinolin-1-one,
246 6-[(S)-1-(1-Methyl-1H-pyrazol-4-ylmethyl)-pyrrolidin-3-ylamino]-2H-isoquinolin-1-one,
247 6-((S)-1-Thiophen-3-ylmethyl-pyrrolidin-3-ylamino)-2H-isoquinolin-1-one,
248 6-((S)-1-Piperidin-3-ylmethyl-pyrrolidin-3-ylamino)-2H-isoquinolin-1-one,
249 6-[1-(3-Chloro-2-fluoro-benzyl)-azetidin-3-ylamino]-2H-isoquinolin-1-one,
250 6-[1-(2,3-Difluoro-4-methyl-benzyl)-azetidin-3-ylamino]-2H-isoquinolin-1-one,
251 6-(1-Isopropyl-azetidin-3-ylamino)-2H-isoquinolin-1-one,
252 6-[1-(1-Ethyl-propyl)-azetidin-3-ylamino]-2H-isoquinolin-1-one,
253 6-(1-Cyclopropylmethyl-azetidin-3-ylamino)-2H-isoquinolin-1-one,
254 6-[1-(3-Methyl-butyl)-azetidin-3-ylamino]-2H-isoquinolin-1-one,
255 6-(1-Cyclohexylmethyl-azetidin-3-ylamino)-2H-isoquinolin-1-one,
256 6-(1-Cyclohexyl-azetidin-3-ylamino)-2H-isoquinolin-1-one,
257 6-[1-(4-Chloro-benzyl)-azetidin-3-ylamino]-2H-isoquinolin-1-one,
258 6-[1-(3-Chloro-benzyl)-azetidin-3-ylamino]-2H-isoquinolin-1-one,
259 6-[1-(2-Chloro-benzyl)-azetidin-3-ylamino]-2H-isoquinolin-1-one,
260 6-(1-Benzyl-azetidin-3-ylamino)-2H-isoquinolin-1-one,
261 2-Chloro-N-[1-dimethylamino-meth-(E)-ylidene]-5-[3-(1-oxo-1,2-dihydro-isoquinolin-6-ylamino)-azetidin-1-ylmethyl]-benzenesulfonamide, and
262 6-[1-(4-Methyl-benzyl)-azetidin-3-ylamino]-2H-isoquinolin-1-one, or stereoisomeric form thereof and/or tautomeric form thereof and/or pharmaceutically acceptable salt thereof.

In a further embodiment, the present invention relates to a compound independently selected from the group consisting of 286 7-Chloro-6-(piperidin-4-ylsulfanyl)-2H-isoquinolin-1-one,
288 7-Chloro-6-(piperidine-4-sulfonyl)-2H-isoquinolin-1-one, and
290 7-Chloro-6-(piperidine-4-sulfinyl)-2H-isoquinolin-1-one, or stereoisomeric form thereof and/or tautomeric form thereof and/or pharmaceutically acceptable salt thereof.

In a further embodiment, the present invention relates to a compound independently selected from the group consisting of 18 4-(Isoquinolin-6-ylamino)-piperidine-1-carboxylic acid tert-butyl ester,
19 4-(Isoquinolin-6-yl-methyl-amino)-piperidine-1-carboxylic acid tert-butyl ester,
20 Isoquinolin-6-yl-(1-methyl-piperidin-4-yl)-amine,
21 2-(Isoquinolin-6-ylaminomethyl)-pyrrolidine-1-carboxylic acid tert-butyl ester,
22 3-(Isoquinolin-6-ylaminomethyl)-pyrrolidine-1-carboxylic acid tert-butyl ester,
23 Isoquinolin-6-yl-methyl-(1-methyl-piperidin-4-yl)-amine,
25 (7-Chloro-isoquinolin-6-yl)-(1-methyl-piperidin-4-yl)-amine, 26 4-(7-Chloro-isoquinolin-6-ylamino)-piperidine-1-carboxylic acid tert-butyl ester,
33 Isoquinolin-6-yl-piperidin-4-yl-amine,
34 Isoquinolin-6-yl-methyl-piperidin-4-yl-amine,
35 Isoquinolin-6-yl-pyrrolidin-2-ylmethyl-amine,
36 Isoquinolin-6-yl-pyrrolidin-3-ylmethyl-amine,
37 (7-Chloro-isoquinolin-6-yl)-piperidin-4-yl-amine,
43 (1-Isopropyl-piperidin-4-yl)-isoquinolin-6-yl-amine,
44 Isoquinolin-6-yl-(S)-pyrrolidin-3-yl-amine,
45 Isoquinolin-6-yl-(R)-piperidin-3-yl-amine,
47 Azetidin-3-yl-isoquinolin-6-yl-amine,
56 (1-Butyl-piperidin-4-ylmethyl)-isoquinolin-6-yl-amine,
58 ((S)-1-Benzyl-pyrrolidin-3-yl)-isoquinolin-6-yl-amine,
61. Isoquinolin-6-yl-(S)-pyrrolidin-3-yl-amine
60 (1-Ethyl-piperidin-3-yl)-isoquinolin-6-yl-amine,
62 Isoquinolin-6-yl-piperidin-3-ylmethyl-amine,
63 Azetidin-3-yl-isoquinolin-6-yl-amine,
64 Isoquinolin-6-yl-piperidin-4-yl-pyridin-3-ylmethyl-amine,
65 Benzyl-isoquinolin-6-yl-piperidin-4-yl-amine,
66 Isoquinolin-6-yl-piperidin-4-yl-pyridin-4-ylmethyl-amine,
67 Isoquinolin-6-yl-(R)-pyrrolidin-3-yl-amine,
68 (1-Ethyl-piperidin-4-yl)-isoquinolin-6-yl-amine,
69 Isoquinolin-6-yl-(1-propyl-piperidin-4-yl)-amine,
70 (1-Butyl-piperidin-4-yl)isoquinolin-6-yl-amine,
71 (1-Isobutyl-piperidin-4-yl)isoquinolin-6-yl-amine,
72 (1-Cyclopropylmethyl-piperidin-4-yl)isoquinolin-6-yl-amine,
73 Isoquinolin-6-yl-[1-(3-methyl-butyl)-piperidin-4-yl]-amine,
74 Isoquinolin-6-yl-[1-(3,3,3-trifluoro-propyl)-piperidin-4-yl]-amine,
75 (1-Cyclohexylmethyl-piperidin-4-yl)isoquinolin-6-yl-amine,
76 (1-Cyclohexyl-piperidin-4-yl)isoquinolin-6-yl-amine,
77 [1-(4-Chloro-benzyl)piperidin-4-yl]-isoquinolin-6-yl-amine,
78 [1-(3-Chloro-benzyl)piperidin-4-yl]-isoquinolin-6-yl-amine,
79 [1-(2-Chloro-benzyl)piperidin-4-yl]-isoquinolin-6-yl-amine,
80 [1-(2,4-Dichloro-benzyl)-piperidin-4-yl]-isoquinolin-6-yl-amine,
81 (1-Benzyl-piperidin-4-yl)isoquinolin-6-yl-amine,
82 2-Chloro-N-[1-dimethylamino-meth-(E)-ylidene]-5-[4-(isoquinolin-6-ylamino)-piperidin-1-ylmethyl]-benzene-sulfonamide,
83 N-[1-Dimethylamino-meth-(E)-ylidene]-3-[4-(isoquinolin-6-ylamino)-piperidin-1-ylmethyl]-4-methoxy-benzenesulfonamide,
84 Isoquinolin-6-yl-[1-(4-methyl-benzyl)-piperidin-4-yl]-amine,
85 Isoquinolin-6-yl-[1-(4-trifluoromethyl-benzyl)-piperidin-4-yl]-amine,
86 Isoquinolin-6-yl-(1-pyridin-4-ylmethyl-piperidin-4-yl) amine,
87 Isoquinolin-6-yl-(1-pyridin-3-ylmethyl-piperidin-4-yl) amine,
88 Isoquinolin-6-yl-(1-pyridin-2-ylmethyl-piperidin-4-yl) amine,
89 Isoquinolin-6-yl-[1-(4-methanesulfonyl-benzyl)-piperidin-4-yl]-amine,
90 [1-(5-Fluoro-2-methanesulfonyl-benzyl)-piperidin-4-yl]-isoquinolin-6-yl-amine,
91 Isoquinolin-6-yl-[1-(4-trifluoromethanesulfonyl-benzyl)-piperidin-4-yl]-amine,
92 Isoquinolin-6-yl-(1-naphthalen-2-ylmethyl-piperidin-4-yl)-amine,
93 Isoquinolin-6-yl-(1-naphthalen-1-ylmethyl-piperidin-4-yl)-amine,
94 Isoquinolin-6-yl-methyl-(1-propyl-piperidin-4-yl)amine,
95 (1-Butyl-piperidin-4-yl)isoquinolin-6-yl-methyl-amine,
96 (1-Isobutyl-piperidin-4-yl)isoquinolin-6-yl-methyl-amine,
97 (1-Cyclopropylmethyl-piperidin-4-yl)-isoquinolin-6-yl-methyl-amine,
98 Isoquinolin-6-yl-methyl-[1-(3-methyl-butyl)-piperidin-4-yl]-amine,
99 Isoquinolin-6-yl-methyl-[1-(3,3,3-trifluoro-propyl)-piperidin-4-yl]-amine,
100 [1-(4-Chloro-benzyl)-piperidin-4-yl]-isoquinolin-6-yl-methyl-amine,
101 Isoquinolin-6-yl-[1-(2,3,5-trifluoro-benzyl)-azetidin-3-yl]-amine,
102 [1-(3-Chloro-2-fluoro-benzyl)-azetidin-3-yl]-isoquinolin-6-yl-amine,
103 [1-(2,3-Difluoro-4-methyl-benzyl)-azetidin-3-yl]-isoquinolin-6-yl-amine,
104 (1-Ethyl-azetidin-3-yl)isoquinolin-6-yl-amine,
105 Isoquinolin-6-yl-(1-propyl-azetidin-3-yl)amine,
106 (1-Butyl-azetidin-3-yl)isoquinolin-6-yl-amine,
107 (1-Isopropyl-azetidin-3-yl)isoquinolin-6-yl-amine,
108 [1-(1-Ethyl-propyl)azetidin-3-yl]-isoquinolin-6-yl-amine,
109 (1-Isobutyl-azetidin-3-yl)isoquinolin-6-yl-amine,
110 (1-Cyclopropylmethyl-azetidin-3-yl)isoquinolin-6-yl-amine,
111 Isoquinolin-6-yl-[1-(3-methyl-butyl)-azetidin-3-yl]-amine,
112 Isoquinolin-6-yl-[1-(3,3,3-trifluoro-propyl)-azetidin-3-yl]-amine,
113 (1-Cyclohexylmethyl-azetidin-3-yl)isoquinolin-6-yl-amine,
114 (1-Cyclohexyl-azetidin-3-yl)isoquinolin-6-yl-amine,
115 [1-(4-Chloro-benzyl)azetidin-3-yl]-isoquinolin-6-yl-amine,
116 [1-(3-Chloro-benzyl)azetidin-3-yl]-isoquinolin-6-yl-amine,
117 [1-(2-Chloro-benzyl)azetidin-3-yl]-isoquinolin-6-yl-amine,
118 [1-(2,4-Dichloro-benzyl)azetidin-3-yl]-isoquinolin-6-yl-amine,
119 (1-Benzyl-azetidin-3-yl)isoquinolin-6-yl-amine,
120 2-Chloro-N-[1-dimethylamino-meth-(E)-ylidene]-5-[3-(isoquinolin-6-ylamino)-azetidin-1-ylmethyl]-benzene-sulfonamide,
121 N-[1-Dimethylamino-meth-(E)-ylidene]-3-[3-(isoquinolin-6-ylamino)-azetidin-1-ylmethyl]-4-methoxy-benzenesulfonamide,
122 Isoquinolin-6-yl-[1-(4-methyl-benzyl)-azetidin-3-yl]-amine,
123 Isoquinolin-6-yl-[1-(4-trifluoromethyl-benzyl)-azetidin-3-yl]-amine,
124 Isoquinolin-6-yl-(1-pyridin-4-ylmethyl-azetidin-3-yl) amine,
125 Isoquinolin-6-yl-(1-pyridin-3-ylmethyl-azetidin-3-yl) amine,
126 Isoquinolin-6-yl-(1-pyridin-2-ylmethyl-azetidin-3-yl) amine,
127 Isoquinolin-6-yl-[1-(4-methanesulfonyl-benzyl)-azetidin-3-yl]-amine,
128 [1-(5-Fluoro-2-methanesulfonyl-benzyl)-azetidin-3-yl]-isoquinolin-6-yl-amine, 129 Isoquinolin-6-yl-(1-naphthalen-2-ylmethyl-azetidin-3-yl)amine,
130 Isoquinolin-6-yl-(1-naphthalen-1-ylmethyl-azetidin-3-yl)amine,
131 [1-((S)-2-Amino-propyl)-azetidin-3-yl]-isoquinolin-6-yl-amine,
132 Isoquinolin-6-yl-(1-pyrrolidin-3-ylmethyl-azetidin-3-yl)amine,
133 Isoquinolin-6-yl-(1-(R)-1-pyrrolidin-2-ylmethyl-azetidin-3-yl)-amine,
134 Isoquinolin-6-yl-[1-(1-methyl-1H-pyrazol-4-ylmethyl)-azetidin-3-yl]-amine,
135 Isoquinolin-6-yl-(1-thiophen-3-ylmethyl-azetidin-3-yl)-amine,
136 Isoquinolin-6-yl-[(R)-1-(2,3,5-trifluoro-benzyl)-pyrrolidin-3-yl]-amine,
137 ((R)-1-Butyl-pyrrolidin-3-yl)isoquinolin-6-yl-amine,
138 ((R)-1-Isopropyl-pyrrolidin-3-yl)-isoquinolin-6-yl-amine,
139 [(R)-1-(1-Ethyl-propyl)-pyrrolidin-3-yl]-isoquinolin-6-yl-amine,
140 ((R)-1-Isobutyl-pyrrolidin-3-yl)-isoquinolin-6-yl-amine,
141 ((R)-1-Cyclopropylmethyl-pyrrolidin-3-yl)-isoquinolin-6-yl-amine,
142 Isoquinolin-6-yl-[(R)-1-(3-methyl-butyl)-pyrrolidin-3-yl]-amine,
143 Isoquinolin-6-yl-[(R)-1-(3,3,3-trifluoro-propyl)-pyrrolidin-3-yl]-amine,
144 ((R)-1-Cyclohexylmethyl-pyrrolidin-3-yl)-isoquinolin-6-yl-amine,
145 [(R)-1-(4-Chloro-benzyl)-pyrrolidin-3-yl]-isoquinolin-6-yl-amine,
146 [(R)-1-(3-Chloro-benzyl)-pyrrolidin-3-yl]-isoquinolin-6-yl-amine,
147 ((R)-1-Benzyl-pyrrolidin-3-yl)-isoquinolin-6-yl-amine,
148 [(R)-1-(3,5-Dichloro-benzyl)-pyrrolidin-3-yl]-isoquinolin-6-yl-amine,
149 2-Chloro-N-[1-dimethylamino-meth-(E)-ylidene]-5-[(R)-3-(isoquinolin-6-ylamino)-pyrrolidin-1-ylmethyl]-benzenesulfonamide,
150 N-[1-Dimethylamino-meth-(E)-ylidene]-3-[(R)-3-(isoquinolin-6-ylamino)-pyrrolidin-1-ylmethyl]-4-methoxy-benzenesulfonamide,
151 Isoquinolin-6-yl-[(R)-1-(4-methyl-benzyl)-pyrrolidin-3-yl]-amine,
152 Isoquinolin-6-yl-[(R)-1-(4-trifluoromethyl-benzyl)-pyrrolidin-3-yl]-amine,
153 Isoquinolin-6-yl-((R)-1-pyridin-4-ylmethyl-pyrrolidin-3-yl)-amine,
154 Isoquinolin-6-yl-((R)-1-pyridin-3-ylmethyl-pyrrolidin-3-yl)-amine,
155 Isoquinolin-6-yl-((R)-1-pyridin-2-ylmethyl-pyrrolidin-3-yl)-amine,
156 Isoquinolin-6-yl-[(R)-1-(4-methanesulfonyl-benzyl)-pyrrolidin-3-yl]-amine,
157 [(R)-1-(5-Fluoro-2-methanesulfonyl-benzyl)-pyrrolidin-3-yl]-isoquinolin-6-yl-amine,
158 Isoquinolin-6-yl-((R)-1-naphthalen-2-ylmethyl-pyrrolidin-3-yl)-amine,
159 Isoquinolin-6-yl-[(R)-1-(2,3,5-trifluoro-benzyl)-piperidin-3-yl]-amine,
160 [(R)-1-(3-Chloro-2-fluoro-benzyl)-piperidin-3-yl]-isoquinolin-6-yl-amine,
161 [(R)-1-(2,3-Difluoro-4-methyl-benzyl)-piperidin-3-yl]-isoquinolin-6-yl-amine,
162 ((R)-1-Ethyl-piperidin-3-yl)isoquinolin-6-yl-amine,
163 Isoquinolin-6-yl-((R)-1-propyl-piperidin-3-yl)amine,
164 ((R)-1-Butyl-piperidin-3-yl)isoquinolin-6-yl-amine,
165 ((R)-1-Isobutyl-piperidin-3-yl)isoquinolin-6-yl-amine,
166 ((R)-1-Cyclopropylmethyl-piperidin-3-yl)-isoquinolin-6-yl-amine,
167 Isoquinolin-6-yl-[(R)-1-(3-methyl-butyl)piperidin-3-yl]-amine,
168 Isoquinolin-6-yl-[(R)-1-(3,3,3-trifluoro-propyl)-piperidin-3-yl]-amine,
169 ((R)-1-Cyclohexylmethyl-piperidin-3-yl)isoquinolin-6-yl-amine,
170 [(R)-1-(4-Chloro-benzyl)-piperidin-3-yl]-isoquinolin-6-yl-amine,
171 [(R)-1-(3-Chloro-benzyl)-piperidin-3-yl]-isoquinolin-6-yl-amine,
172 [(R)-1-(2-Chloro-benzyl)-piperidin-3-yl]-isoquinolin-6-yl-amine,
173 [(R)-1-(2,4-Dichloro-benzyl)-piperidin-3-yl]-isoquinolin-6-yl-amine,
174 ((R)-1-Benzyl-piperidin-3-yl)isoquinolin-6-yl-amine,
175 [(R)-1-(3,5-Dichloro-benzyl)-piperidin-3-yl]-isoquinolin-6-yl-amine,
176 2-Chloro-N-[1-dimethylamino-meth-(E)-ylidene]-5-[(R)-3-(isoquinolin-6-ylamino)-piperidin-1-ylmethyl]-benzenesulfonamide,
177 N-[1-Dimethylamino-meth-(E)-ylidene]-3-[(R)-3-(isoquinolin-6-ylamino)-piperidin-1-ylmethyl]-4-methoxy-benzenesulfonamide,
178 Isoquinolin-6-yl-[(R)-1-(4-methyl-benzyl)-piperidin-3-yl]-amine,
179 Isoquinolin-6-yl-[(R)-1-(4-trifluoromethyl-benzyl)-piperidin-3-yl]-amine,
180 Isoquinolin-6-yl-((R)-1-pyridin-4-ylmethyl-piperidin-3-yl)-amine,
181 Isoquinolin-6-yl-((R)-1-pyridin-3-ylmethyl-piperidin-3-yl)-amine,
182 Isoquinolin-6-yl-((R)-1-pyridin-2-ylmethyl-piperidin-3-yl)-amine,
183 Isoquinolin-6-yl-[(R)-1-(4-methanesulfonyl-benzyl)-piperidin-3-yl]-amine,
184 Isoquinolin-6-yl-((R)-1-naphthalen-2-ylmethyl-piperidin-3-yl)-amine,
185 Isoquinolin-6-yl-((R)-1-naphthalen-1-ylmethyl-piperidin-3-yl)-amine,
186 [(R)-1-((S)-2-Amino-propyl)-piperidin-3-yl]-isoquinolin-6-yl-amine,
187 Isoquinolin-6-yl-((R)-1-pyrrolidin-3-ylmethyl-piperidin-3-yl)-amine, or
188 Isoquinolin-6-yl-((R)-1-(R)-1-pyrrolidin-2-ylmethyl-piperidin-3-yl)-amine, or their stereoisomeric and/or tautomeric forms and/or their pharmaceutically acceptable salts.

In a further embodiment, the present invention relates to a compound independently selected from the group of 267 (S)-3-(7-Chloro-isoquinolin-6-ylsulfanyl)-pyrrolidine-1-carboxylic acid tert-butyl ester,
268 7-Chloro-6-((S)-pyrrolidin-3-ylsulfanyl)-isoquinoline,
269 (Rac)-7-Chloro-6-(piperidin-3-ylsulfanyl)-isoquinoline,
270 (Rac)-6-(Azepan-4-ylsulfanyl)-7-chloro-isoquinoline,
271 (Rac)-6-(Azepan-4-ylsulfanyl)-7-bromo-isoquinoline,
274 4-(7-Chloro-isoquinolin-6-ylsulfanyl)-piperidine-1-carboxylic acid tert-butyl ester,
275 7-Chloro-6-(piperidin-4-ylsulfanyl)-isoquinoline,
276 4-(7-Propyl-isoquinolin-6-ylsulfanyl)-piperidine-1-carboxylic acid tert-butyl ester,
277 6-(Piperidin-4-ylsulfanyl)-7-propyl-isoquinoline,
278 7-Bromo-6-(piperidin-4-ylsulfanyl)-isoquinoline, 279 7-Chloro-6-(piperidin-4-ylmethylsulfanyl)-isoquinoline,
280 7-Chloro-6-(piperidin-3-ylmethylsulfanyl)-isoquinoline,
281 7-Bromo-6-(piperidin-3-ylmethylsulfanyl)-isoquinoline,
282 7-Chloro-6-(pyrrolidin-2-ylmethylsulfanyl)-isoquinoline,
283 7-Chloro-6-(pyrrolidin-3-ylmethylsulfanyl)-isoquinoline,
284 7-Bromo-6-(pyrrolidin-3-ylmethylsulfanyl)-isoquinoline,
291 7-Chloro-6-((S)-1-ethyl-pyrrolidin-3-ylsulfanyl)-isoquinoline,
292 7-Chloro-6-((S)-1-propyl-pyrrolidin-3-ylsulfanyl)-isoquinoline,
293 6-((S)-1-Butyl-pyrrolidin-3-ylsulfanyl)-7-chloro-isoquinoline,
294 7-Chloro-6-((S)-1-isopropyl-pyrrolidin-3-ylsulfanyl)-isoquinoline,
295 7-Chloro-6-((S)-1-isobutyl-pyrrolidin-3-ylsulfanyl)-isoquinoline,
296 7-Chloro-6-((S)-1-cyclopropyl-methyl-pyrrolidin-3-ylsulfanyl)-isoquinoline,
297 7-Chloro-6-[(S)-1-(3-methyl-butyl)-pyrrolidin-3-ylsulfanyl]-isoquinoline,
298 7-Chloro-6-[(S)-1-(3,3,3-trifluoro-propyl)-pyrrolidin-3-ylsulfanyl]-isoquinoline,
299 7-Chloro-6-((S)-1-cyclohexylmethyl-pyrrolidin-3-ylsulfanyl)-isoquinoline,
300 7-Chloro-6-((S)-1-cyclohexyl-pyrrolidin-3-ylsulfanyl)-isoquinoline,
301 7-Chloro-6-[(S)-1-(4-chloro-benzyl)-pyrrolidin-3-ylsulfanyl]-isoquinoline,
302 7-Chloro-6-[(S)-1-(3-chloro-benzyl)-pyrrolidin-3-ylsulfanyl]-isoquinoline,
303 7-Chloro-6-[(S)-1-(2-chloro-benzyl)-pyrrolidin-3-ylsulfanyl]-isoquinoline,
304 7-Chloro-6-[(S)-1-(2,4-dichloro-benzyl)-pyrrolidin-3-ylsulfanyl]-isoquinoline,
305 6-((S)-1-Benzyl-pyrrolidin-3-ylsulfanyl)-7-chloro-isoquinoline,
306 7-Chloro-6-[(S)-1-(3,5-dichloro-benzyl)-pyrrolidin-3-ylsulfanyl]-isoquinoline,
307 2-Chloro-5-[(S)-3-(7-chloro-isoquinolin-6-ylsulfanyl)-pyrrolidin-1-ylmethyl]-N-[1-dimethylamino-meth-(E)-ylidene]-benzenesulfonamide,
308 3-[(S)-3-(7-Chloro-isoquinolin-6-ylsulfanyl)-pyrrolidin-1-ylmethyl]-N-[1-dimethylamino-meth-(E)-ylidene]-4-methoxy-benzenesulfonamide,
309 7-Chloro-6-[(S)-1-(4-methyl-benzyl)-pyrrolidin-3-ylsulfanyl]-isoquinoline,
310 7-Chloro-6-[(S)-1-(4-trifluoromethyl-benzyl)-pyrrolidin-3-ylsulfanyl]-isoquinoline,
311 7-Chloro-6-((S)-1-pyridin-4-ylmethyl-pyrrolidin-3-ylsulfanyl)-isoquinoline,
312 7-Chloro-6-((S)-1-pyridin-3-ylmethyl-pyrrolidin-3-ylsulfanyl)-isoquinoline,
313 7-Chloro-6-((S)-1-pyridin-2-ylmethyl-pyrrolidin-3-ylsulfanyl)-isoquinoline,
314 7-Chloro-6-[(S)-1-(4-methanesulfonyl-benzyl)-pyrrolidin-3-ylsulfanyl]-isoquinoline,
315 7-Chloro-6-[(S)-1-(5-fluoro-2-methanesulfonyl-benzyl)-pyrrolidin-3-ylsulfanyl]-isoquinoline,
316 7-Chloro-6-[(S)-1-(4-trifluoromethanesulfonyl-benzyl)-pyrrolidin-3-ylsulfanyl]-isoquinoline,
317 7-Chloro-6-((S)-1-naphthalen-2-ylmethyl-pyrrolidin-3-ylsulfanyl)-isoquinoline,
318 7-Chloro-6-(1-ethyl-piperidin-4-ylsulfanyl)-isoquinoline,
319 7-Chloro-6-(1-propyl-piperidin-4-ylsulfanyl)-isoquinoline,
320 6-(1-Butyl-piperidin-4-ylsulfanyl)-7-chloro-isoquinoline,
321 7-Chloro-6-(1-isopropyl-piperidin-4-ylsulfanyl)-isoquinoline,
322 7-Chloro-6-(1-isobutyl-piperidin-4-ylsulfanyl)-isoquinoline,
323 7-Chloro-6-(1-cyclopropylmethyl-piperidin-4-ylsulfanyl)-isoquinoline,
324 7-Chloro-6-[1-(3-methyl-butyl)-piperidin-4-ylsulfanyl]-isoquinoline,
325 7-Chloro-6-[1-(3,3,3-trifluoro-propyl)-piperidin-4-ylsulfanyl]-isoquinoline,
326 7-Chloro-6-(1-cyclohexylmethyl-piperidin-4-ylsulfanyl)-isoquinoline,
327 7-Chloro-6-(1-cyclohexyl-piperidin-4-ylsulfanyl)-isoquinoline,
328 7-Chloro-6-[1-(4-chloro-benzyl)-piperidin-3-ylsulfanyl]-isoquinoline,
329 7-Chloro-6-[1-(3-chloro-benzyl)-piperidin-3-ylsulfanyl]-isoquinoline,
330 7-Chloro-6-[1-(2-chloro-benzyl)-piperidin-3-ylsulfanyl]-isoquinoline,
331 7-Chloro-6-[1-(2,4-dichloro-benzyl)-piperidin-3-ylsulfanyl]-isoquinoline,
332 6-(1-Benzyl-piperidin-3-ylsulfanyl)-7-chloro-isoquinoline,
333 7-Chloro-6-[1-(3,5-dichloro-benzyl)-piperidin-3-ylsulfanyl]-isoquinoline,
334 2-Chloro-5-[3-(7-chloro-isoquinolin-6-ylsulfanyl)-piperidin-1-ylmethyl]-N-[1-dimethylamino-meth-(E)-ylidene]-benzenesulfonamide,
335 3-[3-(7-Chloro-isoquinolin-6-ylsulfanyl)-piperidin-1-ylmethyl]-N-[1-dimethylamino-meth-(E)-ylidene]-4-methoxy-benzenesulfonamide,
336 7-Chloro-6-[1-(4-methyl-benzyl)-piperidin-3-ylsulfanyl]-isoquinoline,
337 7-Chloro-6-[1-(4-trifluoromethyl-benzyl)-piperidin-3-ylsulfanyl]-isoquinoline,
338 7-Chloro-6-(1-pyridin-4-ylmethyl-piperidin-3-ylsulfanyl)-isoquinoline,
339 7-Chloro-6-(1-pyridin-3-ylmethyl-piperidin-3-ylsulfanyl)-isoquinoline,
340 7-Chloro-6-(1-pyridin-2-ylmethyl-piperidin-3-ylsulfanyl)-isoquinoline,
341 6-Chloro-7-(pyrrolidin-2-ylmethylsulfanyl)-isoquinoline,
342 7-Bromo-6-(1-ethyl-piperidin-4-ylsulfanyl)-isoquinoline,
343 7-Bromo-6-(1-propyl-piperidin-4-ylsulfanyl)-isoquinoline,
344 7-Bromo-6-(1-butyl-piperidin-4-ylsulfanyl)-isoquinoline,
345 7-Bromo-6-(1-isopropyl-piperidin-4-ylsulfanyl)-isoquinoline,
346 7-Bromo-6-(1-isobutyl-piperidin-4-ylsulfanyl)-isoquinoline,
347 7-Bromo-6-(1-cyclopropylmethyl-piperidin-4-ylsulfanyl)-isoquinoline,
348 7-Bromo-6-[1-(3-methyl-butyl)-piperidin-4-ylsulfanyl]-isoquinoline, 349 7-Bromo-6-[1-(3,3,3-trifluoro-propyl)-piperidin-4-yl-sulfanyl]-isoquinoline, 350 7-Bromo-6-(1-cyclohexylmethyl-piperidin-4-ylsulfanyl)-isoquinoline, 351 7-Bromo-6-(1-cyclohexyl-piperidin-4-ylsulfanyl)-isoquinoline, 352 7-Bromo-6-[1-(4-chloro-benzyl)-piperidin-4-ylsulfanyl]-isoquinoline, 353 7-Bromo-6-[1-(3-chloro-benzyl)-piperidin-4-ylsulfanyl]-isoquinoline, 354 7-Bromo-6-[1-(2-chloro-benzyl)-piperidin-4-ylsulfanyl]-isoquinoline, 355 7-Bromo-6-[1-(2,4-dichloro-benzyl)-piperidin-4-ylsulfanyl]-isoquinoline, 356 7-Bromo-6-[1-benzyl-piperidin-4-ylsulfanyl]-isoquinoline, 357 7-Bromo-6-[1-(3,5-dichloro-benzyl)-piperidin-4-ylsulfanyl]-isoquinoline, 358 2-Chloro-5-[4-(7-bromo-isoquinolin-6-ylsulfanyl)-piperidin-1-ylmethyl]-N-[1-di-methylaminometh-(E)-ylidene]-benzene-sulfonamide, 359 3-[4-(7-Bromo-isoquinolin-6-ylsulfanyl)-pipe-ridin-1-ylmethyl]-N-dimethylamino-meth(E)-ylidene-4-methoxy benzene-sulfonamide, 360 7-Bromo-6-[1-(4-trifluormethyl-benzyl)-piperidin-4-yl-sulfanyl]-isoquinoline, 361 7-Bromo-6-(1-pyridin-2-ylmethyl-piperidin-4-ylsulfanyl)-isoquinoline, 362 7-Bromo-6-[1-(5-fluoro-2-methanesulfonyl-benzyl)-piperidin-4-ylsulfanyl]-isoquinoline, 363 7-Bromo-6-[1-(4-trifluoromethanesulfonyl-benzyl)-piperidin-4-ylsulfanyl]-isoquinoline, 364 7-Bromo-6-(1-naphthalen-2-ylmethyl-piperidin-4-yl-sulfanyl)-isoquinoline, 365 7-Bromo-6-(1-naphthalen-1-ylmethyl-piperidin-4-yl-sulfanyl)-isoquinoline, 366 7-Bromo-6-[1-(1-methyl-1H-pyrrol-3-ylmethyl)-piperidin-4-ylsulfanyl]-isoquinoline, 367 7-Bromo-6-[1-(1-methyl-1H-pyrazol-4-ylmethyl)-piperidin-4-ylsulfanyl]-isoquinoline, 368 7-Chloro-6-(1-ethyl-piperidin-3-ylsulfanyl)-isoquinoline, 369 7-Chloro-6-(1-propyl-piperidin-3-ylsulfanyl)-isoquinoline, 370 6-(1-Butyl-piperidin-3-ylsulfanyl)-7-chloro-isoquinoline, 371 7-Chloro-6-(1-isopropyl-piperidin-3-ylsulfanyl)-isoquinoline, 372 7-Chloro-6-(1-isobutyl-piperidin-3-ylsulfanyl)-isoquinoline, 373 7-Chloro-6-(1-cyclopropylmethyl-piperidin-3-ylsulfanyl)-isoquinoline, 374 7-Chloro-6-[1-(3-methyl-butyl)-piperidin-3-ylsulfanyl]-isoquinoline, 375 7-Chloro-6-[1-(3,3,3-trifluoro-propyl)-piperidin-3-yl-sulfanyl]-isoquinoline, 376 7-Chloro-6-(1-cyclohexylmethyl-piperidin-3-ylsulfanyl)-isoquinoline, 377 7-Chloro-6-(1-cyclohexyl-piperidin-3-ylsulfanyl)-isoquinoline, 378 7-Chloro-6-[1-(4-chloro-benzyl)-piperidin-3-ylsulfanyl]-isoquinoline, 379 7-Chloro-6-[1-(3-chloro-benzyl)-piperidin-3-ylsulfanyl]-isoquinoline, 380 7-Chloro-6-[1-(2-chloro-benzyl)-piperidin-3-ylsulfanyl]-isoquinoline, 381 6-(1-Benzyl-piperidin-3-ylsulfanyl)-7-chloro-isoquinoline, 382 7-Chloro-6-[1-(3,5-dichloro-benzyl)-piperidin-3-ylsulfanyl]-isoquinoline, 383 2-Chloro-5-[3-(7-chloro-isoquinolin-6-ylsulfanyl)-piperidin-1-ylmethyl]-N-[1-dimethylamino-meth-(E)-ylidene]-benzenesulfonamide, 384 3-[3-(7-Chloro-isoquinolin-6-ylsulfanyl)-piperidin-1-ylmethyl]-N-[1-dimethylamino-meth-(E)-ylidene]-4-methoxy-benzenesulfonamide, 385 7-Chloro-6-[1-(4-methyl-benzyl)-piperidin-3-ylsulfanyl]-isoquinoline, 386 7-Chloro-6-[1-(4-trifluoromethyl-benzyl)-piperidin-3-ylsulfanyl]-isoquinoline, 387 7-Chloro-6-(1-pyridin-4-ylmethyl-piperidin-3-ylsulfanyl)-isoquinoline, and 388 7-Chloro-6-(1-pyridin-3-ylmethyl-piperidin-3-ylsulfanyl)-isoquinoline, or stereoisomeric form thereof and/or tautomeric form thereof and/or pharmaceutically acceptable salt thereof.

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Isoquinoline substitution pattern is numbered according to IUPAC rules:

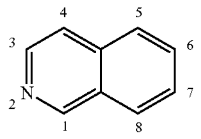

All references to "compound(s) of formula (I)" hereinafter refer to compound(s) of the formula (I), (II), (III), (III') and (IV) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I), (II), (III), (III') or (VI) in the form of their stereoisomeric forms, which include racemates, racemic mixtures, pure enantiomers and diastereomers and mixtures thereof. The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The present invention therefore also relates to the compounds of the formula (I) and/or their pharmaceutically acceptable salts and/or their prodrugs for use as pharmaceuticals (or medicaments), to the use of the compounds of the formula (I) and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formulae (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

Isoquinolines and isoquinolinones can by synthesized via a variety of methods. The following general schemes illustrate some of the possible ways to access isoquinolones, but do not limit the present invention.

Scheme 1:

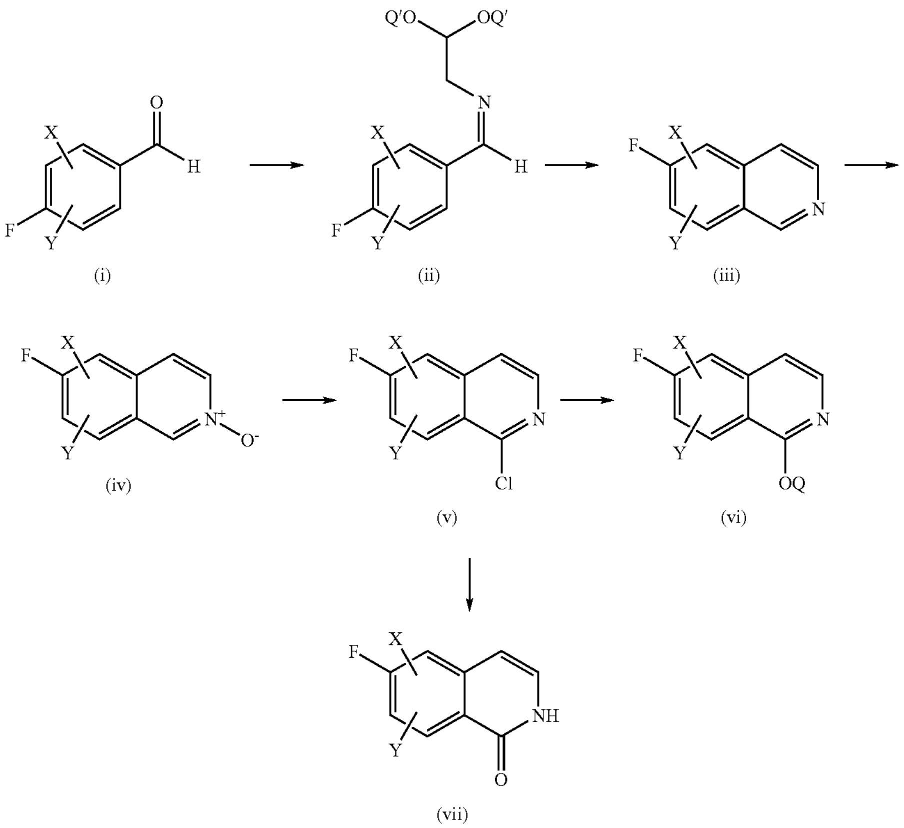

A suitably substituted aldehyde, for example substituted by X or Y being independently from each other hydrogen, alkyl, alkoxy or halide attached in a suitable position, can be reacted with a suitable compound such as for example an actal of aminoacetaldehyde for example in a solvent like THF, chloroform or toluene under acid catalysis by toluene sulfonic acid or another appropriate acid to give imine (ii) wherein Q' can be for instance methyl or ethyl, which in turn can be cyclized by different methods to the isoquinoline (iii). For example this can be done by Lewis acid catalysis by suitable Lewis acids like titanium tetrachloride, ferrous halides, aluminium halides etc. at temperatures ranging from ambient to 100° C. or by reducing the imine to the corresponding amine by action of a suitable reducing agent like sodium borohydride, converting the amine into an amide or sulphonamide by reaction with a suitable acid chloride and subsequent cyclization to the isoquinoline by action of an appropriate lewis acid. The isoquinoline (iii) itself can then be converted to the corresponding N-oxide (iv) by action of a suitable oxidative agent like hydrogen peroxide, m-chloro perbenzoic acid or others at room temperature or elevated temperature. The N-oxide (iv) can then be converted into the 1-chloro-isoquinoline derivative (v) by reacting it with a reagent like phosphorous oxy chloride in or without presence of phosphorous pentachloride. The derivative (v) can then be turned into suitable 1-alkoxy-derivatives by reacting it with various alcohols Q-OH like methanol, ethanol or benzyl alcohol in the presence of a suitable base like sodium hydride and in a suitable solvent like dimethyl formamide, dimethyl acetamide or others. Alternatively (v) can be directly converted into the isoquinolinone derivative (vii) by reacting it with a reagent like ammonium acetate.

Employing suitable bromo derivatives in the described reaction sequences, 6-bromo isoquinolines or 6-bromo-isoquinolones can be obtained.

Scheme 2

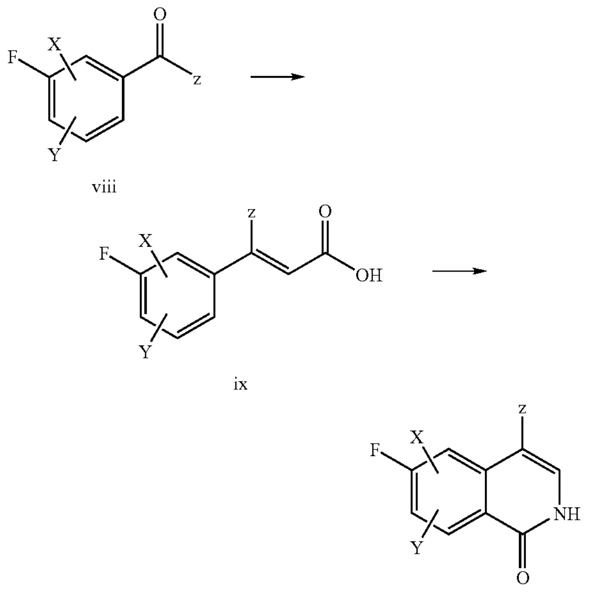

viii ix x

Alternatively isoquinolines can be obtained by reacting suitable 3-formylated or acylated fluorobenzenes (viii), wherein z is for example H or alkyl like methyl or ethyl, with a reagent like triethyl phosphono acetate in the presence of a suitable base like sodium hydride to give the corresponding cinnamic acid ester, which subsequently is cleaved by action of a suitable base like potassium hydroxide, sodium hydroxide or lithium hydroxide in a suitable solvent to deliver acid (ix). (ix) can then be converted in the corresponding acid chloride by well known methods, which can be transferred into the acid azide by reaction with sodium azide in a suitable solvent like ether, chloroform or acetone in or without the presence of water. The corresponding azide then can be converted into isoquinolinone (x) by reacting it in a suitable solvent like diphenylmethane or diphenylether at suitable temperature.

Scheme 3:

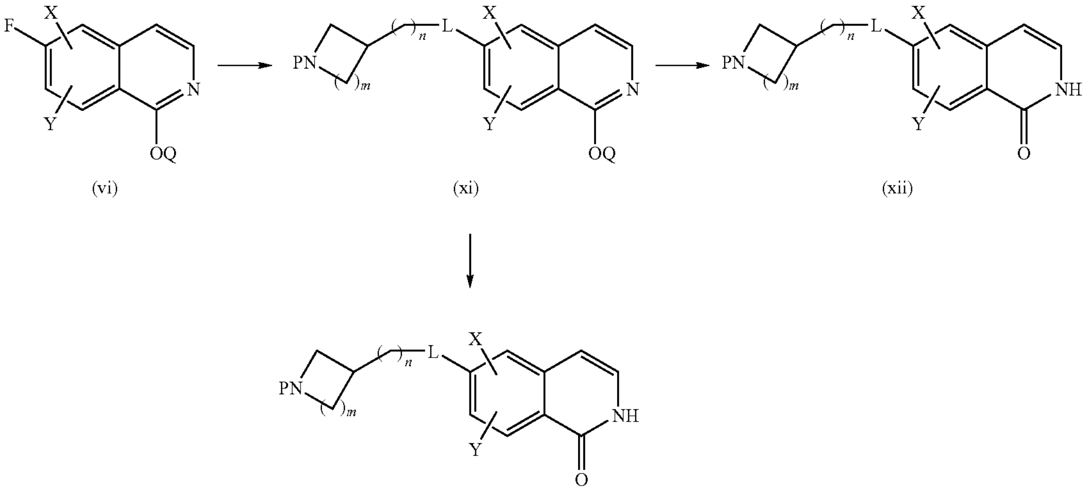

(vi) (xi) (xii)

(xiii)

The above obtained 6-Fluoro-isoquinolones (or the corresponding isoquinolines iii, alternatively), for example (vi), can be reacted with suitable P substituted thiols or amines wherein P is for example hydrogen, alkyl or a protecting group like for example Boc in the presence of base such as DBU, cesium carbonate or sodium hydride to give the corresponding alkylthio or alkylamino substituted derivatives (xi). Eventually, this conversion can already be performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base.

In case of amine substitutions, reaction may also be accomplished by reacting a suitable bromo-derivative with the given amine in the presence of a palladium catalyst like palladium acetate, a ligand like e.g. BINAP and a base like cesium carbonate.

The products like (xi) obtained via this method can then either be liberated or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step like for example acidic removal of Boc-groups. Furthermore an amino group can be acylated by reacting it with a suitable acid chloride in the presence of a base like triethyl amine or Hünig's base or by reacting it with a suitable carboxylic acid in the presence of a base like triethylamine of Hünig's base and a coupling reagent like EDC, PyBOP or TOTU.

In case of use of protected isoquinolones, cleavage of the used protection groups is required to liberate the desired isoquinolone (xii). This liberation, however, can be performed before or after the reductive amination step, depending on the nature of the used aldehyde/ketone and the protection group used.

Isoquinoline and isoquinolone derivatives like (xii) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

Accordingly, the following examples are part of and intended to illustrate but not to limit the present invention.

It is understood that modifications that do not substantially affect the activity of the various embodiments of this invention are included within the invention disclosed herein.

Method A:

| | |
|---|---|
| Stationary phase: | Col YMC Jsphere 33 × 2 |
| Gradient: | ACN + 0.05% TFA:water + 0.05% TFA<br>5:95(0 min) to 95:5(3.4 min) to 95:5(4.4 min) |
| Flow | 1 mL/min |

Method B:

| | |
|---|---|
| Stationary phase: | Col YMC Jsphere 33 × 2 |
| Gradient: | ACN + 0.05% TFA:water + 0.05% TFA<br>5:95(0 min) to 95:5(2.5 min) to 95:5(3.0 min) |
| Flow | 1 mL/min |

Method C:

| | |
|---|---|
| Stationary phase: | Col YMC Jsphere ODS H80 20 × 2 |
| Gradient: | ACN:water + 0.05% TFA<br>4:96(0 min) to 95:5(2.0 min) to 95:5(2.4 min) |
| Flow | 1 mL/min |

Method D:

| | |
|---|---|
| Stationary phase: | Col YMC Jsphere 33 × 2.1 |
| Gradient: | Grad ACN + 0.08% FA:water + 0.1% FA<br>(Formic Acid)<br>5:95 (0 min) to 95:5 (2.5 min) to 95:5 (3 min) |
| Flow | 1.3 mL/min |

Method E:

| | |
|---|---|
| Stationary phase: | Col YMC Jsphere 33 × 2 |
| Gradient: | ACN + 0.05% TFA:water + 0.05% TFA<br>5:95(0 min) to 95:5(2.5 min) to 95:5(3.2 min) |
| Flow | 1.3 mL/min |

Method F:

| | |
|---|---|
| Stationary phase: | Col YMC-Pack Pro C18 RS 33 × 2.1 |
| Gradient: | Grad ACN + 0.1% FA:water + 0.1% FA<br>(Formic Acid)<br>5:95(0 min) to 95:5(2.5 min) to 95:5(3 min) |
| Flow | 1.3 mL/min |

1: (4-Bromo-benzyl)-(2,2-dimethoxy-ethyl)-amine

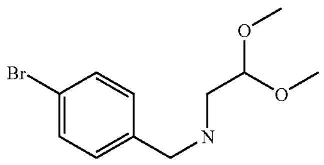

50 g (270.2 mmol) 4-bromobenzaldehyde were dissolved in 200 ml of toluene and 28.4 g (270.2 mmol) aminoacetaldehyde dimethylacetal were added. After the addition of 5.1 g (27.0 mmol) p-toluenesulfonic acid monohydrate, the reaction mixture was heated under reflux in a Dean Stark apparatus. After 4 h, the reaction was cooled to room temperature and washed with saturated sodium hydrogen carbonate-solution (2×) and water. The combined aqueous layers were extracted with Toluene and the combined organic layers were dried over magnesium sulfate and evaporated. The residue was dissolved in 200 ml of ethanol and 5.11 g (135.1 mmol) of sodium borohydride were added in small portions. After stirring for 2 h at room temperature and standing overnight, 5.0 ml acetic acid were added and the solvent was removed i. vac. The residue was taken up in dichloromethane and washed (2×) with water. After drying over magnesium sulfate and evaporation, 60.5 g of the title compound were obtained (crude product), which were used without further purification. $R_t$=0.80 min (Method C). Detected mass: 274.1/276.1 ($M+H^+$).

2: N-(4-Bromo-benzyl)-N-(2,2-dimethoxy-ethyl)-4-methyl-benzenesulfonamide

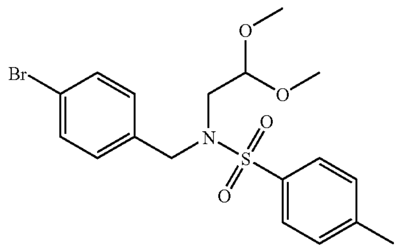 [SMILES: COC(CN(Cc1ccc(Br)cc1)S(=O)(=O)c1ccc(C)cc1)OC]

60.5 g (4-Bromo-benzyl)-(2,2-dimethoxy-ethyl)-amine (1, crude product) were dissolved in 270 ml of dichloromethane/pyridine (8:1). At 0° C. a solution of 76.0 g (386.4 mmol) p-toluenesulfonylchloride in 100 ml of dichloromethane was added and the solution was stirred at room temperature. After 3 h, the reaction mixture was washed twice with 2 N HCl and saturated sodium hydrogen carbonate-solution. The organic layer was dried over magnesium sulfate and evaporated. Final silica gel chromatography (heptane/ethylacetate 4:1) gave 59.9 g of the title compound. $R_t$=1.82 min (Method C). Detected mass: 396.1/398.1 ($M-OMe^-$).

3: 6-Bromo-isoquinoline

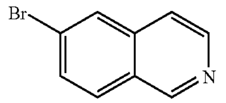 [SMILES: Brc1ccc2cnccc2c1]

To a mechanically stirred suspension of 95.2 g (699.5 mmol) of $AlCl_3$ in 400 ml of dichloromethane a solution of 59.9 g (139.8 mmol) N-(4-bromo-benzyl)-N-(2,2-dimethoxy-ethyl)-4-methyl-benzenesulfonamide (2) in 400 ml of dichloromethane was added and the reaction was stirred at room temperature for 4 h. After standing overnight, the reaction mixture was poured onto ice, the organic layer was separated and the aqueous layer was extracted twice with dichloromethane. The combined dichloromethane solutions were washed with 1 N NaOH (2×) and saturated sodium hydrogen carbonate-solution (2×). After drying with magnesium sulfate and evaporation of the solvent, the crude product was purified by silica gel chromatography (heptane/ethyl acetate 1:1) to yield 17.5 g of the title compound. $R_t$=0.68 min (Method C). Detected mass: 208.1/210.1 ($M+H^+$).

4: 6-Bromo-isoquinoline 2-oxide

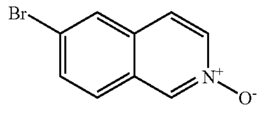 [SMILES: [O-][n+]1ccc2cc(Br)ccc2c1]

To a solution of 51.0 g (245.1 mmol) of 6-bromo-isoquinoline (3) in 800 ml of dichloromethane were added under mechanical stirring 90.6 g (367.6 mmol) of 3-chloro-benzenecarboperoxoic acid (70%). After stirring for 4 h at room temperature and standing overnight, saturated sodium hydrogen carbonate-solution was added until two clear layers were obtained. The dichloromethane solution was separated and washed with saturated NaCl-solution. The aqueous layers were extracted with a chloroform/isopropanol (3:1) mixture and the organic layers were combined, washed again with saturated NaCl-solution, dried over magnesium sulfate and evaporated. The obtained crude product (53.0 g) was used without further purification. $R_t$=0.89 min (Method C). Detected mass: 226.2 ($M+H^+$).

5: 6-Bromo-1-chloro-isoquinoline

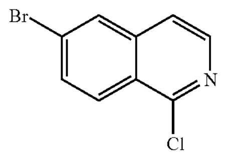 [SMILES: Clc1nccc2cc(Br)ccc12]

53.0 g (236, mmol) of 6-bromo-isoquinoline 2-oxide (4) were heated in 400 ml of $POCl_3$ under reflux conditions in two portions. After 4 h, the reaction was cooled to room temperature and poured carefully on ice with mechanical stirring. The aqueous solution was extracted three times with dichloromethane. The combined organic layers were dried over magnesium sulfate and evaporated, which gave 42.8 g of the title compound, which was used without further purification. $R_t$=1.64 min (Method C). Detected mass: 242.1/244.2 ($M+H^+$).

6: 6-Bromo-2H-isoquinolin-1-one

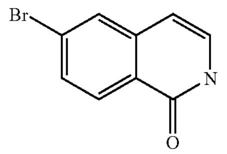 [SMILES: O=c1[nH]ccc2cc(Br)ccc12]

To a solution of 42.8 g (173.5 mmol) of 6-Bromo-1-chloro-isoquinoline (5) in 700 ml of acetic acid were added 133.6 g (1.74 mol) ammonium acetate. After stirring at 100° C. for 3 h, the solution was cooled to room temperature and the solvent was removed i. vac. to a small volume. The residue was poured on water and the suspension was stirred for some minutes. The precipitate was isolated by filtration and dried, to yield 28.2 g of the title compound. $R_t$=1.30 min (Method B). Detected mass: 224.0 ($M+H^+$).

7: (4-Bromo-3-chloro-benzyl)-(2,2-dimethoxy-ethyl)-amine

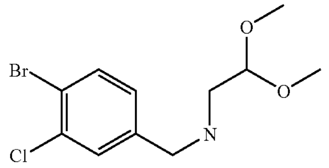 [SMILES: COC(CNCc1ccc(Br)c(Cl)c1)OC]

Starting from 4-Bromo-3-chloro-benzaldehyde, the title compound was prepared by the method described for (4-Bromo-benzyl)-(2,2-dimethoxy-ethyl)-amine (1). $R_t$=0.94 min (Method C). Detected mass: 308.3/310.3 ($M+H^+$).

8: N-(4-Bromo-3-chloro-benzyl)-N-(2,2-dimethoxy-ethyl)-4-methyl-benzene-sulfonamide

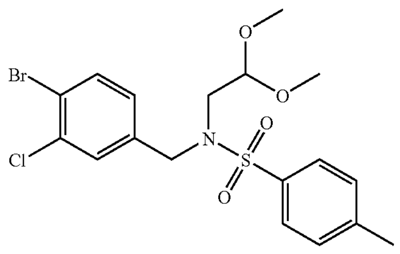 [SMILES: COC(CN(Cc1ccc(Br)c(Cl)c1)S(=O)(=O)c1ccc(C)cc1)OC]

The title compound was prepared by the protocol described for N-(4-Bromo-benzyl)-N-(2,2-dimethoxy-ethyl)-4-methyl-benzenesulfonamide (2), starting from (4-Bromo-3-chloro-benzyl)-(2,2-dimethoxy-ethyl)-amine (7). $R_t$=1.93 min (Method C). Detected mass: 430.3/432.3 ($M-OMe^-$).

9: 6-Bromo-7-chloro-isoquinoline

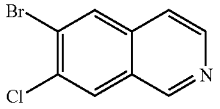

Starting from N-(4-Bromo-3-chloro-benzyl)-N-(2,2-dimethoxy-ethyl)-4-methyl-benzene-sulfonamide (8), the title compound was synthesized by the protocol described for 6-Bromo-isoquinoline (3). $R_t$=1.02 min (Method C). Detected mass: 242.2/244.2 ($M+H^+$).

10: 6-Bromo-7-chloro-isoquinoline 2-oxide

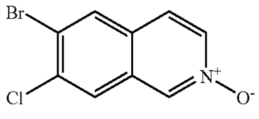 [SMILES: [O-][n+]1ccc2cc(Br)c(Cl)cc2c1]

The title compound was prepared by the method, described for 6-Bromo-isoquinoline 2-oxide (4), starting with 6-Bromo-7-chloro-isoquinoline (9). $R_t$=1.05 min (Method C). Detected mass: 258.1/260.2 ($M+H^+$).

11: 6-Bromo-1,7-dichloro-isoquinoline

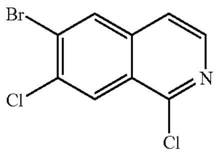

Starting with 6-Bromo-7-chloro-isoquinoline 2-oxide (10), the desired 6-Bromo-1,7-dichloro-isoquinoline was prepared by the method, described for 6-Bromo-1-chloro-isoquinoline (5). $R_t$=1.85 min (Method C). Detected mass: 276.1/278.2 ($M+H^+$).

12: 6-Bromo-7-chloro-2H-isoquinolin-1-one

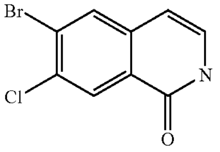 [SMILES: O=c1[nH]ccc2cc(Br)c(Cl)cc12]

The title compound was prepared by the method, described for 6-Bromo-2H-isoquinolin-1-one (6), starting from 6-Bromo-1,7-dichloro-isoquinoline (11). $R_t$=1.26 min (Method C). Detected mass: 258.2/260.2 ($M+H^+$).

13: 6-Bromo-2-(4-methoxy-benzyl)-2H-isoquinolin-1-one

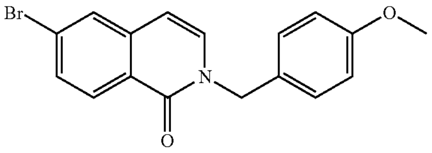 [SMILES: COc1ccc(Cn2ccc3cc(Br)ccc3c2=O)cc1]

28.18 g (125.8 mmol) 6-Bromo-2H-isoquinolin-1-one (6) were dissolved in 200 ml Dimethylacetamide and 7.55 g (188.7 mmol) sodium hydride (60%) were added at room temperature. After stirring for 30 minutes, 29.94 g (188.7 mmol) 4-Methoxy-benzylchloride were added and stirring was continued at room temperature until complete conversion was detected. The solvent was removed under reduced pressure, the residue taken up in saturated sodium hydrogen carbonate-solution and extracted three times with dichloromethane. The organic layers were dried over magnesium sulfate and evaporated. Final purification was achieved by silicagel chromatography. $R_t$=1.93 min (Method B). Detected mass: 344.1 ($M+H^+$).

14: 6-Bromo-7-chloro-2-(4-methoxy-benzyl)-2H-isoquinolin-1-one

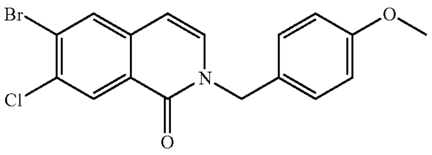

Starting from 6-Bromo-7-chloro-2H-isoquinolin-1-one (12), the title compound was prepared by the method described for 6-Bromo-2-(4-methoxy-benzyl)-2H-isoquinolin-1-one (compound 13). $R_t$=2.12 min (Method B). Detected mass: 378.1/380.1 (M+H$^+$).

15: 1-Benzyloxy-6-bromo-isoquinoline

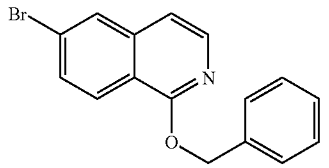 [SMILES: Brc1ccc2c(OCc3ccccc3)nccc2c1]

To a solution of 3.93 g (17.5 mmol) 6-Bromo-2H-isoquinolin-1-one (6) in 150 ml Toluene were added 12.13 g (44.0 mmol) silver carbonate and 3.60 g (21.1 mmol) of benzyl bromide. The reaction mixture was refluxed for 1.5 h and then cooled to room temperature. The solution was filtered. The filtrate was washed with water and the aqueous phase extracted with ethyl acetate. The combined organic layers were dried over magnesium sulfate and evaporated. Final purification was achieved by preparative HPLC. $R_t$=2.47 min (Method B). Detected mass: 314.1/316.5 (M+H$^+$).

16: 4-Ethylamino-piperidine-1-carboxylic acid tert-butyl ester

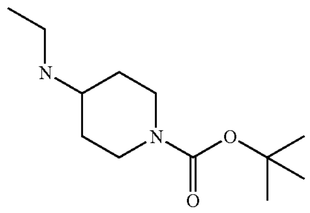 [SMILES: CCNC1CCN(C(=O)OC(C)(C)C)CC1]

3.0 g (15.0 mmol) 4-Amino-piperidine-1-carboxylic acid tert-butyl ester were dissolved in 40 ml Methanol. After adding molecular sieves, 3.0 g (30.0 mmol) Triethylamine, 9.0 g (149.8 mmol) acetic acid and 659.9 mg (15.0 mmol) acetaldehyde, a solution of 2.82 g (44.9 mmol) sodium cyanoborohydride in 2 ml of methanol was added and the reaction mixture was stirred at room temperature until complete conversion of the starting material was detected. For working up, the reaction mixture was filtered and the filtrate was evaporated. The residue was dissolved in dichloromethane and washed with saturated sodium hydrogen carbonate-solution and water. After drying with magnesium sulfate, the solvent was removed under reduced pressure. Purification was achieved by preparative HPLC, which gave the title compound as trifluoroacetate. The product fractions were combined and brought to alkaline pH by adding sodium hydrogen carbonate(s). After evaporation of the solvent i. vac., the residue was dissolved in water and extracted three times with dichloromethane. Drying with magnesium sulfate and evaporation of the solvent gave the title compound as free base. $R_t$=0.95 min (Method B). Detected mass: 229.2 (M+H$^+$).

17: 4-Propylamino-piperidine-1-carboxylic acid tert-butyl ester

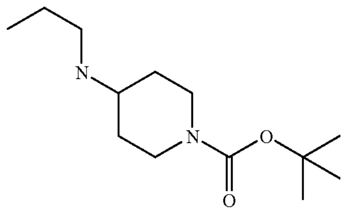 [SMILES: CCCNC1CCN(C(=O)OC(C)(C)C)CC1]

The title compound was synthesized by the method, described for 4-Ethylamino-piperidine-1-carboxylic acid tert-butyl ester (16), using propionaldehyde instead of acetaldehyde. $R_t$=1.43 min (Method B). Detected mass: 243.2 (M+H$^+$).

General Procedure A for the Hartwig-Buchwald Amination Reaction:

1.0 eq of the arylbromide, 1.5 eq cesium carbonate and 1.2 eq of the amine were dissolved in Toluene. If the amine was taken as a salt another equivalent of cesium carbonate was used; if additionally the arylbromide was used as a salt (HCl- or TFA-salt of the isoquinolines) again, 1 additional equivalent of cesium carbonate was used. The solution was degassed and flushed with argon. Then, 0.03 eq $Pd(OAc)_2$ and 0.045 eq BINAP were added and the solution was heated at 100° C. until the reaction was complete or no further improvement could be achieved. For product isolation, the solution was cooled to room temperature, filtered and the filtrate was evaporated. The residue was taken up in water and extracted ethyl acetate. The organic layer was separated, dried over magnesium sulfate and the solvent was removed i. vac. The crude product was purified by preparative HPLC.

General Procedure B for the Hartwig-Buchwald Amination Reaction:

1.0 eq of the arylbromide, 2.5 eq NaO$^t$Bu and 1.2 eq of the amine were dissolved in dry Dioxane. The solution was degassed and flushed with argon. Then, 0.03 eq $Pd(OAc)_2$ and 0.045 eq 1,1'-Bis(di-tert-butylphosphino)ferrocene were added and the solution was heated at 100° C. until the reaction was complete or no further improvement could be achieved. For product isolation, the solvent was removed i. vac. and the residue dissolved in dichloromethane. The organic phase was washed with saturated sodium hydrogen carbonate-solution and water, dried over magnesium sulfate and evaporated. Final purification was achieved by silicagel chromatography (Table 1).

TABLE 1
| Example | Aryl-bromide | Amine | Product |
|---|---|---|---|
| 18 | 3 | 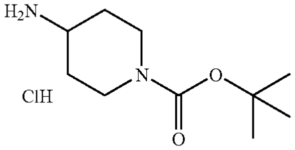 | 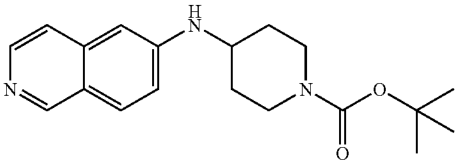 [SMILES: CC(C)(C)OC(=O)N1CCC(Nc2ccc3cnccc3c2)CC1] |
| 19 | 3 | 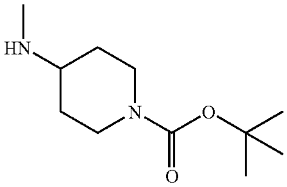 | 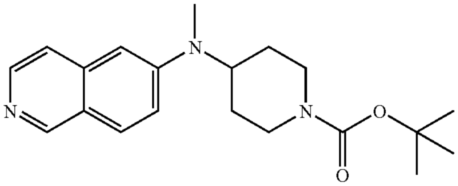 [SMILES: CN(c1ccc2cnccc2c1)C1CCN(C(=O)OC(C)(C)C)CC1] |
| 20 | 3 | 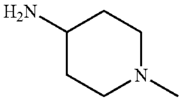 | 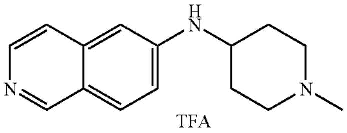 [SMILES: CN1CCC(Nc2ccc3cnccc3c2)CC1] |
| 21 | 3 | 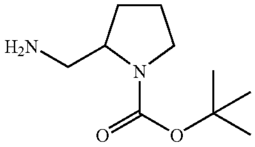 | 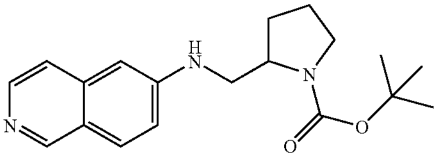 [SMILES: CC(C)(C)OC(=O)N1CCCC1CNc1ccc2cnccc2c1] |
| 22 | 3 | 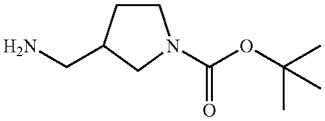 | 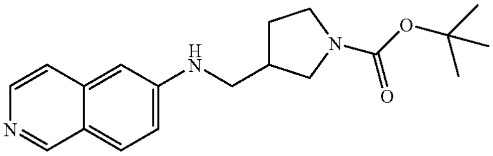 [SMILES: CC(C)(C)OC(=O)N1CCC(CNc2ccc3cnccc3c2)C1] |
| 23 | 3 | 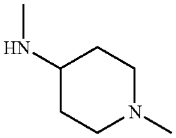 | 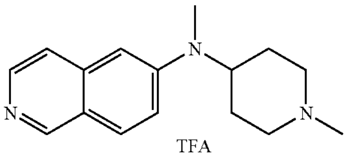 [SMILES: CN1CCC(N(C)c2ccc3cnccc3c2)CC1] |
| 25 | 9 | 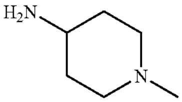 | 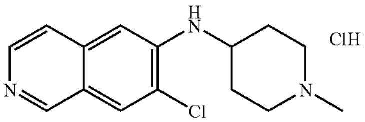 [SMILES: CN1CCC(Nc2cc3ccncc3cc2Cl)CC1 ; Cl] |
| 26 | 9 | 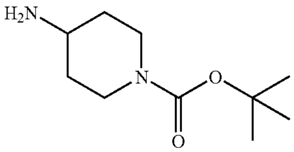 | 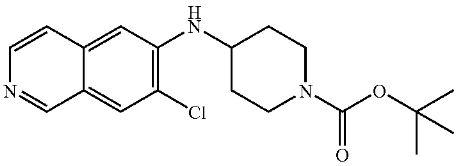 [SMILES: CC(C)(C)OC(=O)N1CCC(Nc2cc3ccncc3cc2Cl)CC1] |
| 27 | 13 | 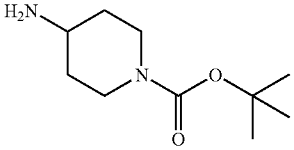 | 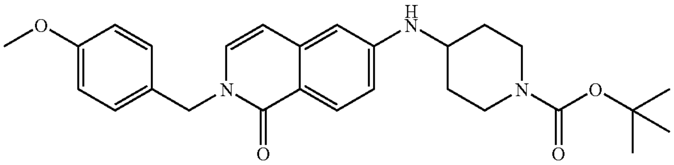 [SMILES: COc1ccc(Cn2ccc3cc(NC4CCN(C(=O)OC(C)(C)C)CC4)ccc3c2=O)cc1] |

TABLE 1-continued

| | | | |
|---|---|---|---|
| 28 | 14 | 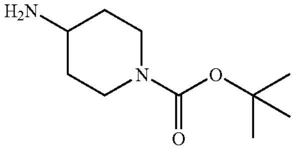 | 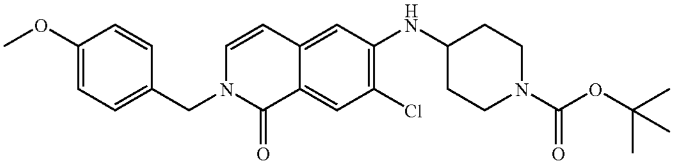 [SMILES: COc1ccc(Cn2ccc3cc(NC4CCN(C(=O)OC(C)(C)C)CC4)c(Cl)cc3c2=O)cc1] |
| 29 | 13 | 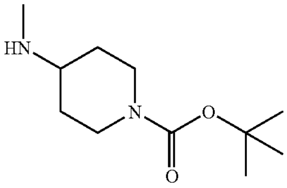 | 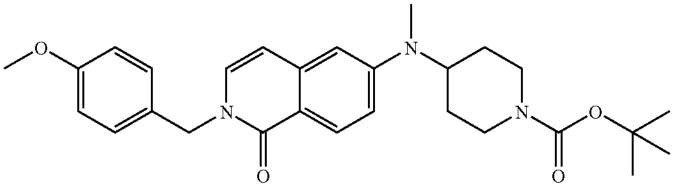 [SMILES: COc1ccc(Cn2ccc3cc(N(C)C4CCN(C(=O)OC(C)(C)C)CC4)ccc3c2=O)cc1] |
| 30 | 13 | 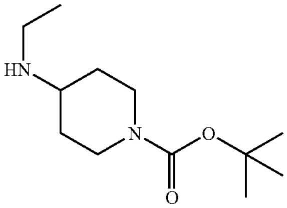 [SMILES: CCNC1CCN(C(=O)OC(C)(C)C)CC1] | 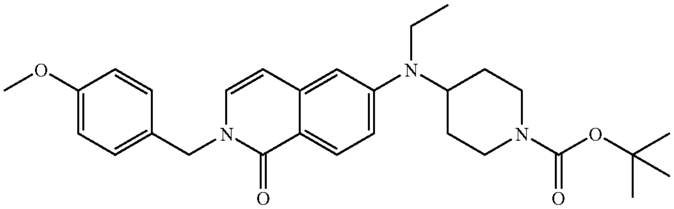 [SMILES: CCN(c1ccc2c(=O)n(Cc3ccc(OC)cc3)ccc2c1)C1CCN(C(=O)OC(C)(C)C)CC1] |
| 31 | 13 | 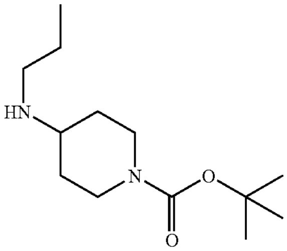 [SMILES: CCCNC1CCN(C(=O)OC(C)(C)C)CC1] | 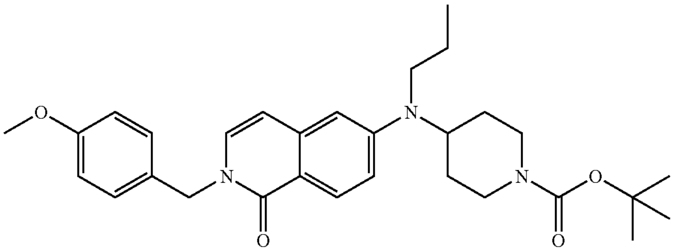 [SMILES: CCCN(c1ccc2c(=O)n(Cc3ccc(OC)cc3)ccc2c1)C1CCN(C(=O)OC(C)(C)C)CC1] |
| 32 | 13 | 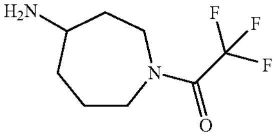 [SMILES: NC1CCCN(C(=O)C(F)(F)F)CC1] | 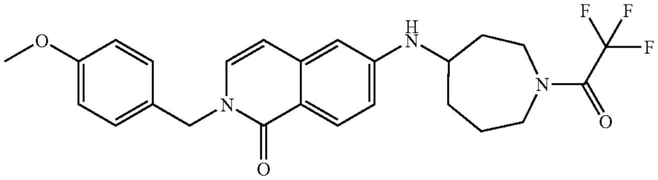 [SMILES: COc1ccc(Cn2ccc3cc(NC4CCCN(C(=O)C(F)(F)F)CC4)ccc3c2=O)cc1] |

| Example | $R_t$ [min] | Mass [M + H$^+$] | LCMS Method | Procedure | Chemical Name |
|---|---|---|---|---|---|
| 18 | 1.05 | 328.2 | C | A | 4-(Isoquinolin-6-ylamino)-piperidine-1-carboxylic acid tert-butyl ester |
| 19 | 1.10 | 342.2 | C | A | 4-(Isoquinolin-6-yl-methyl-amino)-piperidine-1-carboxylic acid tert-butyl ester |
| 20 | 0.57 | 242.2 | B | A | Isoquinolin-6-yl-(1-methyl-piperidin-4-yl)-amine |
| 21 | 1.06 | 328.2 | C | A | 2-(Isoquinolin-6-ylamino-methyl)-pyrrolidine-1-carboxylic acid tert-butyl ester |
| 22 | 1.04 | 328.2 | C | A | 3-(Isoquinolin-6-ylamino-methyl)-pyrrolidine-1-carboxylic acid tert-butyl ester |
| 23 | 0.16 | 256.2 | A | A | Isoquinolin-6-yl-methyl-(1-methyl-piperidin-4-yl)-amine |
| 25 | 0.75 | 276.2 | B | A; NaO$^t$Bu was used instead of cesium carbonate | (7-Chloro-isoquinolin-6-yl)-(1-methyl-piperidin-4-yl)-amine |
| 26 | 1.11 | 362.2 | C | A: NaO$^t$Bu was used instead of cesium carbonate | 4-(7-Chloro-isoquinolin-6-ylamino)-piperidine-1-carboxylic acid tert-butyl ester |

TABLE 1-continued

| | | | | |
|---|---|---|---|---|
| 27 | 1.89 | 464.4 | B | A |
| 28 | 1.83 | 498.5 | C | A |
| 29 | 2.00 | 478.2 | B | B |
| 30 | 1.74 | 492.6 | C | B |
| 31 | 1.86 | 506.7 | C | B |
| 32 | 1.81 | 474.2 | B | A |

General Procedure C for the Deprotection of the Boc-Group:

The Boc-protected compounds were dissolved in Methanol and the same volume of 2 N HCl was added. The solutions were stirred at room temperature until complete conversion was detected. The solvent was removed i. vac. and the residues were dissolved in water. Final lyophilisation gave the desired product as hydrochlorides. (Table 2)

TABLE 2

| Example | Boc-protected compound | Product | $R_t$ [min] | Mass [M + H$^+$] | LCMS Method | Chemical name |
|---|---|---|---|---|---|---|
| 33 | 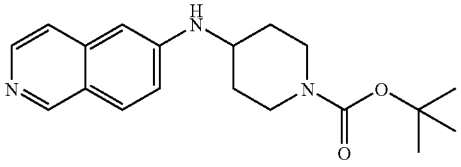 [SMILES: CC(C)(C)OC(=O)N1CCC(Nc2ccc3cnccc3c2)CC1] | 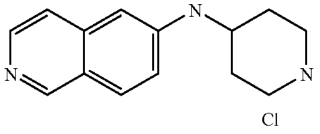 [SMILES: c1cc2cc(NC3CCNCC3)ccc2cn1 ; Cl] | 0.33 | 228.2 | C | Isoquinolin-6-yl-piperidin-4-yl-amine |
| 34 | 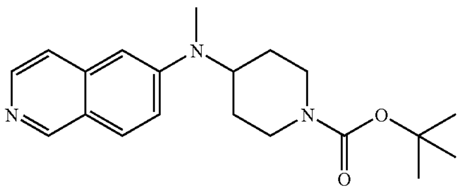 [SMILES: CN(c1ccc2cnccc2c1)C1CCN(C(=O)OC(C)(C)C)CC1] | 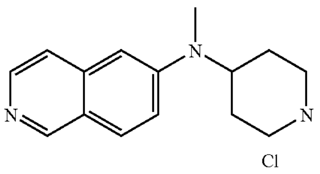 [SMILES: CN(c1ccc2cnccc2c1)C1CCNCC1 ; Cl] | 0.50 | 242.2 | C | Isoquinolin-6-yl-methyl-piperidin-4-yl-amine |
| 35 | 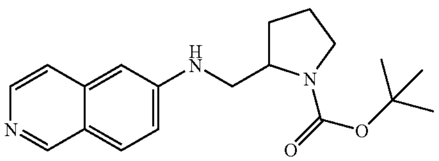 [SMILES: CC(C)(C)OC(=O)N1CCCC1CNc1ccc2cnccc2c1] | 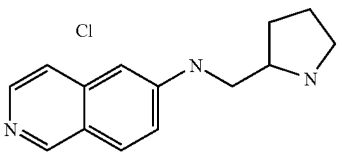 [SMILES: c1cc2cc(NCC3CCCN3)ccc2cn1 ; Cl] | 0.68 | 228.2 | B | Isoquinolin-6-yl-pyrrolidin-2-ylmethyl-amine |
| 36 | 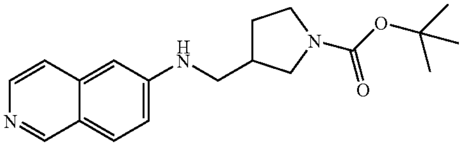 [SMILES: CC(C)(C)OC(=O)N1CCC(CNc2ccc3cnccc3c2)C1] | 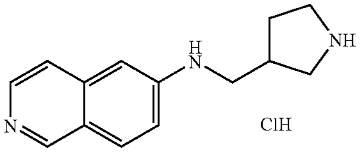 [SMILES: c1cc2cc(NCC3CCNC3)ccc2cn1 ; Cl] | 0.68 | 228.2 | B | Isoquinolin-6-yl-pyrrolidin-3-ylmethyl-amine |
| 37 | 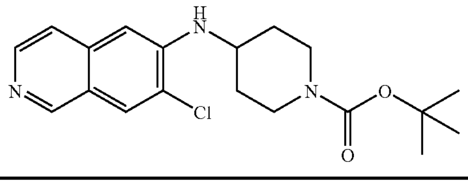 | 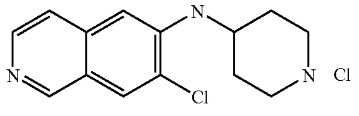 [SMILES: Clc1cc2cnccc2cc1NC1CCNCC1 ; Cl] | 0.63 | 262.0 | B | (7-Chloro-isoquinolin-6-yl)-piperidin-4-yl-amine |

General Procedure D for the Deprotection of PMB-Protected Compounds;

In the case of PMB- and Boc-protected compounds, the starting materials were dissolved in Trifluoroacetic acid and stirred at room temperature for 1 h, followed by 3 h at 140° C. in a microwave. For isolation, the solvent was removed under reduced pressure and the residue was purified by preparative HPLC. The product fractions were combined and evaporated, which gave the desired product as trifluoroacetates, which, in some cases, were dissolved in 2 N HCl and evaporated. After final lyophilisation of the aqueous solutions, these desired products were isolated as hydrochlorides. By this method, the following compounds were synthesized (Table 3):

TABLE 3
| Example | Protected compound | Product | $R_t$ [min] | Mass [M + H$^+$] | Method | Chemical name |
|---|---|---|---|---|---|---|
| 38 | 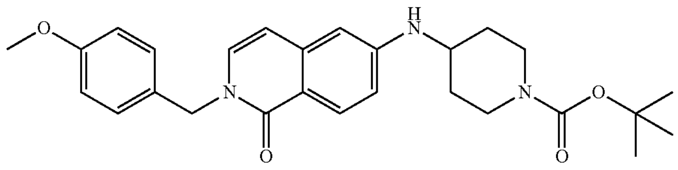 [SMILES: COc1ccc(Cn2ccc3cc(NC4CCN(C(=O)OC(C)(C)C)CC4)ccc3c2=O)cc1] | 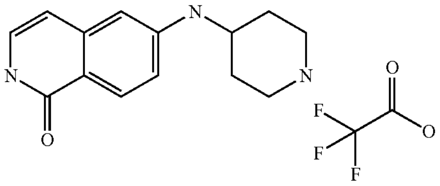 | 0.64 | 244.2 | B | 6-(Piperidin-4-ylamino)-2H-isoquinolin-1-one |
| 39 | 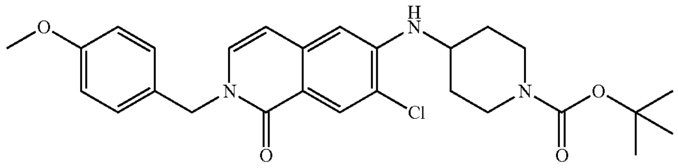 | 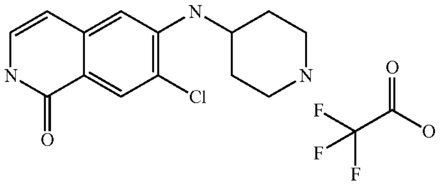 | 0.80 | 278.1 | B | 7-Chloro-6-(piperidin-4-ylamino)-2H-isoquinolin-1-one |
| 40 | 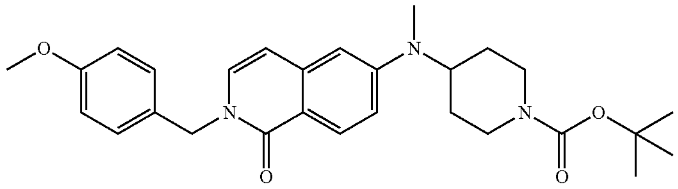 [SMILES: COc1ccc(Cn2ccc3cc(N(C)C4CCN(C(=O)OC(C)(C)C)CC4)ccc3c2=O)cc1] | 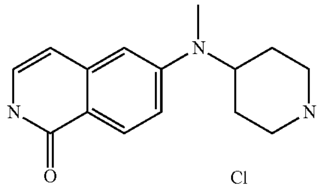 [SMILES: CN(c1ccc2c(=O)[nH]ccc2c1)C1CCNCC1 ; Cl] | 0.75 | 258.2 | B | 6-(Methyl-piperidin-4-yl-amino)-2H-isoquinolin-1-one |
| 41 | 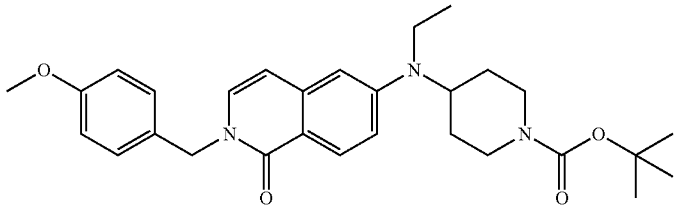 [SMILES: CCN(c1ccc2c(=O)n(Cc3ccc(OC)cc3)ccc2c1)C1CCN(C(=O)OC(C)(C)C)CC1] | 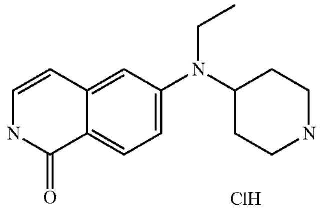 [SMILES: CCN(c1ccc2c(=O)[nH]ccc2c1)C1CCNCC1 ; Cl] | 0.76 | 272.2 | B | 6-(Ethyl-piperidin-4-yl-amino)-2H-isoquinolin-1-one |

TABLE 3-continued
| Example | Protected compound | Product | $R_t$ [min] | Mass [M + H+] | Method | Chemical name |
|---|---|---|---|---|---|---|
| 42 | 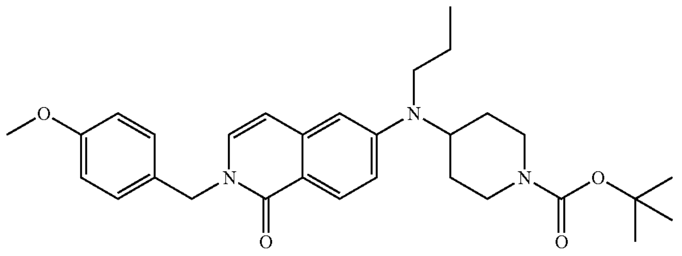 [SMILES: CCCN(c1ccc2c(=O)n(Cc3ccc(OC)cc3)ccc2c1)C1CCN(C(=O)OC(C)(C)C)CC1] | 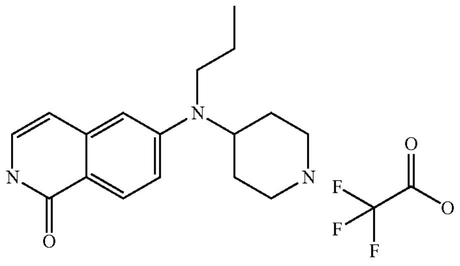 | 0.90 | 286.2 | B | 6-(Propyl-piperidin-4-yl-amino)-2H-isoquinolin-1-one |

General Procedure E for the Reductive Amination:

The starting material (1.0 eq) was dissolved in dry Methanol. After adding freshly dried molecular sieves (4 A), Triethylamine (2.0 eq), acetic acid (10.0 eq), the carbonyl compounds (3.0-6.0 eq) and sodium cyano borohydride (3.0 eq), the mixture was stirred at room temperature. To achieve complete conversion, in some cases the reaction was heated to 70° C. (bath temperature) or further equivalents of the carbonyl compound and sodium cyano borohydride were added. For product isolation, the solution was filtered and the filtrate was evaporated. The residue was dissolved in ethyl acetate and washed with 1 N NaOH. The aqueous layer was separated and extracted twice with ethyl acetate. The combined organic layers were dried over Sodium sulfate and the solvent was removed under reduced pressure. The crude products were purified by preparative HPLC. The product fractions were combined and evaporated, which gave the desired product as trifluoro acetates, which were dissolved in 2 N HCl and evaporated. After final lyophilisation of the aqueous solutions, the desired products were isolated as hydrochlorides.

Isoquinolin-6-yl-(R)-piperidin-3-yl-amine was prepared in analogous fashion as described for 47 starting from (R)-3-Amino-piperidine-1-carboxylic acid tert-butyl ester.

46: 6-(Azepan-4-ylamino)-2H-isoquinolin-1-one

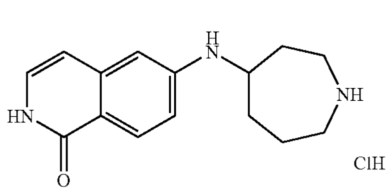

450 mg (0.95 mmol) 2-(4-Methoxy-benzyl)-6-[1-(2,2,2-trifluoro-acetyl)-azepan- 4-ylamino]-2H-isoquinolin-1-one

| Example | Amine | Carbonyl compound | Product | $R_t$ [min] | Mass [M + $H^+$] | LCMS Method | Chemica Name |
|---|---|---|---|---|---|---|---|
| 43 | 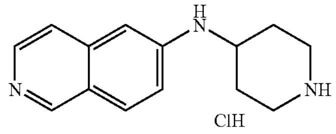 [SMILES: c1cc2cc(NC3CCNCC3)ccc2cn1 ; Cl] | 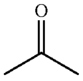 | 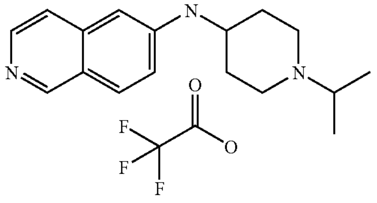 | 0.84 | 270.2 | B | 2.0 + 3.0 eq acetone were used. (1-Isopropyl-piperidin-4-yl)-isoquinolin-6-yl-amine |

44: Isoquinolin-6-yl-(R)-pyrrolidin-3-yl-amine hydrochloride

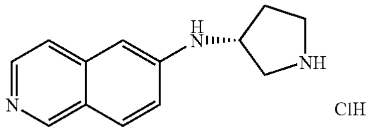 [SMILES: c1cc2cc(N[C@@H]3CCNC3)ccc2cn1 ; Cl]

Isoquinolin-6-yl-(R)-pyrrolidin-3-yl-amine was prepared in analogous fashion as described for 33 starting from (R)-3-Amino-pyrrolidine-1-carboxylic acid tert-butyl ester.

45: Isoquinolin-6-yl-(R)-piperidin-3-yl-amine hydrochloride

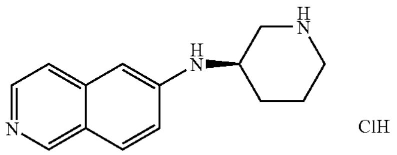 [SMILES: c1cc2cc(N[C@@H]3CCCNC3)ccc2cn1 ; Cl]

(compound 42) were heated in a microwave at 140° C. for 3.5 h. After evaporation of the solvent, the residue was dissolved in 15 ml Ethanol and 2 ml 2 N NaOH were added. The solution was stirred for 1 h at room temperature and the solvent was removed under reduced pressure. The residue was taken up in water and washed with dichloromethane. The aqueous layer was separated and filtered. After lyophilisation, the crude product was stirred in Ethanol, filtered and the solvent evaporated. Final purification by preparative HPLC gave the title compound as trifluoroacetate, which was dissolved in 1 N HCl. The solvent was removed and the residue was dissolved in water. Final lyophilisation gave the desired compound as hydrochloride. $R_t$=0.76 min (Method B). Detected mass: 258.2 (M+$H^+$).

47: Azetidin-3-yl-isoquinolin-6-yl-amine hydrochloride

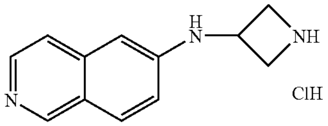 [SMILES: c1cc2cc(NC3CNC3)ccc2cn1 ; Cl]

Azetidin-3-yl-isoquinolin-6-yl-amine was prepared in analogous fashion as described for 33 starting from (3-Amino-azetidine-1-carboxylic acid tert-butyl ester.

18: 4-(Isoquinolin-6-ylamino)-piperidine-1-carboxylic acid tert-butyl ester trifluoroacetate

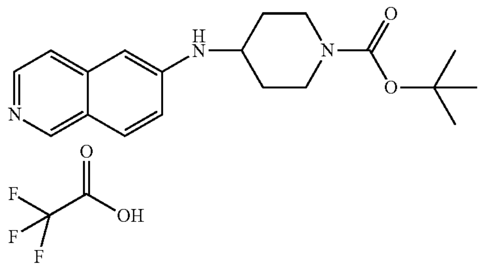

To 187 mg (0.9 mmol) 6-Bromoisoquinoline (3) in 5 ml Dioxan were added 733 mg (2.25 mmol) Cesiumcarbonate, 216 mg (1.08 mmol) 4-Amino-1-BOC-piperidine and the mixture was degassed. 56 mg (0.09 mmol) BINAP and 17.5 mg (78.3 μmol) Palladium acetate were added and the mixture was heated to 100° C. for 16 h. After filtration from solids the volatiles were evaporated and the residue was purified by preparative HPLC (Method A). 258 mg 4-(Isoquinolin-6-ylamino)-piperidine-1-carboxylic acid tert-butyl ester trifluoroacetate could be obtained.

33: Isoquinolin-6-yl-piperidin-4-yl-amine Hydrochloride

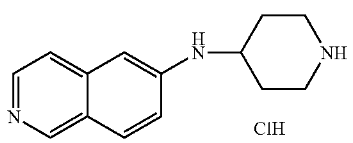 [SMILES: c1cc2cc(NC3CCNCC3)ccc2cn1 ; Cl]

258 mg (0.79 mmol) 4-(Isoquinolin-6-ylamino)-piperidine-1-carboxylic acid tert-butyl ester were stirred in 6N HCl in isopropanol for 2 h. After evaporation the residue was taken up in water and lyophilized. 206 mg of Isoquinolin-6-yl-piperidin-4-yl-amine as the hydrochloride could be obtained.

The compounds described in the following table were synthesized in a similar fashion as described for 18/33 (Table 4).

TABLE 4
| Example | Arylbromide | Amine | Product | $R_t$ [min] | Mass [M + H$^+$] | LCMS Method | Chemical name |
| --- | --- | --- | --- | --- | --- | --- | --- |
| 49 | 13 | 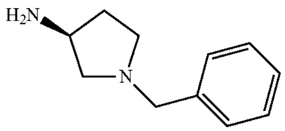 [SMILES: N[C@H]1CCN(Cc2ccccc2)C1] | 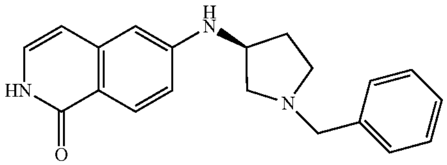 [SMILES: O=c1[nH]ccc2cc(N[C@H]3CCN(Cc4ccccc4)C3)ccc12] | 1.06 | 320.3 | B | 6-((S)-1-Benzyl-pyrrolidin-3-ylamino)-2H-isoquinolin-1-one |
| 50 | 13 | 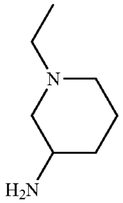 | 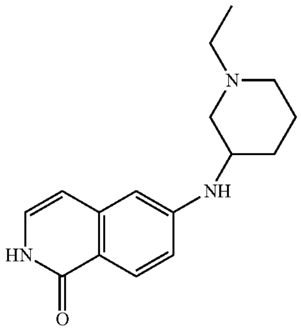 [SMILES: CCN1CCCC(Nc2ccc3c(=O)[nH]ccc3c2)C1] | 0.77 | 272.2 | B | 6-(1-Ethyl-piperidin-3-ylamino)-2H-isoquinolin-1-one |
| 51 | 13 | 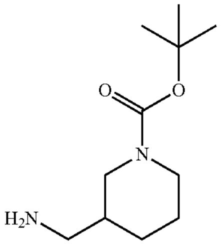 | 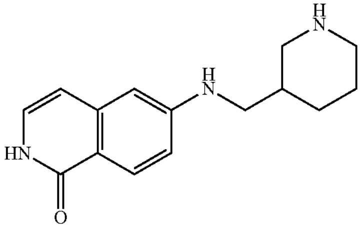 [SMILES: O=c1[nH]ccc2cc(NCC3CCCNC3)ccc12] | 0.99 | 258.3 | B | 6-[(Piperidin-3-ylmethyl)-amino]-2H-isoquinolin-1-one |
| 52 | 13 | 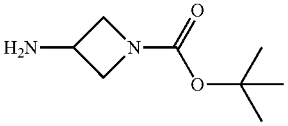 | 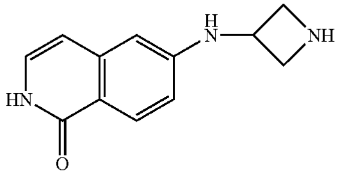 [SMILES: O=c1[nH]ccc2cc(NC3CNC3)ccc12] | 0.59 | 216.2 | B | 6-(Azetidin-3-ylamino)-2H-isoquinolin-1-one |

TABLE 4-continued
| Example | Arylbromide | Amine | Product | $R_t$ [min] | Mass [M + H$^+$] | LCMS Method | Chemical name |
|---|---|---|---|---|---|---|---|
| 53 | 13 | 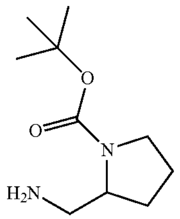 | 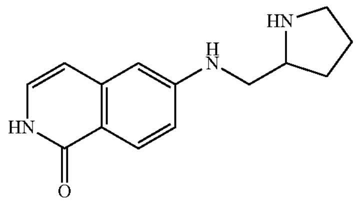 [SMILES: O=c1[nH]ccc2cc(NCC3CCCN3)ccc12] | 0.69 | 244.3 | B | 6-[(Pyrrolidin-2-ylmethyl)-amino]-2H-isoquinolin-1-one |
| 54 | 13 | 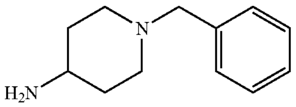 [SMILES: NC1CCN(Cc2ccccc2)CC1] | 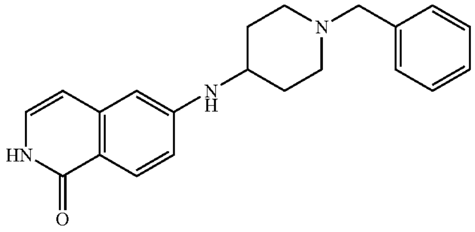 [SMILES: O=c1[nH]ccc2cc(NC3CCN(Cc4ccccc4)CC3)ccc12] | 1.04 | 334.1 | B | 6-(1-Benzyl-piperidin-4-ylamino)-2H-isoquinolin-1-one |
| 55 | 13 | 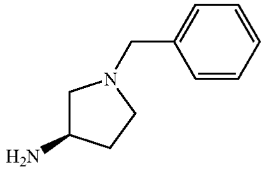 [SMILES: N[C@@H]1CCN(Cc2ccccc2)C1] | 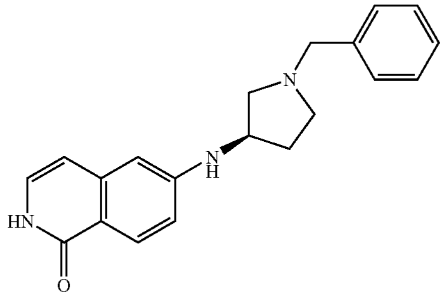 [SMILES: O=c1[nH]ccc2cc(N[C@@H]3CCN(Cc4ccccc4)C3)ccc12] | 0.95 | 320.1 | B | 6-((R)-1-Benzyl-pyrrolidin-3-ylamino)-2H-isoquinolin-1-one |
| 56 | 3 | 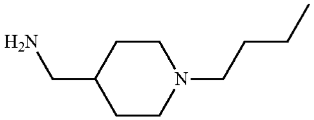 | 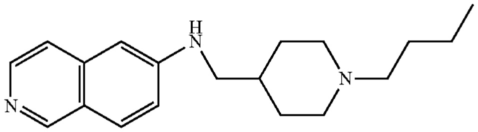 [SMILES: CCCCN1CCC(CNc2ccc3cnccc3c2)CC1] | 1.01 | 298.2 | B | (1-Butyl-piperidin-4-ylmethyl)-isoquinolin-6-yl-amine |
| 58 | 3 | 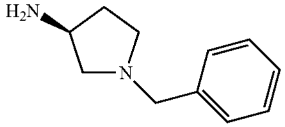 [SMILES: N[C@H]1CCN(Cc2ccccc2)C1] | 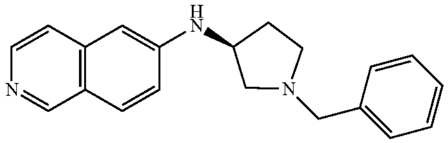 [SMILES: c1ccc(CN2CC[C@H](Nc3ccc4cnccc4c3)C2)cc1] | 0.89 | 304.2 | B | ((S)-1-Benzyl-pyrrolidin-3-yl)-isoquinolin-6-yl-amine |

TABLE 4-continued
| Example | Arylbromide | Amine | Product | $R_t$ [min] | Mass [M + H$^+$] | LCMS Method | Chemical name |
|---|---|---|---|---|---|---|---|
| 60 | 3 | 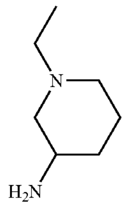 | 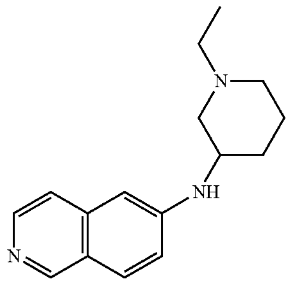 [SMILES: CCN1CCCC(Nc2ccc3cnccc3c2)C1] | 0.87 | 256.2 | B | (1-Ethyl-piperidin-3-yl)-isoquinolin-6-yl-amine |
| 61 | 3 | 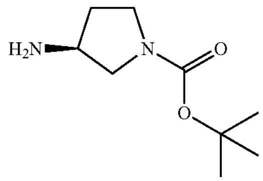 | 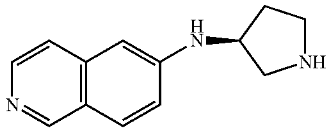 [SMILES: c1cc2cc(N[C@H]3CCNC3)ccc2cn1] | 0.60 | 214.2 | B | Isoquinolin-6-yl-(S)-pyrrolidin-3-yl-amine |
| 62 | 3 | 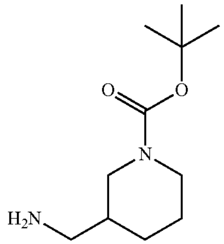 | 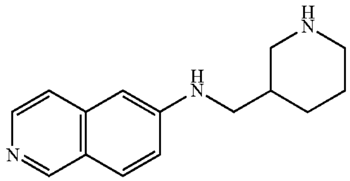 [SMILES: c1cc2cc(NCC3CCCNC3)ccc2cn1] | 0.70 | 242.3 | B | Isoquinolin-6-yl-piperidin-3-ylmethyl-amine |
| 63 | 3 | 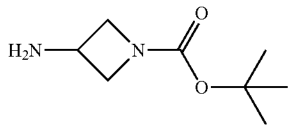 | 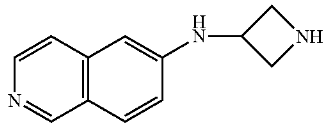 [SMILES: c1cc2cc(NC3CNC3)ccc2cn1] | 0.85 | 200.2 | B | Azetidin-3-yl-isoquinolin-6-yl-amine |

TABLE 4-continued
| Example | Arylbromide | Amine | Product | $R_t$ [min] | Mass [M + H$^+$] | LCMS Method | Chemical name |
|---|---|---|---|---|---|---|---|
| 64 | 3 | 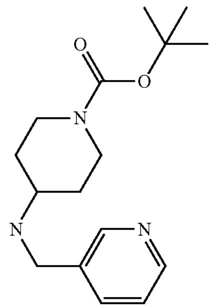 [SMILES: CC(C)(C)OC(=O)N1CCC(NCc2cccnc2)CC1] | 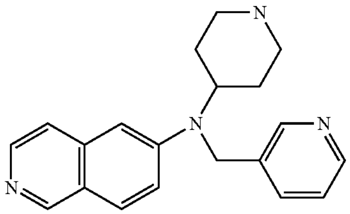 [SMILES: c1cncc(CN(c2ccc3cnccc3c2)C2CCNCC2)c1] | 0.32 | 319.4 | B | Isoquinolin-6-yl-piperidin-4-yl-pyridin-3-ylmethyl-amine |
| 65 | 3 | 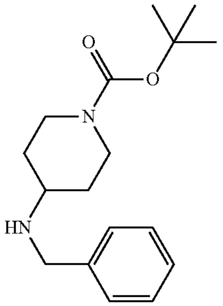 [SMILES: CC(C)(C)OC(=O)N1CCC(NCc2ccccc2)CC1] | 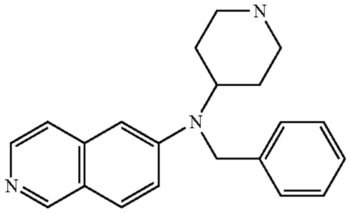 [SMILES: c1ccc(CN(c2ccc3cnccc3c2)C2CCNCC2)cc1] | 1.09 | 318.3 | B | Benzyl-isoquinolin-6-yl-piperidin-4-yl-amine |
| 66 | 3 | 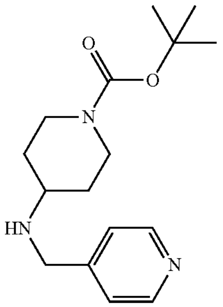 [SMILES: CC(C)(C)OC(=O)N1CCC(NCc2ccncc2)CC1] | 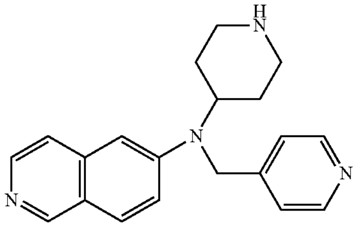 [SMILES: c1cc(CN(c2ccc3cnccc3c2)C2CCNCC2)ccn1] | 0.69 | 319.3 | B | Isoquinolin-6-yl-piperidin-4-yl-pyridin-4-ylmethyl-amine |

TABLE 4-continued
| Example | Arylbromide | Amine | Product | $R_t$ [min] | Mass [M + H$^+$] | LCMS Method | Chemical name |
|---|---|---|---|---|---|---|---|
| 67 | 3 | 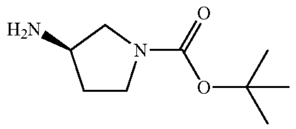 | 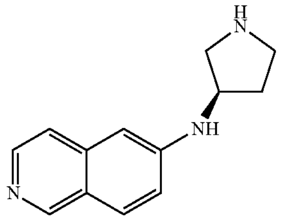 [SMILES: c1cc2cc(N[C@@H]3CCNC3)ccc2cn1] | 0.19 | 214.2 | B | Isoquinolin-6-yl-(R)-pyrrolidin-3-yl-amine |

68: (1-Ethyl-piperidin-4-yl)-isoquinolin-6-yl-amine hydrochloride

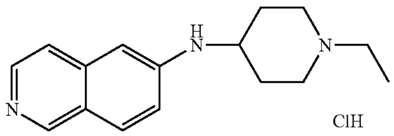 [SMILES: CCN1CCC(Nc2ccc3cnccc3c2)CC1 ; Cl]

To 32 mg (0.12 mmol) Isoquinolin-6-yl-piperidin-4-yl-amine Hydrochloride (48) in 4 ml THF was added (0.12 mmol) acetaldehyde and 104 mg MP-Cyano borohydride resin (2.3 mmol/g) and stirred over night. After filtration from the resin and evaporation the residue was purified by preparative HPLC (Method A) to obtain (1-Ethyl-piperidin-4-yl)-isoquinolin-6-yl-amine as the trifluoroacetate. The obtained trifluoroacetate was dissolved in 6 N HCl in Isopropanol and evaporated. Final lyophilization gave 2 mg of the title compound $R_t$=0.63 min (Method B). Detected mass: 256.2 $(M+H^+)$.

The compounds described in the following table were synthesized in an analogous fashion as described for 68 (Table 5):

TABLE 5

| Example | Amine | Aldehyde | Product |
|---|---|---|---|
| 69 | 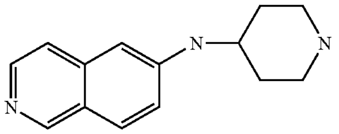 | 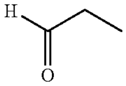 | 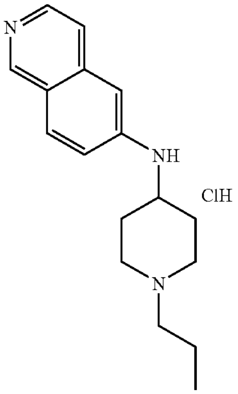 [SMILES: CCCN1CCC(Nc2ccc3cnccc3c2)CC1 ; Cl] |
| 70 | 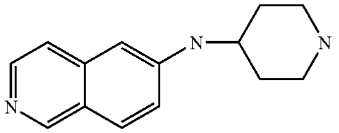 [SMILES: c1cc2cc(NC3CCNCC3)ccc2cn1] | 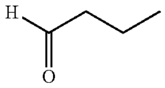 | 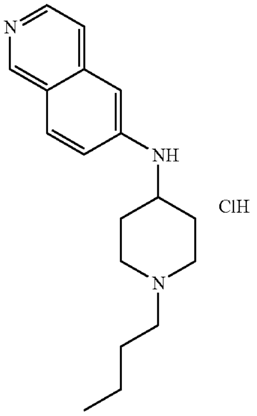 [SMILES: CCCCN1CCC(Nc2ccc3cnccc3c2)CC1 ; Cl] |
| 71 | 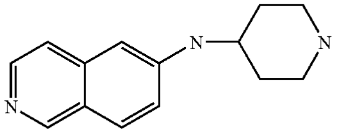 | 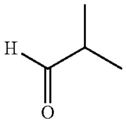 | 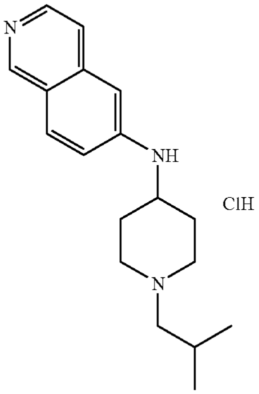 [SMILES: CC(C)CN1CCC(Nc2ccc3cnccc3c2)CC1 ; Cl] |

TABLE 5-continued
| | | | |
|---|---|---|---|
| 72 | 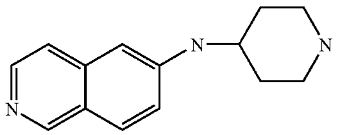 | 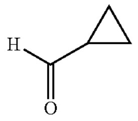 | 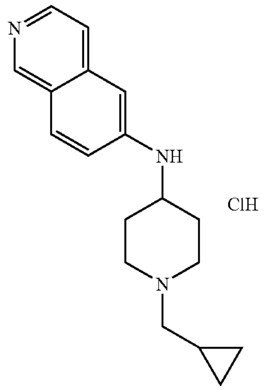 [SMILES: c1cc2cc(NC3CCN(CC4CC4)CC3)ccc2cn1 ; Cl] |
| 73 | 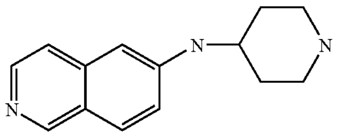 | 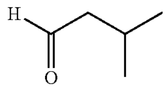 | 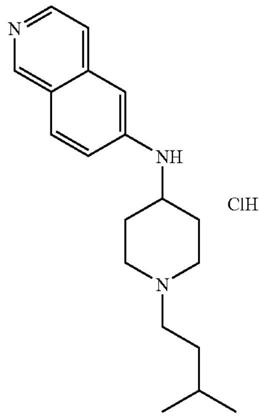 [SMILES: CC(C)CCN1CCC(Nc2ccc3cnccc3c2)CC1 ; Cl] |
| 74 | 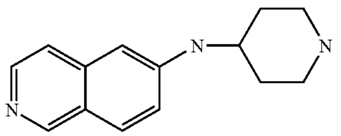 [SMILES: c1cc2cc(NC3CCNCC3)ccc2cn1] | 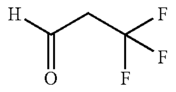 | 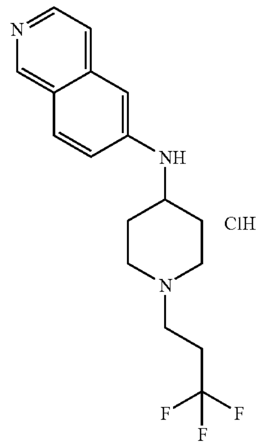 [SMILES: FC(F)(F)CCN1CCC(Nc2ccc3cnccc3c2)CC1 ; Cl] |

TABLE 5-continued
| | | | |
|---|---|---|---|
| 75 | 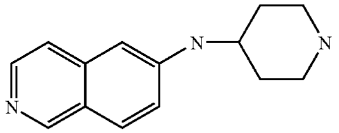 | 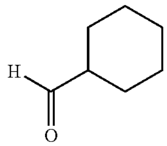 | 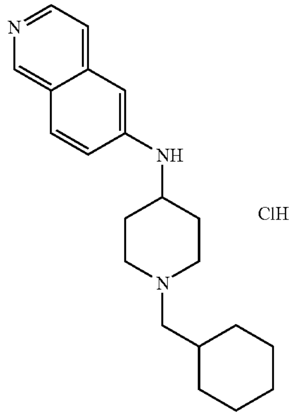 [SMILES: c1cc2cc(NC3CCN(CC4CCCCC4)CC3)ccc2cn1 ; Cl] |
| 76 | 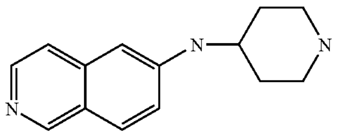 [SMILES: c1cc2cc(NC3CCNCC3)ccc2cn1] | 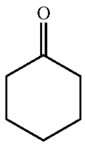 | 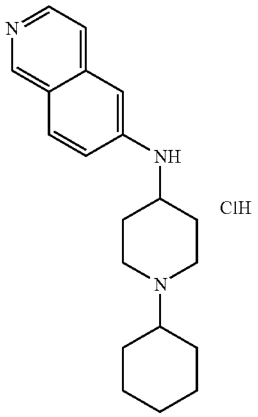 [SMILES: c1cc2cc(NC3CCN(C4CCCCC4)CC3)ccc2cn1 ; Cl] |
| 77 | 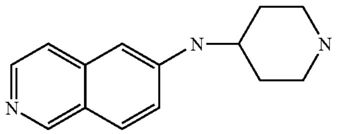 | 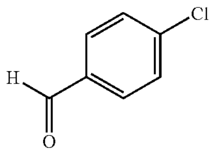 | 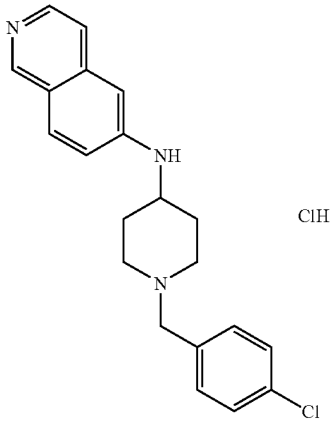 [SMILES: Clc1ccc(CN2CCC(Nc3ccc4cnccc4c3)CC2)cc1 ; Cl] |

TABLE 5-continued
| | | | |
|---|---|---|---|
| 78 | 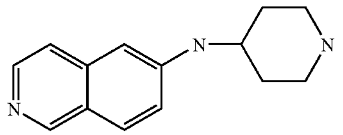 | 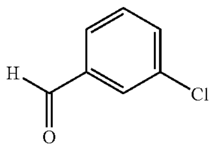 | 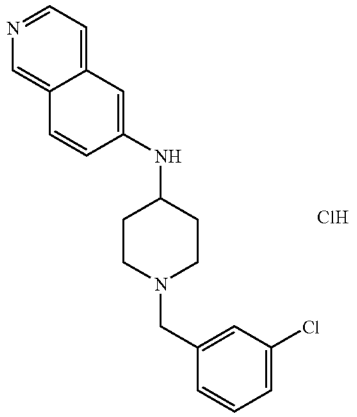 [SMILES: Clc1cccc(CN2CCC(Nc3ccc4cnccc4c3)CC2)c1 ; Cl] |
| 79 | 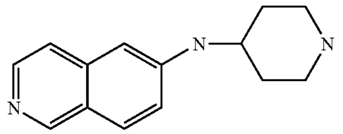 [SMILES: c1cc2cc(NC3CCNCC3)ccc2cn1] | 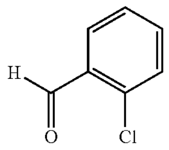 | 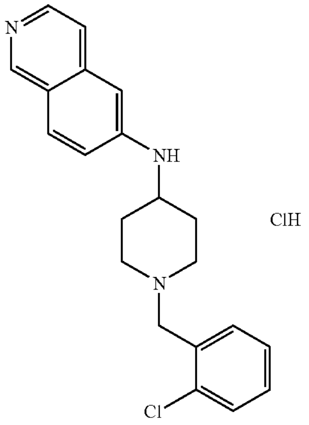 [SMILES: Clc1ccccc1CN1CCC(Nc2ccc3cnccc3c2)CC1 ; Cl] |
| 80 | 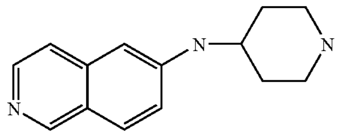 | 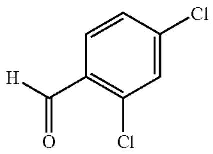 | 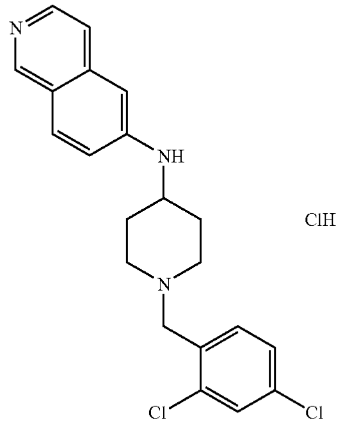 [SMILES: Clc1ccc(CN2CCC(Nc3ccc4cnccc4c3)CC2)c(Cl)c1 ; Cl] |

TABLE 5-continued
| | | | |
|---|---|---|---|
| 81 | 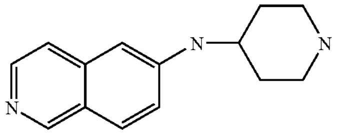 [SMILES: c1cc2cc(NC3CCNCC3)ccc2cn1] | 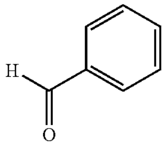 | 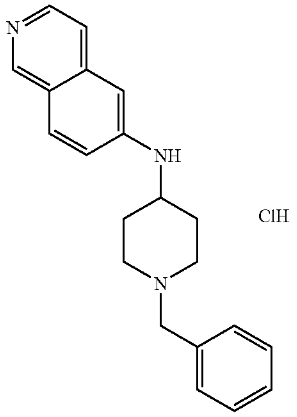 [SMILES: c1ccc(CN2CCC(Nc3ccc4cnccc4c3)CC2)cc1 ; Cl] |
| 82 | 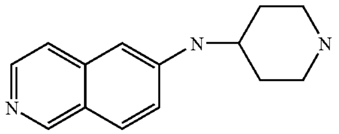 | 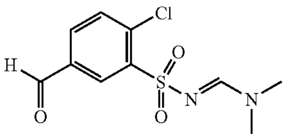 [SMILES: CN(C)/C=N/S(=O)(=O)c1cc(C=O)ccc1Cl] | 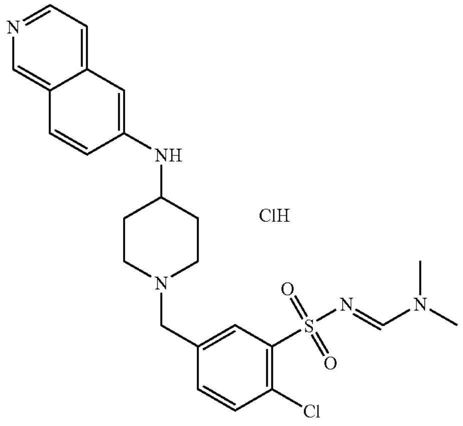 [SMILES: CN(C)/C=N/S(=O)(=O)c1cc(CN2CCC(Nc3ccc4cnccc4c3)CC2)ccc1Cl ; Cl] |
| 83 | 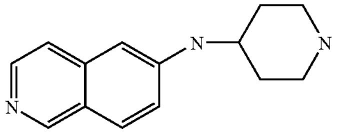 | 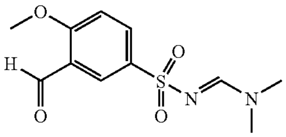 [SMILES: COc1ccc(S(=O)(=O)/N=C/N(C)C)cc1C=O] | 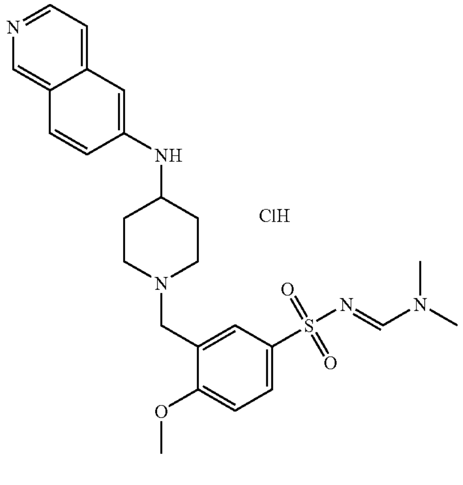 [SMILES: COc1ccc(S(=O)(=O)/N=C/N(C)C)cc1CN1CCC(Nc2ccc3cnccc3c2)CC1 ; Cl] |

TABLE 5-continued
| | | | |
|---|---|---|---|
| 84 | 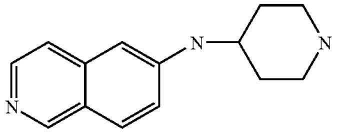 [SMILES: c1cc2cc(NC3CCNCC3)ccc2cn1] | 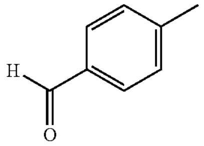 | 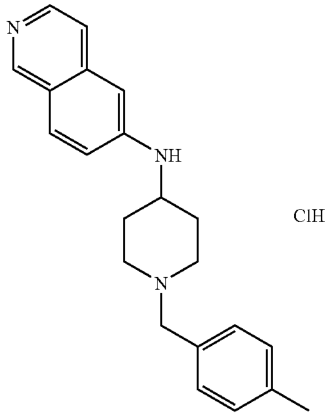 [SMILES: Cc1ccc(CN2CCC(Nc3ccc4cnccc4c3)CC2)cc1 ; Cl] |
| 85 | 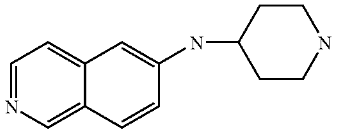 | 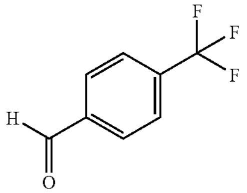 [SMILES: O=Cc1ccc(C(F)(F)F)cc1] | 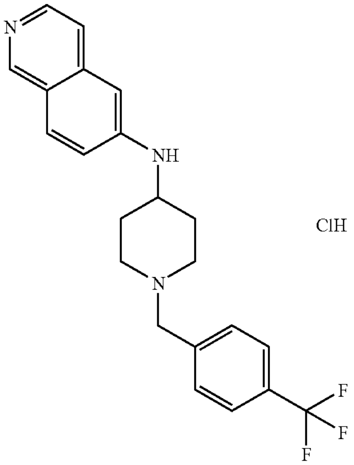 [SMILES: FC(F)(F)c1ccc(CN2CCC(Nc3ccc4cnccc4c3)CC2)cc1 ; Cl] |
| 86 | 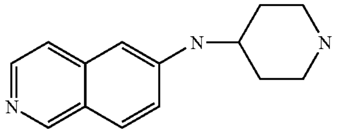 [SMILES: c1cc2cc(NC3CCNCC3)ccc2cn1] | 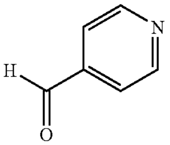 | 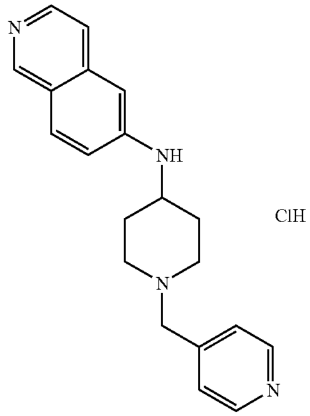 [SMILES: c1cc(CN2CCC(Nc3ccc4cnccc4c3)CC2)ccn1 ; Cl] |

TABLE 5-continued
| | | | |
|---|---|---|---|
| 87 | 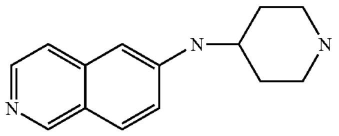 | 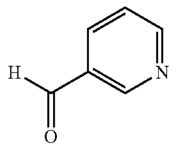 | 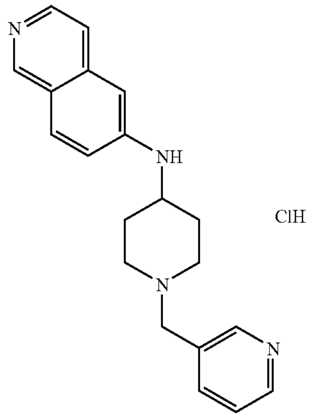 [SMILES: c1cncc(CN2CCC(Nc3ccc4cnccc4c3)CC2)c1 ; Cl] |
| 88 | 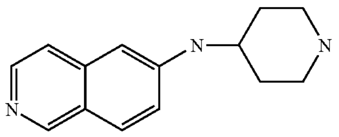 [SMILES: c1cc2cc(NC3CCNCC3)ccc2cn1] | 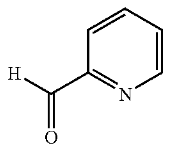 | 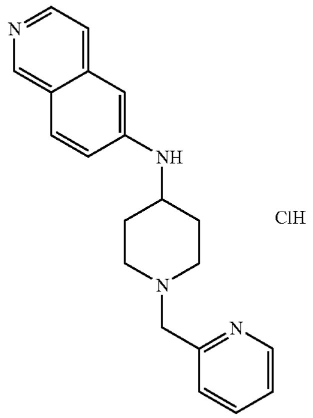 [SMILES: c1ccc(CN2CCC(Nc3ccc4cnccc4c3)CC2)nc1 ; Cl] |
| 89 | 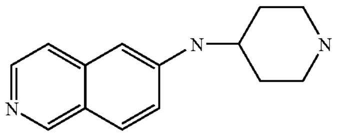 | 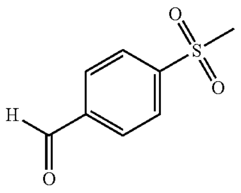 | 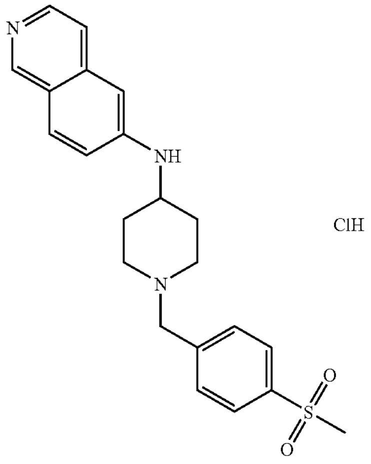 [SMILES: CS(=O)(=O)c1ccc(CN2CCC(Nc3ccc4cnccc4c3)CC2)cc1 ; Cl] |

TABLE 5-continued
| | | | |
|---|---|---|---|
| 90 | 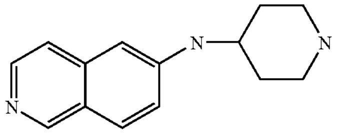 | 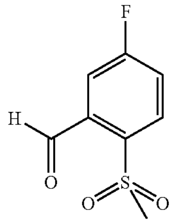 | 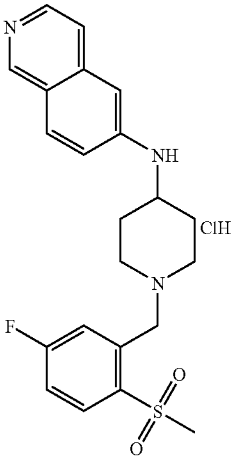 [SMILES: CS(=O)(=O)c1ccc(F)cc1CN1CCC(Nc2ccc3cnccc3c2)CC1 ; Cl] |
| 91 | 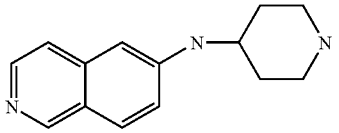 [SMILES: c1cc2cc(NC3CCNCC3)ccc2cn1] | 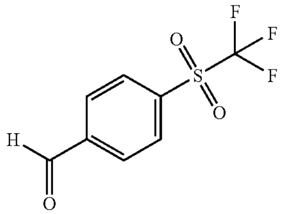 [SMILES: O=Cc1ccc(S(=O)(=O)C(F)(F)F)cc1] | 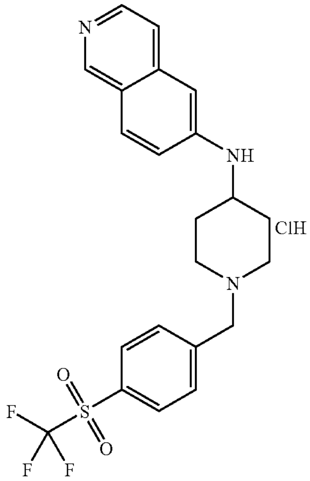 [SMILES: O=S(=O)(c1ccc(CN2CCC(Nc3ccc4cnccc4c3)CC2)cc1)C(F)(F)F ; Cl] |
| 92 | 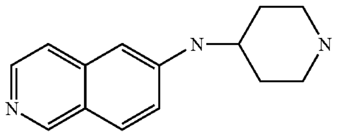 | 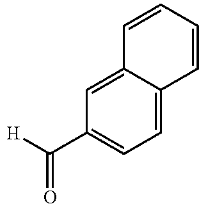 [SMILES: O=Cc1ccc2ccccc2c1] | 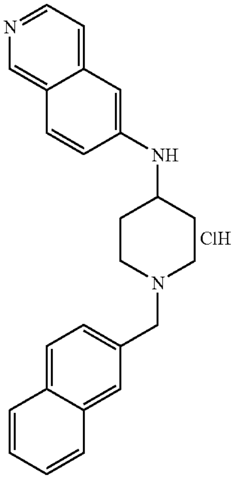 [SMILES: c1ccc2cc(CN3CCC(Nc4ccc5cnccc5c4)CC3)ccc2c1 ; Cl] |

TABLE 5-continued
| | | | |
|---|---|---|---|
| 93 | 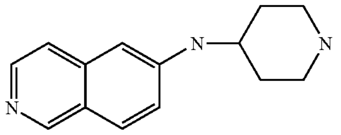 [SMILES: c1cc2cc(NC3CCNCC3)ccc2cn1] | 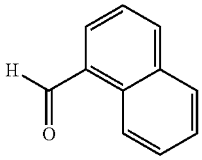 [SMILES: O=Cc1cccc2ccccc12] | 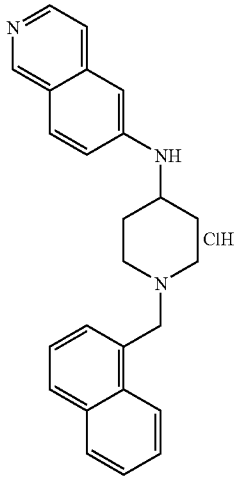 [SMILES: c1ccc2c(CN3CCC(Nc4ccc5cnccc5c4)CC3)cccc2c1 ; Cl] |
| 94 | 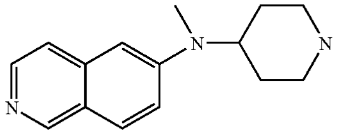 [SMILES: CN(c1ccc2cnccc2c1)C1CCNCC1] | 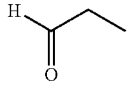 | 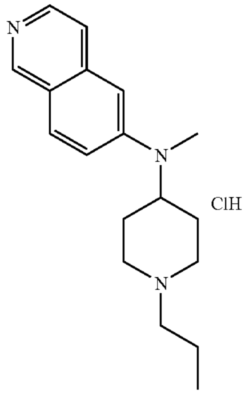 [SMILES: CCCN1CCC(N(C)c2ccc3cnccc3c2)CC1 ; Cl] |
| 95 | 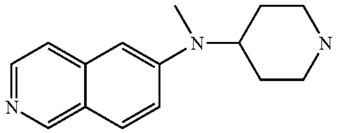 [SMILES: CN(c1ccc2cnccc2c1)C1CCNCC1] | 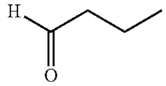 | 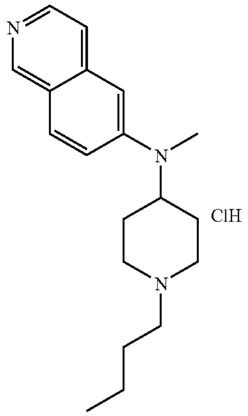 [SMILES: CCCCN1CCC(N(C)c2ccc3cnccc3c2)CC1 ; Cl] |

TABLE 5-continued
| | | | |
|---|---|---|---|
| 96 | 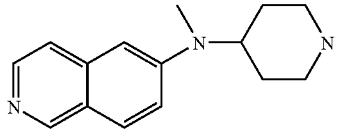 [SMILES: CN(c1ccc2cnccc2c1)C1CCNCC1] | 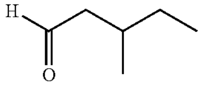 | 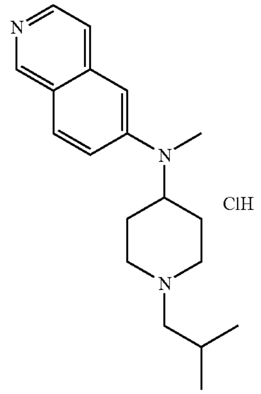 [SMILES: CC(C)CN1CCC(N(C)c2ccc3cnccc3c2)CC1 ; Cl] |
| 97 | 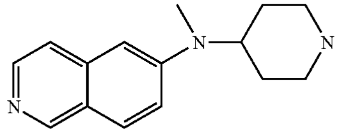 [SMILES: CN(c1ccc2cnccc2c1)C1CCNCC1] | 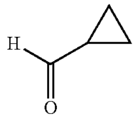 | 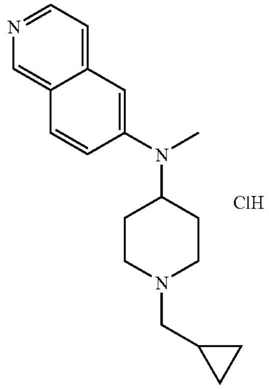 [SMILES: CN(c1ccc2cnccc2c1)C1CCN(CC2CC2)CC1 ; Cl] |
| 98 | 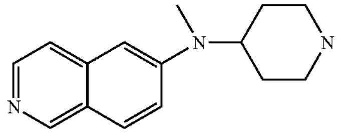 [SMILES: CN(c1ccc2cnccc2c1)C1CCNCC1] | 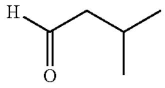 | 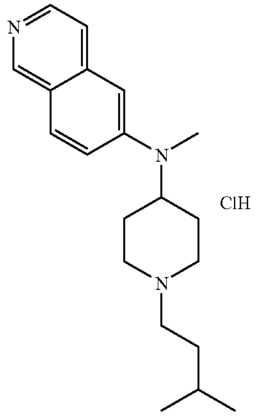 [SMILES: CC(C)CCN1CCC(N(C)c2ccc3cnccc3c2)CC1 ; Cl] |
| 99 | 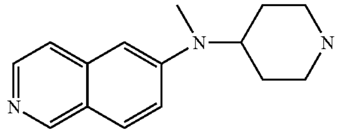 [SMILES: CN(c1ccc2cnccc2c1)C1CCNCC1] | 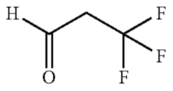 | 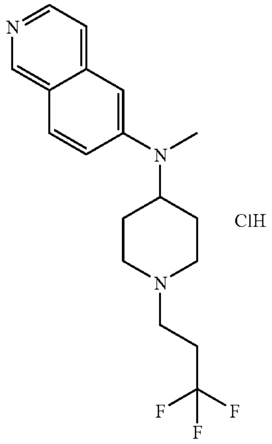 [SMILES: CN(c1ccc2cnccc2c1)C1CCN(CCC(F)(F)F)CC1 ; Cl] |

TABLE 5-continued
| | | | |
|---|---|---|---|
| 100 | 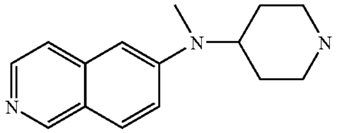 [SMILES: CN(c1ccc2cnccc2c1)C1CCNCC1] | 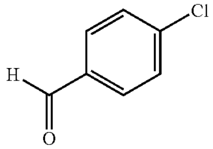 | 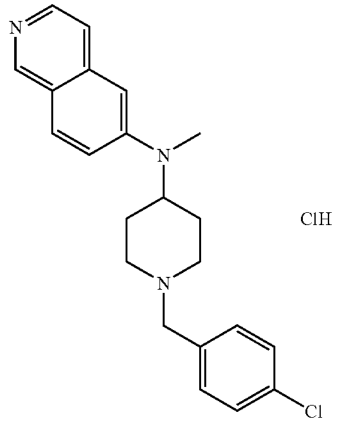 [SMILES: CN(c1ccc2cnccc2c1)C1CCN(Cc2ccc(Cl)cc2)CC1 ; Cl] |
| 101 | 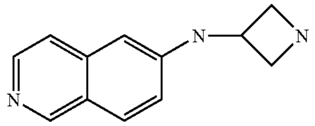 [SMILES: c1cc2cc(NC3CNC3)ccc2cn1] | 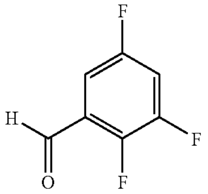 [SMILES: O=Cc1cc(F)cc(F)c1F] | 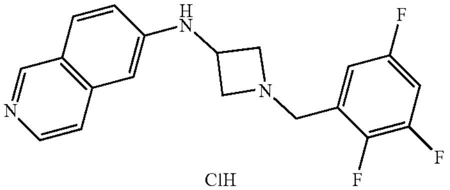 [SMILES: Fc1cc(F)c(F)c(CN2CC(Nc3ccc4cnccc4c3)C2)c1 ; Cl] |
| 102 | 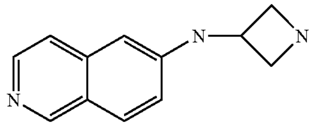 [SMILES: c1cc2cc(NC3CNC3)ccc2cn1] | 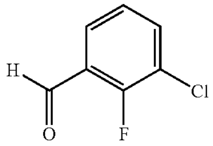 | 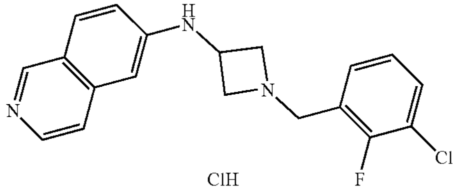 [SMILES: Fc1c(Cl)cccc1CN1CC(Nc2ccc3cnccc3c2)C1 ; Cl] |
| 103 | 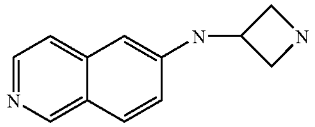 [SMILES: c1cc2cc(NC3CNC3)ccc2cn1] | 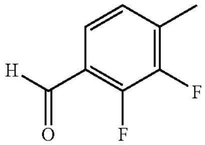 | 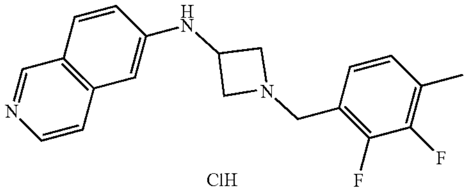 [SMILES: Cc1ccc(CN2CC(Nc3ccc4cnccc4c3)C2)c(F)c1F ; Cl] |
| 104 | 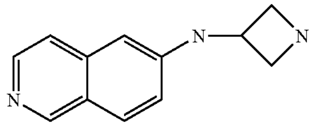 [SMILES: c1cc2cc(NC3CNC3)ccc2cn1] | 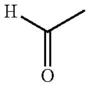 | 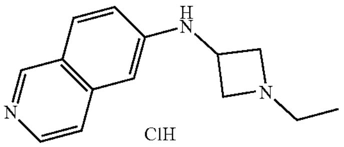 [SMILES: CCN1CC(Nc2ccc3cnccc3c2)C1 ; Cl] |
| 105 | 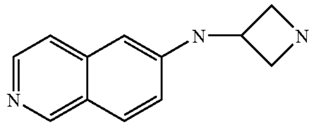 [SMILES: c1cc2cc(NC3CNC3)ccc2cn1] | 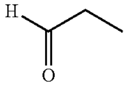 | 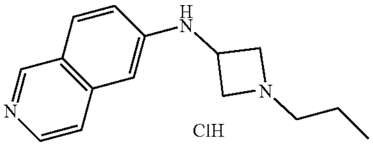 [SMILES: CCCN1CC(Nc2ccc3cnccc3c2)C1 ; Cl] |
| 106 | 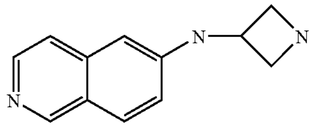 | 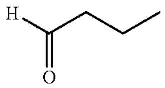 | 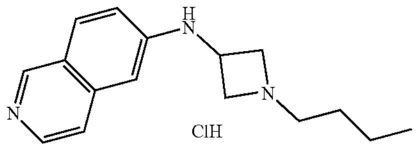 [SMILES: CCCCN1CC(Nc2ccc3cnccc3c2)C1 ; Cl] |

TABLE 5-continued
| | | | |
|---|---|---|---|
| 107 | 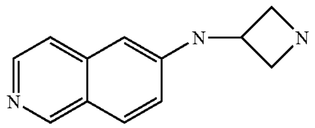 [SMILES: c1cc2cc(NC3CNC3)ccc2cn1] | 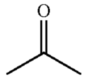 | 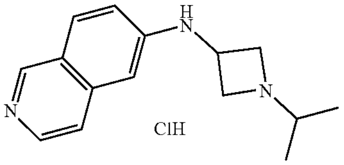 [SMILES: CC(C)N1CC(Nc2ccc3cnccc3c2)C1 ; Cl] |
| 108 | 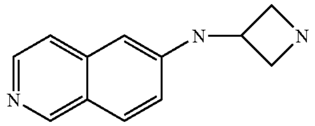 [SMILES: c1cc2cc(NC3CNC3)ccc2cn1] | 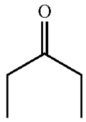 | 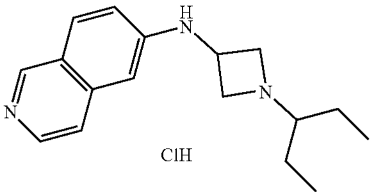 [SMILES: CCC(CC)N1CC(Nc2ccc3cnccc3c2)C1 ; Cl] |
| 109 | 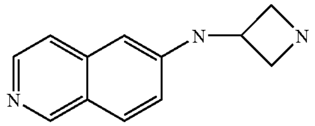 [SMILES: c1cc2cc(NC3CNC3)ccc2cn1] | 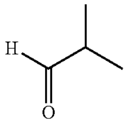 | 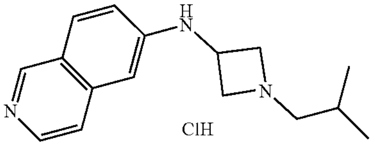 [SMILES: CC(C)CN1CC(Nc2ccc3cnccc3c2)C1 ; Cl] |
| 110 | 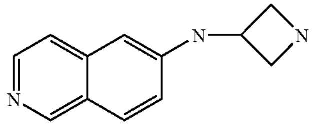 [SMILES: c1cc2cc(NC3CNC3)ccc2cn1] | 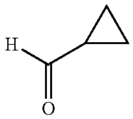 | 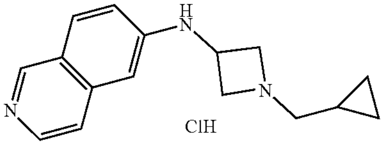 [SMILES: c1cc2cc(NC3CN(CC4CC4)C3)ccc2cn1 ; Cl] |
| 111 | 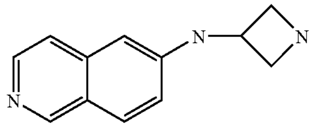 [SMILES: c1cc2cc(NC3CNC3)ccc2cn1] | 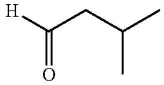 | 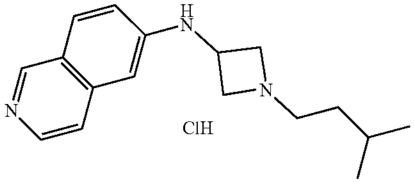 [SMILES: CC(C)CCN1CC(Nc2ccc3cnccc3c2)C1 ; Cl] |
| 112 | 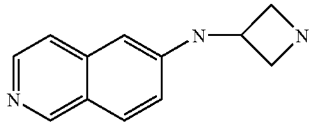 [SMILES: c1cc2cc(NC3CNC3)ccc2cn1] | 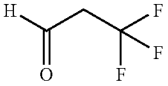 | 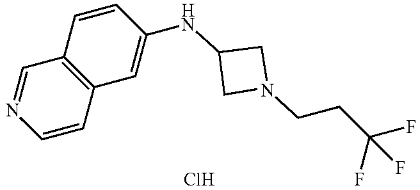 [SMILES: FC(F)(F)CCN1CC(Nc2ccc3cnccc3c2)C1 ; Cl] |
| 113 | 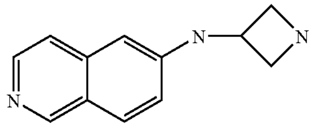 [SMILES: c1cc2cc(NC3CNC3)ccc2cn1] | 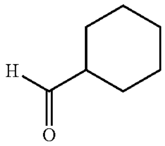 | 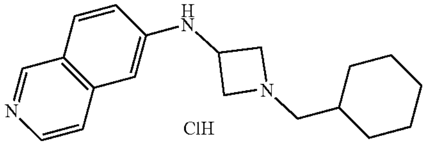 [SMILES: c1cc2cc(NC3CN(CC4CCCCC4)C3)ccc2cn1 ; Cl] |
| 114 | 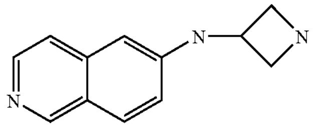 | 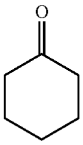 | 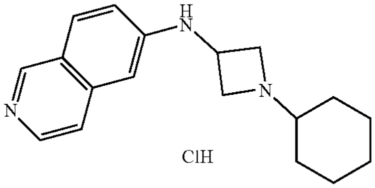 [SMILES: c1cc2cc(NC3CN(C4CCCCC4)C3)ccc2cn1 ; Cl] |
| 115 | 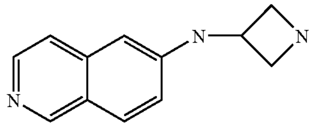 [SMILES: c1cc2cc(NC3CNC3)ccc2cn1] | 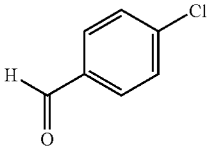 | 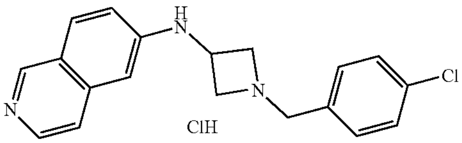 [SMILES: Clc1ccc(CN2CC(Nc3ccc4cnccc4c3)C2)cc1 ; Cl] |

TABLE 5-continued
| | | | |
|---|---|---|---|
| 116 | 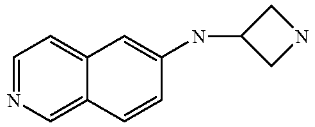 [SMILES: c1cc2cc(NC3CNC3)ccc2cn1] | 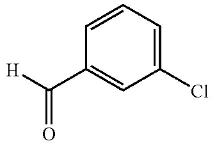 | 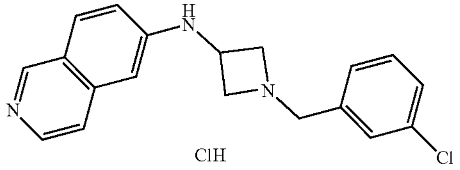 [SMILES: Clc1cccc(CN2CC(Nc3ccc4cnccc4c3)C2)c1 ; Cl] |
| 117 | 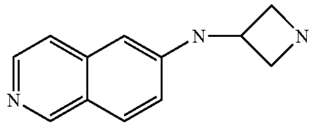 [SMILES: c1cc2cc(NC3CNC3)ccc2cn1] | 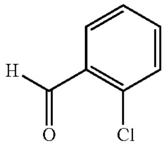 | 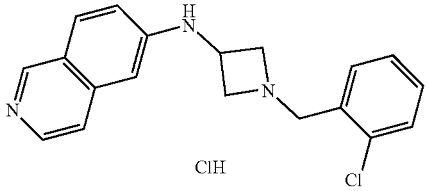 [SMILES: Clc1ccccc1CN1CC(Nc2ccc3cnccc3c2)C1 ; Cl] |
| 118 | 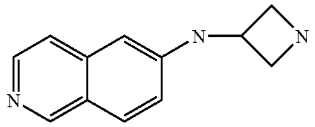 [SMILES: c1cc2cc(NC3CNC3)ccc2cn1] | 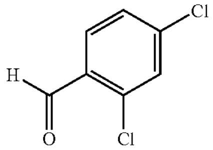 | 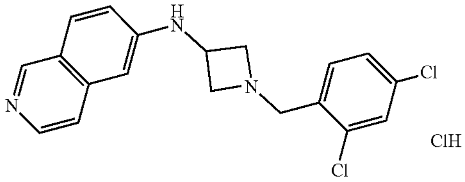 [SMILES: Clc1ccc(CN2CC(Nc3ccc4cnccc4c3)C2)c(Cl)c1 ; Cl] |
| 119 | 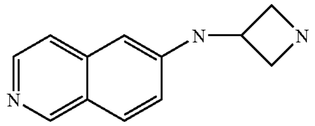 [SMILES: c1cc2cc(NC3CNC3)ccc2cn1] | 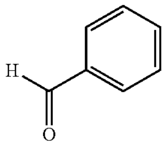 | 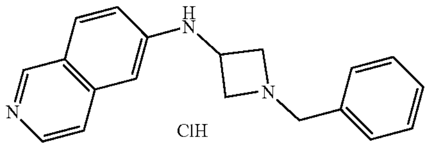 [SMILES: c1ccc(CN2CC(Nc3ccc4cnccc4c3)C2)cc1 ; Cl] |
| 120 | 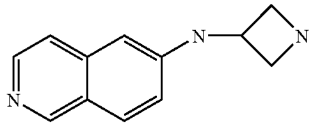 [SMILES: c1cc2cc(NC3CNC3)ccc2cn1] | 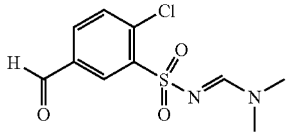 [SMILES: CN(C)/C=N/S(=O)(=O)c1cc(C=O)ccc1Cl] | 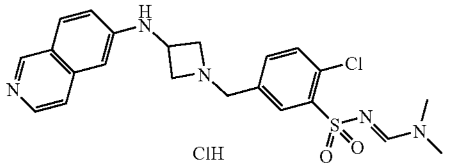 [SMILES: CN(C)/C=N/S(=O)(=O)c1cc(CN2CC(Nc3ccc4cnccc4c3)C2)ccc1Cl ; Cl] |
| 121 | 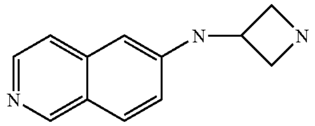 [SMILES: c1cc2cc(NC3CNC3)ccc2cn1] | 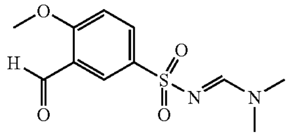 [SMILES: COc1ccc(S(=O)(=O)/N=C/N(C)C)cc1C=O] | 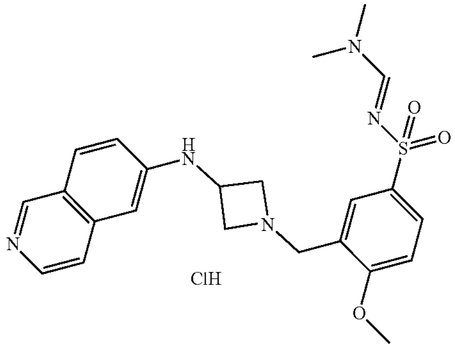 [SMILES: COc1ccc(S(=O)(=O)/N=C/N(C)C)cc1CN1CC(Nc2ccc3cnccc3c2)C1 ; Cl] |
| 122 | 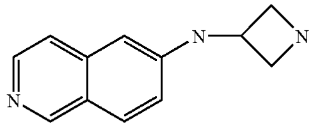 [SMILES: c1cc2cc(NC3CNC3)ccc2cn1] | 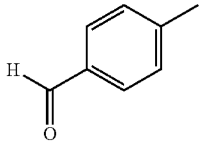 | 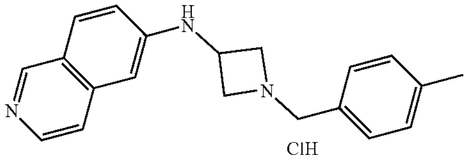 [SMILES: Cc1ccc(CN2CC(Nc3ccc4cnccc4c3)C2)cc1 ; Cl] |
| 123 | 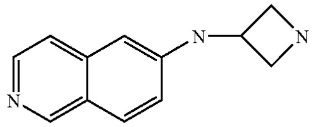 [SMILES: c1cc2cc(NC3CNC3)ccc2cn1] | 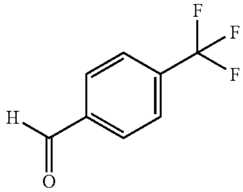 [SMILES: O=Cc1ccc(C(F)(F)F)cc1] | 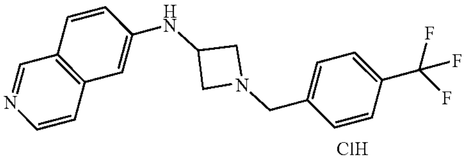 [SMILES: FC(F)(F)c1ccc(CN2CC(Nc3ccc4cnccc4c3)C2)cc1 ; Cl] |

TABLE 5-continued
| | | | |
|---|---|---|---|
| 124 | 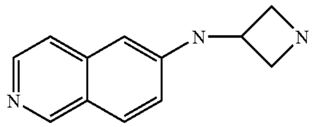 [SMILES: c1cc2cc(NC3CNC3)ccc2cn1] | 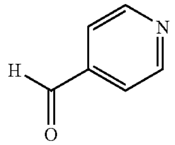 | 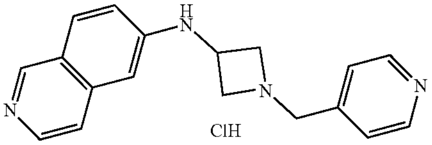 [SMILES: c1cc(CN2CC(Nc3ccc4cnccc4c3)C2)ccn1 ; Cl] |
| 125 | 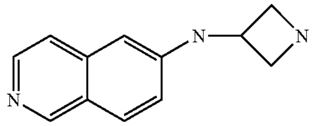 [SMILES: c1cc2cc(NC3CNC3)ccc2cn1] | 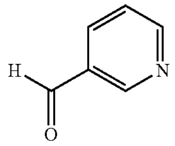 | 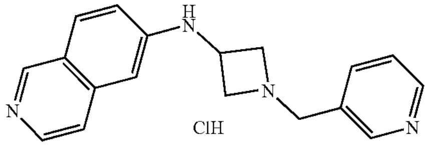 [SMILES: c1cncc(CN2CC(Nc3ccc4cnccc4c3)C2)c1 ; Cl] |
| 126 | 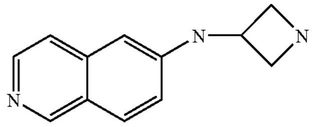 [SMILES: c1cc2cc(NC3CNC3)ccc2cn1] | 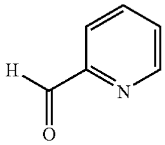 | 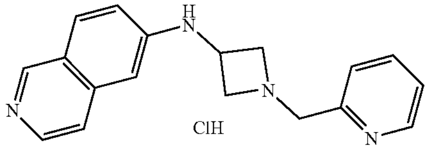 [SMILES: c1ccc(CN2CC(Nc3ccc4cnccc4c3)C2)nc1 ; Cl] |
| 127 | 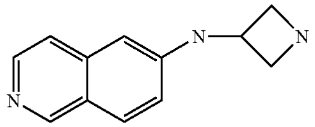 [SMILES: c1cc2cc(NC3CNC3)ccc2cn1] | 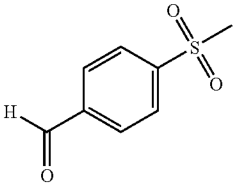 | 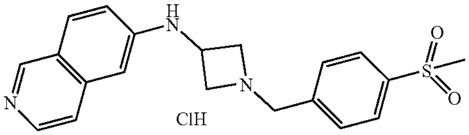 [SMILES: CS(=O)(=O)c1ccc(CN2CC(Nc3ccc4cnccc4c3)C2)cc1 ; Cl] |
| 128 | 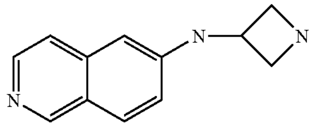 [SMILES: c1cc2cc(NC3CNC3)ccc2cn1] | 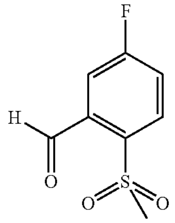 | 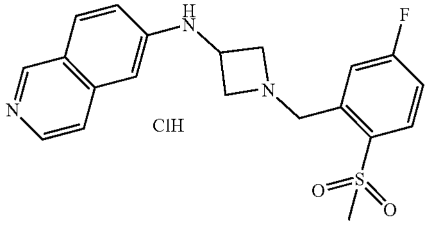 [SMILES: CS(=O)(=O)c1ccc(F)cc1CN1CC(Nc2ccc3cnccc3c2)C1 ; Cl] |
| 129 | 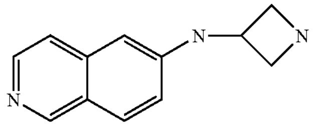 [SMILES: c1cc2cc(NC3CNC3)ccc2cn1] | 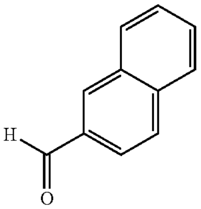 [SMILES: O=Cc1ccc2ccccc2c1] | 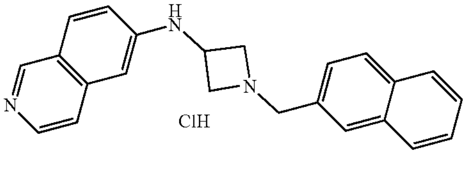 [SMILES: c1ccc2cc(CN3CC(Nc4ccc5cnccc5c4)C3)ccc2c1 ; Cl] |
| 130 | 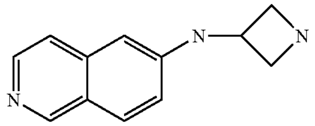 [SMILES: c1cc2cc(NC3CNC3)ccc2cn1] | 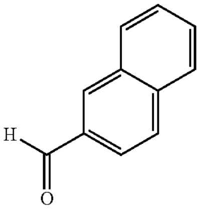 [SMILES: O=Cc1ccc2ccccc2c1] | 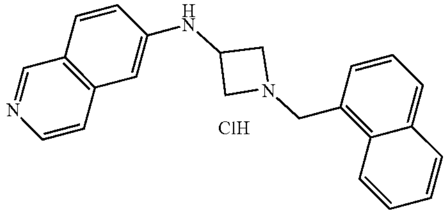 [SMILES: c1ccc2c(CN3CC(Nc4ccc5cnccc5c4)C3)cccc2c1 ; Cl] |
| 131 | 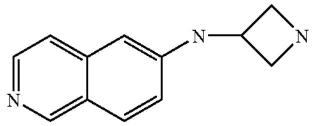 [SMILES: c1cc2cc(NC3CNC3)ccc2cn1] | 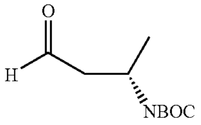 | 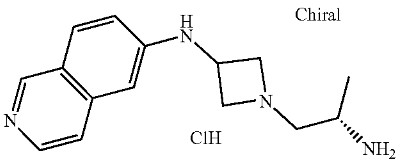 [SMILES: C[C@H](N)CN1CC(Nc2ccc3cnccc3c2)C1 ; Cl] |

TABLE 5-continued
| | | | |
|---|---|---|---|
| 132 | 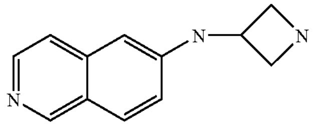 [SMILES: c1cc2cc(NC3CNC3)ccc2cn1] | 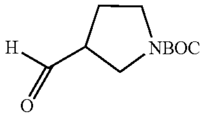 | 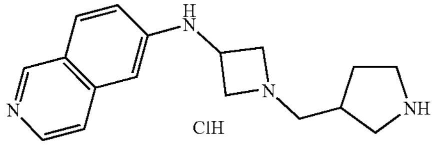 [SMILES: c1cc2cc(NC3CN(CC4CCNC4)C3)ccc2cn1 ; Cl] |
| 133 | 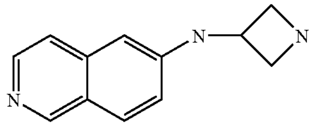 [SMILES: c1cc2cc(NC3CNC3)ccc2cn1] | 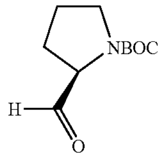 | 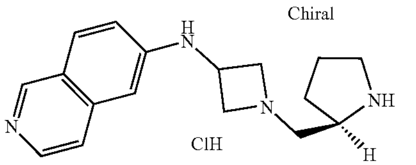 [SMILES: c1cc2cc(NC3CN(C[C@H]4CCCN4)C3)ccc2cn1 ; Cl] |
| 134 | 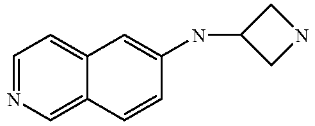 [SMILES: c1cc2cc(NC3CNC3)ccc2cn1] | 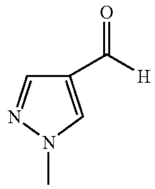 | 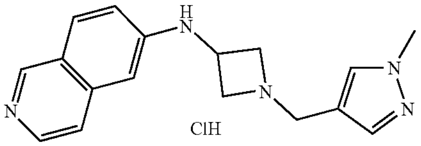 [SMILES: Cn1cc(CN2CC(Nc3ccc4cnccc4c3)C2)cn1 ; Cl] |
| 135 | 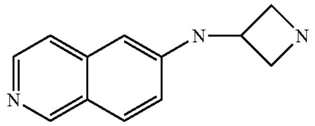 [SMILES: c1cc2cc(NC3CNC3)ccc2cn1] | 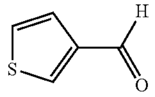 | 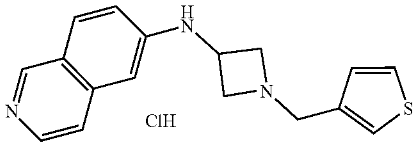 [SMILES: c1cc2cc(NC3CN(Cc4ccsc4)C3)ccc2cn1 ; Cl] |
| 136 | 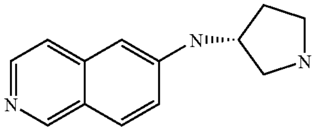 [SMILES: c1cc2cc(N[C@@H]3CCNC3)ccc2cn1] | 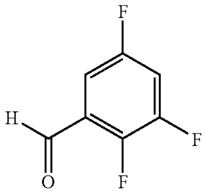 [SMILES: O=Cc1cc(F)cc(F)c1F] | 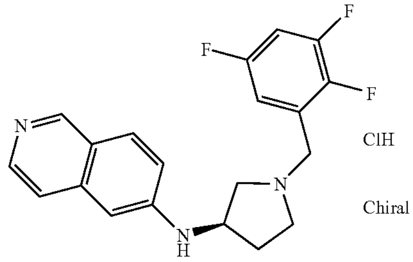 [SMILES: Fc1cc(F)c(F)c(CN2CC[C@@H](Nc3ccc4cnccc4c3)C2)c1 ; "Chiral" ; Cl] |
| 137 | 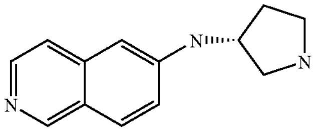 [SMILES: c1cc2cc(N[C@@H]3CCNC3)ccc2cn1] | 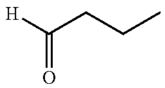 | 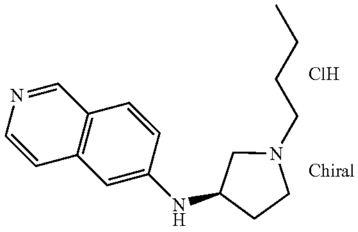 |
| 138 | 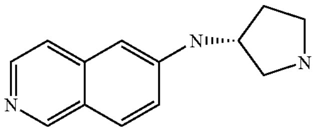 [SMILES: c1cc2cc(N[C@@H]3CCNC3)ccc2cn1] | 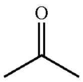 | 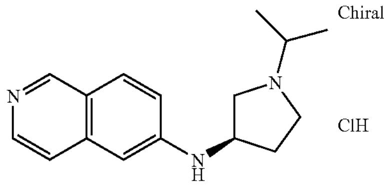 |
| 139 | 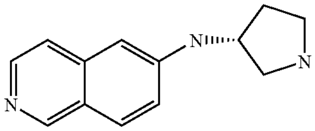 [SMILES: c1cc2cc(N[C@@H]3CCNC3)ccc2cn1] | 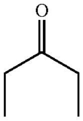 | 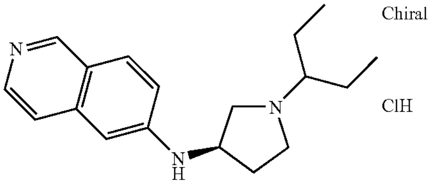 |

TABLE 5-continued
| | | | |
|---|---|---|---|
| 140 | 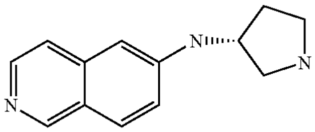 [SMILES: c1cc2cc(N[C@@H]3CCNC3)ccc2cn1] | 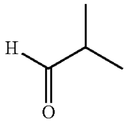 | 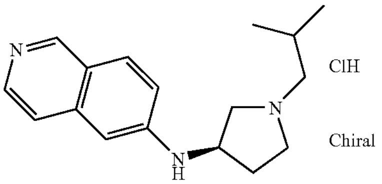 |
| 141 | 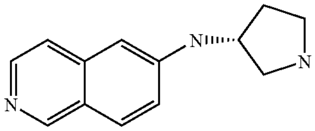 [SMILES: c1cc2cc(N[C@@H]3CCNC3)ccc2cn1] | 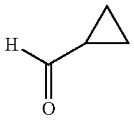 | 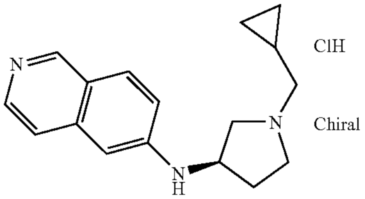 |
| 142 | 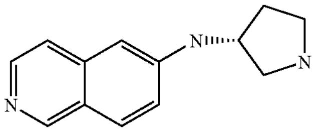 [SMILES: c1cc2cc(N[C@@H]3CCNC3)ccc2cn1] | 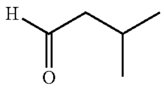 | 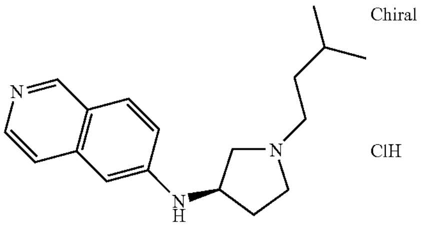 |
| 143 | 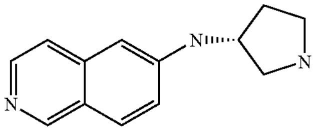 [SMILES: c1cc2cc(N[C@@H]3CCNC3)ccc2cn1] | 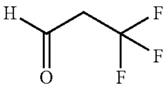 | 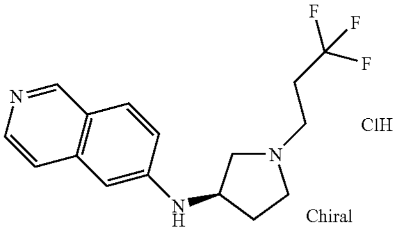 |
| 144 | 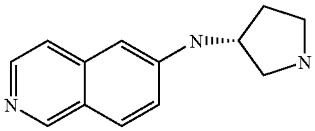 [SMILES: c1cc2cc(N[C@@H]3CCNC3)ccc2cn1] | 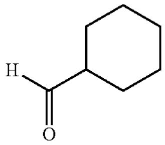 | 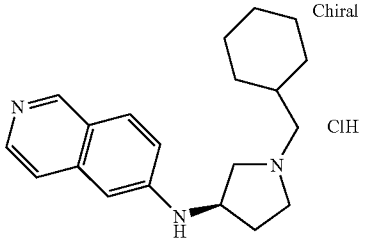 |
| 145 | 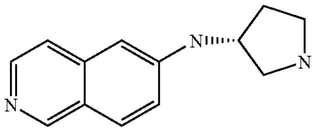 [SMILES: c1cc2cc(N[C@@H]3CCNC3)ccc2cn1] | 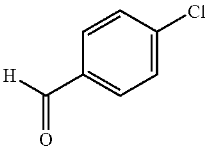 | 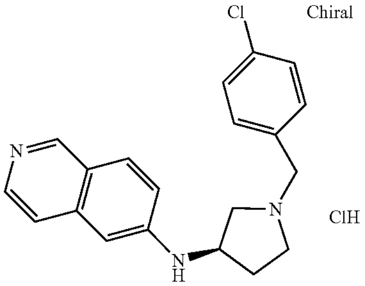 |

TABLE 5-continued
| | | | |
|---|---|---|---|
| 146 | 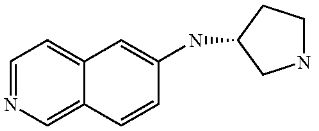 [SMILES: c1cc2cc(N[C@@H]3CCNC3)ccc2cn1] | 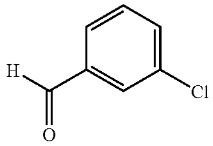 | 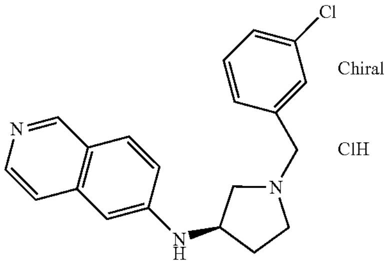 |
| 147 | 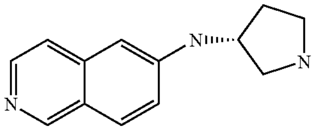 [SMILES: c1cc2cc(N[C@@H]3CCNC3)ccc2cn1] | 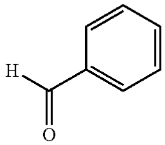 | 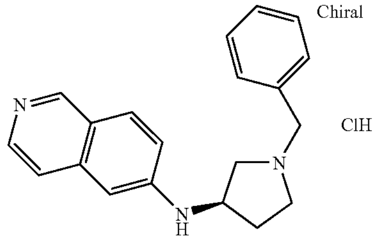 |
| 148 | 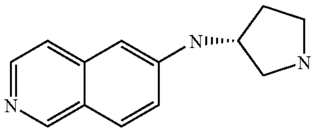 [SMILES: c1cc2cc(N[C@@H]3CCNC3)ccc2cn1] | 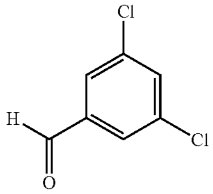 | 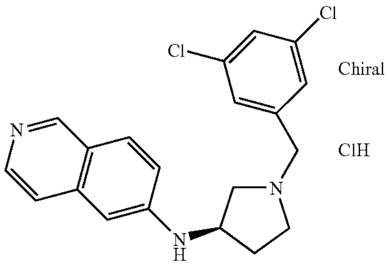 |
| 149 | 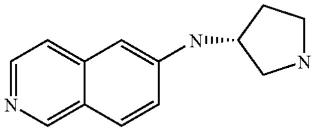 [SMILES: c1cc2cc(N[C@@H]3CCNC3)ccc2cn1] | 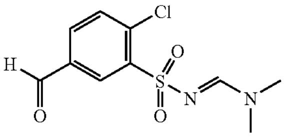 [SMILES: CN(C)/C=N/S(=O)(=O)c1cc(C=O)ccc1Cl] | 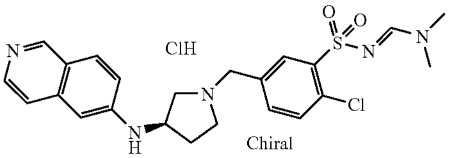 |
| 150 | 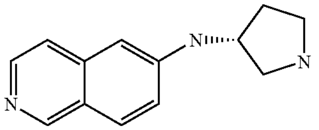 [SMILES: c1cc2cc(N[C@@H]3CCNC3)ccc2cn1] | 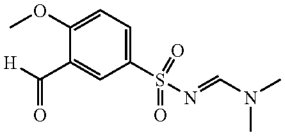 [SMILES: COc1ccc(S(=O)(=O)/N=C/N(C)C)cc1C=O] | 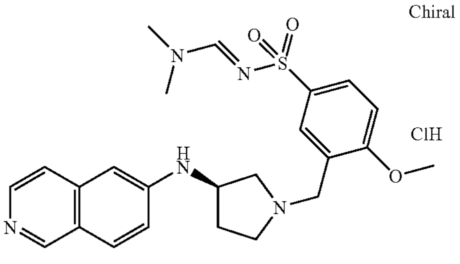 [SMILES: COc1ccc(S(=O)(=O)/N=C/N(C)C)cc1CN1CC[C@@H](Nc2ccc3cnccc3c2)C1 ; Cl] |
| 151 | 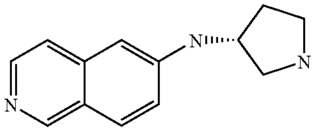 [SMILES: c1cc2cc(N[C@@H]3CCNC3)ccc2cn1] | 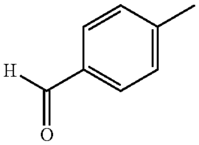 | 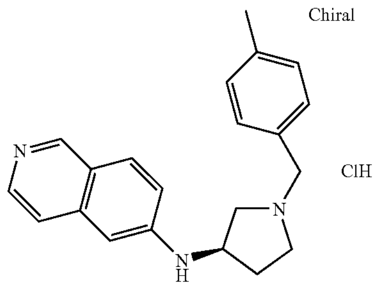 |

TABLE 5-continued
| | | | |
|---|---|---|---|
| 152 | 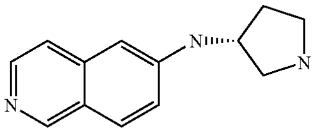 [SMILES: c1cc2cc(N[C@@H]3CCNC3)ccc2cn1] | 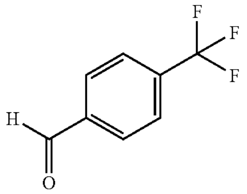 [SMILES: O=Cc1ccc(C(F)(F)F)cc1] | 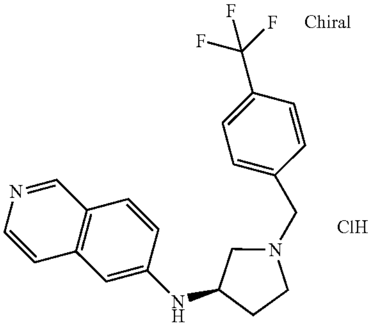 |
| 153 | 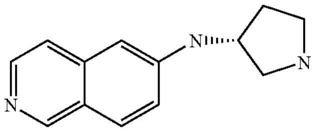 [SMILES: c1cc2cc(N[C@@H]3CCNC3)ccc2cn1] | 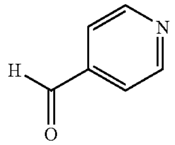 | 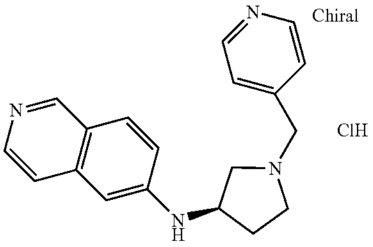 |
| 154 | 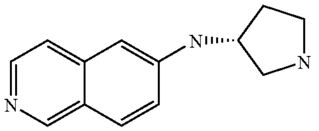 [SMILES: c1cc2cc(N[C@@H]3CCNC3)ccc2cn1] | 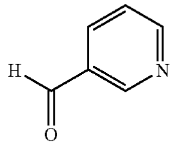 | 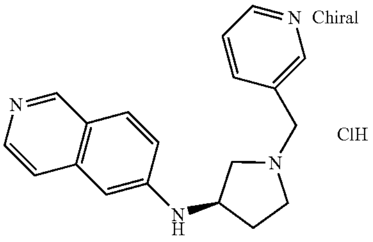 |
| 155 | 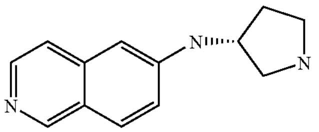 [SMILES: c1cc2cc(N[C@@H]3CCNC3)ccc2cn1] | 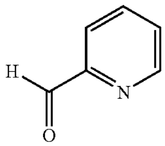 | 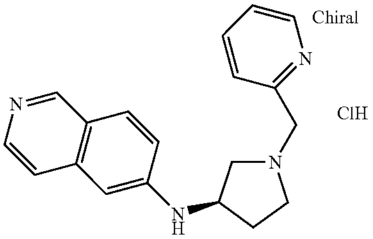 |
| 156 | 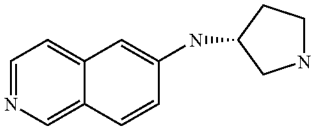 [SMILES: c1cc2cc(N[C@@H]3CCNC3)ccc2cn1] | 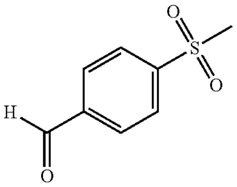 | 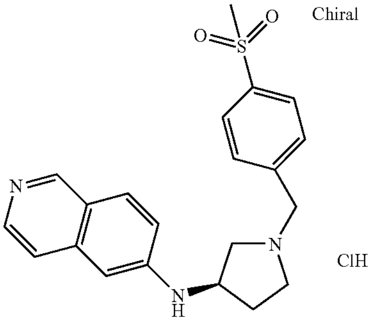 |

TABLE 5-continued
| | | | |
|---|---|---|---|
| 157 | 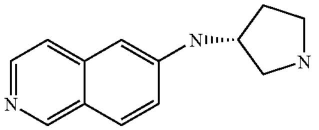 [SMILES: c1cc2cc(N[C@@H]3CCNC3)ccc2cn1] | 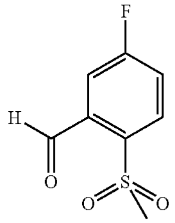 | 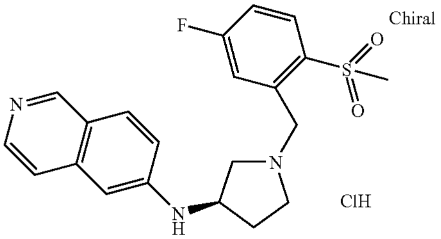 |
| 158 | 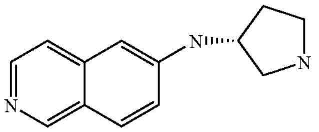 [SMILES: c1cc2cc(N[C@@H]3CCNC3)ccc2cn1] | 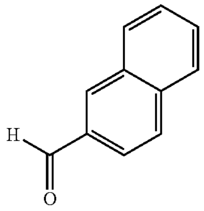 | 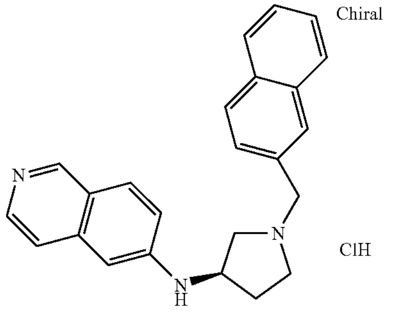 |
| 159 | 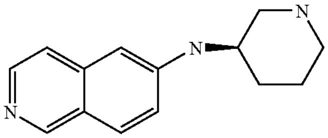 [SMILES: c1cc2cc(N[C@@H]3CCCNC3)ccc2cn1] | 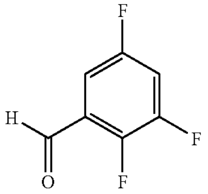 [SMILES: O=Cc1cc(F)cc(F)c1F] | 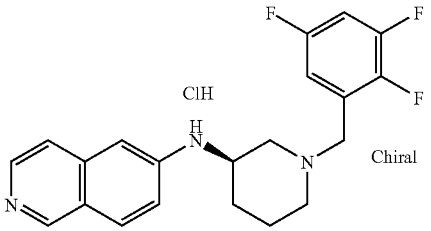 [SMILES: Fc1cc(F)c(F)c(CN2CCC[C@@H](Nc3ccc4cnccc4c3)C2)c1 ; Cl] |
| 160 | 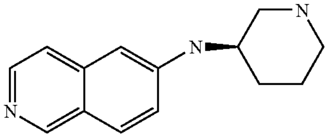 [SMILES: c1cc2cc(N[C@@H]3CCCNC3)ccc2cn1] | 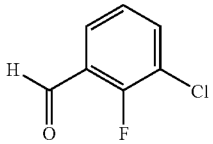 | 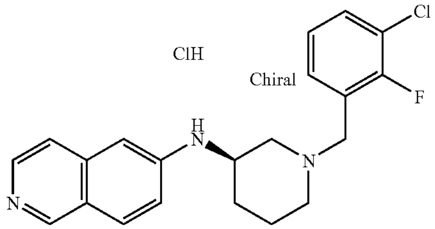 [SMILES: Fc1c(Cl)cccc1CN1CCC[C@@H](Nc2ccc3cnccc3c2)C1 ; Cl] |
| 161 | 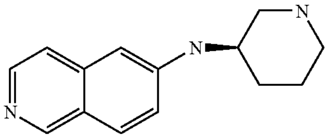 [SMILES: c1cc2cc(N[C@@H]3CCCNC3)ccc2cn1] | 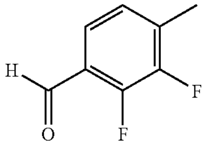 | 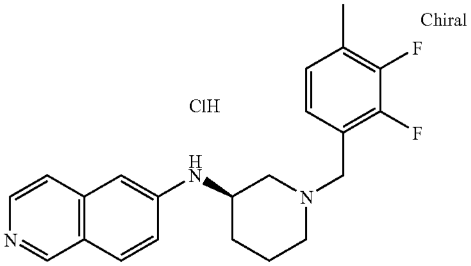 [SMILES: Cc1ccc(CN2CCC[C@@H](Nc3ccc4cnccc4c3)C2)c(F)c1F ; Cl] |
| 162 | 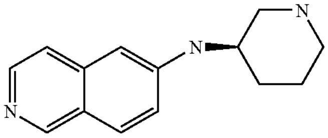 [SMILES: c1cc2cc(N[C@@H]3CCCNC3)ccc2cn1] | 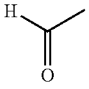 | 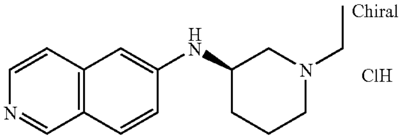 [SMILES: CCN1CCC[C@@H](Nc2ccc3cnccc3c2)C1 ; Cl] |
| 163 | 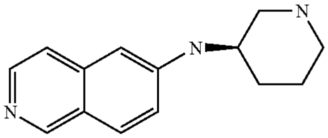 [SMILES: c1cc2cc(N[C@@H]3CCCNC3)ccc2cn1] | 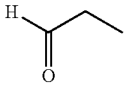 | 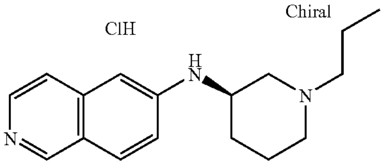 [SMILES: CCCN1CCC[C@@H](Nc2ccc3cnccc3c2)C1 ; Cl] |

TABLE 5-continued
| | | | |
|---|---|---|---|
| 164 | 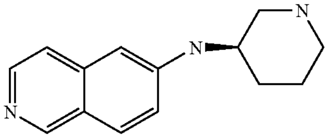 [SMILES: c1cc2cc(N[C@@H]3CCCNC3)ccc2cn1] | 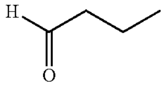 | 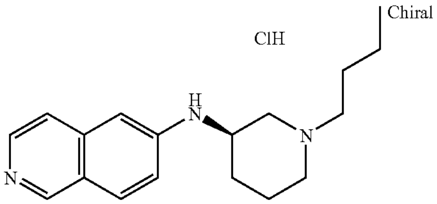 [SMILES: CCCCN1CCC[C@@H](Nc2ccc3cnccc3c2)C1 ; Cl] |
| 165 | 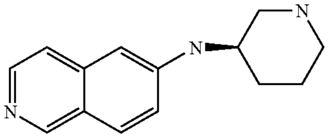 [SMILES: c1cc2cc(N[C@@H]3CCCNC3)ccc2cn1] | 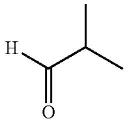 | 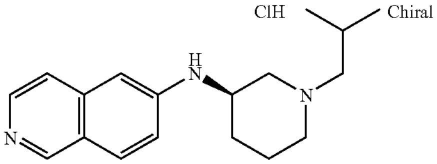 [SMILES: CC(C)CN1CCC[C@@H](Nc2ccc3cnccc3c2)C1 ; Cl] |
| 166 | 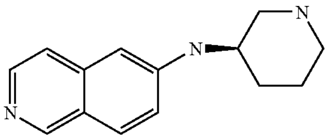 [SMILES: c1cc2cc(N[C@@H]3CCCNC3)ccc2cn1] | 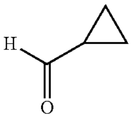 | 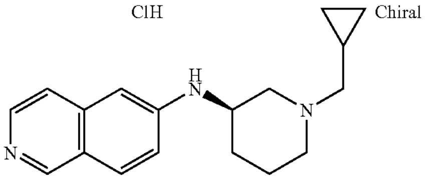 [SMILES: c1cc2cc(N[C@@H]3CCCN(CC4CC4)C3)ccc2cn1 ; Cl] |
| 167 | 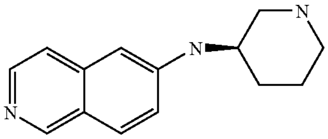 [SMILES: c1cc2cc(N[C@@H]3CCCNC3)ccc2cn1] | 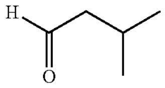 | 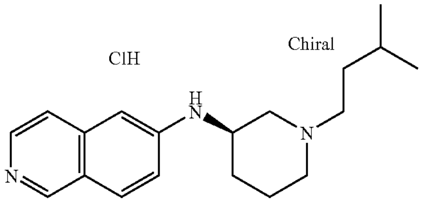 [SMILES: CC(C)CCN1CCC[C@@H](Nc2ccc3cnccc3c2)C1 ; Cl] |
| 168 | 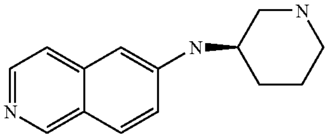 [SMILES: c1cc2cc(N[C@@H]3CCCNC3)ccc2cn1] | 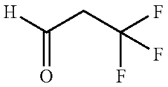 | 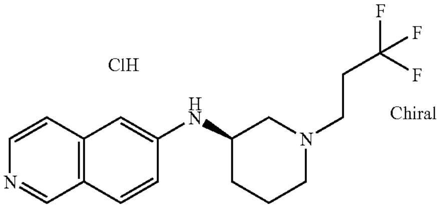 [SMILES: FC(F)(F)CCN1CCC[C@@H](Nc2ccc3cnccc3c2)C1 ; Cl] |
| 169 | 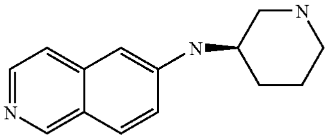 [SMILES: c1cc2cc(N[C@@H]3CCCNC3)ccc2cn1] | 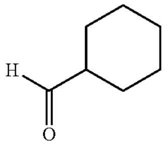 | 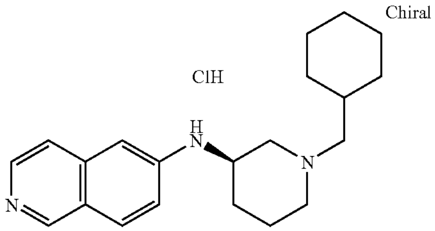 [SMILES: c1cc2cc(N[C@@H]3CCCN(CC4CCCCC4)C3)ccc2cn1 ; Cl] |
| 170 | 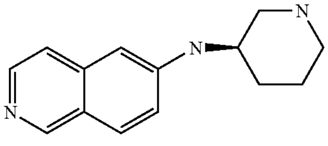 [SMILES: c1cc2cc(N[C@@H]3CCCNC3)ccc2cn1] | 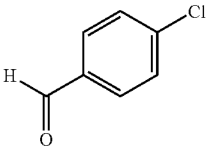 | 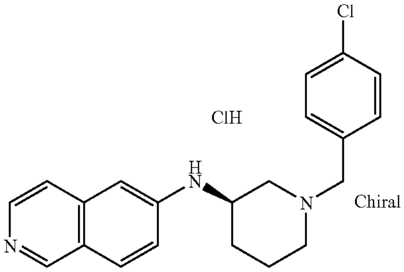 [SMILES: Clc1ccc(CN2CCC[C@@H](Nc3ccc4cnccc4c3)C2)cc1 ; Cl] |

TABLE 5-continued
| | | | |
|---|---|---|---|
| 171 | 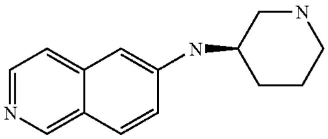 [SMILES: c1cc2cc(N[C@@H]3CCCNC3)ccc2cn1] | 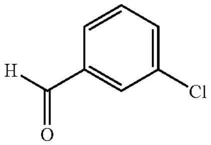 | 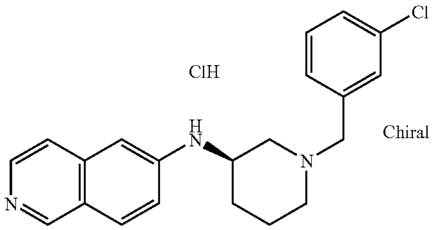 [SMILES: Clc1cccc(CN2CCC[C@@H](Nc3ccc4cnccc4c3)C2)c1 ; Cl] |
| 172 | 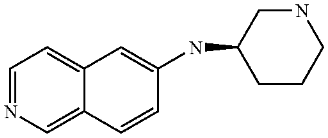 [SMILES: c1cc2cc(N[C@@H]3CCCNC3)ccc2cn1] | 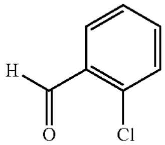 | 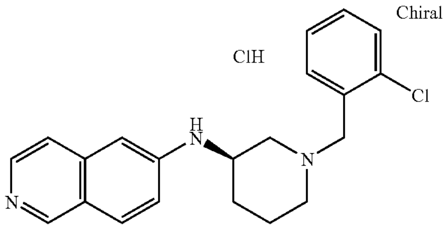 [SMILES: Clc1ccccc1CN1CCC[C@@H](Nc2ccc3cnccc3c2)C1 ; Cl] |
| 173 | 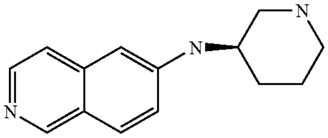 [SMILES: c1cc2cc(N[C@@H]3CCCNC3)ccc2cn1] | 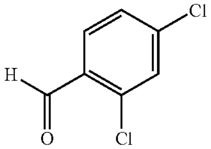 | 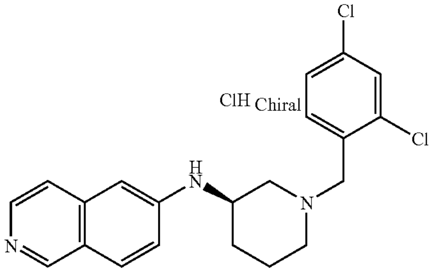 [SMILES: Clc1ccc(CN2CCC[C@@H](Nc3ccc4cnccc4c3)C2)c(Cl)c1 ; Cl] |
| 174 | 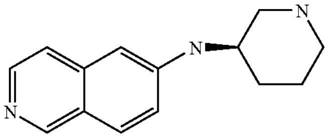 [SMILES: c1cc2cc(N[C@@H]3CCCNC3)ccc2cn1] | 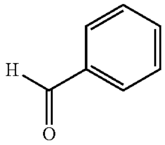 | 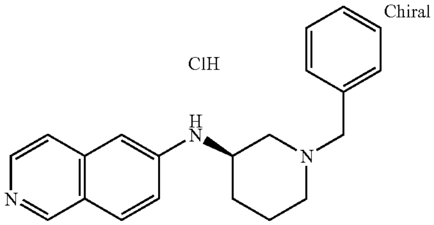 [SMILES: c1ccc(CN2CCC[C@@H](Nc3ccc4cnccc4c3)C2)cc1 ; Cl] |
| 175 | 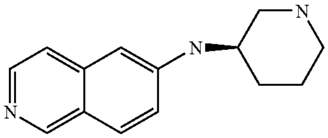 [SMILES: c1cc2cc(N[C@@H]3CCCNC3)ccc2cn1] | 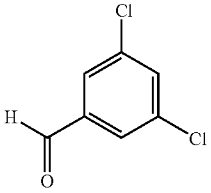 | 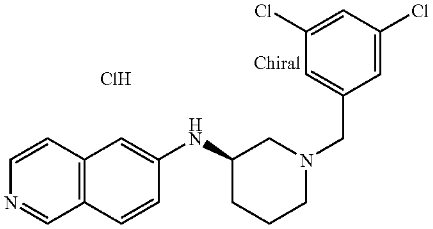 [SMILES: Clc1cc(Cl)cc(CN2CCC[C@@H](Nc3ccc4cnccc4c3)C2)c1 ; Cl] |
| 176 | 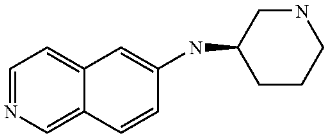 [SMILES: c1cc2cc(N[C@@H]3CCCNC3)ccc2cn1] | 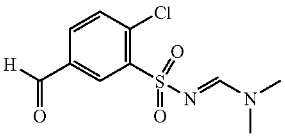 [SMILES: CN(C)/C=N/S(=O)(=O)c1cc(C=O)ccc1Cl] | 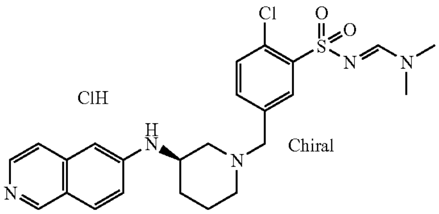 [SMILES: CN(C)/C=N/S(=O)(=O)c1cc(CN2CCC[C@@H](Nc3ccc4cnccc4c3)C2)ccc1Cl ; Cl] |

TABLE 5-continued
| | | | |
|---|---|---|---|
| 177 | 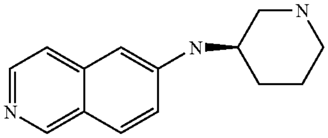 [SMILES: c1cc2cc(N[C@@H]3CCCNC3)ccc2cn1] | 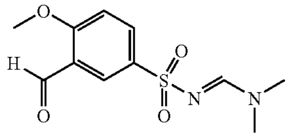 [SMILES: COc1ccc(S(=O)(=O)/N=C/N(C)C)cc1C=O] | 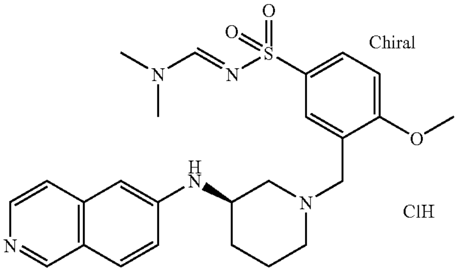 [SMILES: COc1ccc(S(=O)(=O)/N=C/N(C)C)cc1CN1CCC[C@@H](Nc2ccc3cnccc3c2)C1 ; Cl] |
| 178 | 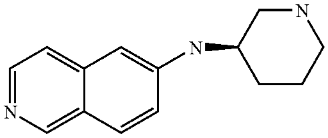 [SMILES: c1cc2cc(N[C@@H]3CCCNC3)ccc2cn1] | 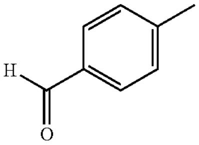 | 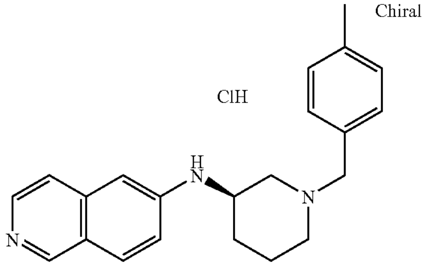 [SMILES: Cc1ccc(CN2CCC[C@@H](Nc3ccc4cnccc4c3)C2)cc1 ; Cl] |
| 179 | 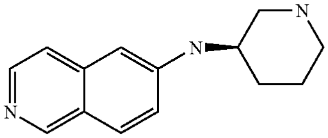 [SMILES: c1cc2cc(N[C@@H]3CCCNC3)ccc2cn1] | 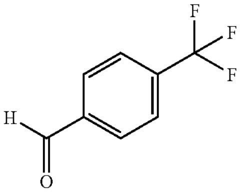 [SMILES: O=Cc1ccc(C(F)(F)F)cc1] | 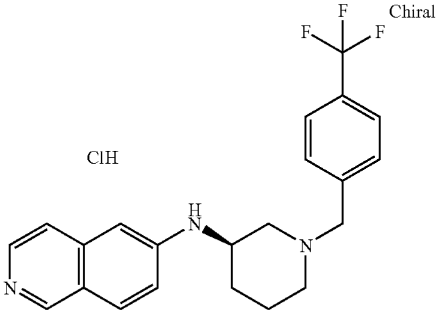 [SMILES: FC(F)(F)c1ccc(CN2CCC[C@@H](Nc3ccc4cnccc4c3)C2)cc1 ; Cl] |
| 180 | 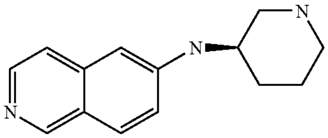 [SMILES: c1cc2cc(N[C@@H]3CCCNC3)ccc2cn1] | 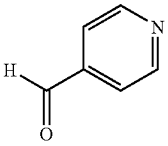 | 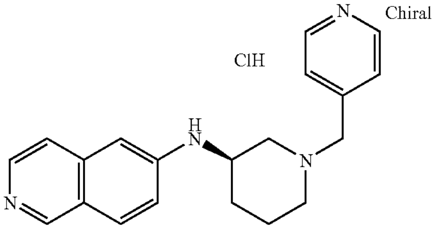 [SMILES: c1cc(CN2CCC[C@@H](Nc3ccc4cnccc4c3)C2)ccn1 ; Cl] |
| 181 | 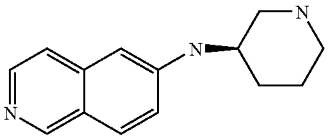 [SMILES: c1cc2cc(N[C@@H]3CCCNC3)ccc2cn1] | 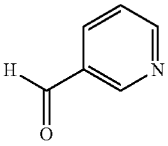 | 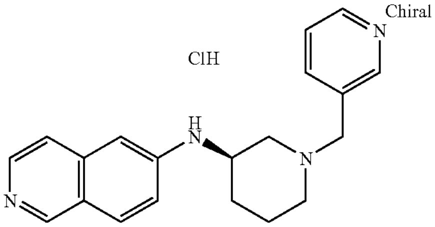 [SMILES: c1cncc(CN2CCC[C@@H](Nc3ccc4cnccc4c3)C2)c1 ; Cl] |
| 182 | 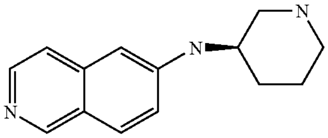 [SMILES: c1cc2cc(N[C@@H]3CCCNC3)ccc2cn1] | 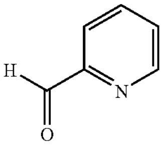 | 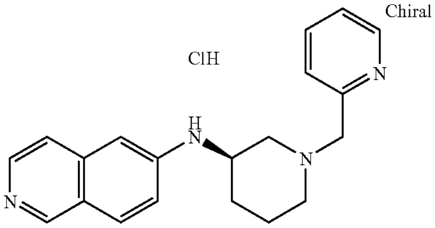 [SMILES: c1ccc(CN2CCC[C@@H](Nc3ccc4cnccc4c3)C2)nc1 ; Cl] |

TABLE 5-continued
| | | | |
|---|---|---|---|
| 183 | 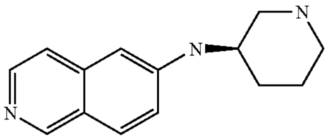 [SMILES: c1cc2cc(N[C@@H]3CCCNC3)ccc2cn1] | 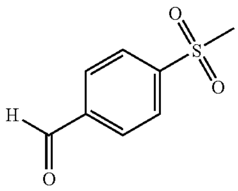 | 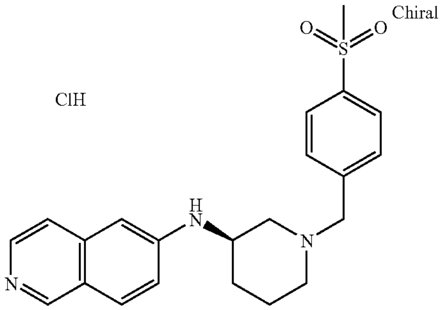 [SMILES: CS(=O)(=O)c1ccc(CN2CCC[C@@H](Nc3ccc4cnccc4c3)C2)cc1 ; Cl] |
| 48 | 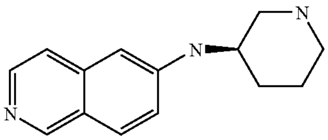 [SMILES: c1cc2cc(N[C@@H]3CCCNC3)ccc2cn1] | 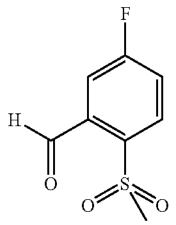 | 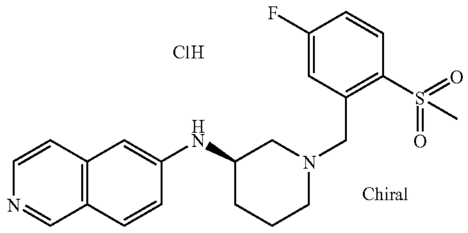 [SMILES: CS(=O)(=O)c1ccc(F)cc1CN1CCC[C@@H](Nc2ccc3cnccc3c2)C1 ; Cl] |
| 184 | 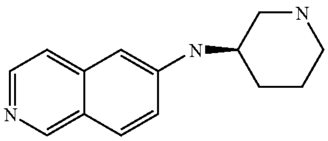 [SMILES: c1cc2cc(N[C@@H]3CCCNC3)ccc2cn1] | 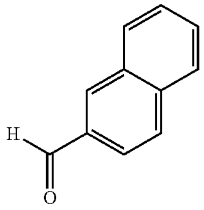 | 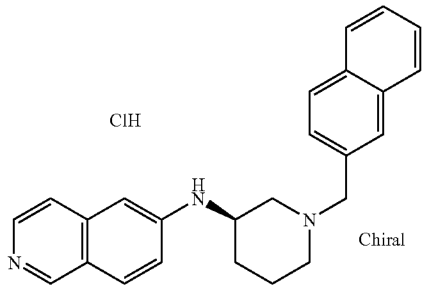 [SMILES: c1ccc2cc(CN3CCC[C@@H](Nc4ccc5cnccc5c4)C3)ccc2c1 ; Cl] |
| 185 | 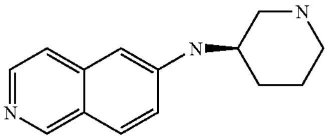 [SMILES: c1cc2cc(N[C@@H]3CCCNC3)ccc2cn1] | 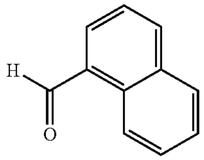 [SMILES: O=Cc1cccc2ccccc12] | 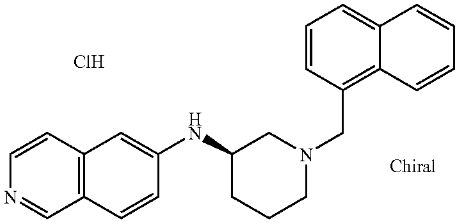 [SMILES: c1ccc2c(CN3CCC[C@@H](Nc4ccc5cnccc5c4)C3)cccc2c1 ; Cl] |
| 186 | 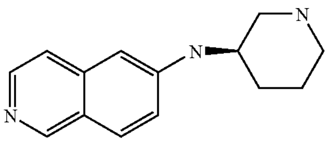 [SMILES: c1cc2cc(N[C@@H]3CCCNC3)ccc2cn1] | 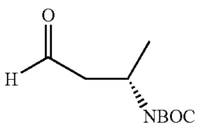 | 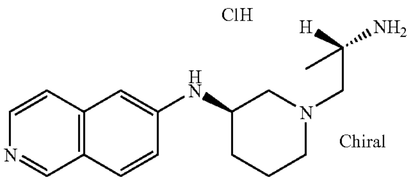 [SMILES: Cl ; C[C@H](N)CN1CCC[C@@H](Nc2ccc3cnccc3c2)C1] |
| 187 | 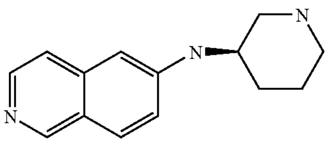 [SMILES: c1cc2cc(N[C@@H]3CCCNC3)ccc2cn1] | 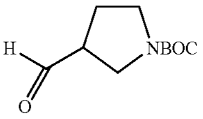 | 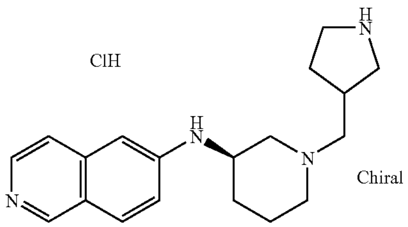 [SMILES: c1cc2cc(N[C@@H]3CCCN(CC4CCNC4)C3)ccc2cn1 ; Cl] |

TABLE 5-continued

188

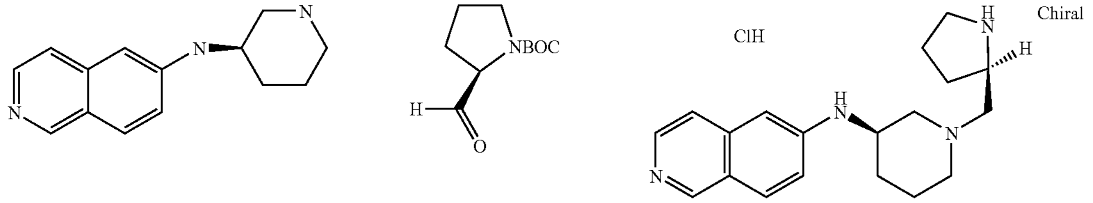

| Example | $R_t$ [min] | Mass [M + H$^+$] | LCMS Method | Chemical name |
|---|---|---|---|---|
| 69 | 0.68 | 270.2 | B | Isoquinolin-6-yl-(1-propyl-piperidin-4-yl)-amine |
| 70 | 0.82 | 284.2 | B | (1-Butyl-piperidin-4-yl)-isoquinolin-6-yl-amine |
| 71 | 0.82 | 284.2 | B | (1-Isobutyl-piperidin-4-yl)-isoquinolin-6-yl-amine |
| 72 | 0.72 | 282.2 | B | (1-Cyclopropylmethyl-piperidin-4-yl)-isoquinolin-6-yl-amine |
| 73 | 0.97 | 298.2 | B | Isoquinolin-6-yl-[1-(3-methyl-butyl)-piperidin-4-yl]-amine |
| 74 | 0.79 | 324.2 | B | Isoquinolin-6-yl-[1-(3,3,3-trifluoro-propyl)-piperidin-4-yl]-amine |
| 75 | 1.00 | 324.3 | B | (1-Cyclohexylmethyl-piperidin-4-yl)-isoquinolin-6-yl-amine |
| 76 | 0.82 | 310.3 | B | (1-Cyclohexyl-piperidin-4-yl)-isoquinolin-6-yl-amine |
| 77 | 0.99 | 352.2 | B | [1-(4-Chloro-benzyl)-piperidin-4-yl]-isoquinolin-6-yl-amine |
| 78 | 0.99 | 352.2 | B | [1-(3-Chloro-benzyl)-piperidin-4-yl]-isoquinolin-6-yl-amine |
| 79 | 0.91 | 352.2 | B | [1-(2-Chloro-benzyl)-piperidin-4-yl]-isoquinolin-6-yl-amine |
| 80 | 1.06 | 386.2 | B | [1-(2,4-Dichloro-benzyl)-piperidin-4-yl]-isoquinolin-6-yl-amine |
| 81 | 0.82 | 318.2 | B | (1-Benzyl-piperidin-4-yl)-isoquinolin-6-yl-amine |
| 82 | 1.00 | 486.2 | B | 2-Chloro-N-[1-dimethylamino-meth-(E)-ylidene]-5-[4-(isoquinolin-6-ylamino)-piperidin-1-ylmethyl]-benzenesulfonamide |
| 83 | 0.87 | 482.3 | B | N-[1-Dimethylamino-meth-(E)-ylidene]-3-[4-(isoquinolin-6-ylamino)-piperidin-1-ylmethyl]-4-methoxy-benzenesulfonamide |
| 84 | 0.92 | 332.2 | B | Isoquinolin-6-yl-[1-(4-methyl-benzyl)-piperidin-4-yl]-amine |
| 85 | 1.04 | 386.2 | B | Isoquinolin-6-yl-[1-(4-trifluoromethyl-benzyl)-piperidin-4-yl]-amine |
| 86 | 0.77 | 319.2 | B | Isoquinolin-6-yl-(1-pyridin-4-ylmethyl-piperidin-4-yl)-amine |
| 87 | 0.50 | 319.2 | B | Isoquinolin-6-yl-(1-pyridin-3-ylmethyl-piperidin-4-yl)-amine |
| 88 | 0.73 | 319.2 | B | Isoquinolin-6-yl-(1-pyridin-2-ylmethyl-piperidin-4-yl)-amine |
| 89 | 0.78 | 396.2 | B | Isoquinolin-6-yl-[1-(4-methanesulfonyl-benzyl)-piperidin-4-yl]-amine |
| 90 | 0.82 | 414.2 | B | [1-(5-Fluoro-2-methanesulfonyl-benzyl)-piperidin-4-yl]-isoquinolin-6-yl-amine |
| 91 | 1.15 | 450.1 | B | Isoquinolin-6-yl-[1-(4-trifluoromethanesulfonyl-benzyl)-piperidin-4-yl]-amine |
| 92 | 1.13 | 368.2 | B | Isoquinolin-6-yl-(1-naphthalen-2-ylmethyl-piperidin-4-yl)-amine |
| 93 | 1.05 | 368.2 | B | Isoquinolin-6-yl-(1-naphthalen-1-ylmethyl-piperidin-4-yl)-amine |
| 94 | 0.82 | 284.3 | B | Isoquinolin-6-yl-methyl-(1-propyl-piperidin-4-yl)-amine |
| 95 | 0.79 | 298.3 | B | (1-Butyl-piperidin-4-yl)-isoquinolin-6-yl-methyl-amine |
| 96 | 0.82 | 298.2 | B | (1-Isobutyl-piperidin-4-yl)-isoquinolin-6-yl-methyl-amine |
| 97 | 0.79 | 296.2 | B | (1-Cyclopropylmethyl-piperidin-4-yl)-isoquinolin-6-yl-methyl-amine |
| 98 | 0.95 | 312.3 | B | Isoquinolin-6-yl-methyl-[1-(3-methyl-butyl)-piperidin-4-yl]-amine |
| 99 | 0.74 | 338.2 | B | Isoquinolin-6-yl-methyl-[1-(3,3,3-trifluoro-propyl)-piperidin-4-yl]-amine |
| 100 | 1.02 | 366.2 | B | [1-(4-Chloro-benzyl)-piperidin-4-yl]-isoquinolin-6-yl-methyl-amine |
| 101 | 0.78 | 344.2 | A | Isoquinolin-6-yl-[1-(2,3,5-trifluoro-benzyl)-azetidin-3-yl]-amine |
| 102 | 0.86 | 342.2/344.2 | A | [1-(3-Chloro-2-fluoro-benzyl)-azetidin-3-yl]-isoquinolin-6-yl-amine |
| 103 | 0.87 | 340.2 | A | [1-(2,3-Difluoro-4-methyl-benzyl)-azetidin-3-yl]-isoquinolin-6-yl-amine |
| 104 | 0.14 | 228.2 | A | (1-Ethyl-azetidin-3-yl)-isoquinolin-6-yl-amine |
| 105 | 0.18 | 242.2 | A | Isoquinolin-6-yl-(1-propyl-azetidin-3-yl)-amine |
| 106 | 0.12 | 256.3 | A | (1-Butyl-azetidin-3-yl)-isoquinolin-6-yl-amine |
| 107 | 0.4$ | 242.2 | A | (1-Isopropyl-azetidin-3-yl)-isoquinolin-6-yl-amin |
| 108 | 0.68 | 270.3 | A | [1-(1-Ethyl-propyl)-azetidin-3-yl]-isoquinolin-6-yl-amine |
| 109 | 0.66 | 256.3 | A | (1-Isobutyl-azetidin-3-yl)-isoquinolin-6-yl-amine |
| 110 | 0.5§ | 254.3 | A | (1-Cyclopropylmethyl-azetidin-3-yl)-isoquinolin-6-yl-amine |
| 111 | 0.77 | 270.2 | A | Isoquinolin-6-yl-[1-(3-methyl-butyl)-azetidin-3-yl]-amine |
| 112 | 0.54 | 296.2 | A | Isoquinolin-6-yl-[1-(3,3,3-trifluoro-propyl)-azetidin-3-yl]-amine |
| 113 | 0.81 | 296.3 | A | (1-Cyclohexylmethyl-azetidin-3-yl)-isoquinolin-6-yl-amine |
| 114 | 0.79 | 282.3 | A | (1-Cyclohexyl-azetidin-3-yl)-isoquinolin-6-yl-amine |
| 115 | 0.76 | 324.2/326.2 | A | [1-(4-Chloro-benzyl)-azetidin-3-yl]-isoquinolin-6-yl-amine |
| 116 | 0.84 | 324.2/326.2 | A | [1-(3-Chloro-benzyl)-azetidin-3-yl]-isoquinolin-6-yl-amine |
| 117 | 0.79 | 324.2/326.2 | A | [1-(2-Chloro-benzyl)-azetidin-3-yl]-isoquinolin-6-yl-amine |
| 118 | 0.93 | 358.2 | A | [1-(2,4-Dichloro-benzyl)-azetidin-3-yl]-isoquinolin-6-yl-amine |
| 119 | 0.72 | 290.2 | A | (1-Benzyl-azetidin-3-yl)-isoquinolin-6-yl-amine |
| 120 | 0.75 | 458.3/460.3 | A | 2-Chloro-N-[1-dimethylamino-meth-(E)-ylidene]-5-[3-(isoquinolin-6-ylamino)-azetidin-1-ylmethyl]-benzenesulfonamide |
| 121 | 0.73 | 454.3 | A | N-[1-Dimethylamino-meth-(E)-ylidene]-3-[3-(isoquinolin-6-ylamino)-azetidin-1-ylmethyl]-4-methoxy-benzenesulfonamide |
| 122 | 0.84 | 304.3 | A | Isoquinolin-6-yl-[1-(4-methyl-benzyl)-azetidin-3-yl]-amine |
| 123 | 0.92 | 358.2 | A | Isoquinolin-6-yl-[1-(4-trifluoromethyl-benzyl)-azetidin-3-yl]-amine |
| 124 | 0.18 | 291.2 | A | Isoquinolin-6-yl-(1-pyridin-4-ylmethyl-azetidin-3-yl)-amine |
| 125 | 0.21 | 291.2 | A | Isoquinolin-6-yl-(1-pyridin-3-ylmethyl-azetidin-3-yl)-amine |
| 126 | 0.23 | 291.3 | A | Isoquinolin-6-yl-(1-pyridin-2-ylmethyl-azetidin-3-yl)-amine |
| 127 | 0.61 | 368.3 | A | Isoquinolin-6-yl-[1-(4-methanesulfonyl-benzyl)-azetidin-3-yl]-amine |
| 128 | 0.74 | 386.2 | A | [1-(5-Fluoro-2-methanesulfonyl-benzyl)-azetidin-3-yl]-isoquinolin-6-yl-amine |
| 129 | 1.03 | 340.3 | A | Isoquinolin-6-yl-(1-naphthalen-2-ylmethyl-azetidin-3-yl)-amine |
| 130 | 0.96 | 340.3 | A | Isoquinolin-6-yl-(1-naphthalen-1-ylmethyl-azetidin-3-yl)-amine |
| 131 | 0.14 | 257.3 | A | [1-((S)-2-Amino-propyl)-azetidin-3-yl]-isoquinolin-6-yl-amine |

TABLE 5-continued

| | | | | |
|---|---|---|---|---|
| 132 | 0.14 | 283.3 | A | Isoquinolin-6-yl-(1-pyrrolidin-3-ylmethyl-azetidin-3-yl)-amine |
| 133 | 0.12 | 283.3 | A | Isoquinolin-6-yl-(1-(R)-1-pyrrolidin-2-ylmethyl-azetidin-3-yl)-amine |
| 134 | 0.46 | 294.3 | A | Isoquinolin-6-yl-[1-(1-methyl-1H-pyrazol-4-ylmethyl)-azetidin-3-yl]-amine |
| 135 | 0.70 | 296.2 | A | Isoquinolin-6-yl-(1-thiophen-3-ylmethyl-azetidin-3-yl)-amine |
| 136 | 0.82 | 358.2 | B | Isoquinolin-6-yl-[(R)-1-(2,3,5-trifluoro-benzyl)-pyrrolidin-3-yl]-amine |
| 137 | 0.70 | 270.2 | B | ((R)-1-Butyl-pyrrolidin-3-yl)-isoquinolin-6-yl-amine |
| 138 | 0.49 | 256.2 | B | ((R)-1-Isopropyl-pyrrolidin-3-yl)-isoquinolin-6-yl-amine |
| 139 | 0.74 | 284.2 | B | [(R)-1-(1-Ethyl-propyl)-pyrrolidin-3-yl]-isoquinolin-6-yl-amine |
| 140 | 0.65 | 270.2 | B | ((R)-1-Isobutyl-pyrrolidin-3-yl)-isoquinolin-6-yl-amine |
| 141 | 0.64 | 268.2 | B | ((R)-1-Cyclopropylmethyl-pyrrolidin-3-yl)-isoquinolin-6-yl-amine |
| 142 | 0.80 | 284.2 | B | Isoquinolin-6-yl-[(R)-1-(3-methyl-butyl)-pyrrolidin-3-yl]-amine |
| 143 | 0.62 | 310.2 | B | Isoquinolin-6-yl-[(R)-1-(3,3,3-trifluoro-propyl)-pyrrolidin-3-yl]-amine |
| 144 | 0.87 | 310.2 | B | ((R)-1-Cyclohexylmethyl-pyrrolidin-3-yl)-isoquinolin-6-yl-amine |
| 145 | 0.58 | 338.4/340.4 | B | [(R)-1-(4-Chloro-benzyl)-pyrrolidin-3-yl]-isoquinolin-6-yl-amine |
| 146 | 0.60 | 338.5/340.4 | B | [(R)-1-(3-Chloro-benzyl)-pyrrolidin-3-yl]-isoquinolin-6-yl-amine |
| 147 | 0.79 | 304.1 | B | ((R)-1-Benzyl-pyrrolidin-3-yl)-isoquinolin-6-yl-amine |
| 148 | 1.02 | 372..0/374.0 | B | [(R)-1-(3,5-Dichloro-benzyl)-pyrrolidin-3-yl]-isoquinolin-6-yl-amine |
| 149 | 0.86 | 472.0 | B | 2-Chloro-N-[1-dimethylamino-meth-(E)-ylidene]-5-[(R)-3-(isoquinolin-6-ylamino)-pyrrolidin-1-ylmethyl]-benzenesulfonamide |
| 150 | 0.82 | 468.3 | A | N-[1-Dimethylamino-meth-(E)-ylidene]-3-[(R)-3-(isoquinolin-6-ylamino)-pyrrolidin-1-ylmethyl]-4-methoxy-benzenesulfonamide |
| 151 | 0.81 | 318.3 | A | Isoquinolin-6-yl-[(R)-1-(4-methyl-benzyl)-pyrrolidin-3-yl]-amine |
| 152 | 1.03 | 372.2 | A | Isoquinolin-6-yl-[(R)-1-(4-trifluoromethyl-benzyl)-pyrrolidin-3-yl]-amine |
| 153 | 0.16 | 305.3 | A | Isoquinolin-6-yl-((R)-1-pyridin-4-ylmethyl-pyrrolidin-3-yl)-amine |
| 154 | 0.14 | 305.3 | A | Isoquinolin-6-yl-((R)-1-pyridin-3-ylmethyl-pyrrolidin-3-yl)-amine |
| 155 | 0.16 | 305.3 | A | Isoquinolin-6-yl-((R)-1-pyridin-2-ylmethyl-pyrrolidin-3-yl)-amine |
| 156 | 0.60 | 382.3 | A | Isoquinolin-6-yl-[(R)-1-(4-methanesulfonyl-benzyl)-pyrrolidin-3-yl]-amine |
| 157 | 0.64 | 400.2 | A | [(R)-1-(5-Fluoro-2-methanesulfonyl-benzyl)-pyrrolidin-3-yl]-isoquinolin-6-yl-amine |
| 158 | 0.97 | 354.3 | A | Isoquinolin-6-yl-((R)-1-naphthalen-2-ylmethyl-pyrrolidin-3-yl)-amine |
| 159 | 0.81 | 372.3 | A | Isoquinolin-6-yl-[(R)-1-(2,3,5-trifluoro-benzyl)-piperidin-3-yl]-amine |
| 160 | 0.93 | 370.3 | A | [(R)-1-(3-Chloro-2-fluoro-benzyl)-piperidin-3-yl]-isoquinolin-6-yl-amine |
| 161 | 0.91 | 368.2 | A | [(R)-1-(2,3-Difluoro-4-methyl-benzyl)-piperidin-3-yl]-isoquinolin-6-yl-amine |
| 162 | 0.77 | 256.2 | A | ((R)-1-Ethyl-piperidin-3-yl)-isoquinolin-6-yl-amine |
| 163 | 0.21 | 270.3 | A | Isoquinolin-6-yl-((R)-1-propyl-piperidin-3-yl)-amine |
| 164 | 0.69 | 284.3 | A | ((R)-1-Butyl-piperidin-3-yl)-isoquinolin-6-yl-amine |
| 165 | 0.65 | 284.3 | A | ((R)-1-Isobutyl-piperidin-3-yl)-isoquinolin-6-yl-amine |
| 166 | 0.59 | 282.3 | A | ((R)-1-Cyclopropylmethyl-piperidin-3-yl)-isoquinolin-6-yl-amine |
| 167 | 0.80 | 298.3 | A | Isoquinolin-6-yl-[(R)-1-(3-methyl-butyl)-piperidin-3-yl]-amine |
| 168 | 0.62 | 324.3 | A | Isoquinolin-6-yl-[(R)-1-(3,3,3-trifluoro-propyl)-piperidin-3-yl]-amine |
| 169 | 0.75 | 324.3 | A | ((R)-1-Cyclohexylmethyl-piperidin-3-yl)-isoquinolin-6-yl-amine |
| 170 | 0.91 | 352.3/354.3 | A | [(R)-1-(4-Chloro-benzyl)-piperidin-3-yl]-isoquinolin-6-yl-amine |
| 171 | 0.73 | 352.3/354.3 | A | [(R)-1-(3-Chloro-benzyl)-piperidin-3-yl]-isoquinolin-6-yl-amine |
| 172 | 0.85 | 352.3/354.3 | A | [(R)-1-(2-Chloro-benzyl)-piperidin-3-yl]-isoquinolin-6-yl-amine |
| 173 | 1.00 | 386.2/388.2 | A | [(R)-1-(2,4-Dichloro-benzyl)-piperidin-3-yl]-isoquinolin-6-yl-amine |
| 174 | 0.77 | 318.4 | A | ((R)-1-Benzyl-piperidin-3-yl)-isoquinolin-6-yl-amine |
| 175 | 1.00 | 386.2/388.2 | A | [(R)-1-(3,5-Dichloro-benzyl)-piperidin-3-yl]-isoquinolin-6-yl-amine |
| 176 | 0.64 | 486.3 | A | 2-Chloro-N-[1-dimethylamino-meth-(E)-ylidene]-5-[(R)-3-(isoquinolin-6-ylamino)-piperidin-1-ylmethyl]-benzenesulfonamide |
| 177 | 0.80 | 482.4 | A | N-[1-Dimethyl-amino-meth-(E)-ylidene]-3-[(R)-3-(isoquinolin-6-ylamino)-piperidin-1-ylmethyl]-4-methoxy-benzenesulfonamide |
| 178 | 0.90 | 332.3 | A | Isoquinolin-6-yl-[(R)-1-(4-methyl-benzyl)-piperidin-3-yl]-amine |
| 179 | 0.96 | 386.3 | A | Isoquinolin-6-yl-[(R)-1-(4-trifluoromethyl-benzyl)-piperidin-3-yl]-amine |
| 180 | 0.12 | 319.3 | A | Isoquinolin-6-yl-((R)-1-pyridin-4-ylmethyl-piperidin-3-yl)-amine |
| 181 | 0.16 | 319.3 | A | Isoquinolin-6-yl-((R)-1-pyridin-3-ylmethyl-piperidin-3-yl)-amine |
| 182 | 0.18 | 319.3 | A | Isoquinolin-6-yl-((R)-1-pyridin-2-ylmethyl-piperidin-3-yl)-amin |
| 183 | 0.67 | 396.3 | A | Isoquinolin-6-yl-[(R)-1-(4-methanesulfonyl-benzyl)-piperidin-3-yl]-amine |
| 48 | 0.70 | 414.3 | A | [(R)-1-(5-Fluoro-2-methanesulfonyl-benzyl)-piperidin-3-yl]-isoquinolin-6-yl-amine |
| 184 | 1.06 | 368.3 | A | Isoquinolin-6-yl-((R)-1-naphthalen-2-ylmethyl-piperidin-3-yl)-amine |
| 185 | 0.97 | 368.3 | A | Isoquinolin-6-yl-((R)-1-naphthalen-1-ylmethyl-piperidin-3-yl)-amine |
| 186 | 0.18 | 285.3 | A | [(R)-1-((S)-2-Amino-propyl)-piperidin-3-yl]-isoquinolin-6-yl-amine |
| 187 | 0.14 | 311.3 | A | Isoquinolin-6-yl-((R)-1-pyrrolidin-3-ylmethyl-piperidin-3-yl)-amine |
| 188 | 0.21 | 311 .3 | A | Isoquinolin-6-yl-((R)-1-(R)-1-pyrrolidin-2-ylmethyl-piperidin-3-yl)-amine |

189: 6-(Azetidin-3-ylamino)-2H-isoquinolin-1-one hydrochloride

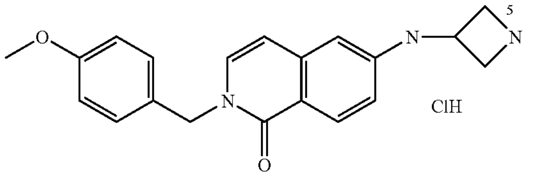 [SMILES: COc1ccc(Cn2ccc3cc(NC4CNC4)ccc3c2=O)cc1 ; Cl]

6-(Azetidin-3-ylamino)-2H-isoquinolin-1-one hydrochloride was prepared by Buchwald Reaction starting from 6-Bromo-2-(4-methoxy-benzyl)-2H-isoquinolin-1-one (13) and 3-Amino-azetidine-1-carboxylic acid tert-butyl ester. BOC deprotection was performed as described for Isoquinolin-6-yl-piperidin-4-yl-amine (48).

190: 2-(4-Methoxy-benzyl)-6-((R)-piperidin-3-ylamino)-2H-isoquinolin-1-one hydrochloride

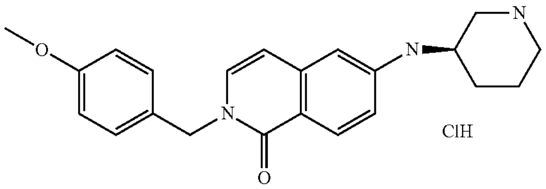 [SMILES: COc1ccc(Cn2ccc3cc(N[C@@H]4CCCNC4)ccc3c2=O)cc1 ; Cl]

2-(4-Methoxy-benzyl)-6-((R)-piperidin-3-ylamino)-2H-isoquinolin-1-one hydrochloride was prepared in analogy to 189.

191: 2-(4-Methoxy-benzyl)-6-((S)-pyrrolidin-3-ylamino)-2H-isoquinolin-1-one hydrochloride

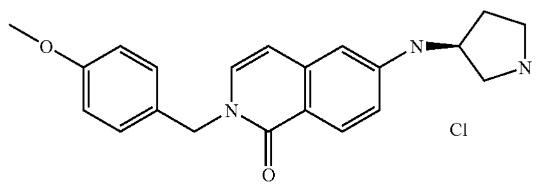 [SMILES: COc1ccc(Cn2ccc3cc(N[C@H]4CCNC4)ccc3c2=O)cc1 ; Cl]

2-(4-Methoxy-benzyl)-6-((S)-Pyrrolidin-3-ylamino)-2H-isoquinolin-1-one hydrochloride was prepared in analogy to 189.

Reductive aminations were carried out in analogy to (1-Ethyl-piperidin-4-yl)-isoquinolin-6-yl-amine (68). PMB deprotection was carried out as described in general procedure D with a reaction time of 1.5 h to give the products listed in table below as hydrochloride salts.

TABLE 6

| Example | Amine | Aldehyde |
|---|---|---|
| 192 | 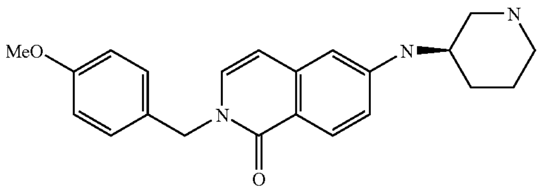 [SMILES: COc1ccc(Cn2ccc3cc(N[C@@H]4CCCNC4)ccc3c2=O)cc1] | 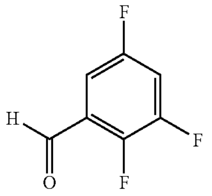 [SMILES: O=Cc1cc(F)cc(F)c1F] |
| 193 | 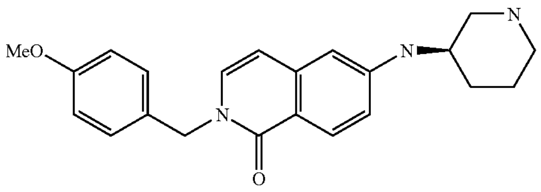 [SMILES: COc1ccc(Cn2ccc3cc(N[C@@H]4CCCNC4)ccc3c2=O)cc1] | 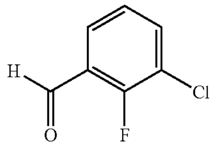 |
| 194 | 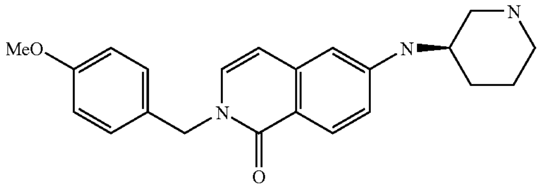 [SMILES: COc1ccc(Cn2ccc3cc(N[C@@H]4CCCNC4)ccc3c2=O)cc1] | 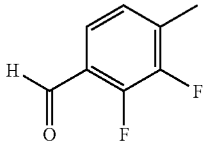 |
| 195 | 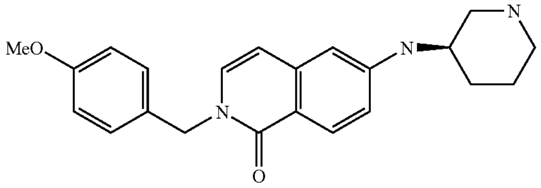 [SMILES: COc1ccc(Cn2ccc3cc(N[C@@H]4CCCNC4)ccc3c2=O)cc1] | 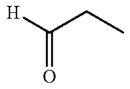 |

TABLE 6-continued
| | | |
|---|---|---|
| 196 | 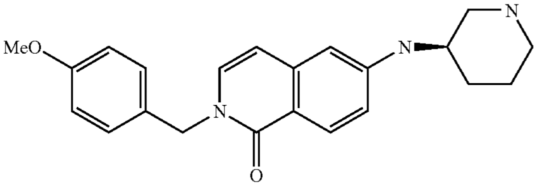 [SMILES: COc1ccc(Cn2ccc3cc(N[C@@H]4CCCNC4)ccc3c2=O)cc1] | 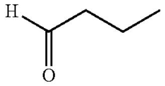 |
| 197 | 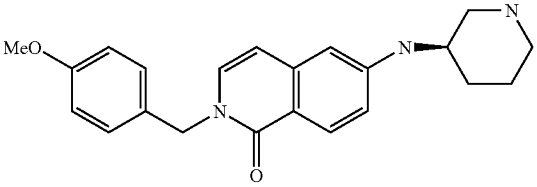 [SMILES: COc1ccc(Cn2ccc3cc(N[C@@H]4CCCNC4)ccc3c2=O)cc1] | 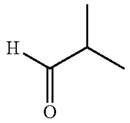 |
| 198 | 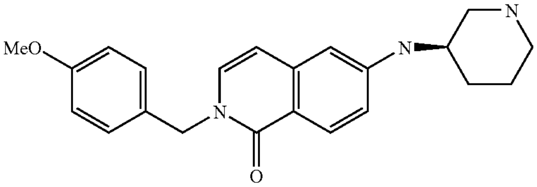 [SMILES: COc1ccc(Cn2ccc3cc(N[C@@H]4CCCNC4)ccc3c2=O)cc1] | 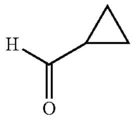 |
| 199 | 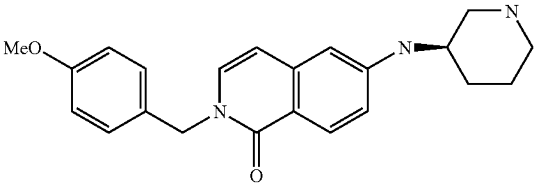 [SMILES: COc1ccc(Cn2ccc3cc(N[C@@H]4CCCNC4)ccc3c2=O)cc1] | 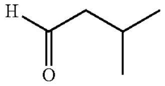 |
| 200 | 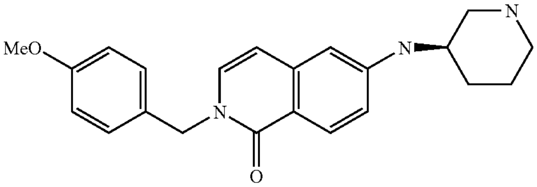 [SMILES: COc1ccc(Cn2ccc3cc(N[C@@H]4CCCNC4)ccc3c2=O)cc1] | 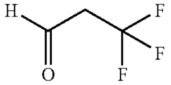 |
| 201 | 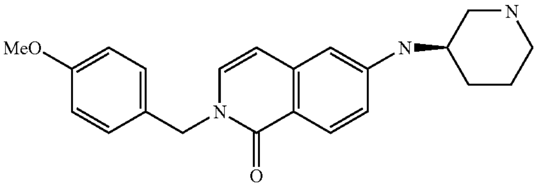 [SMILES: COc1ccc(Cn2ccc3cc(N[C@@H]4CCCNC4)ccc3c2=O)cc1] | 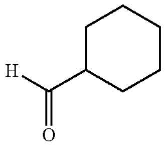 |
| 202 | 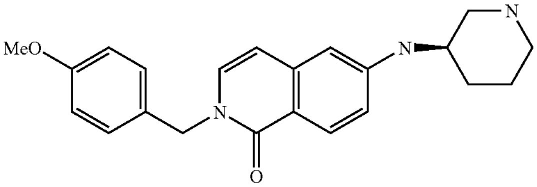 [SMILES: COc1ccc(Cn2ccc3cc(N[C@@H]4CCCNC4)ccc3c2=O)cc1] | 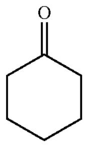 |
| 203 | 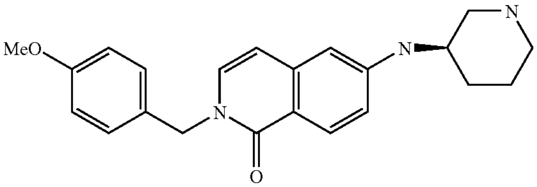 [SMILES: COc1ccc(Cn2ccc3cc(N[C@@H]4CCCNC4)ccc3c2=O)cc1] | 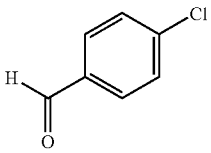 |

TABLE 6-continued
| | | |
|---|---|---|
| 204 | 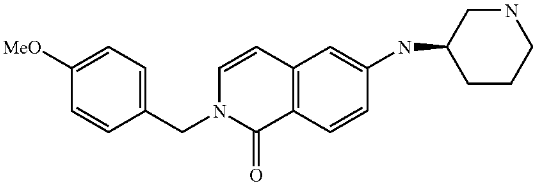 [SMILES: COc1ccc(Cn2ccc3cc(N[C@@H]4CCCNC4)ccc3c2=O)cc1] | 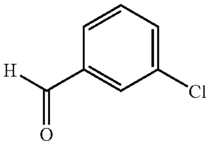 |
| 205 | 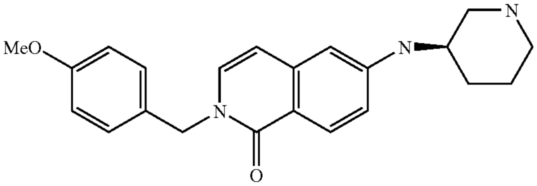 [SMILES: COc1ccc(Cn2ccc3cc(N[C@@H]4CCCNC4)ccc3c2=O)cc1] | 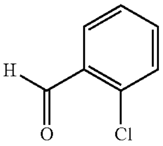 |
| 206 | 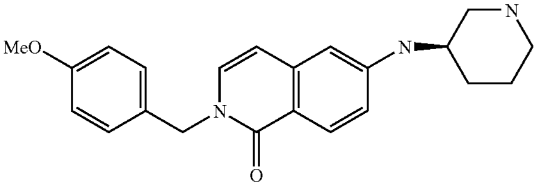 [SMILES: COc1ccc(Cn2ccc3cc(N[C@@H]4CCCNC4)ccc3c2=O)cc1] | 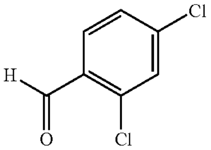 |
| 207 | 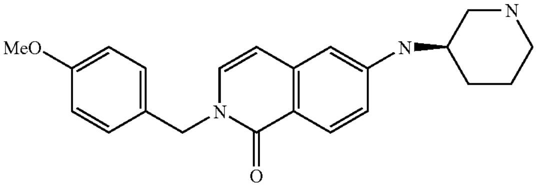 [SMILES: COc1ccc(Cn2ccc3cc(N[C@@H]4CCCNC4)ccc3c2=O)cc1] | 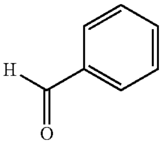 |
| 208 | 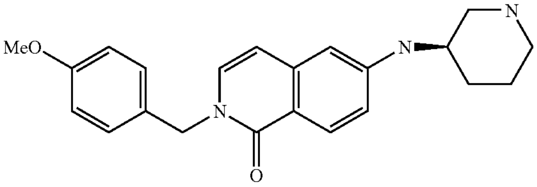 [SMILES: COc1ccc(Cn2ccc3cc(N[C@@H]4CCCNC4)ccc3c2=O)cc1] | 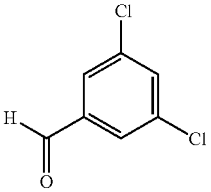 |
| 209 | 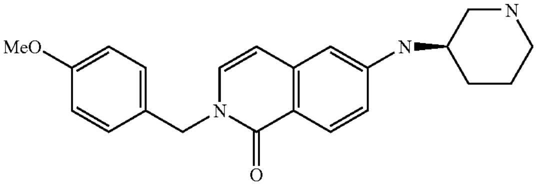 [SMILES: COc1ccc(Cn2ccc3cc(N[C@@H]4CCCNC4)ccc3c2=O)cc1] | 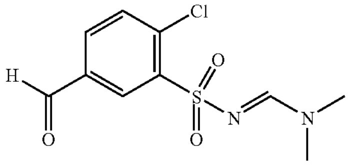 [SMILES: CN(C)/C=N/S(=O)(=O)c1cc(C=O)ccc1Cl] |
| 210 | 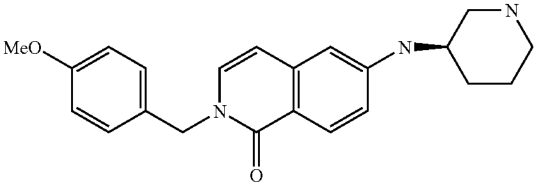 [SMILES: COc1ccc(Cn2ccc3cc(N[C@@H]4CCCNC4)ccc3c2=O)cc1] | 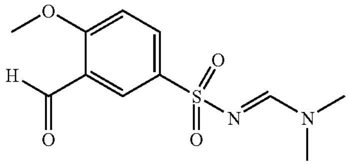 [SMILES: COc1ccc(S(=O)(=O)/N=C/N(C)C)cc1C=O] |
| 211 | 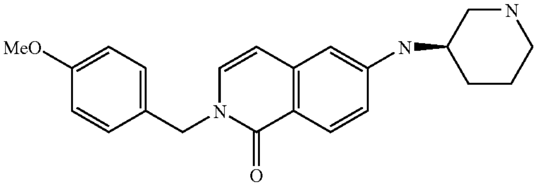 [SMILES: COc1ccc(Cn2ccc3cc(N[C@@H]4CCCNC4)ccc3c2=O)cc1] | 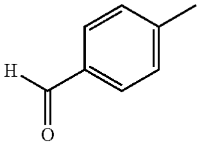 |

TABLE 6-continued
| | | |
|---|---|---|
| 212 | 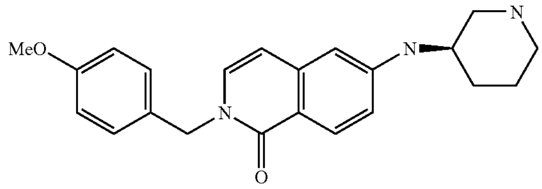 [SMILES: COc1ccc(Cn2ccc3cc(N[C@@H]4CCCNC4)ccc3c2=O)cc1] | 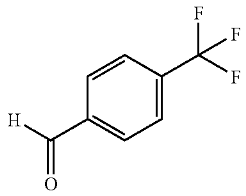 [SMILES: O=Cc1ccc(C(F)(F)F)cc1] |
| 213 | 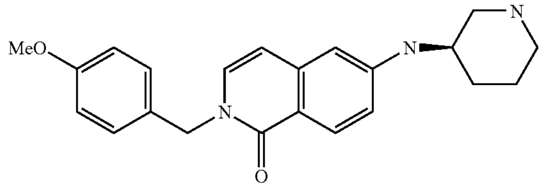 [SMILES: COc1ccc(Cn2ccc3cc(N[C@@H]4CCCNC4)ccc3c2=O)cc1] | 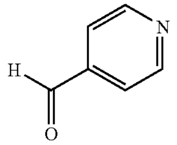 |
| 214 | 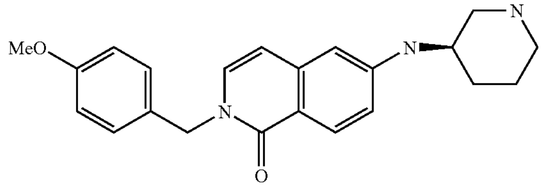 [SMILES: COc1ccc(Cn2ccc3cc(N[C@@H]4CCCNC4)ccc3c2=O)cc1] | 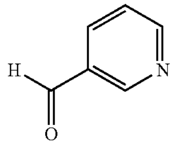 |
| 215 | 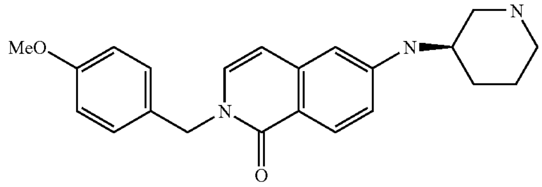 [SMILES: COc1ccc(Cn2ccc3cc(N[C@@H]4CCCNC4)ccc3c2=O)cc1] | 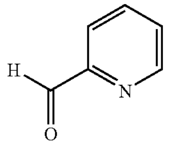 |
| 216 | 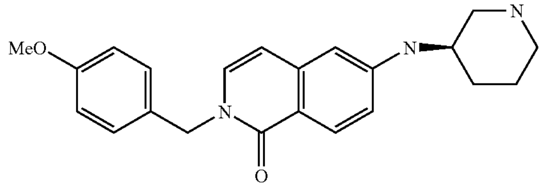 [SMILES: COc1ccc(Cn2ccc3cc(N[C@@H]4CCCNC4)ccc3c2=O)cc1] | 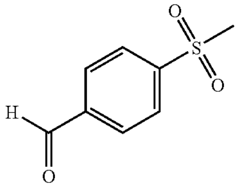 |
| 217 | 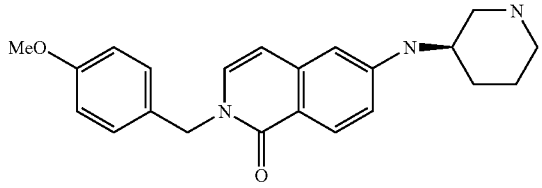 [SMILES: COc1ccc(Cn2ccc3cc(N[C@@H]4CCCNC4)ccc3c2=O)cc1] | 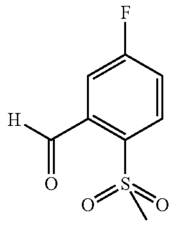 |
| 218 | 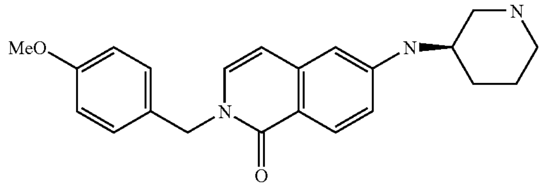 [SMILES: COc1ccc(Cn2ccc3cc(N[C@@H]4CCCNC4)ccc3c2=O)cc1] | 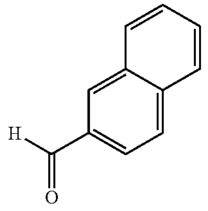 [SMILES: O=Cc1ccc2ccccc2c1] |

TABLE 6-continued
| | | |
|---|---|---|
| 219 | 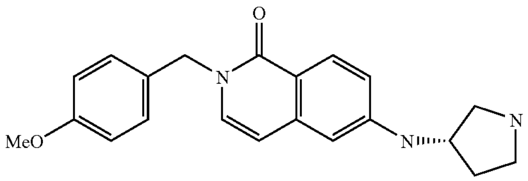 [SMILES: COc1ccc(Cn2ccc3cc(N[C@H]4CCNC4)ccc3c2=O)cc1] | 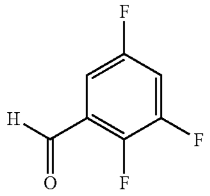 [SMILES: O=Cc1cc(F)cc(F)c1F] |
| 220 | 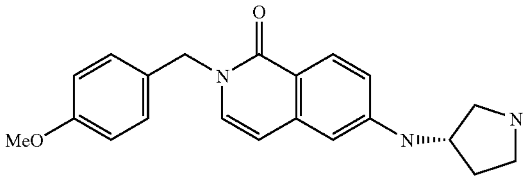 [SMILES: COc1ccc(Cn2ccc3cc(N[C@H]4CCNC4)ccc3c2=O)cc1] | 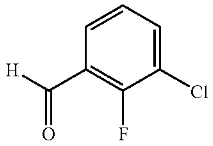 |
| 221 | 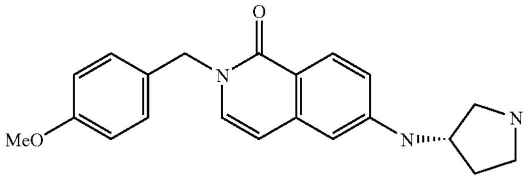 [SMILES: COc1ccc(Cn2ccc3cc(N[C@H]4CCNC4)ccc3c2=O)cc1] | 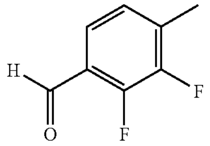 |
| 222 | 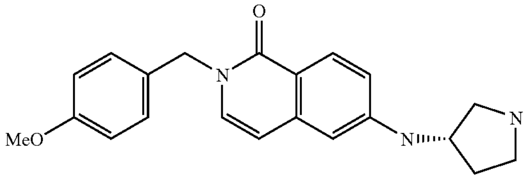 [SMILES: COc1ccc(Cn2ccc3cc(N[C@H]4CCNC4)ccc3c2=O)cc1] | 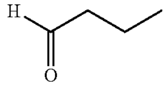 |
| 223 | 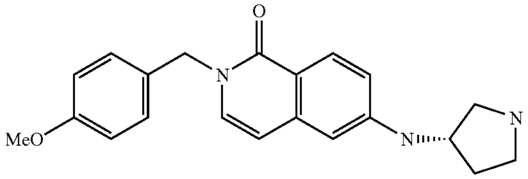 [SMILES: COc1ccc(Cn2ccc3cc(N[C@H]4CCNC4)ccc3c2=O)cc1] | 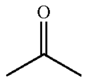 |
| 224 | 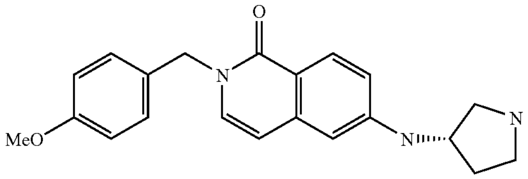 [SMILES: COc1ccc(Cn2ccc3cc(N[C@H]4CCNC4)ccc3c2=O)cc1] | 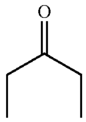 |
| 225 | 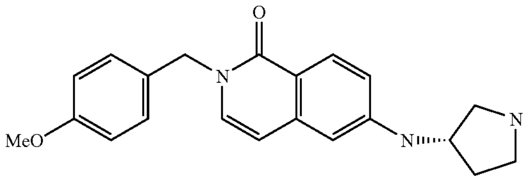 [SMILES: COc1ccc(Cn2ccc3cc(N[C@H]4CCNC4)ccc3c2=O)cc1] | 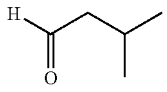 |
| 226 | 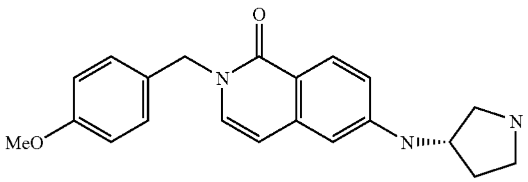 [SMILES: COc1ccc(Cn2ccc3cc(N[C@H]4CCNC4)ccc3c2=O)cc1] | 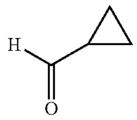 |

TABLE 6-continued
| | | |
|---|---|---|
| 227 | 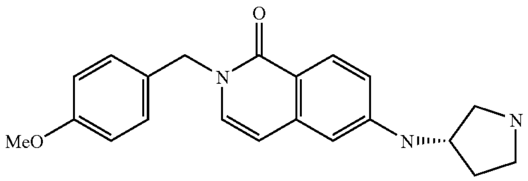 [SMILES: COc1ccc(Cn2ccc3cc(N[C@H]4CCNC4)ccc3c2=O)cc1] | 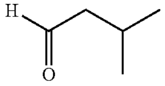 |
| 228 | 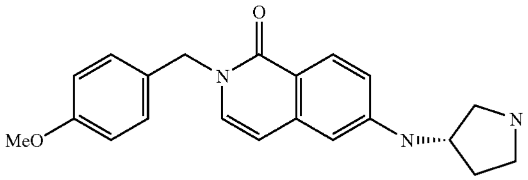 [SMILES: COc1ccc(Cn2ccc3cc(N[C@H]4CCNC4)ccc3c2=O)cc1] | 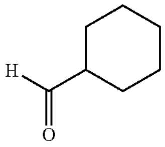 |
| 229 | 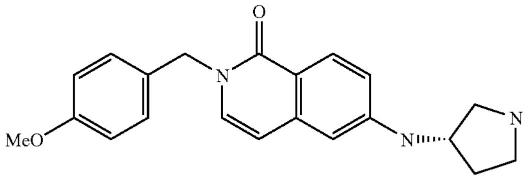 [SMILES: COc1ccc(Cn2ccc3cc(N[C@H]4CCNC4)ccc3c2=O)cc1] | 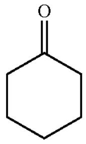 |
| 230 | 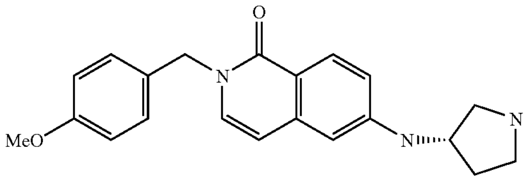 [SMILES: COc1ccc(Cn2ccc3cc(N[C@H]4CCNC4)ccc3c2=O)cc1] | 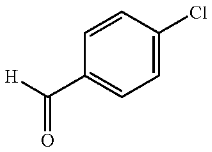 |
| 231 | 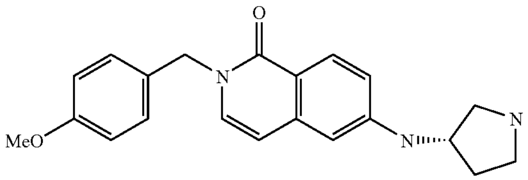 [SMILES: COc1ccc(Cn2ccc3cc(N[C@H]4CCNC4)ccc3c2=O)cc1] | 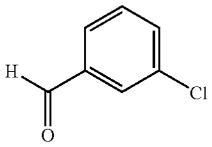 |
| 232 | 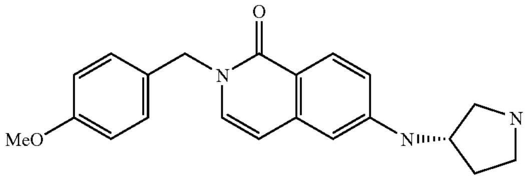 [SMILES: COc1ccc(Cn2ccc3cc(N[C@H]4CCNC4)ccc3c2=O)cc1] | 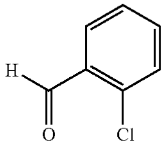 |
| 233 | 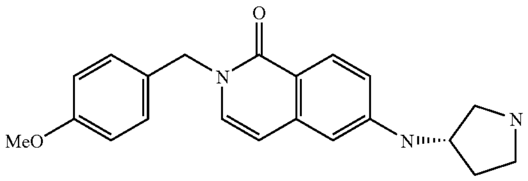 [SMILES: COc1ccc(Cn2ccc3cc(N[C@H]4CCNC4)ccc3c2=O)cc1] | 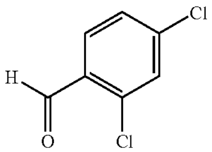 |
| 234 | 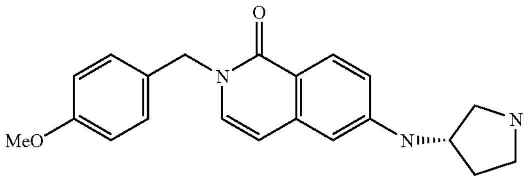 [SMILES: COc1ccc(Cn2ccc3cc(N[C@H]4CCNC4)ccc3c2=O)cc1] | 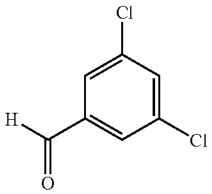 |

TABLE 6-continued
| | | |
|---|---|---|
| 235 | 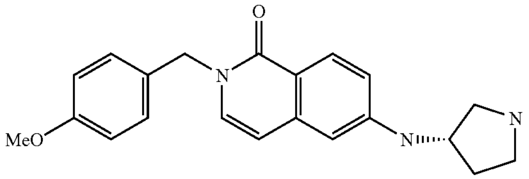 [SMILES: COc1ccc(Cn2ccc3cc(N[C@H]4CCNC4)ccc3c2=O)cc1] | 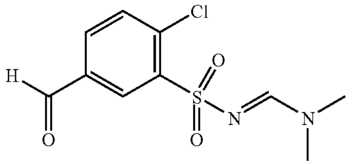 [SMILES: CN(C)/C=N/S(=O)(=O)c1cc(C=O)ccc1Cl] |
| 236 | 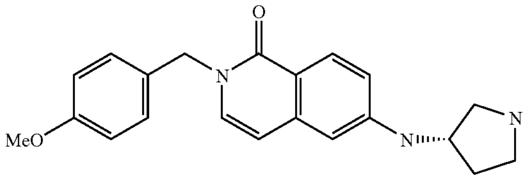 [SMILES: COc1ccc(Cn2ccc3cc(N[C@H]4CCNC4)ccc3c2=O)cc1] | 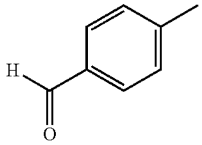 |
| 237 | 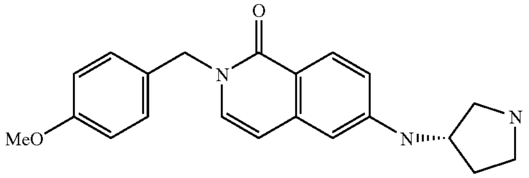 [SMILES: COc1ccc(Cn2ccc3cc(N[C@H]4CCNC4)ccc3c2=O)cc1] | 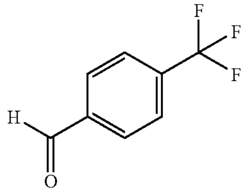 [SMILES: O=Cc1ccc(C(F)(F)F)cc1] |
| 238 | 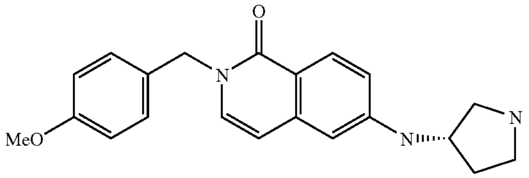 [SMILES: COc1ccc(Cn2ccc3cc(N[C@H]4CCNC4)ccc3c2=O)cc1] | 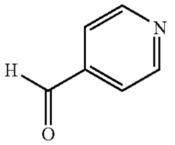 |
| 239 | 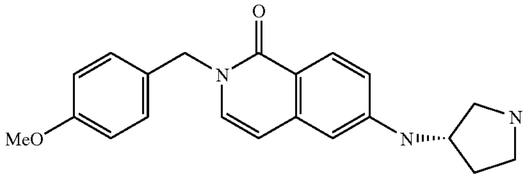 [SMILES: COc1ccc(Cn2ccc3cc(N[C@H]4CCNC4)ccc3c2=O)cc1] | 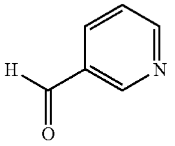 |
| 240 | 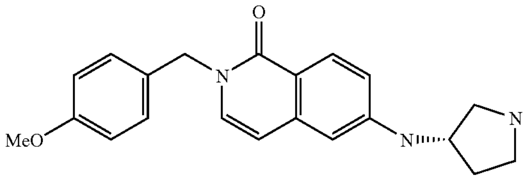 [SMILES: COc1ccc(Cn2ccc3cc(N[C@H]4CCNC4)ccc3c2=O)cc1] | 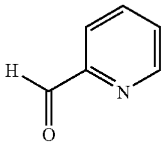 |
| 241 | 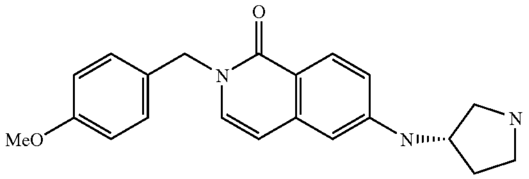 [SMILES: COc1ccc(Cn2ccc3cc(N[C@H]4CCNC4)ccc3c2=O)cc1] | 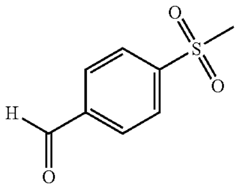 |
| 242 | 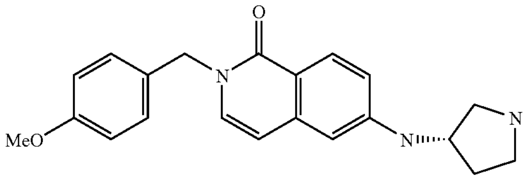 [SMILES: COc1ccc(Cn2ccc3cc(N[C@H]4CCNC4)ccc3c2=O)cc1] | 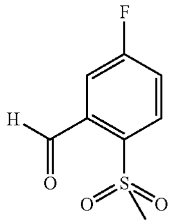 |

TABLE 6-continued
| | | |
|---|---|---|
| 243 | 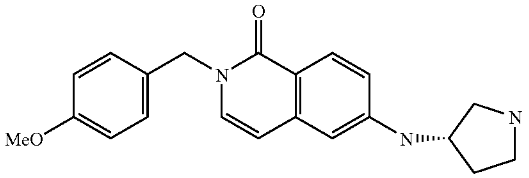 [SMILES: COc1ccc(Cn2ccc3cc(N[C@H]4CCNC4)ccc3c2=O)cc1] | 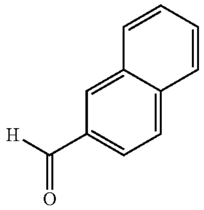 [SMILES: O=Cc1ccc2ccccc2c1] |
| 244 | 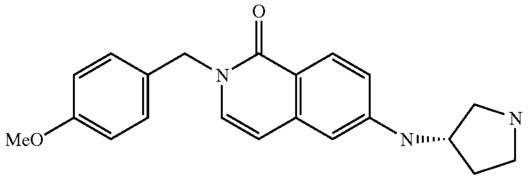 [SMILES: COc1ccc(Cn2ccc3cc(N[C@H]4CCNC4)ccc3c2=O)cc1] | 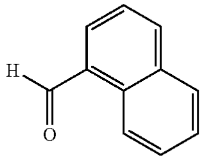 [SMILES: O=Cc1cccc2ccccc12] |
| 245 | 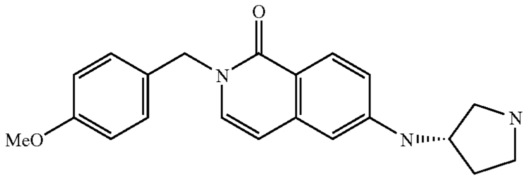 [SMILES: COc1ccc(Cn2ccc3cc(N[C@H]4CCNC4)ccc3c2=O)cc1] | 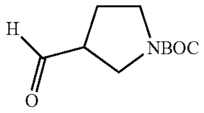 |
| 246 | 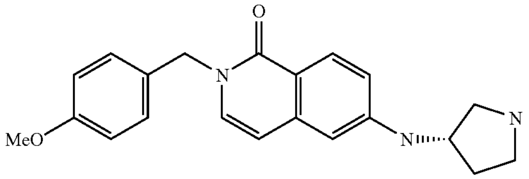 [SMILES: COc1ccc(Cn2ccc3cc(N[C@H]4CCNC4)ccc3c2=O)cc1] | 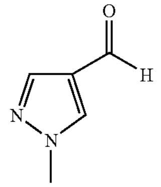 |
| 247 | 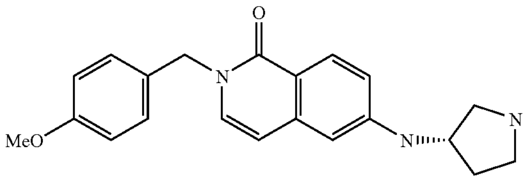 [SMILES: COc1ccc(Cn2ccc3cc(N[C@H]4CCNC4)ccc3c2=O)cc1] | 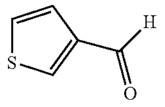 |
| 248 | 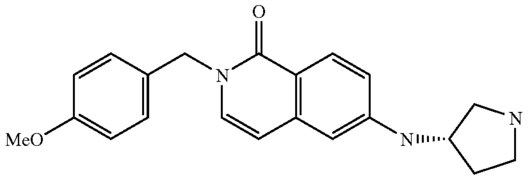 [SMILES: COc1ccc(Cn2ccc3cc(N[C@H]4CCNC4)ccc3c2=O)cc1] | 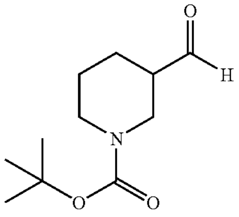 |
| 249 | 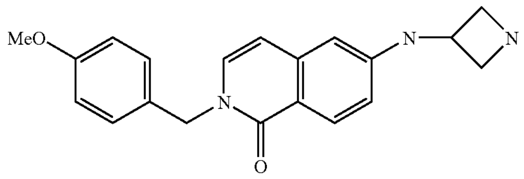 [SMILES: COc1ccc(Cn2ccc3cc(NC4CNC4)ccc3c2=O)cc1] | 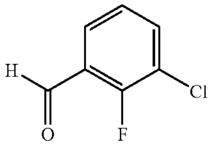 |
| 250 | 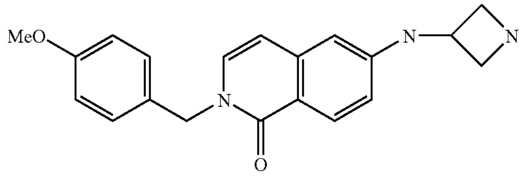 [SMILES: COc1ccc(Cn2ccc3cc(NC4CNC4)ccc3c2=O)cc1] | 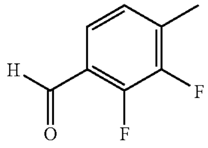 |

TABLE 6-continued
| | | |
|---|---|---|
| 251 | 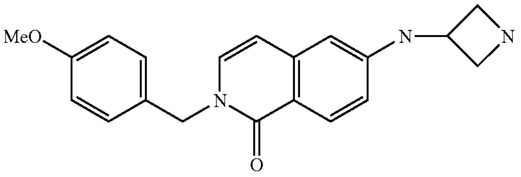 | 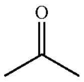 |
| 252 | 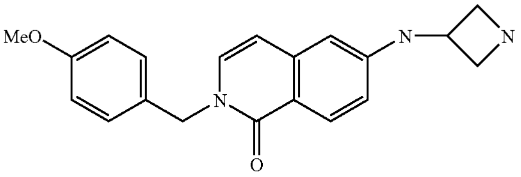 [SMILES: COc1ccc(Cn2ccc3cc(NC4CNC4)ccc3c2=O)cc1] | 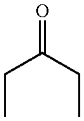 |
| 253 | 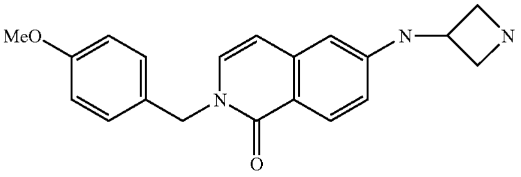 [SMILES: COc1ccc(Cn2ccc3cc(NC4CNC4)ccc3c2=O)cc1] | 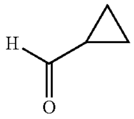 |
| 254 | 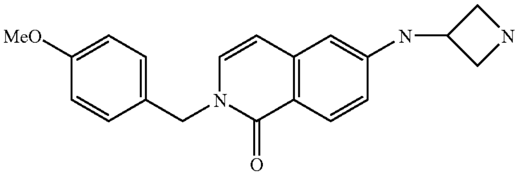 [SMILES: COc1ccc(Cn2ccc3cc(NC4CNC4)ccc3c2=O)cc1] | 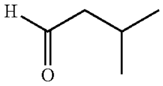 |
| 255 | 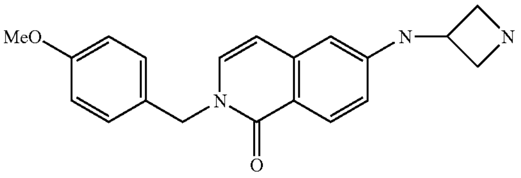 | 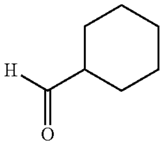 |
| 256 | 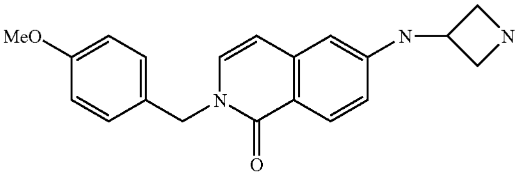 | 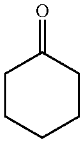 |
| 257 | 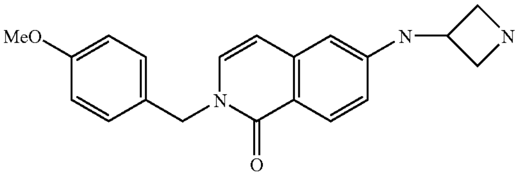 [SMILES: COc1ccc(Cn2ccc3cc(NC4CNC4)ccc3c2=O)cc1] | 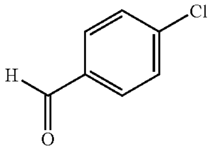 |
| 258 | 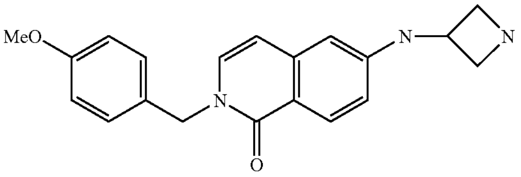 [SMILES: COc1ccc(Cn2ccc3cc(NC4CNC4)ccc3c2=O)cc1] | 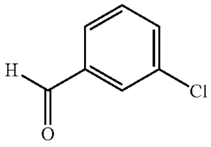 |

TABLE 6-continued
| | | |
|---|---|---|
| 259 | 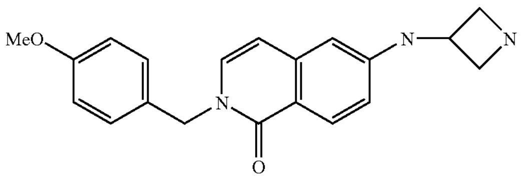 [SMILES: COc1ccc(Cn2ccc3cc(NC4CNC4)ccc3c2=O)cc1] | 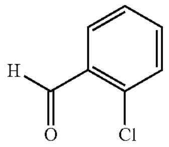 |
| 260 | 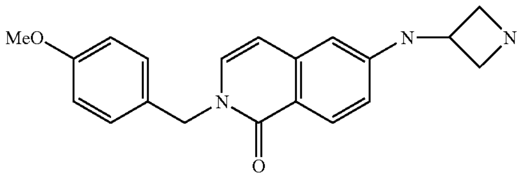 [SMILES: COc1ccc(Cn2ccc3cc(NC4CNC4)ccc3c2=O)cc1] | 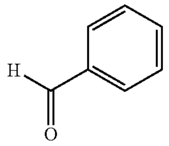 |
| 261 | 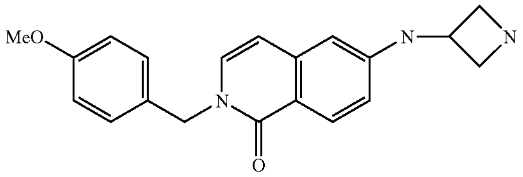 | 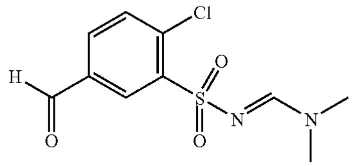 [SMILES: CN(C)/C=N/S(=O)(=O)c1cc(C=O)ccc1Cl] |
| 262 | 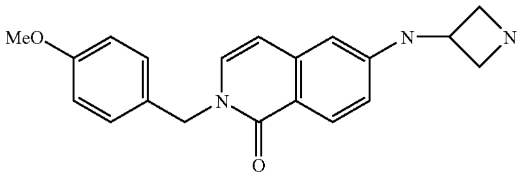 [SMILES: COc1ccc(Cn2ccc3cc(NC4CNC4)ccc3c2=O)cc1] | 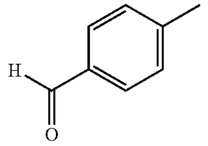 |
| Example | Product | $R_t$ [min] | Mass [M + H$^+$] | LCMS Method | Chemical name |
|---|---|---|---|---|---|
| 192 | 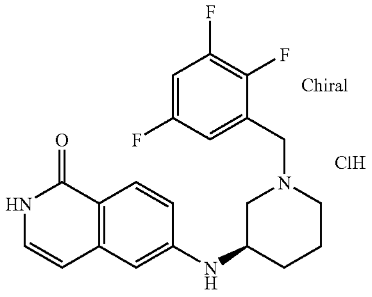 [SMILES: O=c1[nH]ccc2cc(N[C@@H]3CCCN(Cc4cc(F)cc(F)c4F)C3)ccc12 ; Cl] | 1.07 | 388.1 | B | 6-[(R)-1-(2,3,5-Trifluoro-benzyl)-piperidin-3-ylamino]-2H-isoquinolin-1-one |
| 193 | 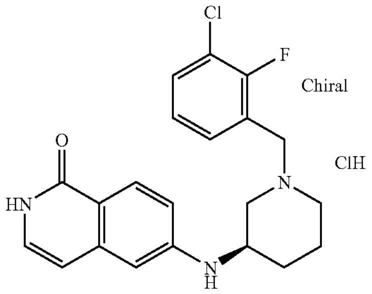 [SMILES: O=c1[nH]ccc2cc(N[C@@H]3CCCN(Cc4cccc(Cl)c4F)C3)ccc12 ; Cl] | 1.04 | 386.1 | B | 6-[(R)-1-(3-Chloro-2-fluoro-benzyl)-piperidin-3-ylamino]-2H-isoquinolin-1-one |

TABLE 6-continued
| | | | | | |
|---|---|---|---|---|---|
| 194 | 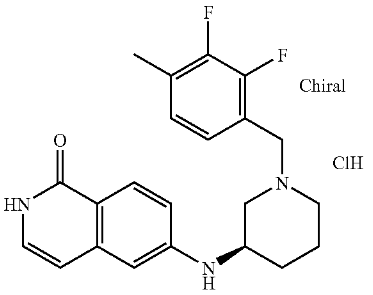 [SMILES: Cc1ccc(CN2CCC[C@@H](Nc3ccc4c(=O)[nH]ccc4c3)C2)c(F)c1F ; Cl] | 1.12 | 384.1 | B | 6-[(R)-1-(2,3-Difluoro-4-methyl-benzyl)-piperidin-3-ylamino]-2H-isoquinolin-1-one |
| 195 | 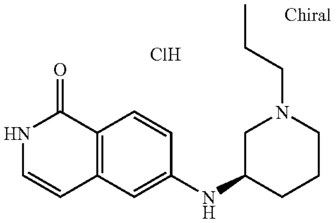 [SMILES: CCCN1CCC[C@@H](Nc2ccc3c(=O)[nH]ccc3c2)C1 ; Cl] | 0.79 | 286.2 | B | 6-((R)-1-Propyl-piperidin-3-ylamino)-2H-isoquinolin-1-one |
| 196 | 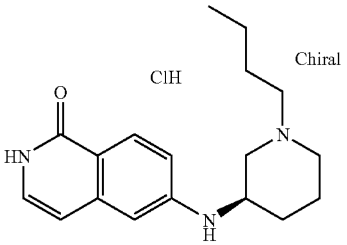 [SMILES: CCCCN1CCC[C@@H](Nc2ccc3c(=O)[nH]ccc3c2)C1 ; Cl] | 0.83 | 300.2 | B | 6-((R)-1-Butyl-piperidin-3-ylamino)-2H-isoquinolin-1-one |
| 197 | 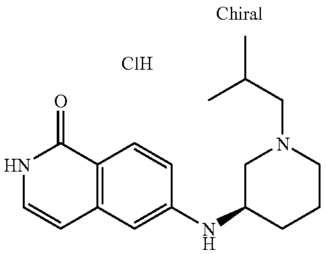 [SMILES: CC(C)CN1CCC[C@@H](Nc2ccc3c(=O)[nH]ccc3c2)C1 ; Cl] | 0.80 | 300.2 | B | 6-((R)-1-Isobutyl-piperidin-3-ylamino)-2H-isoquinolin-1-one |
| 198 | 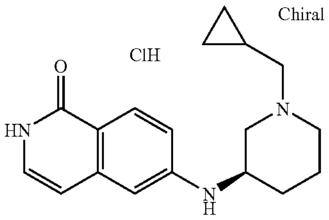 [SMILES: O=c1[nH]ccc2cc(N[C@@H]3CCCN(CC4CC4)C3)ccc12 ; Cl] | 0.76 | 298.2 | B | 6-((R)-1-Cyclopropylmethyl-piperidin-3-ylamino)-2H-isoquinolin-1-one |
| 199 | 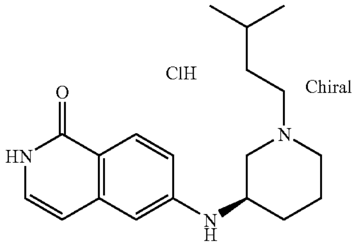 [SMILES: CC(C)CCN1CCC[C@@H](Nc2ccc3c(=O)[nH]ccc3c2)C1 ; Cl] | 0.95 | 314.2 | B | 6-[(R)-1-(3-Methyl-butyl)-piperidin-3-ylamino]-2H-isoquinolin-1-one |

TABLE 6-continued
| | | | | | |
|---|---|---|---|---|---|
| 200 | 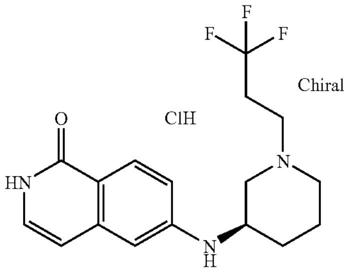 [SMILES: O=c1[nH]ccc2cc(N[C@@H]3CCCN(CCC(F)(F)F)C3)ccc12 ; Cl] | 0.81 | 340.1 | B | 6-[(R)-1-(3,3,3-Trifluoro-propyl)-piperidin-3-ylamino]-2H-isoquinolin-1-one |
| 201 | 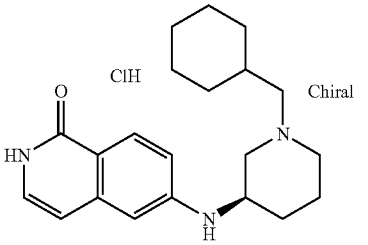 [SMILES: O=c1[nH]ccc2cc(N[C@@H]3CCCN(CC4CCCCC4)C3)ccc12 ; Cl] | 1.02 | 340.2 | B | 6-((R)-1-Cyclohexylmethyl-piperidin-3-ylamino)-2H-isoquinolin-1-one |
| 202 | 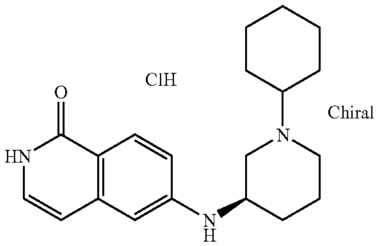 [SMILES: O=c1[nH]ccc2cc(N[C@@H]3CCCN(C4CCCCC4)C3)ccc12 ; Cl] | 0.98 | 326.2 | B | 6-((R)-1-Cyclohexyl-piperidin-3-ylamino)-2H-isoquinolin-1-one |
| 203 | 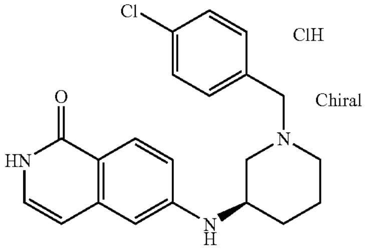 [SMILES: O=c1[nH]ccc2cc(N[C@@H]3CCCN(Cc4ccc(Cl)cc4)C3)ccc12 ; Cl] | 1.05 | 368.1 | B | 6-[(R)-1-(4-Chloro-benzyl)-piperidin-3-ylamino]-2H-isoquinolin-1-one |
| 204 | 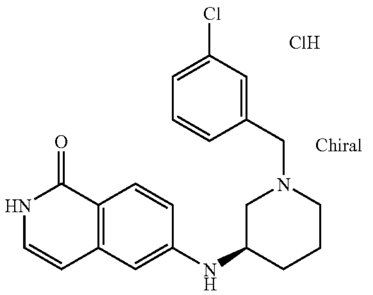 [SMILES: O=c1[nH]ccc2cc(N[C@@H]3CCCN(Cc4cccc(Cl)c4)C3)ccc12 ; Cl] | 1.05 | 368.1 | B | 6-[(R)-1-(3-Chloro-benzyl)-piperidin-3-ylamino]-2H-isoquinolin-1-one |
| 205 | 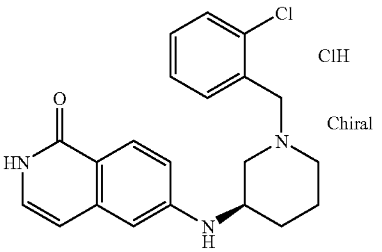 [SMILES: O=c1[nH]ccc2cc(N[C@@H]3CCCN(Cc4ccccc4Cl)C3)ccc12 ; Cl] | 0.98 | 368.1 | B | 6-[(R)-1-(2-Chloro-benzyl)-piperidin-3-ylamino]-2H-isoquinolin-1-one |

TABLE 6-continued

| | | | | | |
|---|---|---|---|---|---|
| 206 | 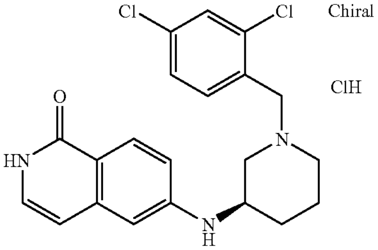 [SMILES: O=c1[nH]ccc2cc(N[C@@H]3CCCN(Cc4ccc(Cl)cc4Cl)C3)ccc12 ; Cl] Chiral | 1.17 | 402.1/ 404.1 | B | 6-[(R)-1-(2,4-Dichloro-benzyl)-piperidin-3-ylamino]-2H-isoquinolin-1-one |
| 207 | 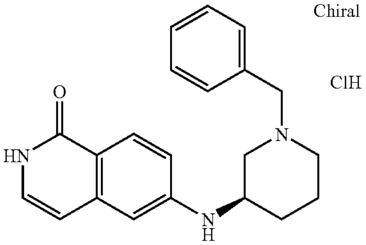 [SMILES: O=c1[nH]ccc2cc(N[C@@H]3CCCN(Cc4ccccc4)C3)ccc12 ; Cl] Chiral | 0.92 | 334.2 | B | 6-((R)-1-Benzyl-piperidin-3-ylamino)-2H-isoquinolin-1-one |
| 208 | 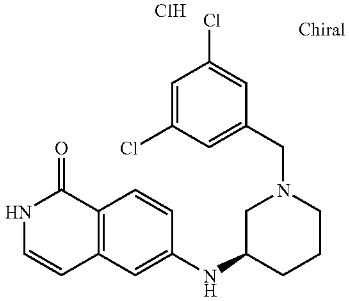 [SMILES: Cl ; O=c1[nH]ccc2cc(N[C@@H]3CCCN(Cc4cc(Cl)cc(Cl)c4)C3)ccc12] Chiral | 1.18 | 402.1/ 404.1 | B | 6-[(R)-1-(3,5-Dichloro-benzyl)-piperidin-3-ylamino]-2H-isoquinolin-1-one |
| 209 | Chiral 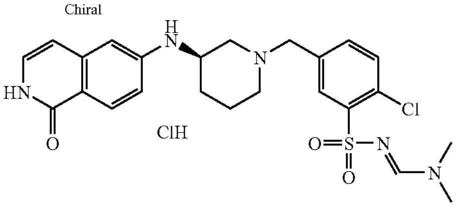 [SMILES: CN(C)/C=N/S(=O)(=O)c1cc(CN2CCC[C@@H](Nc3ccc4c(=O)[nH]ccc4c3)C2)ccc1Cl ; Cl] | 0.95 | 502.1 | B | 2-Chloro-N-[1-dimethylamino-meth-(E)-ylidene]-5-[(R)-3-(1-oxo-1,2-dihydro-isoquinolin-6-ylamino)-piperidin-1-ylmethyl]-benzenesulfonamide |
| 210 | 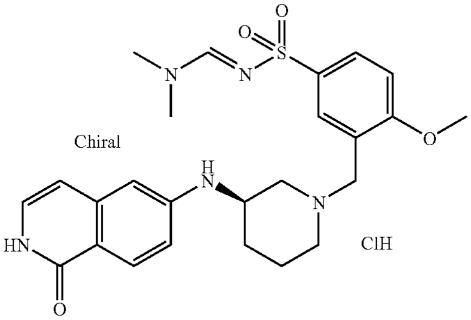 [SMILES: COc1ccc(S(=O)(=O)/N=C/N(C)C)cc1CN1CCC[C@@H](Nc2ccc3c(=O)[nH]ccc3c2)C1 ; Cl] Chiral | 0.92 | 498.2 | B | N-[1-Dimethylamino-meth-(E)-ylidene]-4-methoxy-3-[(R)-3-(1-oxo-1,2-dihydro-isoquinolin-6-ylamino)-piperidin-1-ylmethyl]-benzenesulfonamide |
| 211 | 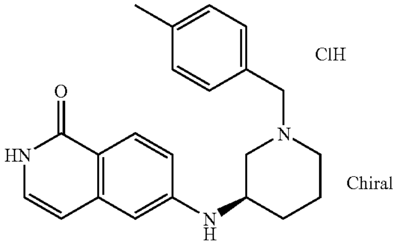 [SMILES: Cc1ccc(CN2CCC[C@@H](Nc3ccc4c(=O)[nH]ccc4c3)C2)cc1 ; Cl] Chiral | 1.06 | 348.2 | B | 6-[(R)-1-(4-Methyl-benzyl)-piperidin-3-ylamino]-2H-isoquinolin-1-one |

TABLE 6-continued
| | | | | | |
|---|---|---|---|---|---|
| 212 | 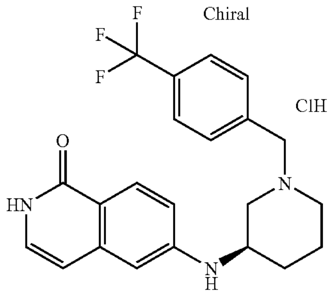 [SMILES: O=c1[nH]ccc2cc(N[C@@H]3CCCN(Cc4ccc(C(F)(F)F)cc4)C3)ccc12 ; Cl] | 1.13 | 402.1 | B | 6-[(R)-1-(4-Trifluoromethyl-benzyl)-piperidin-3-ylamino]-2H-isoquinolin-1-one |
| 213 | 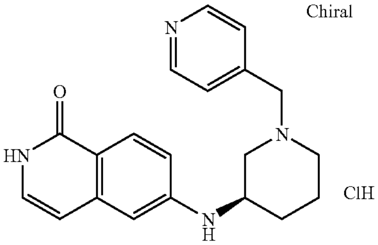 [SMILES: O=c1[nH]ccc2cc(N[C@@H]3CCCN(Cc4ccncc4)C3)ccc12 ; Cl] | 0.77 | 355.2 | B | 6-((R)-1-Pyridin-4-ylmethyl-piperidin-3-ylamino)-2H-isoquinolin-1-one |
| 214 | 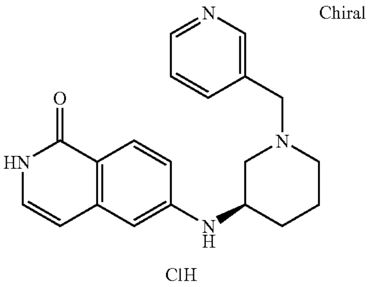 [SMILES: O=c1[nH]ccc2cc(N[C@@H]3CCCN(Cc4cccnc4)C3)ccc12 ; Cl] | 0.69 | 355.2 | B | 6-((R)-1-Pyridin-3-ylmethyl-piperidin-3-ylamino)-2H-isoquinolin-1-one |
| 215 | 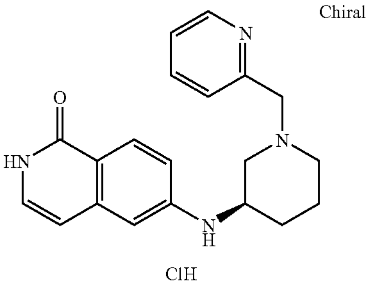 [SMILES: O=c1[nH]ccc2cc(N[C@@H]3CCCN(Cc4ccccn4)C3)ccc12 ; Cl] | 0.78 | 355.2 | B | 6-((R)-1-Pyridin-2-ylmethyl-piperidin-3-ylamino)-2H-isoquinolin-1-one |
| 216 | 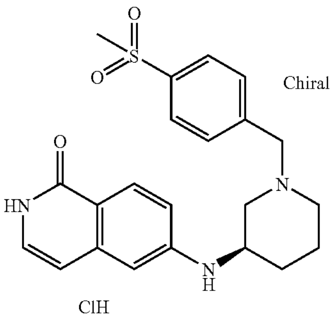 [SMILES: CS(=O)(=O)c1ccc(CN2CCC[C@@H](Nc3ccc4c(=O)[nH]ccc4c3)C2)cc1 ; Cl] | 0.80 | 412.1 | B | 6-[(R)-1-(4-Methanesulfonyl-benzyl)-piperidin-3-ylamino]-2H-isoquinolin-1-one |

TABLE 6-continued

| | | | | | |
|---|---|---|---|---|---|
| 217 | 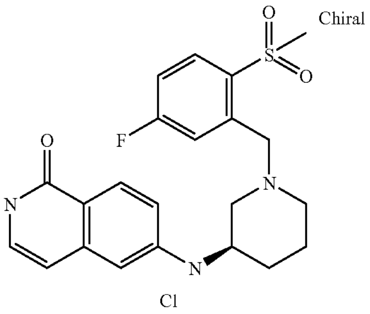 [SMILES: CS(=O)(=O)c1ccc(F)cc1CN1CCC[C@@H](Nc2ccc3c(=O)[nH]ccc3c2)C1 ; Cl] | 0.92 | 430.1 | B | 6-[(R)-1-(5-Fluoro-2-methanesulfonyl-benzyl)-piperidin-3-ylamino]-2H-isoquinolin-1-one |
| 218 | 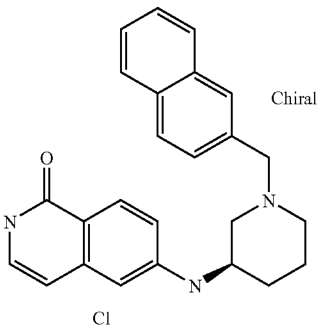 [SMILES: O=c1[nH]ccc2cc(N[C@@H]3CCCN(Cc4ccc5ccccc5c4)C3)ccc12 ; Cl] | 1.12 | 384.2 | B | 6-((R)-1-Naphthalen-2-ylmethyl-piperidin-3-ylamino)-2H-isoquinolin-1-one |
| 219 | 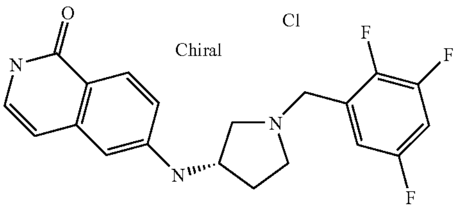 [SMILES: O=c1[nH]ccc2cc(N[C@H]3CCN(Cc4cc(F)cc(F)c4F)C3)ccc12 ; Cl] | 0.97 | 374.1 | B | 6-[(S)-1-(2,3,5-Trifluoro-benzyl)-pyrrolidin-3-ylamino]-2H-isoquinolin-1-one |
| 220 | 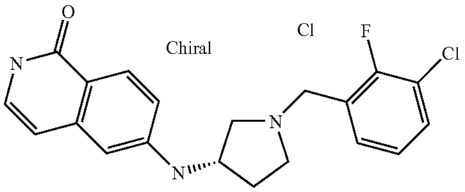 [SMILES: O=c1[nH]ccc2cc(N[C@H]3CCN(Cc4cccc(Cl)c4F)C3)ccc12 ; Cl] | 1.00 | 372.1 | B | 6-[(S)-1-(3-Chloro-2-fluoro-benzyl)-pyrrolidin-3-ylamino]-2H-isoquinolin-1-one |
| 221 | 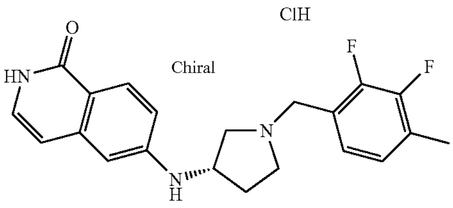 [SMILES: Cl ; Cc1ccc(CN2CC[C@H](Nc3ccc4c(=O)[nH]ccc4c3)C2)c(F)c1F] | 1.06 | 370.1 | B | 6-[(S)-1-(2,3-Difluoro-4-methyl-benzyl)-pyrrolidin-3-ylamino]-2H-isoquinolin-1-one |
| 222 | 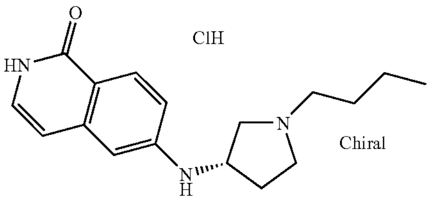 [SMILES: CCCCN1CC[C@H](Nc2ccc3c(=O)[nH]ccc3c2)C1 ; Cl] | 0.87 | 286.2 | D | 6-((S)-1-Butyl-pyrrolidin-3-ylamino)-2H-isoquinolin-1-one |

TABLE 6-continued

| | | | | | |
|---|---|---|---|---|---|
| 223 | 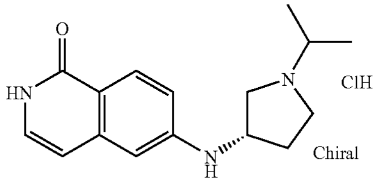 [SMILES: CC(C)N1CC[C@H](Nc2ccc3c(=O)[nH]ccc3c2)C1 ; Cl] | 1.32 | 272.2 | D | 6-((S)-1-Isopropyl-pyrrolidin-3-ylamino)-2H-isoquinolin-1-one |
| 224 | 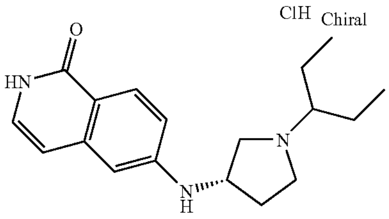 [SMILES: Cl ; CCC(CC)N1CC[C@H](Nc2ccc3c(=O)[nH]ccc3c2)C1] | 0.94 | 300.2 | D | 6-[(S)-1-(1-Ethyl-propyl)-pyrrolidin-3-ylamino]-2H-isoquinolin-1-one |
| 225 | 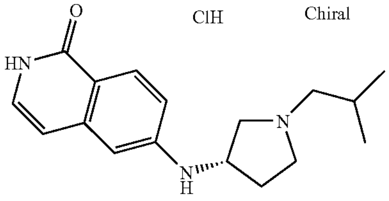 [SMILES: CC(C)CN1CC[C@H](Nc2ccc3c(=O)[nH]ccc3c2)C1 ; Cl] | 0.76 | 286.2 | B | 6-((S)-1-Isobutyl-pyrrolidin-3-ylamino)-2H-isoquinolin-1-one |
| 226 | 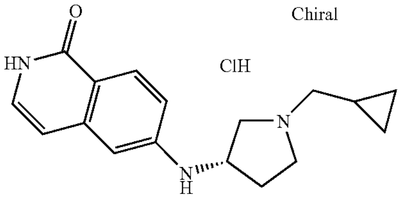 [SMILES: O=c1[nH]ccc2cc(N[C@H]3CCN(CC4CC4)C3)ccc12 ; Cl] | 0.69 | 284.2 | B | 6-((S)-1-Cyclopropylmethyl-pyrrolidin-3-ylamino)-2H-isoquinolin-1-one |
| 227 | 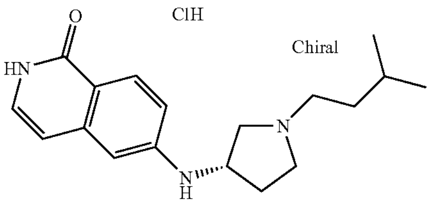 [SMILES: Cl ; CC(C)CCN1CC[C@H](Nc2ccc3c(=O)[nH]ccc3c2)C1] | 0.89 | 300.2 | B | 6-[(S)-1-(3-Methyl-butyl)-pyrrolidin-3-ylamino]-2H-isoquinolin-1-one |
| 228 | 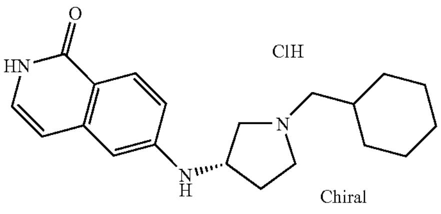 [SMILES: O=c1[nH]ccc2cc(N[C@H]3CCN(CC4CCCCC4)C3)ccc12 ; Cl] | 1.04 | 326.2 | B | 6-((S)-1-Cyclohexylmethyl-pyrrolidin-2-ylamino)-2H-isoquinolin-1-one |
| 229 | 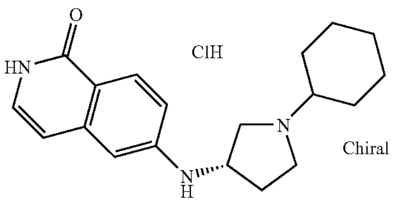 [SMILES: O=c1[nH]ccc2cc(N[C@H]3CCN(C4CCCCC4)C3)ccc12 ; Cl] | 0.85 | 312.2 | B | 6-((S)-1-Cyclohexyl-pyrrolidin-3-ylamino)-2H-isoquinolin-1-one |

TABLE 6-continued

| | | | | | |
|---|---|---|---|---|---|
| 230 | 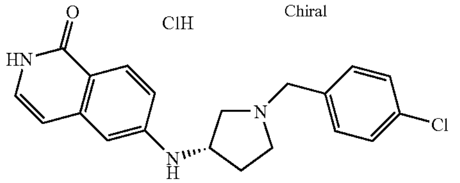 [SMILES: O=c1[nH]ccc2cc(N[C@H]3CCN(Cc4ccc(Cl)cc4)C3)ccc12 ; Cl] | 1.05 | 354.1/ 356.1 | B | 6-[(S)-1-(4-Chloro-benzyl)-pyrrolidin-3-ylamino]-2H-isoquinolin-1-one |
| 231 | 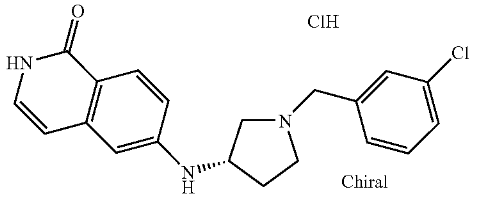 [SMILES: O=c1[nH]ccc2cc(N[C@H]3CCN(Cc4cccc(Cl)c4)C3)ccc12 ; Cl] | 1.03 | 354.1/ 356.1 | B | 6-[(S)-1-(3-Chloro-benzyl)-pyrrolidin-3-ylamino]-2H-isoquinolin-1-one |
| 232 | 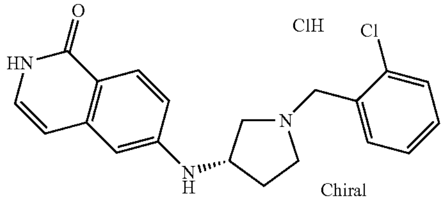 [SMILES: O=c1[nH]ccc2cc(N[C@H]3CCN(Cc4ccccc4Cl)C3)ccc12 ; Cl] | 0.95 | 354.1/ 356.1 | B | 6-[(S)-1-(2-Chloro-benzyl)-pyrrolidin-3-ylamino]-2H-isoquinolin-1-one |
| 233 | 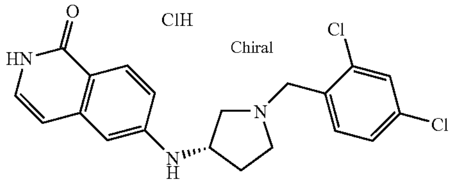 [SMILES: O=c1[nH]ccc2cc(N[C@H]3CCN(Cc4ccc(Cl)cc4Cl)C3)ccc12 ; Cl] | 1.12 | 388.1 | B | 6-[(S)-1-(2,4-Dichloro-benzyl)-pyrrolidin-3-ylamino]-2H-isoquinolin-1-one |
| 234 | 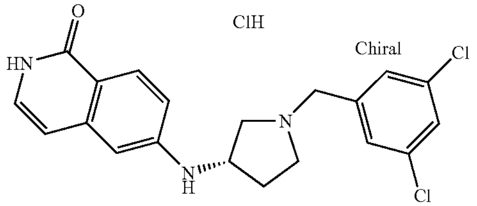 [SMILES: O=c1[nH]ccc2cc(N[C@H]3CCN(Cc4cc(Cl)cc(Cl)c4)C3)ccc12 ; Cl] | 1.16 | 388.1 | B | 6-[(S)-1-(3,5-Dichloro-benzyl)-pyrrolidin-3-ylamino]-2H-isoquinolin-1-one |
| 235 | 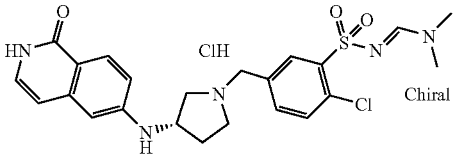 [SMILES: CN(C)/C=N/S(=O)(=O)c1cc(CN2CC[C@H](Nc3ccc4c(=O)[nH]ccc4c3)C2)ccc1Cl ; Cl] | 0.96 | 488.1 | B | 2-Chloro-N-[1-dimethylamino-meth-(E)-ylidene]-5-[(S)-3-(1-oxo-1,2-dihydro-isoquinolin-6-ylamino)-pyrrolidin-1-ylmethyl]-benzenesulfonamide |
| 236 | 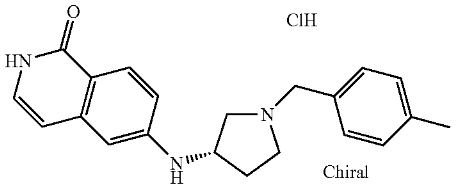 [SMILES: Cc1ccc(CN2CC[C@H](Nc3ccc4c(=O)[nH]ccc4c3)C2)cc1 ; Cl] | 1.04 | 334.2 | B | 6-[(S)-1-(4-Methyl-benzyl)-pyrrolidin-3-ylamino]-2H-isoquinolin-1-one |
| 237 | 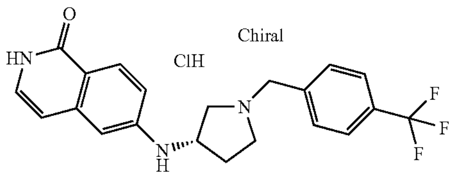 [SMILES: O=c1[nH]ccc2cc(N[C@H]3CCN(Cc4ccc(C(F)(F)F)cc4)C3)ccc12 ; Cl] | 1.20 | 388.1 | B | 6-[(S)-1-(4-Trifluoromethyl-benzyl)-pyrrolidin-3-ylamino]-2H-isoquinolin-1-one |

TABLE 6-continued

| | | | | | |
|---|---|---|---|---|---|
| 238 | 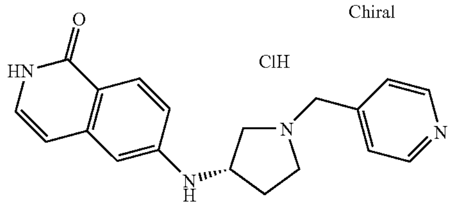 [SMILES: O=c1[nH]ccc2cc(N[C@H]3CCN(Cc4ccncc4)C3)ccc12 ; Cl] | 0.46 | 321.2 | B | 6-((S)-1-Pyridin-4-ylmethyl-pyrrolidin-3-ylamino)-2H-isoquinolin-1-one |
| 239 | 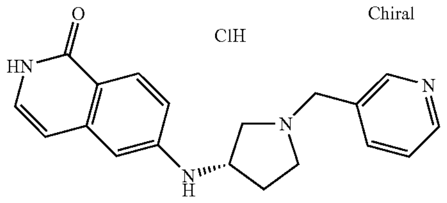 [SMILES: O=c1[nH]ccc2cc(N[C@H]3CCN(Cc4cccnc4)C3)ccc12 ; Cl] | 0.50 | 321.2 | B | 6-((S)-1-Pyridin-3-ylmethyl-pyrrolidin-3-ylamino)-2H-isoquinolin-1-one |
| 240 | 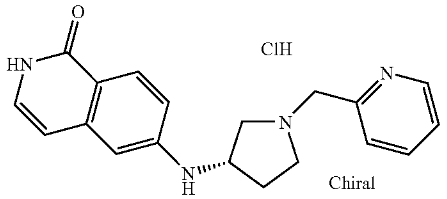 [SMILES: O=c1[nH]ccc2cc(N[C@H]3CCN(Cc4ccccn4)C3)ccc12 ; Cl] | 0.80 | 321.2 | B | 6-((S)-1-Pyridin-2-ylmethyl-pyrrolidin-3-ylamino)-2H-isoquinolin-1-one |
| 241 | 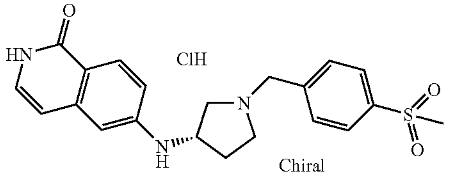 [SMILES: CS(=O)(=O)c1ccc(CN2CC[C@H](Nc3ccc4c(=O)[nH]ccc4c3)C2)cc1 ; Cl] | 0.92 | 398.1 | B | 6-[(S)-1-(4-Methanesulfonyl-benzyl)-pyrrolidin-3-ylamino]-2H-isoquinolin-1-one |
| 242 | 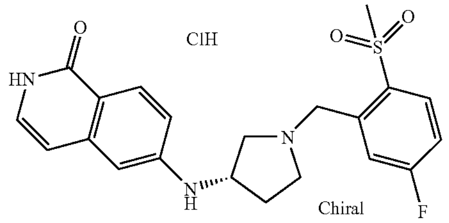 [SMILES: CS(=O)(=O)c1ccc(F)cc1CN1CC[C@H](Nc2ccc3c(=O)[nH]ccc3c2)C1 ; Cl] | 0.78 | 416.1 | B | 6-[(S)-1-(5-Fluoro-2-methanesulfonyl-benzyl)-pyrrolidin-3-ylamino]-2H-isoquinolin-1-one |
| 243 | 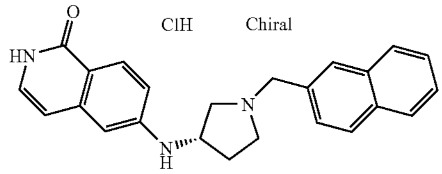 [SMILES: O=c1[nH]ccc2cc(N[C@H]3CCN(Cc4ccc5ccccc5c4)C3)ccc12 ; Cl] | 1.17 | 370.2 | B | 6-((S)-1-Naphthalen-2-ylmethyl-pyrrolidin-3-ylamino)-2H-isoquinolin-1-one |
| 244 | 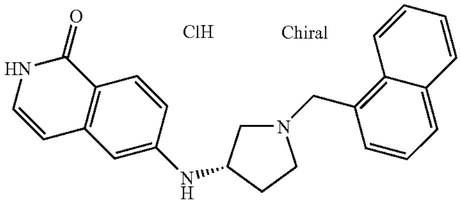 [SMILES: O=c1[nH]ccc2cc(N[C@H]3CCN(Cc4cccc5ccccc45)C3)ccc12 ; Cl] | 1.13 | 370.2 | B | 6-((S)-1-Naphthalen-1-ylmethyl-pyrrolidin-3-ylamino)-2H-isoquinolin-1-one |

TABLE 6-continued

| | | | | | |
|---|---|---|---|---|---|
| 245 | 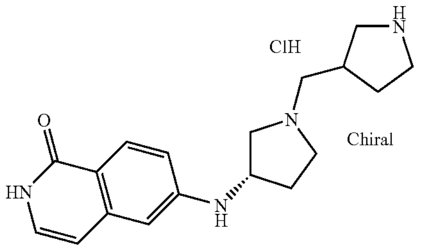 [SMILES: O=c1[nH]ccc2cc(N[C@H]3CCN(CC4CCNC4)C3)ccc12 ; Cl] | 0.43 | 313.2 | A | 6-((S)-1-Pyrrolidin-3-ylmethyl-pyrrolidin-3-ylamino)-2H-isoquinolin-1-one |
| 246 | 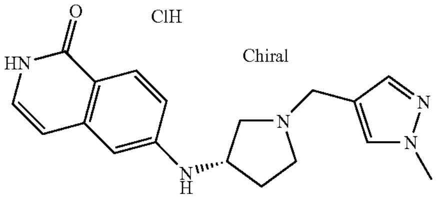 [SMILES: Cn1cc(CN2CC[C@H](Nc3ccc4c(=O)[nH]ccc4c3)C2)cn1 ; Cl] | 0.69 | 324.2 | A | 6-[(S)-1-(1-Methyl-1H-pyrazol-4-ylmethyl)-pyrrolidin-3-ylamino]-2H-isoquinolin-1-one |
| 247 | 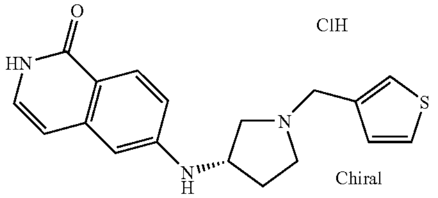 [SMILES: O=c1[nH]ccc2cc(N[C@H]3CCN(Cc4ccsc4)C3)ccc12 ; Cl] | 0.83 | 326.1 | A | 6-((S)-1-Thiophen-3-ylmethyl-pyrrolidin-3-ylamino)-2H-isoquinolin-1-one |
| 248 | 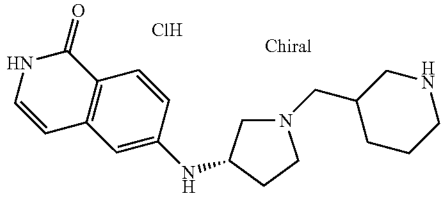 [SMILES: O=c1[nH]ccc2cc(N[C@H]3CCN(CC4CCCNC4)C3)ccc12 ; Cl] | 0.50 | 327.2 | B | 6-((S)-1-Piperidin-3-ylmethyl-pyrrolidin-3-ylamino)-2H-isoquinolin-1-one |
| 249 | 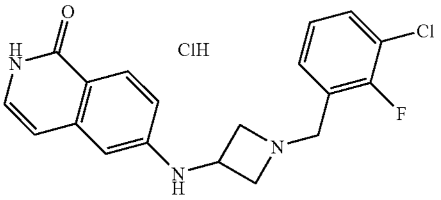 [SMILES: O=c1[nH]ccc2cc(NC3CN(Cc4cccc(Cl)c4F)C3)ccc12 ; Cl] | 1.02 | 358.1 | A | 6-[1-(3-Chloro-2-fluoro-benzyl)-azetidin-3-ylamino]-2H-isoquinolin-1-one |
| 250 | 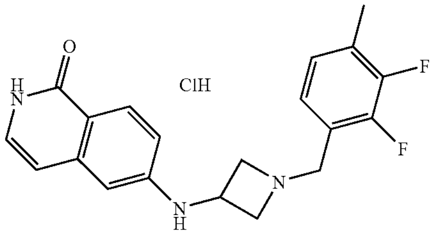 [SMILES: Cc1ccc(CN2CC(Nc3ccc4c(=O)[nH]ccc4c3)C2)c(F)c1F ; Cl] | 1.08 | 356.2 | A | 6-[1-(2,3-Difluoro-4-methyl-benzyl)-azetidin-3-ylamino]-2H-isoquinolin-1-one |
| 251 | 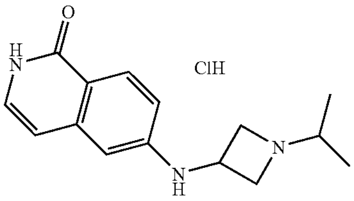 [SMILES: CC(C)N1CC(Nc2ccc3c(=O)[nH]ccc3c2)C1 ; Cl] | 0.61 | 258.2 | A | 6-(1-Isopropyl-azetidin-3-ylamino)-2H-isoquinolin-1-one |

TABLE 6-continued

| | | | | | |
|---|---|---|---|---|---|
| 252 | 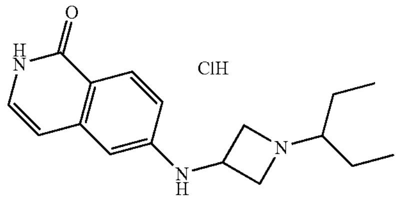 [SMILES: CCC(CC)N1CC(Nc2ccc3c(=O)[nH]ccc3c2)C1 ; Cl] | 0.78 | 286.2 | A | 6-[1-(1-Ethyl-propyl)-azetidin-3-ylamino]-2H-isoquinolin-1-one |
| 253 | 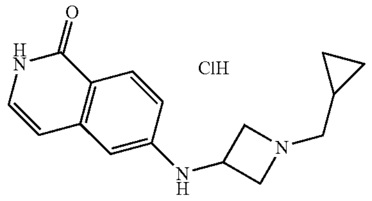 [SMILES: O=c1[nH]ccc2cc(NC3CN(CC4CC4)C3)ccc12 ; Cl] | 0.67 | 270.2 | A | 6-(1-Cyclopropylmethyl-azetidin-3-ylamino)-2H-isoquinolin-1-one |
| 254 | 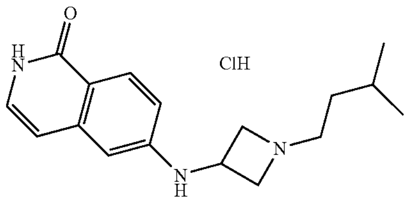 [SMILES: CC(C)CCN1CC(Nc2ccc3c(=O)[nH]ccc3c2)C1 ; Cl] | 0.92 | 286.2 | A | 6-[1-(3-Methyl-butyl)-azetidin-3-ylamino]-2H-isoquinolin-1-one |
| 255 | 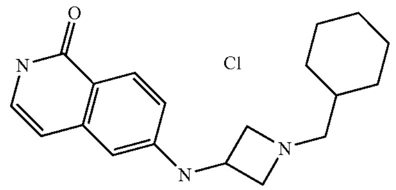 [SMILES: O=c1[nH]ccc2cc(NC3CN(CC4CCCCC4)C3)ccc12 ; Cl] | 1.06 | 312.2 | A | 6-(1-Cyclohexylmethyl-azetidin-3-ylamino)-2H-isoquinolin-1-one |
| 256 | 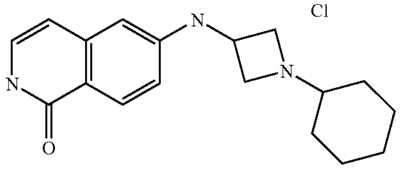 [SMILES: Cl ; O=c1[nH]ccc2cc(NC3CN(C4CCCCC4)C3)ccc12] | 0.88 | 298.2 | A | 6-(1-Cyclohexyl-azetidin-3-ylamino)-2H-isoquinolin-1-one |
| 257 | 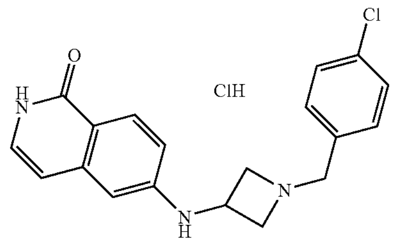 [SMILES: O=c1[nH]ccc2cc(NC3CN(Cc4ccc(Cl)cc4)C3)ccc12 ; Cl] | 1.04 | 340.2 | A | 6-[1-(4-Chloro-benzyl)-azetidin-3-ylamino]-2H-isoquinolin-1-one |
| 258 | 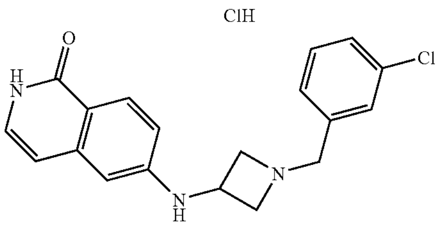 [SMILES: Cl ; O=c1[nH]ccc2cc(NC3CN(Cc4cccc(Cl)c4)C3)ccc12] | 1.08 | 340.2 | A | 6-[1-(3-Chloro-benzyl)-azetidin-3-ylamino]-2H-isoquinolin-1-one |

TABLE 6-continued

| | | | | | |
|---|---|---|---|---|---|
| 259 | 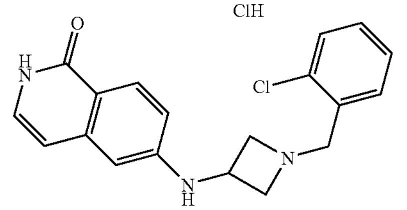 [SMILES: Cl ; O=c1[nH]ccc2cc(NC3CN(Cc4ccccc4Cl)C3)ccc12] | 0.91 | 340.2 | A | 6-[1-(2-Chloro-benzyl)-azetidin-3-ylamino]-2H-isoquinolin-1-one |
| 260 | 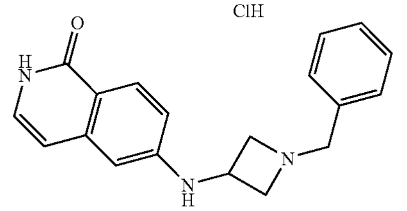 [SMILES: Cl ; O=c1[nH]ccc2cc(NC3CN(Cc4ccccc4)C3)ccc12] | 0.75 | 306.2 | A | 6-(1-Benzyl-azetidin-3-ylamino)-2H-isoquinolin-1-one |
| 261 | 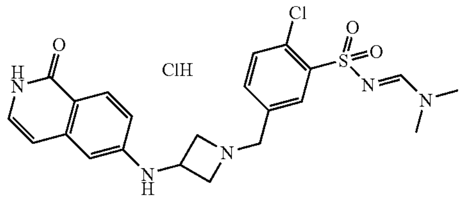 [SMILES: CN(C)/C=N/S(=O)(=O)c1cc(CN2CC(Nc3ccc4c(=O)[nH]ccc4c3)C2)ccc1Cl ; Cl] | 0.92 | 492.2 | A | 2-Chloro-N-[1-dimethylamino-meth-(E)-ylidene]-5-[3-(1-oxo-1,2-dihydro-isoquinolin-6-ylamino)-azetidin-1-ylmethyl]-benzenesulfonamide |
| 262 | 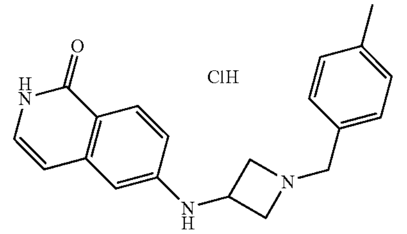 [SMILES: Cc1ccc(CN2CC(Nc3ccc4c(=O)[nH]ccc4c3)C2)cc1 ; Cl] | 1.03 | 320.2 | A | 6-[1-(4-Methyl-benzyl)-azetidin-3-ylamino]-2H-isoquinolin-1-one |

263: 6-Fluoro-7-chloro-isoquinoline

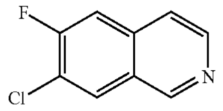 [SMILES: Fc1cc2ccncc2cc1Cl]

Starting from 4-Fluoro-3-chlorobenzaldehyde, the title compound was synthesized by the protocol described for 6-Bromo-isoquinoline (3). Rt=0.77 min (Method A). Detected mass: 182.1/184.1 (M+H+).

264: 6-Bromo-7-chloro-2-(4-methoxy-benzyl)-2H-isoquinolin-1-one

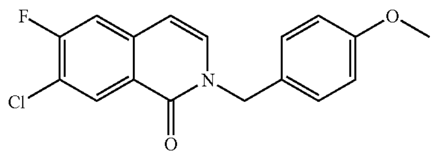 [SMILES: COc1ccc(Cn2ccc3cc(F)c(Cl)cc3c2=O)cc1]

Starting from 6-Bromo-7-chloro-isoquinoline (263), the title compound was prepared by the method described for 6-Bromo-2-(4-methoxy-benzyl)-2H-isoquinolin-1-one (13). $R_t$=1.66 min (Method C). Detected mass: 318.3 (M+H$^+$).

265: 6-Fluoro-7-bromo-isoquinoline

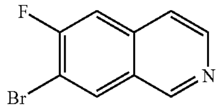 [SMILES: Fc1cc2ccncc2cc1Br]

Starting from 4-Fluoro-3-bromobenzaldehyde, the title compound was synthesized by the protocol described for 6-Bromo-isoquinoline (3). $R_t$=0.91 min (Method B). Detected mass: 226.0/228.0 (M+H$^+$).

266: (S)-3-Acetylsulfanyl-pyrrolidine-1-carboxylic acid tert-butyl ester

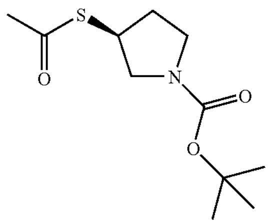 [SMILES: CC(=O)S[C@H]1CCN(C(=O)OC(C)(C)C)C1]

3 g (16 mmol) (R)-3-Hydroxy-pyrrolidine-1-carboxylic acid tert-butyl ester and 4.63 g Triphenylphosphine were dissolved in 70 ml THF. Over a period of 10 min 2.8 ml (17.6 mmol) Diethylazodicarboxylate were added at 0° C. After 10 min 1.26 ml (17.6 mmol) Thioacetic acid was added and the mixture was allowed to come to RT and stirring was continued for 18 h. After evaporation the residue was purified over silica gel (heptane to 20% ethyl acetate in heptane) to give 3.5 g of the expected compound.

267: (S)-3-(7-Chloro-isoquinolin-6-ylsulfanyl)-pyrrolidine-1-carboxylic acid tert-butyl ester

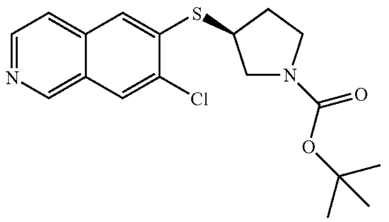 [SMILES: CC(C)(C)OC(=O)N1CC[C@H](Sc2cc3ccncc3cc2Cl)C1]

3.5 g (14.2 mmol) (S)-3-Acetylsulfanyl-pyrrolidine-1-carboxylic acid tert-butyl ester (266) were dissolved in 95 ml MeOH and treated with 2.34 g (16.9 mmol) potassium carbonate and stirred over night. After evaporation of all volatiles the residue was taken up in 60 ml of degassed DMF, 1.27 g (15 mmol) 6-Fluoro-7-chloroisoquinoline and 2.25 ml (15 mmol) DBU were added. After 3 h at RRT the mixture was concentrated, taken up in ethyl acetate and washed with brine. The organic phases were dried over Sodium sulfate and evaporated. Purification over silica gel (10% to 40% ethyl acetate in heptane) gave 4.5 g of the expected compound.

268: 7-Chloro-6-((S)-pyrrolidin-3-ylsulfanyl)-isoquinoline hydrochloride

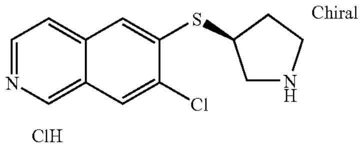 [SMILES: Clc1cc2cnccc2cc1S[C@H]1CCNC1 ; Cl]

4.5 g (6.1 mmol) (S)-3-(7-Chloro-isoquinolin-6-ylsulfanyl)-pyrrolidine-1-carboxylic acid tert-butyl ester in 15 ml dichloromethane and 7.5 ml 6N HCl in isopropanol were stirred over night. After evaporation water was added and lyophilized. 1.98 g of 7-Chloro-6-((S)-pyrrolidin-3-ylsulfanyl)-isoquinoline hydrochloride were obtained. $R_t$=0.76 min (Method B). Detected mass: 264.1/266.1 (M+H$^+$).

269: (Rac)-7-Chloro-6-(piperidin-3-ylsulfanyl)-isoquinoline hydrochloride

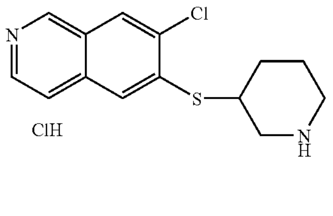 [SMILES: Clc1cc2cnccc2cc1SC1CCCNC1 ; Cl]

Starting from 6-Fluoro-7-chloroisoquinoline (263) and 3-Hydroxy-piperidine-1-carboxylic acid tert-butyl ester (Rac)-7-Chloro-6-(piperidin-3-ylsulfanyl)-isoquinoline could be obtained as the hydrochloride as described for compound (268). $R_t$=0.80 min (Method B). Detected mass: 279.1/281.1 (M+H$^+$).

270: (Rac)-6-(Azepan-4-ylsulfanyl)-7-chloro-isoquinoline hydrochloride

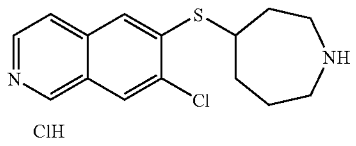 [SMILES: Clc1cc2cnccc2cc1SC1CCCNCC1 ; Cl]

Starting from 6-Fluoro-7-chloroisoquinoline (263) and 4-Hydroxy-azepane-1-carboxylic acid tert-butyl ester (Rac)-6-(Azepan-4-ylsulfanyl)-7-chloro-isoquinoline could be obtained as the hydrochloride as described for compound (268). $R_t$=0.83 min (Method B). Detected mass: 293.1/295.1 (M+H$^+$).

271: (Rac)-6-(Azepan-4-ylsulfanyl)-7-bromo-isoquinoline hydrochloride

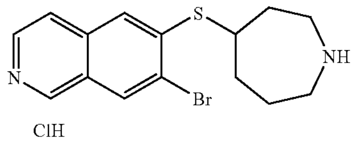 [SMILES: Brc1cc2cnccc2cc1SC1CCCNCC1 ; Cl]

Starting from 6-Fluoro-7-bromoisoquinoline (265) and 4-Hydroxy-azepane-1-carboxylic acid tert-butyl ester (Rac)-6-(Azepan-4-ylsulfanyl)-7-bromo-isoquinoline could be obtained as the hydrochloride as described for compound (268). $R_t$=0.83 min (Method B). Detected mass: 337.1 (M+H$^+$).

272: 4-Acetylsulfanyl-piperidine-1-carboxylic acid tert-butyl ester

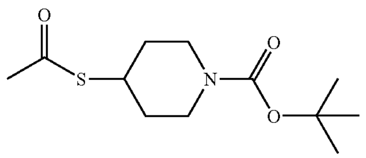 [SMILES: CC(=O)SC1CCN(C(=O)OC(C)(C)C)CC1]

2.2 g (19.3 mmol) Potassium thioacetate and 2.65 g (10 mmol) 4-Bromo-piperidine-1-carboxylic acid tert-butyl ester were dissolved in 50 ml of DMF and stirred at 100° C. for 4 h. The mixture was taken up in ethyl acetate and washed with brine. The organic phases were dried over Sodium sulfate and evaporated. Purification over silica gel (10% to 20% ethyl acetate in heptane) gave 2.15 g of the expected compound.

273: 4-Mercapto-piperidine-1-carboxylic acid tert-butyl ester

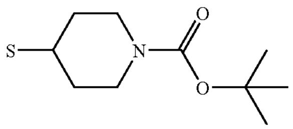

2.15 g 4-Acetylsulfanyl-piperidine-1-carboxylic acid tert-butyl ester (272) were dissolved in 84 ml MeOH and treated with 2.1 g (55.5 mmol) sodium borohydride at 0° C. after stirring for 2 h at RT all volatiles were removed in vacuo and to the residue was added slowly water and 2.3 g (11 mmol) citric acid monohydrate. Extraction with dichloromethane, drying with Sodium sulfate and evaporation gave 1.78 g of crude 4-Mercapto-piperidine-1-carboxylic acid tert-butyl ester 274: 4-(7-Chloro-isoquinolin-6-ylsulfanyl)-piperidine-1-carboxylic acid tert-butyl ester

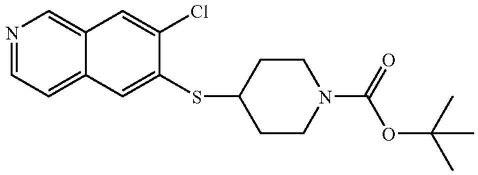 [SMILES: CC(C)(C)OC(=O)N1CCC(Sc2cc3ccncc3cc2Cl)CC1]

To 1.78 g of crude 4-Mercapto-piperidine-1-carboxylic acid tert-butyl ester (273) were dissolved in 20 ml degassed DMF was added 1.3 g (7.1 mmol) 6-Fluoro-7-chloroisoquinoline (263) and 1.23 ml (8.2 mmol) DBU. After stirring for 90 min at 80° C. the solvent was evaporated. The residue was taken up in ethyl acetate and washed with brine. The organic phases were dried over Sodium sulfate and evaporated. Purification over silica gel (40% to 60% ethyl acetate in heptane) gave 1.98 g of the expected compound.

275: 7-Chloro-6-(piperidin-4-ylsulfanyl)-isoquinoline hydrochloride

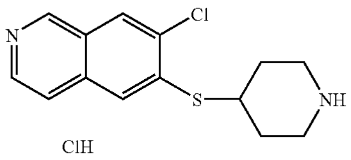 [SMILES: Clc1cc2cnccc2cc1SC1CCNCC1 ; Cl]

1.98 g of 4-(7-Chloro-isoquinolin-6-ylsulfanyl)-piperidine-1-carboxylic acid tert-butyl ester (274) were dissolved in 7 ml dichloromethane and 5 ml 6N HCl in isopropanol. After 18 h at RT the volatiles were evaporated, water was added and lyophilized. 1.85 g of the expected compound were obtained. $R_t$=0.70 min (Method B). Detected mass: 279.1/281.1 ($M+H^+$).

276: 4-(7-Propyl-isoquinolin-6-ylsulfanyl)-piperidine-1-carboxylic acid tert-butyl ester trifluoroacetate

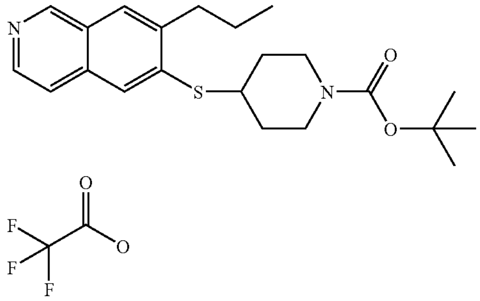

To 200 mg (0.52 mmol) 4-(7-Chloro-isoquinolin-6-ylsulfanyl)-piperidine-1-carboxylic acid tert-butyl ester (274) dissolved in 5 ml THF and 1 ml NMP were added 20 mg (0.055 mmol) Ferric (III) acetylacetonate. To the red solution 0.3 ml of propylmagnesium-chloride (2M in THF) were added and 2 min stirred at RT. 1 ml 1N HCl and 20 ml diethyl ether were added and the organic layer was washed with brine. The organic phases were dried over Sodium sulfate and evaporated. The residue was purified by HPLC. 85 mg of 4-(7-Propyl-isoquinolin-6-ylsulfanyl)-piperidine-1-carboxylic acid tert-butyl ester could be obtained as the trifluoroacetate.

277: 6-(Piperidin-4-ylsulfanyl)-7-propyl-isoquinoline hydrochloride

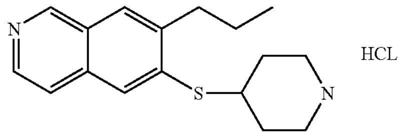 [SMILES: CCCc1cc2cnccc2cc1SC1CCNCC1]

85 mg (107 mmol) 4-(7-Propyl-isoquinolin-6-ylsulfanyl)-piperidine-1-carboxylic acid tert-butyl ester trifluoroacetate (276) were stirred in 6N HCl in iPrOH for 1 h at RT. After evaporation water was added and lyophilized. 42 mg of 6-(Piperidin-4-ylsulfanyl)-7-propyl-isoquinoline hydrochloride were obtained. $R_t$=0.94 min (Method B). Detected mass: 287.1 ($M+H^+$).

278: 7-Bromo-6-(piperidin-4-ylsulfanyl)-isoquinoline hydrochloride

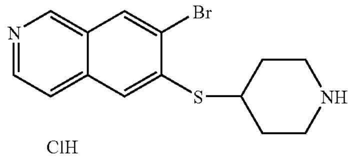 [SMILES: Brc1cc2cnccc2cc1SC1CCNCC1 ; Cl]

Starting from 6-Fluoro-7-bromoisoquinoline (265) 7-Bromo-6-(piperidin-4-ylsulfanyl)-isoquinoline could be obtained as the hydrochloride as described for compound (275). $R_t$=0.26 min (Method B). Detected mass: 325.3 ($M+H^+$).

279: 7-Chloro-6-(piperidin-4-ylmethylsulfanyl)-isoquinoline hydrochloride

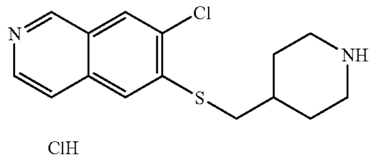 [SMILES: Clc1cc2cnccc2cc1SCC1CCNCC1 ; Cl]

Starting from 6-Fluoro-7-chloroisoquinoline (263) and 4-Bromomethyl-piperidine-1-carboxylic acid tert-butyl ester 7-Chloro-6-(piperidin-4-ylmethylsulfanyl)-isoquinoline could be obtained according to the procedures described for 272, 267, 268 as the hydrochloride. $R_t$=0.78 min (Method B). Detected mass: 293.1/295.1 ($M+H^+$).

280: 7-Chloro-6-(piperidin-3-ylmethylsulfanyl)-isoquinoline hydrochloride

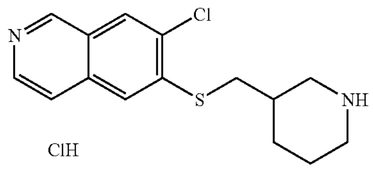 [SMILES: Clc1cc2cnccc2cc1SCC1CCCNC1 ; Cl]

Starting from 6-Fluoro-7-chloroisoquinoline (263) and 3-Bromomethyl-piperidine-1-carboxylic acid tert-butyl ester 7-Chloro-6-(piperidin-3-ylmethylsulfanyl)-isoquinoline could be obtained according to the procedures described for 272, 267, 268 as the hydrochloride. $R_t$=0.75 min (Method B). Detected mass: 293.1/295.1 ($M+H^+$).

281: 7-Bromo-6-(piperidin-3-ylmethylsulfanyl)-isoquinoline hydrochloride

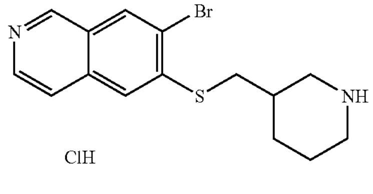 [SMILES: Brc1cc2cnccc2cc1SCC1CCCNC1 ; Cl]

Starting from 7-Bromo-6-chloroisoquinoline (265) and 3-Bromomethyl-piperidine-1-carboxylic acid tert-butyl ester 7-Bromo-6-(piperidin-3-ylmethylsulfanyl)-isoquinoline could be obtained according to the procedures described for 272, 267, 268 as the hydrochloride. $R_t$=0.82 min (Method B). Detected mass: 337.1 ($M+H^+$).

282: 7-Chloro-6-(pyrrolidin-2-ylmethylsulfanyl)-isoquinoline hydrochloride

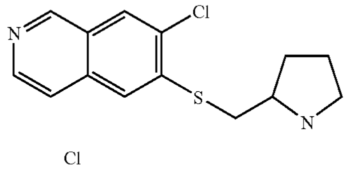 [SMILES: Clc1cc2cnccc2cc1SCC1CCCN1 ; Cl]

Starting from 6-Chloro-7-chloroisoquinoline (263) and 2-Bromomethyl-pyrrolidine-1-carboxylic acid tert-butyl ester 7-Chloro-6-(pyrrolidin-2-ylmethylsulfanyl)-isoquinoline could be obtained according to the procedures described for 272, 267, 268 as the hydrochloride. $R_t$=0.85 min (Method B). Detected mass: 279.1/281.2 ($M+H^+$).

283: 7-Chloro-6-(pyrrolidin-3-ylmethylsulfanyl)-isoquinoline hydrochloride

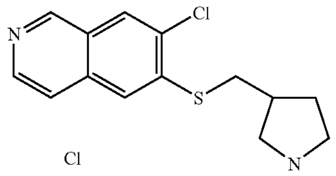 [SMILES: Clc1cc2cnccc2cc1SCC1CCNC1 ; Cl]

Starting from 6-Fluoro-7-chloroisoquinoline (263) and 3-Bromomethyl-pyrrolidine-1-carboxylic acid tert-butyl ester 7-Chloro-6-(pyrrolidin-3-ylmethylsulfanyl)-isoquinoline could be obtained according to the procedures described for 272, 267, 268 as the hydrochloride. $R_t$=0.87 min (Method B). Detected mass: 279.1/281.2 ($M+H^+$).

284: 7-Bromo-6-(pyrrolidin-3-ylmethylsulfanyl)-isoquinoline hydrochloride

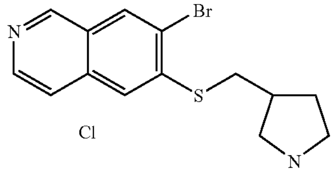 [SMILES: Brc1cc2cnccc2cc1SCC1CCNC1 ; Cl]

Starting from 7-Bromo-6-chloroisoquinoline (265) and 3-Bromomethyl-pyrrolidine-1-carboxylic acid tert-butyl ester 7-Bromo-6-(pyrrolidin-3-ylmethylsulfanyl)-isoquinoline could be obtained according to the procedures described for 272, 267, 268 as the hydrochloride. $R_t$=0.72 min (Method B). Detected mass: 323.1/325.2 (M+H$^+$).

285: 4-[7-Chloro-2-(4-methoxy-benzyl)-1-oxo-1,2-dihydro-isoquinolin-6-ylsulfanyl]-piperidine-1-carboxylic acid tert-butyl ester

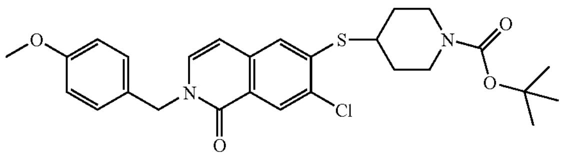 [SMILES: COc1ccc(Cn2ccc3cc(SC4CCN(C(=O)OC(C)(C)C)CC4)c(Cl)cc3c2=O)cc1]

Starting from 7-Chloro-6-fluoro-2-(4-methoxy-benzyl)-2H-isoquinolin-1-one (264) 4-[7-Chloro-2-(4-methoxy-benzyl)-1-oxo-1,2-dihydro-isoquinolin-6-ylsulfanyl]-piperidine-1-carboxylic acid tert-butyl ester could be obtained as described for compound (274). 7-Chloro-6-(piperidin-4-ylsulfanyl)-2H-isoquinolin-1-one.

286: 7-Chloro-6-(piperidin-4-ylsulfanyl)-2H-isoquinolin-1-one hydrochloride

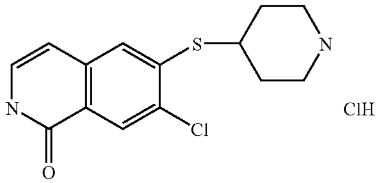 [SMILES: O=c1[nH]ccc2cc(SC3CCNCC3)c(Cl)cc12 ; Cl]

188 mg 4-[7-Chloro-2-(4-methoxy-benzyl)-1-oxo-1,2-dihydro-isoquinolin-6-ylsulfanyl]-piperidine-1-carboxylic acid tert-butyl ester (285) in 2 ml TFA were heated in the microwave at 150° C. for 1.5 h. After evaporation the residue is taken up in 1N HCl and extracted with dichloromethane and lyophilized. 79 mg of 7-Chloro-6-(piperidin-4-ylsulfanyl)-2H-isoquinolin-1-one could be obtained as the hydrochloride. $R_t$=0.93 min (Method B). Detected mass: 295.1/297.1 (M+H$^+$).

287: 4-[7-Chloro-2-(4-methoxy-benzyl)-1-oxo-1,2-dihydro-isoquinoline-6-sulfonyl]-piperidine-1-carboxylic acid tert-butyl ester

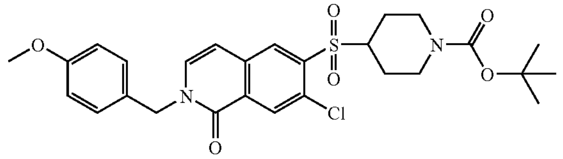 [SMILES: COc1ccc(Cn2ccc3cc(S(=O)(=O)C4CCN(C(=O)OC(C)(C)C)CC4)c(Cl)cc3c2=O)cc1]

103 mg 4-[7-Chloro-2-(4-methoxy-benzyl)-1-oxo-1,2-dihydro-isoquinolin-6-ylsulfanyl]-piperidine-1-carboxylic acid tert-butyl ester (285) in 2 ml of dichloromethane were treated with 123 mg m-Chloroperbenzoic acid in total over 2 h. The mixture was diluted with dichloromethane and washed with sodium hydrogen carbonate solution and brine. After drying over sodium sulfate all volatiles were evaporated and the crude product purified by chromatography 2:1 (ethyl acetate/Heptane) to obtain 4-[7-Chloro-2-(4-methoxy-benzyl)-1-oxo-1,2-dihydro-isoquinoline-6-sulfonyl]-piperidine-1-carboxylic acid tert-butyl ester as an off white solid.

288: 7-Chloro-6-(piperidine-4-sulfonyl)-2H-isoquinolin-1-one hydrochloride

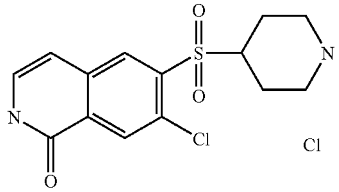 [SMILES: O=c1[nH]ccc2cc(S(=O)(=O)C3CCNCC3)c(Cl)cc12 ; Cl]

190 mg 4-[7-Chloro-2-(4-methoxy-benzyl)-1-oxo-1,2-dihydro-isoquinoline-6-sulfonyl]-piperidine-1-carboxylic acid tert-butyl ester (287) were dissolved in 2 ml of TFA and heated in a microwave at 150° C. for 50 min in total. After evaporation the mixture was dissolved in 1 N HCl and extracted with dichloromethane and lyophilized. 58 mg of 7-Chloro-6-(piperidine-4-sulfonyl)-2H-isoquinolin-1-one could be obtained as the hydrochloride. $R_t$=0.81 min (Method B). Detected mass: 327.1/329.1 (M+H$^+$).

289: 4-[7-Chloro-2-(4-methoxy-benzyl)-1-oxo-1,2-dihydro-isoquinoline-6-sulfinyl]-piperidine-1-carboxylic acid tert-butyl ester

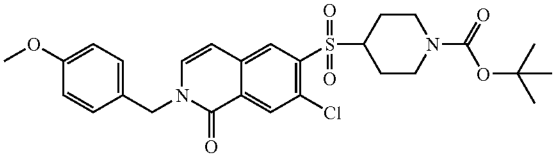 [SMILES: COc1ccc(Cn2ccc3cc(S(=O)(=O)C4CCN(C(=O)OC(C)(C)C)CC4)c(Cl)cc3c2=O)cc1]

206 mg 4-[7-Chloro-2-(4-methoxy-benzyl)-1-oxo-1,2-dihydro-isoquinolin-6-ylsulfanyl]-piperidine-1-carboxylic acid tert-butyl ester (285) in 6 ml of dichloromethane were treated with 83 mg m-Chloroperbenzoic acid over 2 h. The mixture was diluted with dichloromethane and washed with sodium hydrogen carbonate solution and brine. After drying over sodium sulfate all volatiles were evaporated and the crude product purified by chromatography 2:1 (ethyl acetate/Heptane) to obtain 4-[7-Chloro-2-(4-methoxy-benzyl)-1-oxo-1,2-dihydro-isoquinoline-6-sulfinyl]-piperidine-1-carboxylic acid tert-butyl ester as an off white solid.

290: 7-Chloro-6-(piperidine-4-sulfinyl)-2H-isoquinolin-1-one hydrochloride

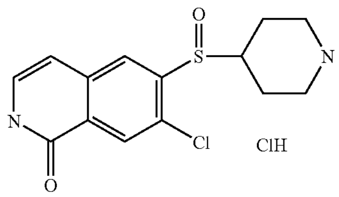 [SMILES: O=c1[nH]ccc2cc(S(=O)C3CCNCC3)c(Cl)cc12 ; Cl]

180 mg 4-[7-Chloro-2-(4-methoxy-benzyl)-1-oxo-1,2-dihydro-isoquinoline-6-sulfinyl]-piperidine-1-carboxylic acid tert-butyl ester (289) were dissolved in 2 ml of TFA and heated in a microwave at 150° C. for 40 min in total. After evaporation the mixture was dissolved in 1 N HCl and extracted with dichloromethane and lyophilized. 58 mg of 7-Chloro-6-(piperidine-4-sulfinyl)-2H-isoquinolin-1-one could be obtained as the hydrochloride. $R_t$=0.78 min (Method B). Detected mass: 311.1/313.1 (M+H$^+$).

291: 7-Chloro-6-((S)-1-ethyl-pyrrolidin-3-ylsulfanyl)-isoquinoline hydrochloride

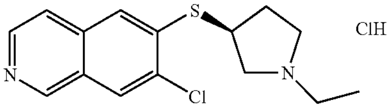 [SMILES: CCN1CC[C@H](Sc2cc3ccncc3cc2Cl)C1 ; Cl]

ClH

To 36 mg (0.12 mmol) 7-Chloro-6-((S)-pyrrolidin-3-ylsulfanyl)-isoquinoline hydrochloride (268) in 4 ml THF was added (0.12 mmol) acetaldehyde and 104 mg MP-Cyano borohydride resin (2.3 mmol/g) and stirred over night. After filtration from the resin and evaporation the residue was purified by preparative HPLC (Method A) to obtain 7-Chloro-6-((S)-1-ethyl-pyrrolidin-3-ylsulfanyl)-isoquinoline as the trifluoroacetate. The obtained trifluoroacetate was dissolved in 6 N HCl in isopropanol and evaporated. Final lyophilization gave 12 mg of the title compound as the hydrochloride $R_t$=0.71 min (Method B). Detected mass: 293.1/295.1 ($M+H^+$).

The compounds described in the following table were obtained in an analogous fashion as described for 291 (Table 7).

TABLE 7

| Example. | Amine | Carbonyl compound | Product |
|---|---|---|---|
| 292 | 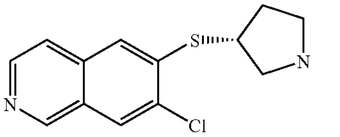 | 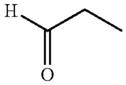 | 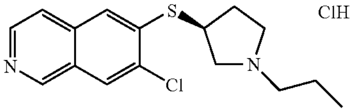 [SMILES: CCCN1CC[C@H](Sc2cc3ccncc3cc2Cl)C1 ; Cl] ClH |
| 293 | 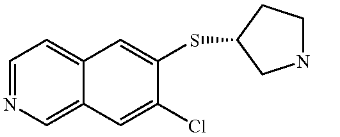 [SMILES: Clc1cc2cnccc2cc1S[C@@H]1CCNC1] | 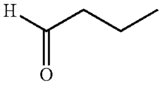 | 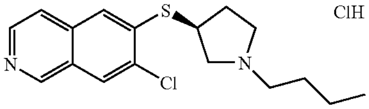 [SMILES: CCCCN1CC[C@H](Sc2cc3ccncc3cc2Cl)C1 ; Cl] ClH |
| 294 | 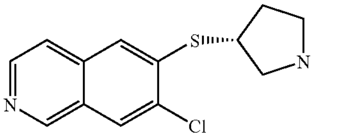 | 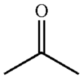 | 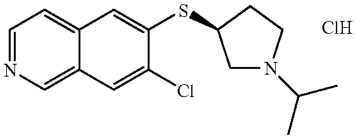 [SMILES: CC(C)N1CC[C@H](Sc2cc3ccncc3cc2Cl)C1 ; Cl] ClH |
| 295 | 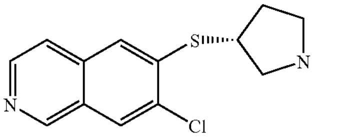 [SMILES: Clc1cc2cnccc2cc1S[C@@H]1CCNC1] | 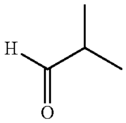 | 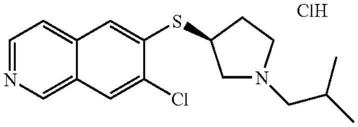 [SMILES: Cl ; CC(C)CN1CC[C@H](Sc2cc3ccncc3cc2Cl)C1] ClH |
| 296 | 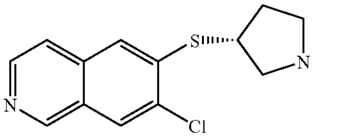 [SMILES: Clc1cc2cnccc2cc1S[C@@H]1CCNC1] | 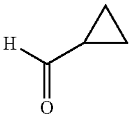 | 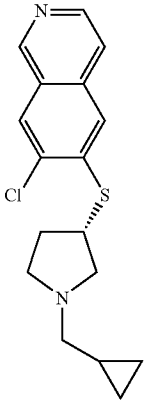 Chiral ClH |

TABLE 7-continued
| | | | |
|---|---|---|---|
| 298 | 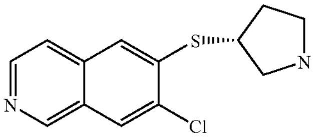 [SMILES: Clc1cc2cnccc2cc1S[C@@H]1CCNC1] | 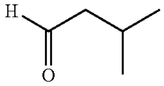 | 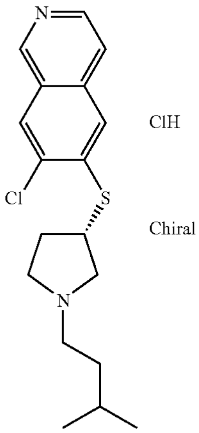 [SMILES: CC(C)CCN1CC[C@H](Sc2cc3ccncc3cc2Cl)C1 ; Cl] |
| 299 | 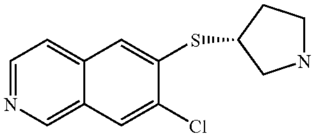 [SMILES: Clc1cc2cnccc2cc1S[C@@H]1CCNC1] | 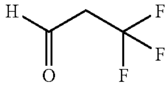 | 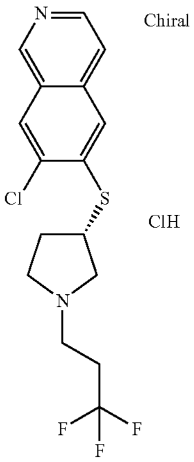 [SMILES: FC(F)(F)CCN1CC[C@H](Sc2cc3ccncc3cc2Cl)C1 ; Cl] |
| 300 | 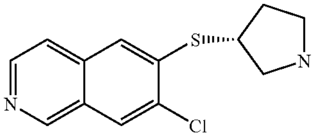 [SMILES: Clc1cc2cnccc2cc1S[C@@H]1CCNC1] | 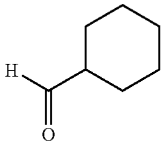 | 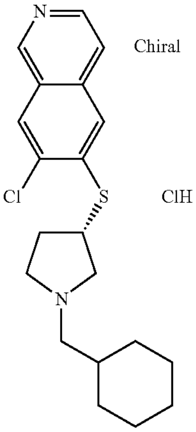 [SMILES: Clc1cc2cnccc2cc1S[C@H]1CCN(CC2CCCCC2)C1 ; Cl] |

TABLE 7-continued
| | | | |
|---|---|---|---|
| 301 | 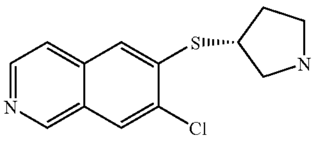 [SMILES: Clc1cc2cnccc2cc1S[C@@H]1CCNC1] | 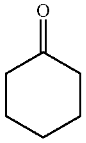 | 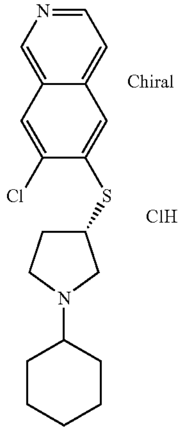 [SMILES: Clc1cc2cnccc2cc1S[C@H]1CCN(C2CCCCC2)C1 ; Cl] |
| 302 | 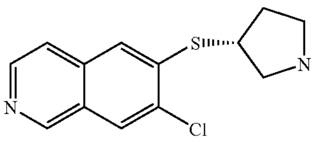 [SMILES: Clc1cc2cnccc2cc1S[C@@H]1CCNC1] | 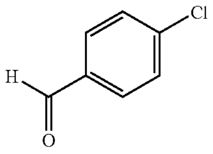 | 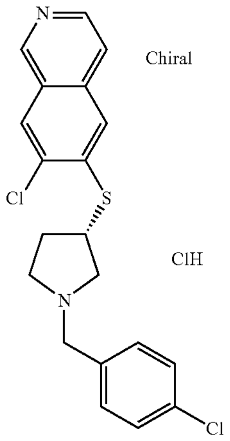 [SMILES: Clc1ccc(CN2CC[C@H](Sc3cc4ccncc4cc3Cl)C2)cc1 ; Cl] |
| 303 | 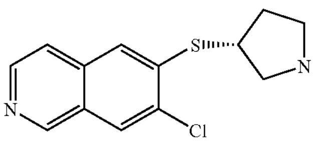 | 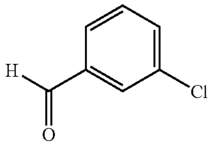 | 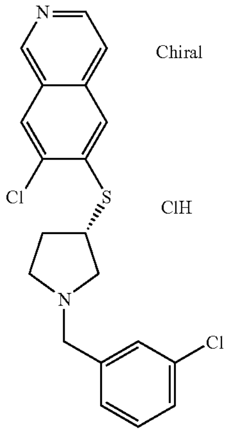 [SMILES: Clc1cccc(CN2CC[C@H](Sc3cc4ccncc4cc3Cl)C2)c1 ; Cl] |

TABLE 7-continued
| | | | |
|---|---|---|---|
| 304 | 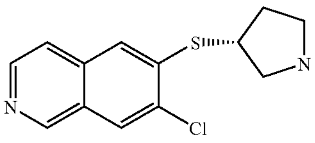 [SMILES: Clc1cc2cnccc2cc1S[C@@H]1CCNC1] | 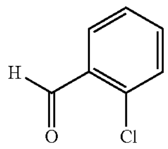 | 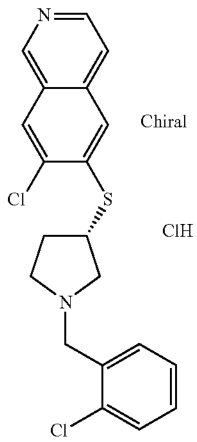 [SMILES: Clc1ccccc1CN1CC[C@H](Sc2cc3ccncc3cc2Cl)C1 ; Cl] |
| 305 | 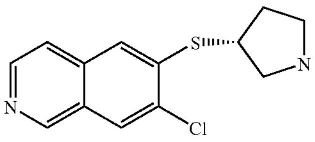 [SMILES: Clc1cc2cnccc2cc1S[C@@H]1CCNC1] | 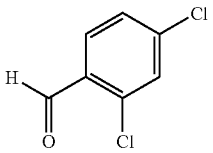 | 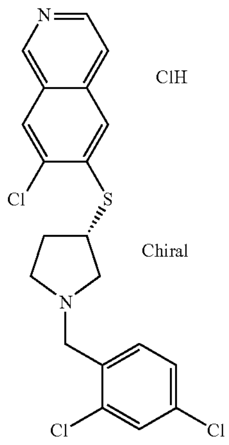 [SMILES: Clc1ccc(CN2CC[C@H](Sc3cc4ccncc4cc3Cl)C2)c(Cl)c1 ; Cl] |
| 306 | 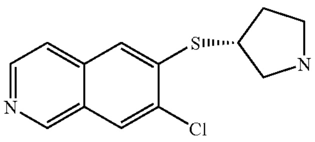 [SMILES: Clc1cc2cnccc2cc1S[C@@H]1CCNC1] | 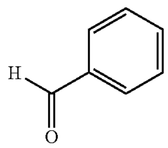 | 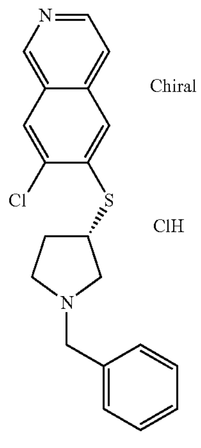 [SMILES: Clc1cc2cnccc2cc1S[C@H]1CCN(Cc2ccccc2)C1 ; Cl] |

TABLE 7-continued
| | | | |
|---|---|---|---|
| 307 | 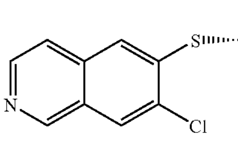 | 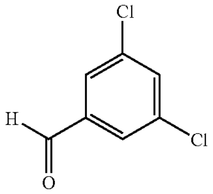 | 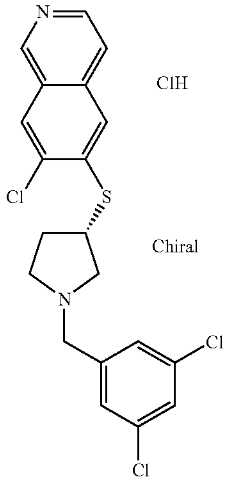 [SMILES: Clc1cc(Cl)cc(CN2CC[C@H](Sc3cc4ccncc4cc3Cl)C2)c1 ; Cl] |
| 308 | 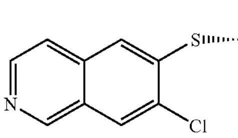 | 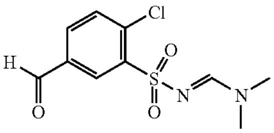 | 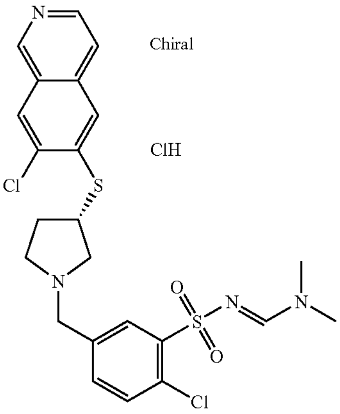 [SMILES: CN(C)/C=N/S(=O)(=O)c1cc(CN2CC[C@H](Sc3cc4ccncc4cc3Cl)C2)ccc1Cl ; Cl] |
| 309 | 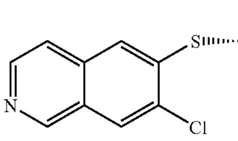 | 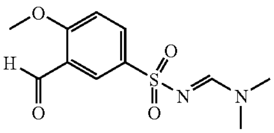 [SMILES: COc1ccc(S(=O)(=O)/N=C/N(C)C)cc1C=O] | 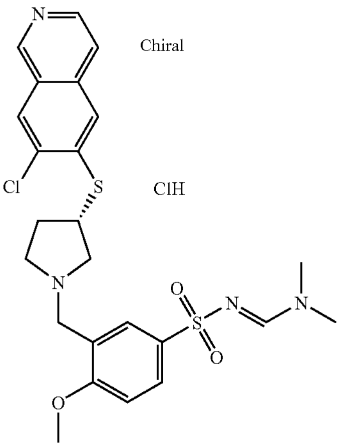 [SMILES: COc1ccc(S(=O)(=O)/N=C/N(C)C)cc1CN1CC[C@H](Sc2cc3ccncc3cc2Cl)C1 ; Cl] |

TABLE 7-continued
| | | | |
|---|---|---|---|
| 310 | 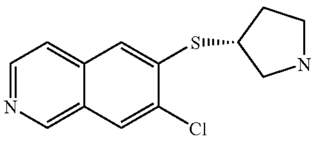 [SMILES: Clc1cc2cnccc2cc1S[C@@H]1CCNC1] | 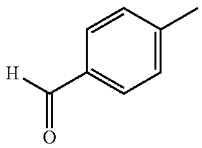 | 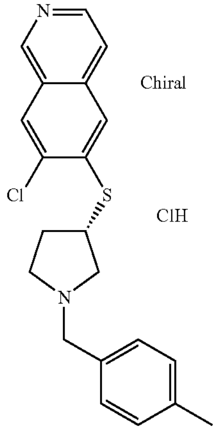 [SMILES: Cc1ccc(CN2CC[C@H](Sc3cc4ccncc4cc3Cl)C2)cc1 ; Cl] |
| 311 | 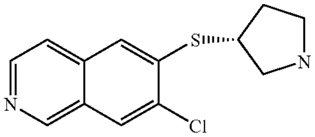 [SMILES: Clc1cc2cnccc2cc1S[C@@H]1CCNC1] | 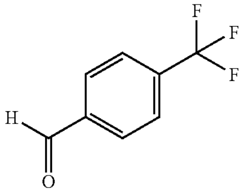 [SMILES: O=Cc1ccc(C(F)(F)F)cc1] | 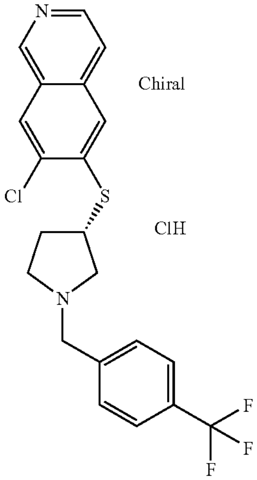 [SMILES: FC(F)(F)c1ccc(CN2CC[C@H](Sc3cc4ccncc4cc3Cl)C2)cc1 ; Cl] |
| 312 | 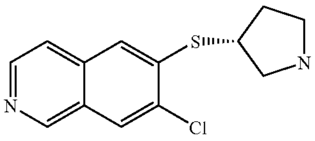 [SMILES: Clc1cc2cnccc2cc1S[C@@H]1CCNC1] | 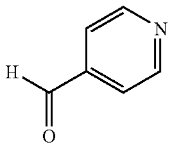 | 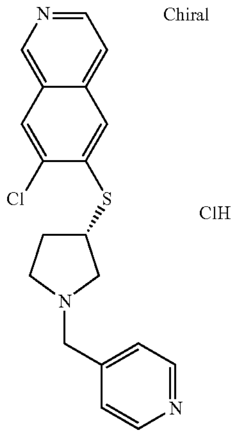 [SMILES: Clc1cc2cnccc2cc1S[C@H]1CCN(Cc2ccncc2)C1 ; Cl] |

TABLE 7-continued
| | | | |
|---|---|---|---|
| 313 | 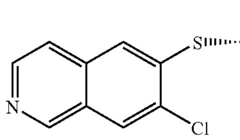 | 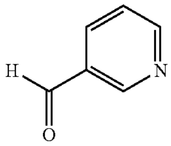 | 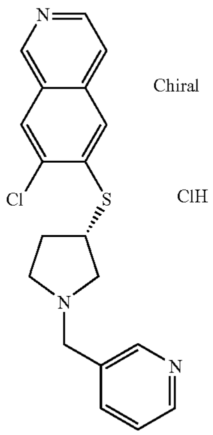 [SMILES: Clc1cc2cnccc2cc1S[C@H]1CCN(Cc2cccnc2)C1 ; Cl] |
| 314 | 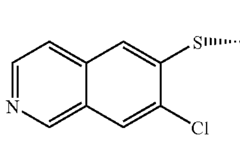 | 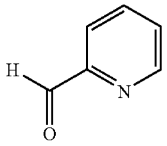 | 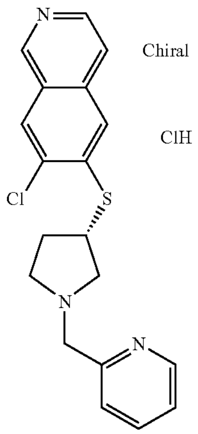 [SMILES: Clc1cc2cnccc2cc1S[C@H]1CCN(Cc2ccccn2)C1 ; Cl] |
| 315 | 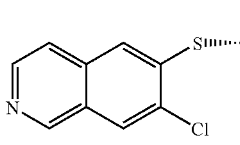 | 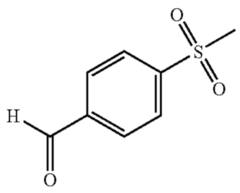 | 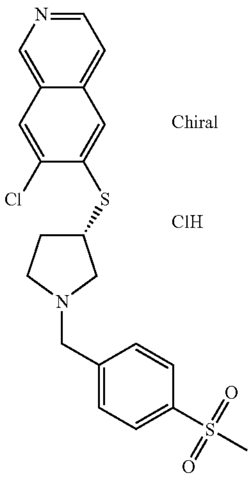 [SMILES: CS(=O)(=O)c1ccc(CN2CC[C@H](Sc3cc4ccncc4cc3Cl)C2)cc1 ; Cl] |

TABLE 7-continued
| | | | |
|---|---|---|---|
| 316 | 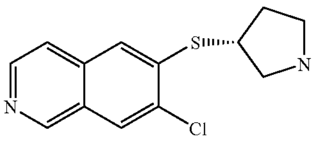 [SMILES: Clc1cc2cnccc2cc1S[C@@H]1CCNC1] | 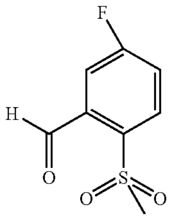 | 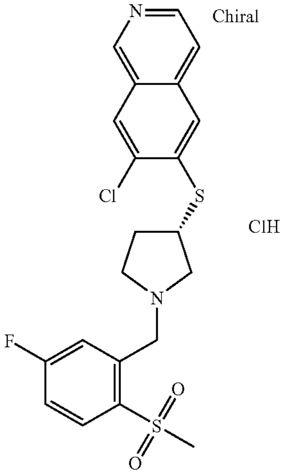 [SMILES: CS(=O)(=O)c1ccc(F)cc1CN1CC[C@H](Sc2cc3ccncc3cc2Cl)C1 ; Cl] |
| 317 | 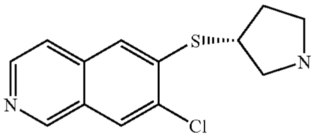 [SMILES: Clc1cc2cnccc2cc1S[C@@H]1CCNC1] | 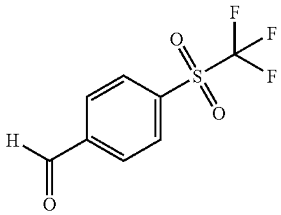 [SMILES: O=Cc1ccc(S(=O)(=O)C(F)(F)F)cc1] | 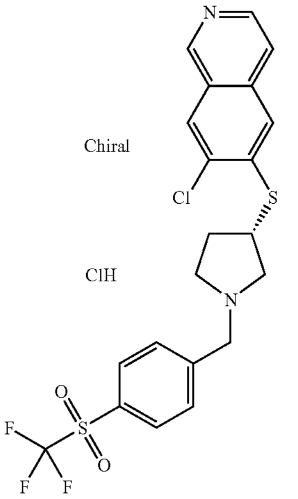 [SMILES: O=S(=O)(c1ccc(CN2CC[C@H](Sc3cc4ccncc4cc3Cl)C2)cc1)C(F)(F)F ; Cl] |
| 317 | 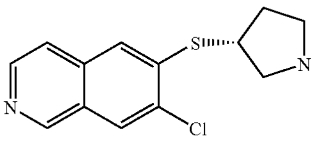 [SMILES: Clc1cc2cnccc2cc1S[C@@H]1CCNC1] | 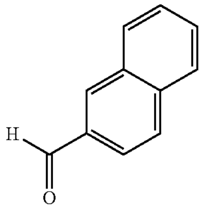 [SMILES: O=Cc1ccc2ccccc2c1] | 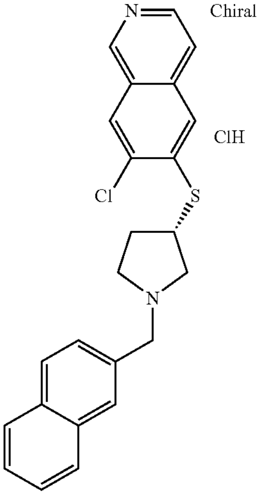 [SMILES: Clc1cc2cnccc2cc1S[C@H]1CCN(Cc2ccc3ccccc3c2)C1 ; Cl] |

TABLE 7-continued
| | | | |
|---|---|---|---|
| 318 | 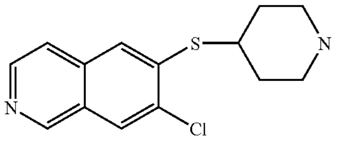 | 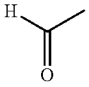 | 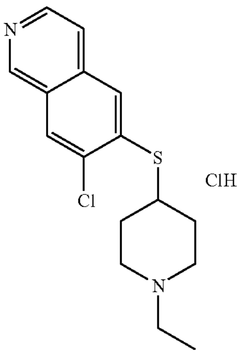 [SMILES: CCN1CCC(Sc2cc3ccncc3cc2Cl)CC1 ; Cl] |
| 319 | 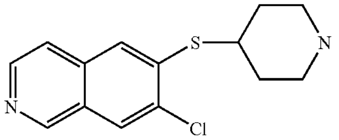 | 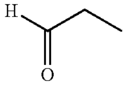 | 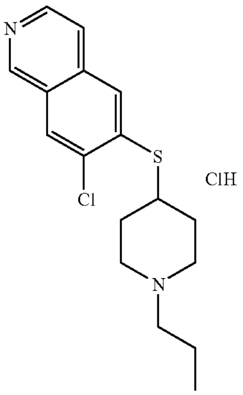 [SMILES: CCCN1CCC(Sc2cc3ccncc3cc2Cl)CC1 ; Cl] |
| 320 | 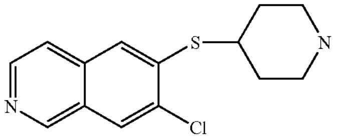 | 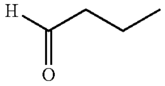 | 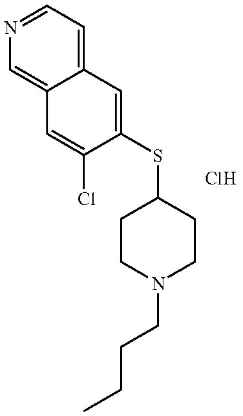 [SMILES: CCCCN1CCC(Sc2cc3ccncc3cc2Cl)CC1 ; Cl] |
| 321 | 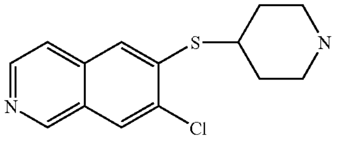 | 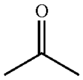 | 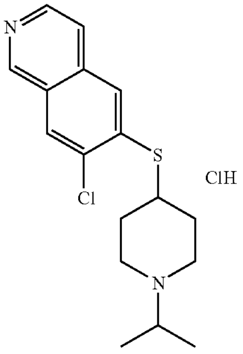 [SMILES: CC(C)N1CCC(Sc2cc3ccncc3cc2Cl)CC1 ; Cl] |

TABLE 7-continued
| | | | |
|---|---|---|---|
| 322 | 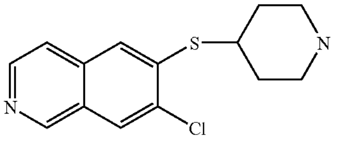 | 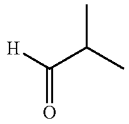 | 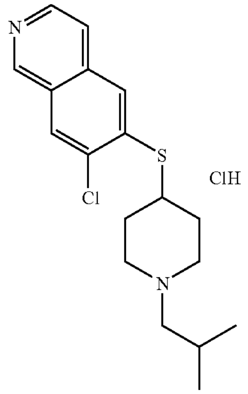 [SMILES: CC(C)CN1CCC(Sc2cc3ccncc3cc2Cl)CC1 ; Cl] |
| 323 | 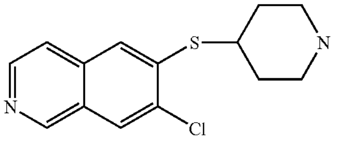 | 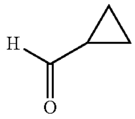 | 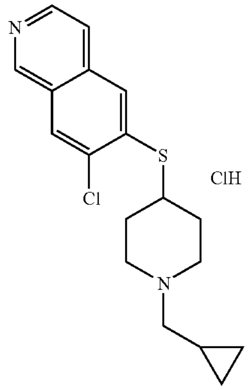 [SMILES: Clc1cc2cnccc2cc1SC1CCN(CC2CC2)CC1 ; Cl] |
| 324 | 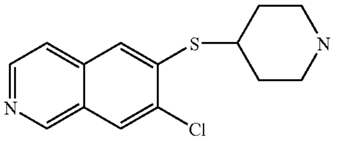 | 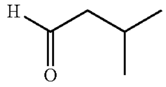 | 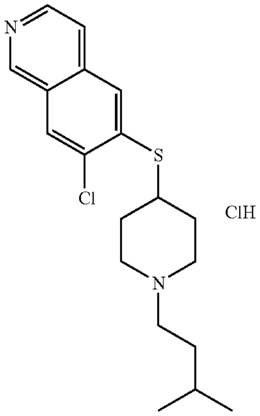 [SMILES: CC(C)CCN1CCC(Sc2cc3ccncc3cc2Cl)CC1 ; Cl] |
| 325 | 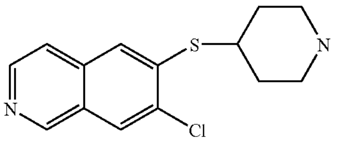 | 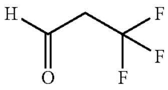 | 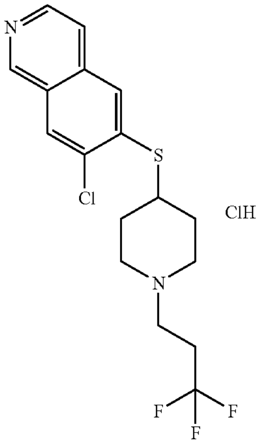 [SMILES: FC(F)(F)CCN1CCC(Sc2cc3ccncc3cc2Cl)CC1 ; Cl] |

TABLE 7-continued
326
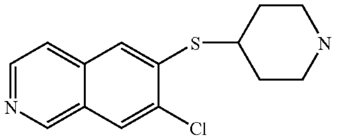
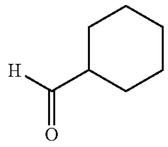
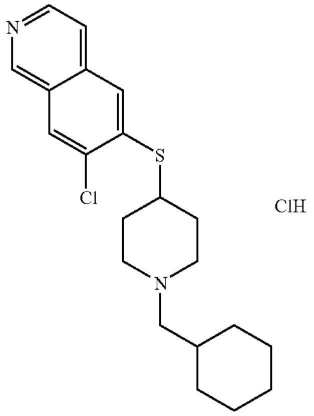 [SMILES: Clc1cc2cnccc2cc1SC1CCN(CC2CCCCC2)CC1 ; Cl]
327
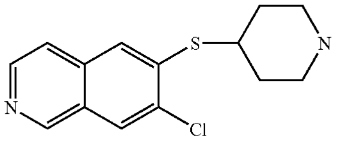 [SMILES: Clc1cc2cnccc2cc1SC1CCNCC1]
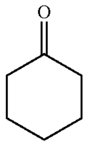
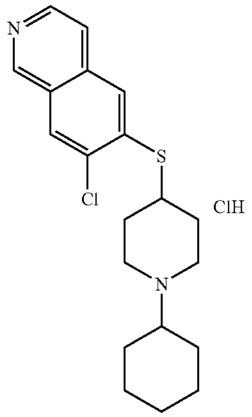 [SMILES: Clc1cc2cnccc2cc1SC1CCN(C2CCCCC2)CC1 ; Cl]
328
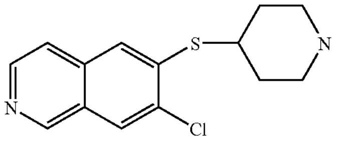
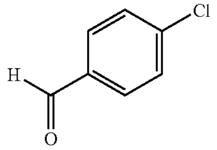
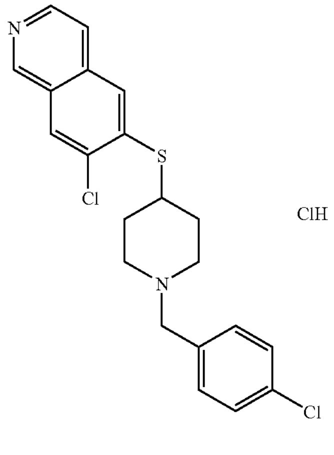 [SMILES: Clc1ccc(CN2CCC(Sc3cc4ccncc4cc3Cl)CC2)cc1 ; Cl]

TABLE 7-continued
329 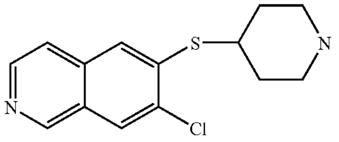 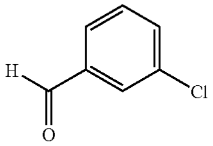 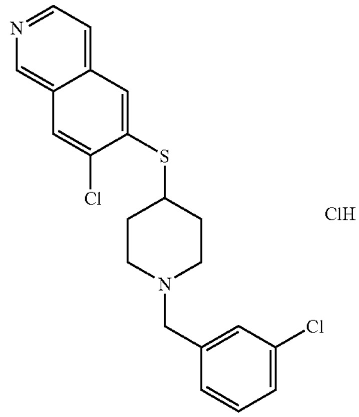 [SMILES: Clc1cccc(CN2CCC(Sc3cc4ccncc4cc3Cl)CC2)c1 ; Cl]
330 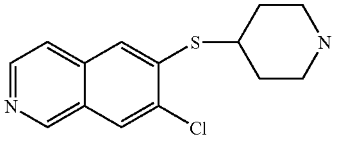 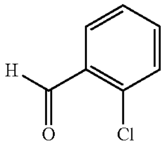 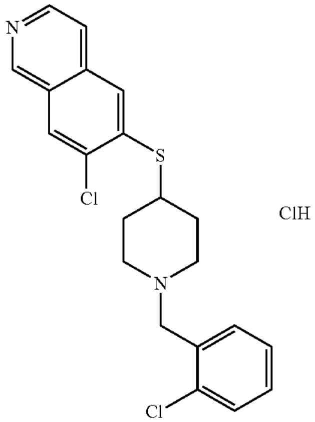 [SMILES: Clc1ccccc1CN1CCC(Sc2cc3ccncc3cc2Cl)CC1 ; Cl]
331 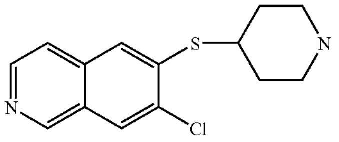 [SMILES: Clc1cc2cnccc2cc1SC1CCNCC1] 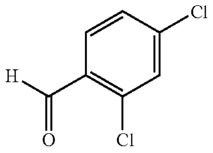 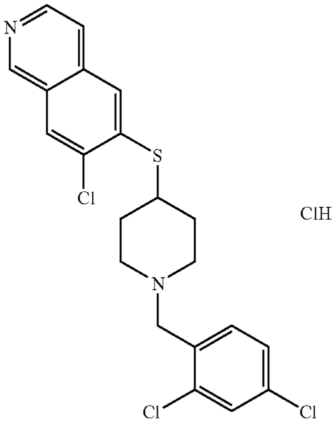 [SMILES: Clc1ccc(CN2CCC(Sc3cc4ccncc4cc3Cl)CC2)c(Cl)c1 ; Cl]

TABLE 7-continued
| | | | |
|---|---|---|---|
| 332 | 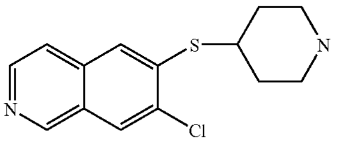 | 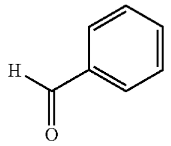 | 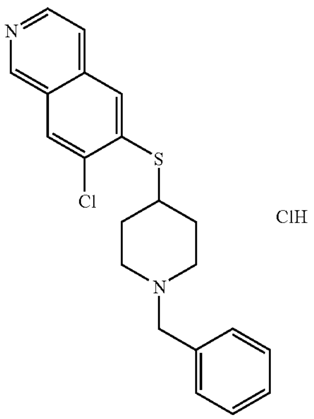 [SMILES: Clc1cc2cnccc2cc1SC1CCN(Cc2ccccc2)CC1 ; Cl] |
| 333 | 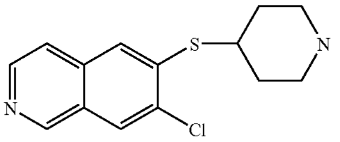 | 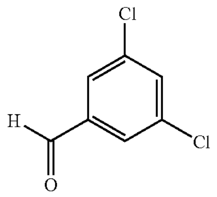 | 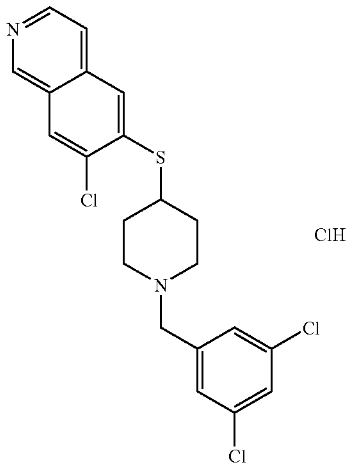 [SMILES: Clc1cc(Cl)cc(CN2CCC(Sc3cc4ccncc4cc3Cl)CC2)c1 ; Cl] |
| 334 | 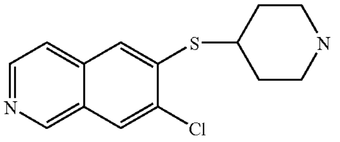 | 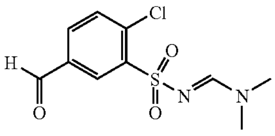 [SMILES: CN(C)/C=N/S(=O)(=O)c1cc(C=O)ccc1Cl] | 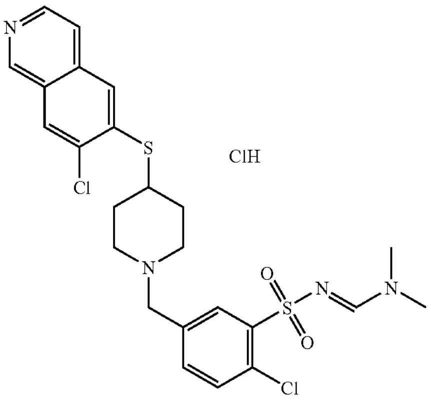 [SMILES: CN(C)/C=N/S(=O)(=O)c1cc(CN2CCC(Sc3cc4ccncc4cc3Cl)CC2)ccc1Cl ; Cl] |

TABLE 7-continued
335
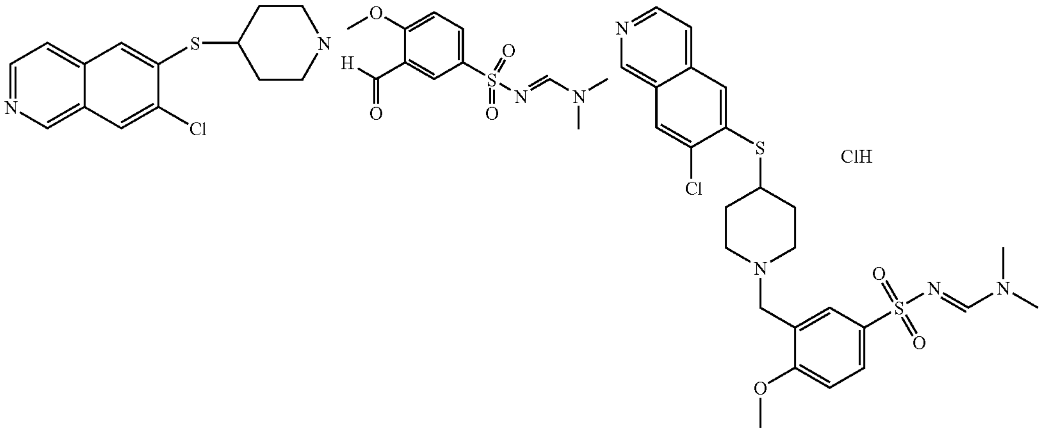
336
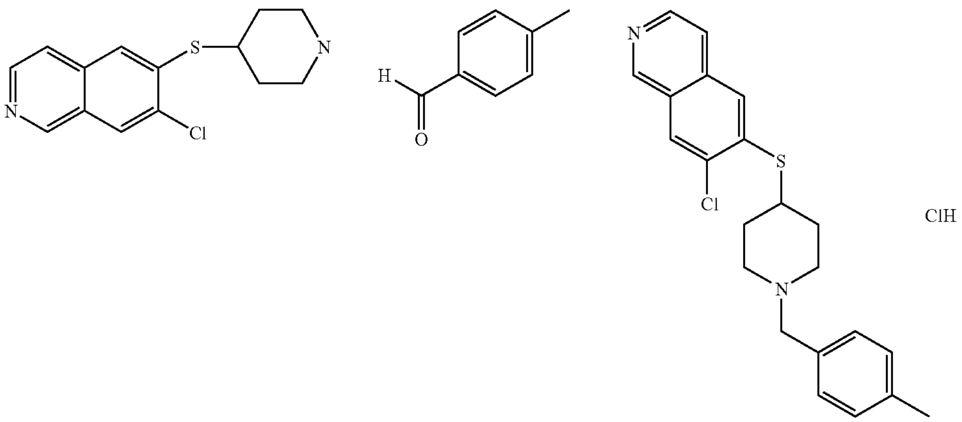
337
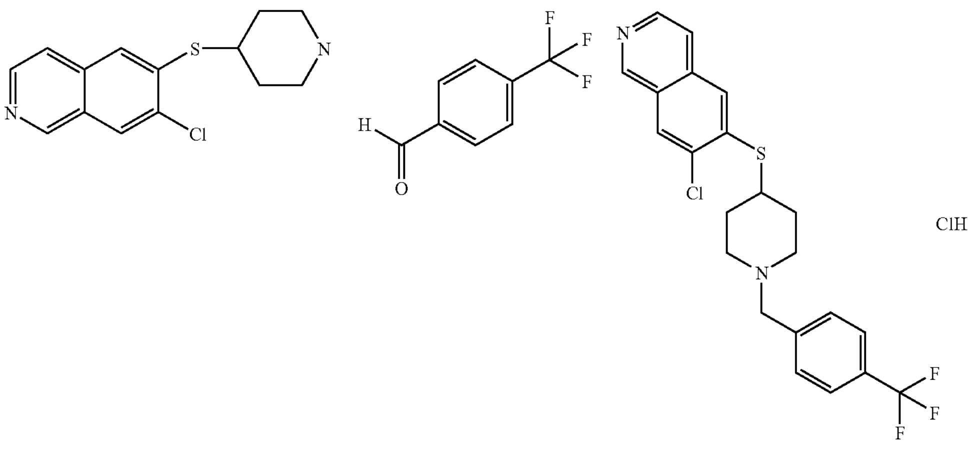

TABLE 7-continued
338
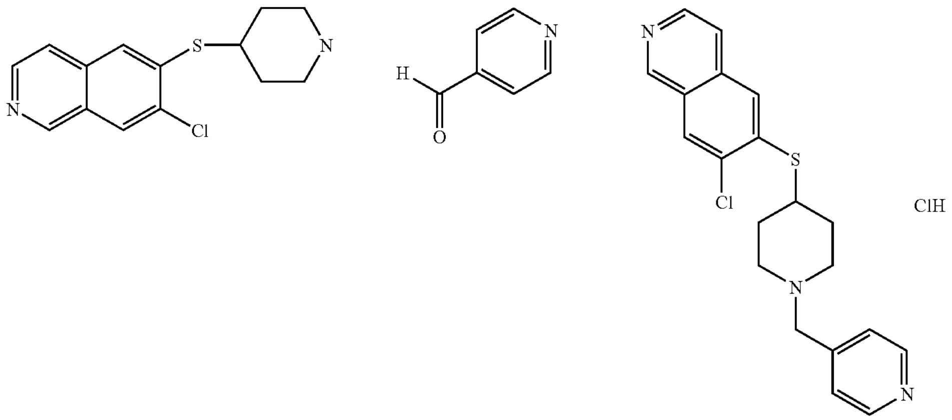
339
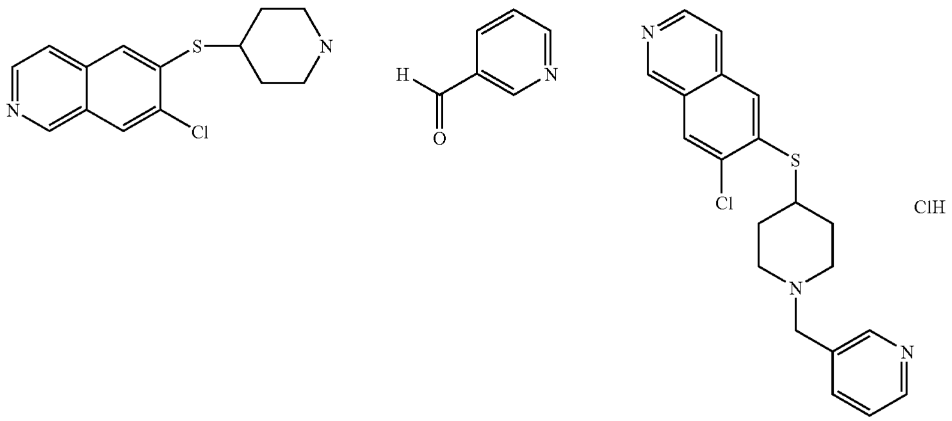
340
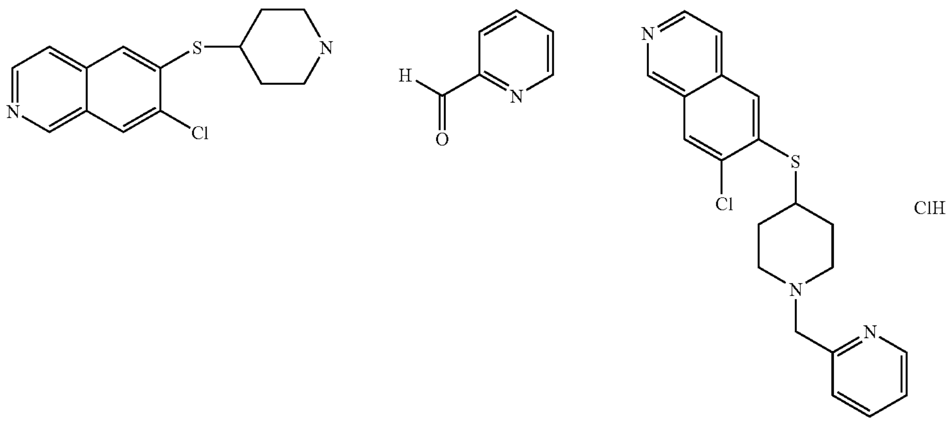

TABLE 7-continued
| | | | |
|---|---|---|---|
| 341 | 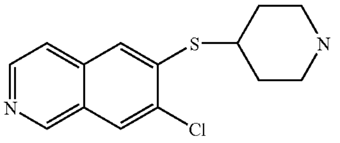 | 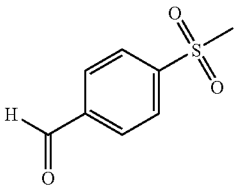 | 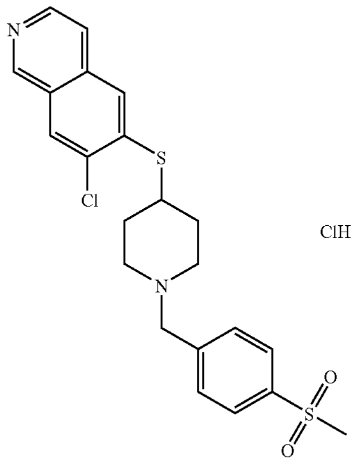 [SMILES: CS(=O)(=O)c1ccc(CN2CCC(Sc3cc4ccncc4cc3Cl)CC2)cc1 ; Cl] |
| 342 | 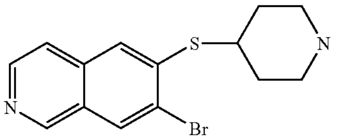 [SMILES: Brc1cc2cnccc2cc1SC1CCNCC1] | 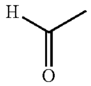 | 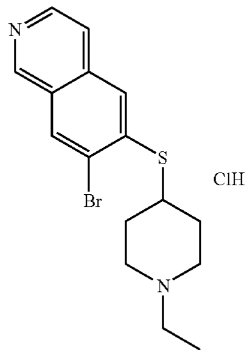 [SMILES: CCN1CCC(Sc2cc3ccncc3cc2Br)CC1 ; Cl] |
| 343 | 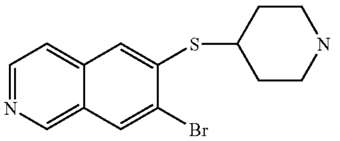 [SMILES: Brc1cc2cnccc2cc1SC1CCNCC1] | 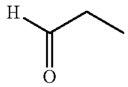 | 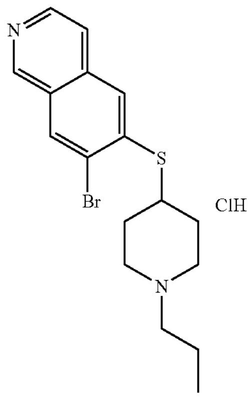 [SMILES: CCCN1CCC(Sc2cc3ccncc3cc2Br)CC1 ; Cl] |
| 344 | 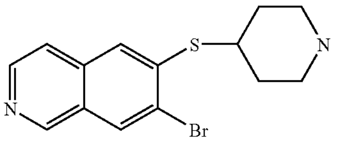 [SMILES: Brc1cc2cnccc2cc1SC1CCNCC1] | 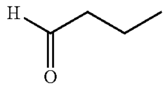 | 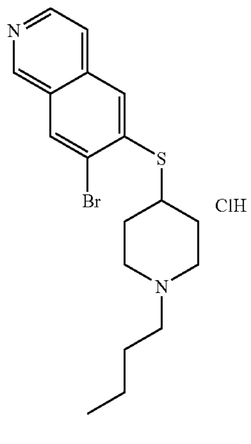 [SMILES: CCCCN1CCC(Sc2cc3ccncc3cc2Br)CC1 ; Cl] |

TABLE 7-continued
| | | | |
|---|---|---|---|
| 345 | 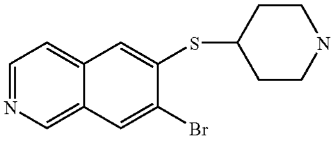 [SMILES: Brc1cc2cnccc2cc1SC1CCNCC1] | 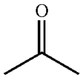 | 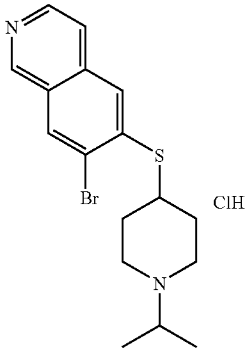 [SMILES: CC(C)N1CCC(Sc2cc3ccncc3cc2Br)CC1 ; Cl] |
| 346 | 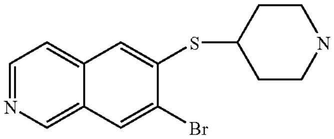 [SMILES: Brc1cc2cnccc2cc1SC1CCNCC1] | 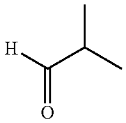 | 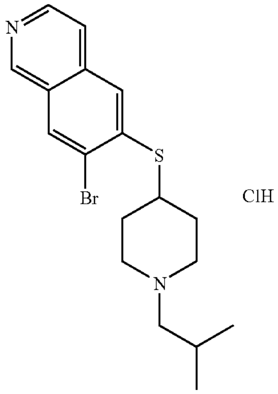 [SMILES: CC(C)CN1CCC(Sc2cc3ccncc3cc2Br)CC1 ; Cl] |
| 347 | 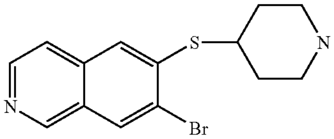 [SMILES: Brc1cc2cnccc2cc1SC1CCNCC1] | 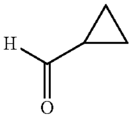 | 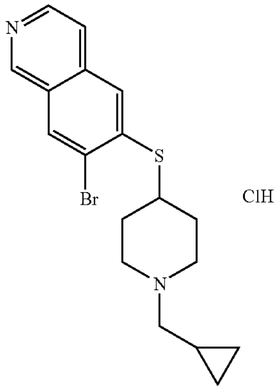 [SMILES: Brc1cc2cnccc2cc1SC1CCN(CC2CC2)CC1 ; Cl] |
| 348 | 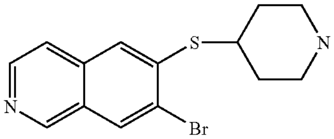 [SMILES: Brc1cc2cnccc2cc1SC1CCNCC1] | 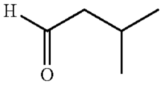 | 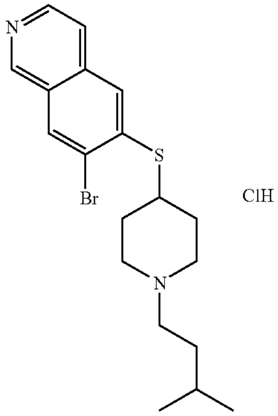 [SMILES: CC(C)CCN1CCC(Sc2cc3ccncc3cc2Br)CC1 ; Cl] |

TABLE 7-continued
| | | | |
|---|---|---|---|
| 349 | 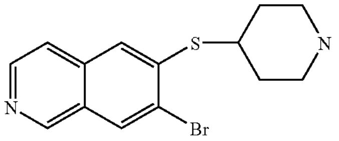 [SMILES: Brc1cc2cnccc2cc1SC1CCNCC1] | 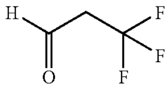 | 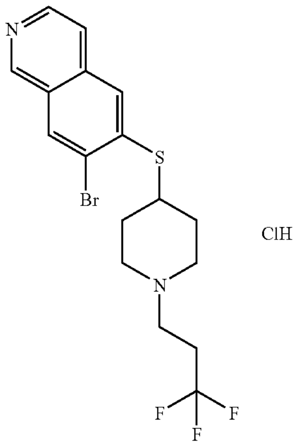 [SMILES: FC(F)(F)CCN1CCC(Sc2cc3ccncc3cc2Br)CC1 ; Cl] |
| 350 | 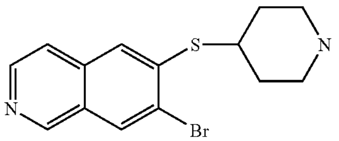 [SMILES: Brc1cc2cnccc2cc1SC1CCNCC1] | 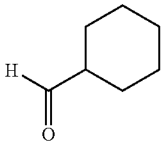 | 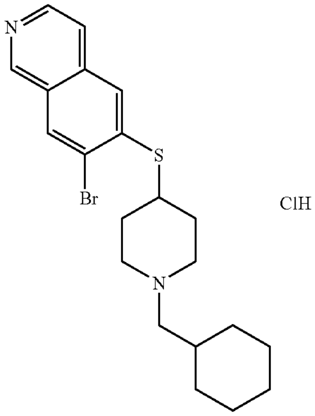 [SMILES: Brc1cc2cnccc2cc1SC1CCN(CC2CCCCC2)CC1 ; Cl] |
| 351 | 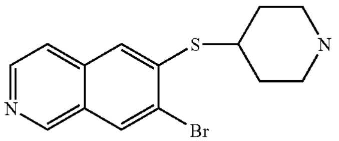 [SMILES: Brc1cc2cnccc2cc1SC1CCNCC1] | 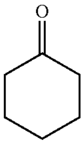 | 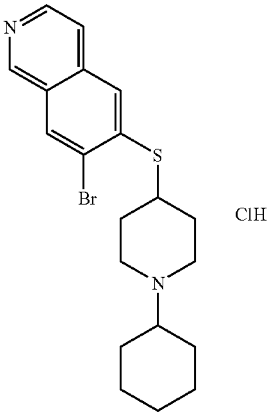 [SMILES: Brc1cc2cnccc2cc1SC1CCN(C2CCCCC2)CC1 ; Cl] |

TABLE 7-continued
| | | | | |
|---|---|---|---|---|
| 352 | 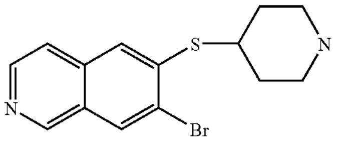 [SMILES: Brc1cc2cnccc2cc1SC1CCNCC1] | 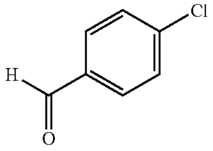 | 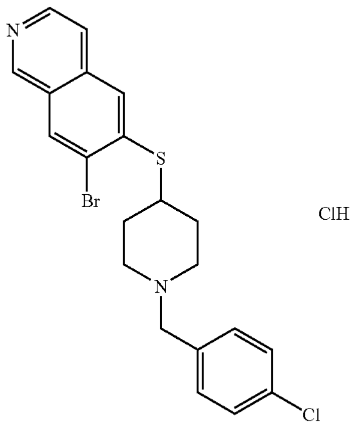 [SMILES: Clc1ccc(CN2CCC(Sc3cc4ccncc4cc3Br)CC2)cc1 ; Cl] | ClH |
| 353 | 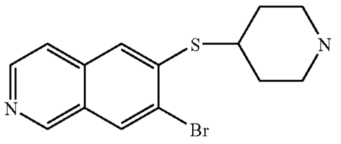 [SMILES: Brc1cc2cnccc2cc1SC1CCNCC1] | 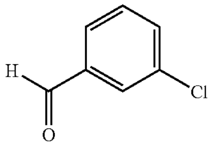 | 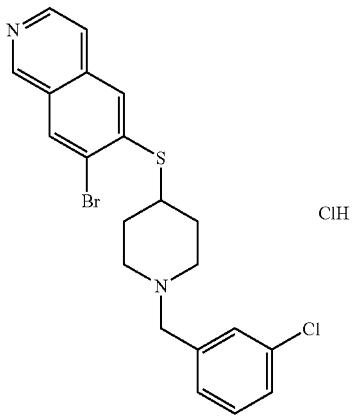 [SMILES: Clc1cccc(CN2CCC(Sc3cc4ccncc4cc3Br)CC2)c1 ; Cl] | ClH |
| 354 | 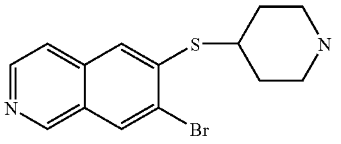 [SMILES: Brc1cc2cnccc2cc1SC1CCNCC1] | 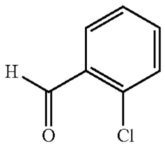 | 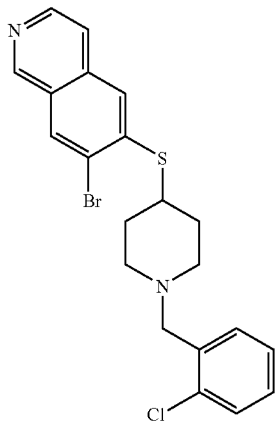 | ClH |

TABLE 7-continued
| | | | |
|---|---|---|---|
| 355 | 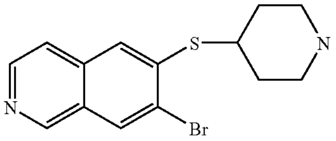 [SMILES: Brc1cc2cnccc2cc1SC1CCNCC1] | 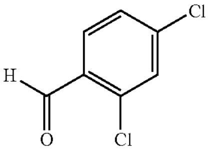 | 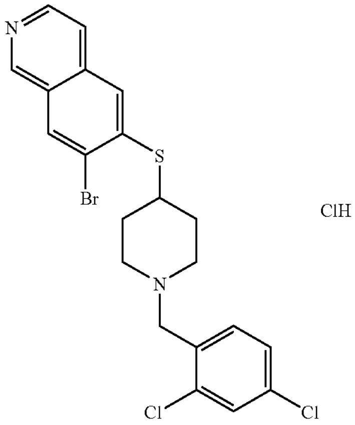 [SMILES: Clc1ccc(CN2CCC(Sc3cc4ccncc4cc3Br)CC2)c(Cl)c1 ; Cl] |
| 356 | 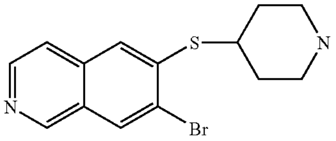 [SMILES: Brc1cc2cnccc2cc1SC1CCNCC1] | 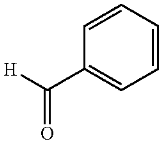 | 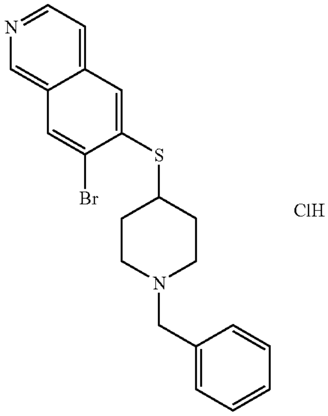 [SMILES: Brc1cc2cnccc2cc1SC1CCN(Cc2ccccc2)CC1 ; Cl] |
| 357 | 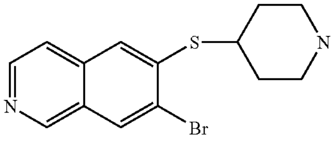 [SMILES: Brc1cc2cnccc2cc1SC1CCNCC1] | 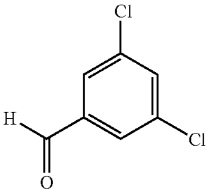 | 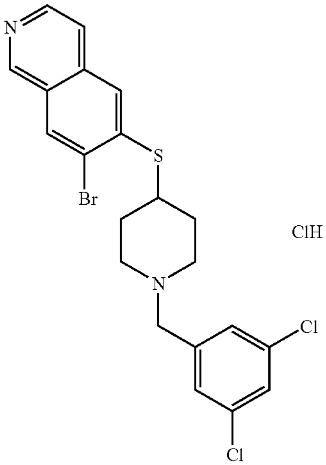 [SMILES: Clc1cc(Cl)cc(CN2CCC(Sc3cc4ccncc4cc3Br)CC2)c1 ; Cl] |

TABLE 7-continued
| | | | |
|---|---|---|---|
| 358 | 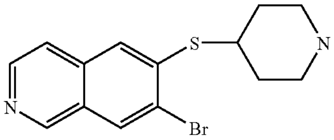 [SMILES: Brc1cc2cnccc2cc1SC1CCNCC1] | 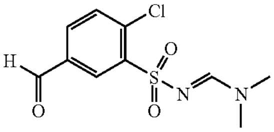 [SMILES: CN(C)/C=N/S(=O)(=O)c1cc(C=O)ccc1Cl] | 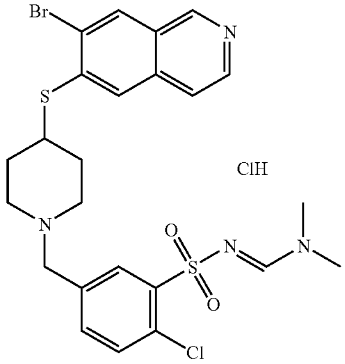 [SMILES: CN(C)/C=N/S(=O)(=O)c1cc(CN2CCC(Sc3cc4ccncc4cc3Br)CC2)ccc1Cl ; Cl] |
| 359 | 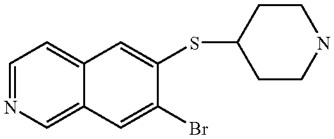 [SMILES: Brc1cc2cnccc2cc1SC1CCNCC1] | 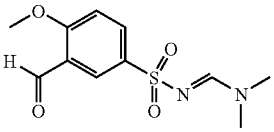 [SMILES: COc1ccc(S(=O)(=O)/N=C/N(C)C)cc1C=O] | 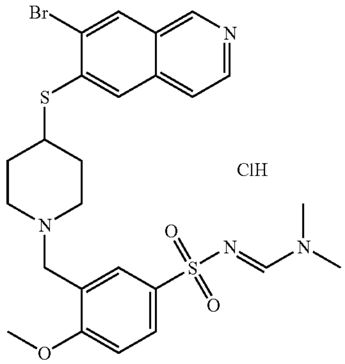 [SMILES: COc1ccc(S(=O)(=O)/N=C/N(C)C)cc1CN1CCC(Sc2cc3ccncc3cc2Br)CC1 ; Cl] |
| 360 | 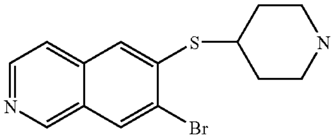 [SMILES: Brc1cc2cnccc2cc1SC1CCNCC1] | 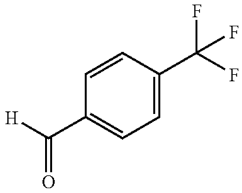 [SMILES: O=Cc1ccc(C(F)(F)F)cc1] | 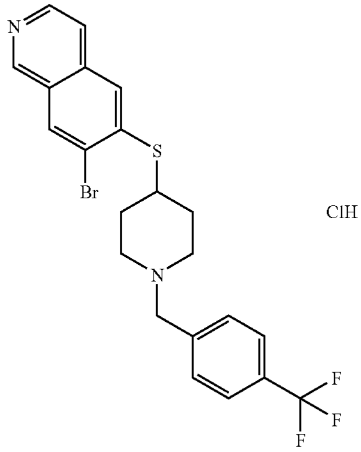 [SMILES: FC(F)(F)c1ccc(CN2CCC(Sc3cc4ccncc4cc3Br)CC2)cc1 ; Cl] |
| 361 | 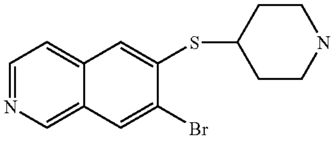 [SMILES: Brc1cc2cnccc2cc1SC1CCNCC1] | 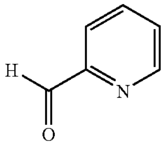 | 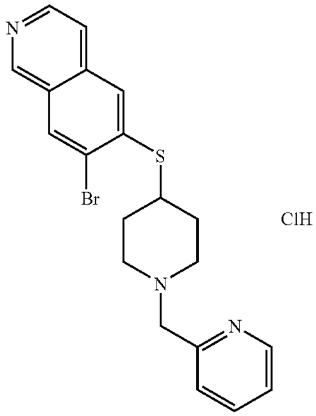 [SMILES: Brc1cc2cnccc2cc1SC1CCN(Cc2ccccn2)CC1 ; Cl] |

TABLE 7-continued
362 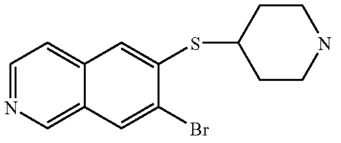 [SMILES: Brc1cc2cnccc2cc1SC1CCNCC1] 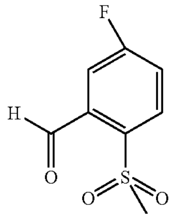 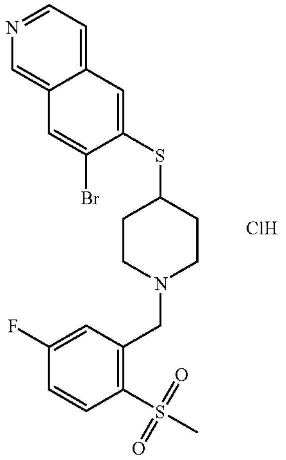 [SMILES: CS(=O)(=O)c1ccc(F)cc1CN1CCC(Sc2cc3ccncc3cc2Br)CC1 ; Cl]
363 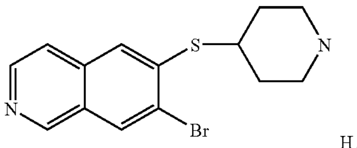 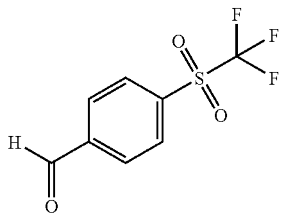 [SMILES: O=Cc1ccc(S(=O)(=O)C(F)(F)F)cc1] 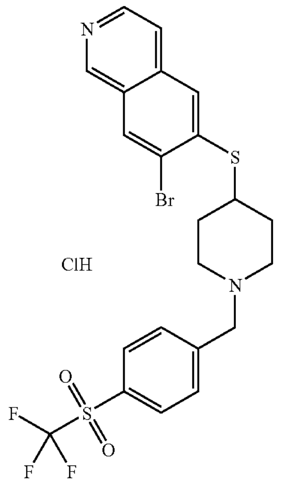 [SMILES: O=S(=O)(c1ccc(CN2CCC(Sc3cc4ccncc4cc3Br)CC2)cc1)C(F)(F)F ; Cl]
364 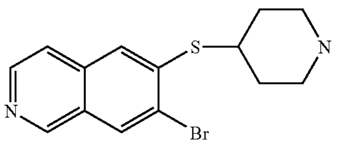 [SMILES: Brc1cc2cnccc2cc1SC1CCNCC1] 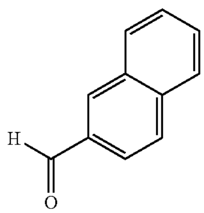 [SMILES: O=Cc1ccc2ccccc2c1] 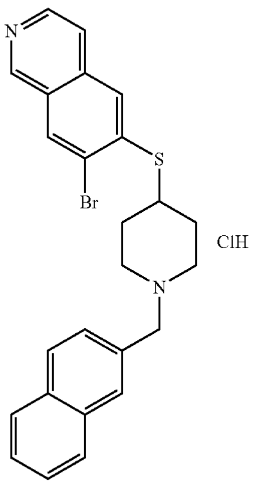 [SMILES: Brc1cc2cnccc2cc1SC1CCN(Cc2ccc3ccccc3c2)CC1 ; Cl]

TABLE 7-continued
| | | | |
|---|---|---|---|
| 365 | 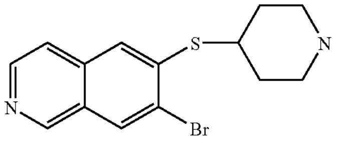 [SMILES: Brc1cc2cnccc2cc1SC1CCNCC1] | 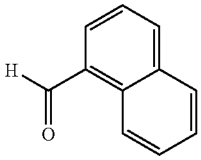 [SMILES: O=Cc1cccc2ccccc12] | 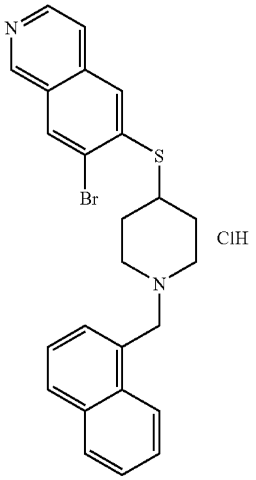 [SMILES: Brc1cc2cnccc2cc1SC1CCN(Cc2cccc3ccccc23)CC1 ; Cl] |
| 366 | 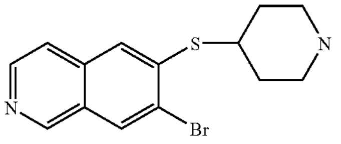 | 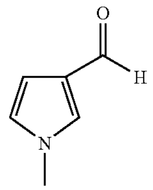 | 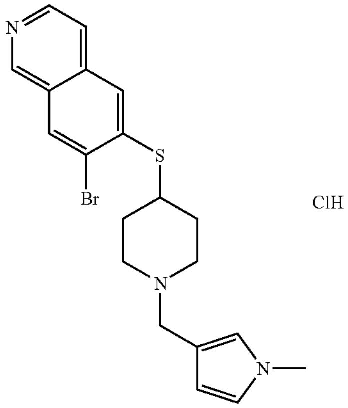 [SMILES: Cn1ccc(CN2CCC(Sc3cc4ccncc4cc3Br)CC2)c1 ; Cl] |
| 367 | 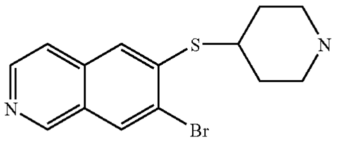 [SMILES: Brc1cc2cnccc2cc1SC1CCNCC1] | 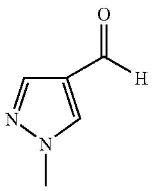 | 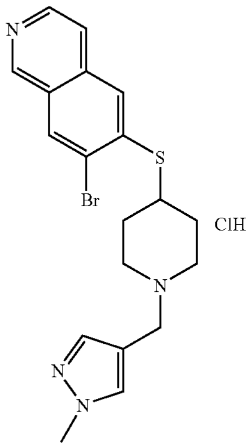 [SMILES: Cn1cc(CN2CCC(Sc3cc4ccncc4cc3Br)CC2)cn1 ; Cl] |

TABLE 7-continued
| | | | |
|---|---|---|---|
| 368 | 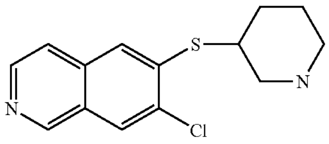 [SMILES: Clc1cc2cnccc2cc1SC1CCCNC1] | 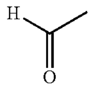 | 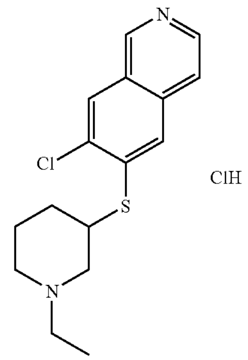 [SMILES: CCN1CCCC(Sc2cc3ccncc3cc2Cl)C1 ; Cl] |
| 369 | 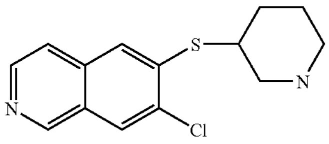 [SMILES: Clc1cc2cnccc2cc1SC1CCCNC1] | 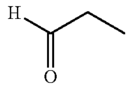 | 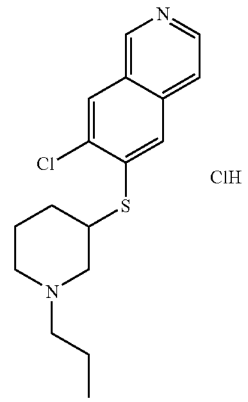 [SMILES: CCCN1CCCC(Sc2cc3ccncc3cc2Cl)C1 ; Cl] |
| 370 | 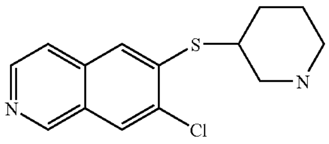 [SMILES: Clc1cc2cnccc2cc1SC1CCCNC1] | 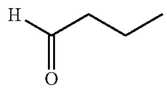 | 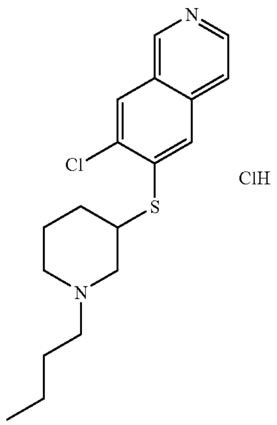 [SMILES: CCCCN1CCCC(Sc2cc3ccncc3cc2Cl)C1 ; Cl] |
| 371 | 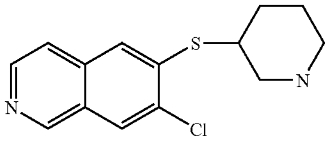 [SMILES: Clc1cc2cnccc2cc1SC1CCCNC1] | 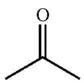 | 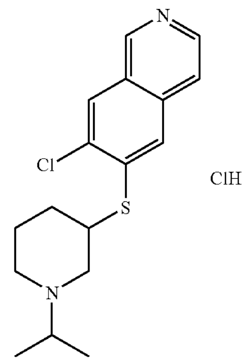 [SMILES: CC(C)N1CCCC(Sc2cc3ccncc3cc2Cl)C1 ; Cl] |

TABLE 7-continued
| | | | |
|---|---|---|---|
| 372 | 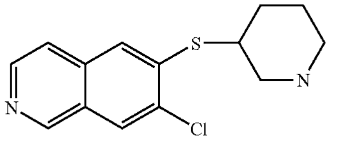 [SMILES: Clc1cc2cnccc2cc1SC1CCCNC1] | 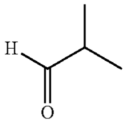 | 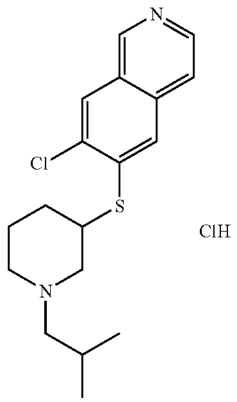 [SMILES: CC(C)CN1CCCC(Sc2cc3ccncc3cc2Cl)C1 ; Cl] |
| 373 | 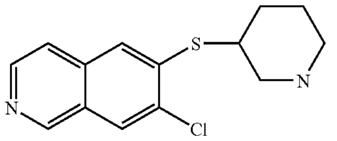 [SMILES: Clc1cc2cnccc2cc1SC1CCCNC1] | 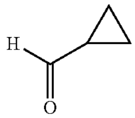 | 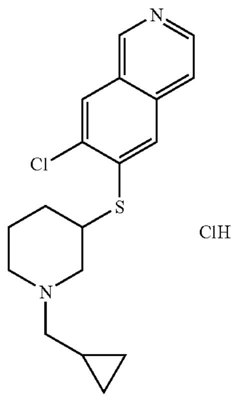 [SMILES: Clc1cc2cnccc2cc1SC1CCCN(CC2CC2)C1 ; Cl] |
| 374 | 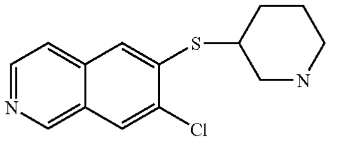 [SMILES: Clc1cc2cnccc2cc1SC1CCCNC1] | 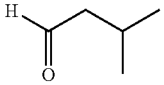 | 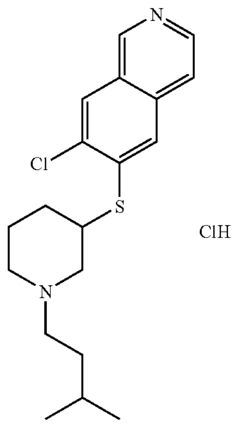 [SMILES: CC(C)CCN1CCCC(Sc2cc3ccncc3cc2Cl)C1 ; Cl] |

TABLE 7-continued
| | | | |
|---|---|---|---|
| 375 | 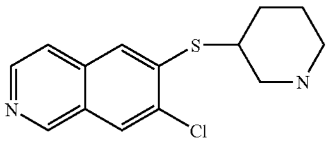 [SMILES: Clc1cc2cnccc2cc1SC1CCCNC1] | 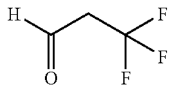 | 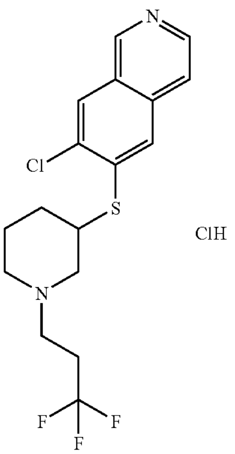 [SMILES: FC(F)(F)CCN1CCCC(Sc2cc3ccncc3cc2Cl)C1 ; Cl] |
| 376 | 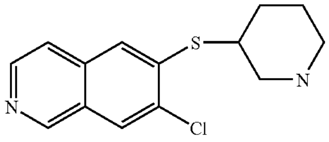 [SMILES: Clc1cc2cnccc2cc1SC1CCCNC1] | 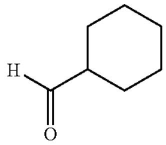 | 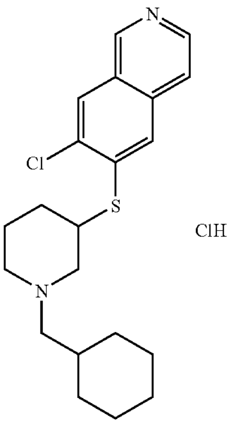 [SMILES: Clc1cc2cnccc2cc1SC1CCCN(CC2CCCCC2)C1 ; Cl] |
| 377 | 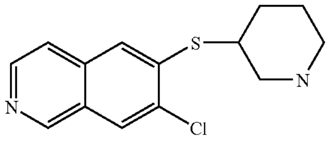 [SMILES: Clc1cc2cnccc2cc1SC1CCCNC1] | 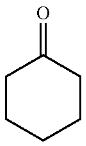 | 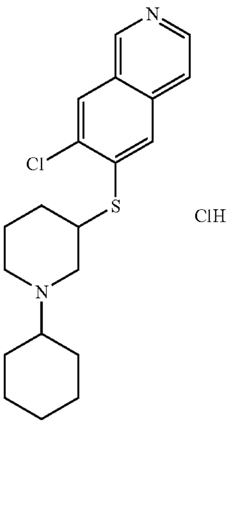 [SMILES: Clc1cc2cnccc2cc1SC1CCCN(C2CCCCC2)C1 ; Cl] |

TABLE 7-continued
| | | | |
|---|---|---|---|
| 378 | 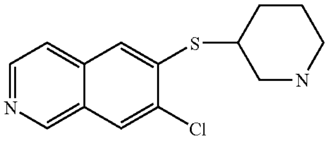 [SMILES: Clc1cc2cnccc2cc1SC1CCCNC1] | 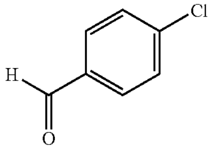 | 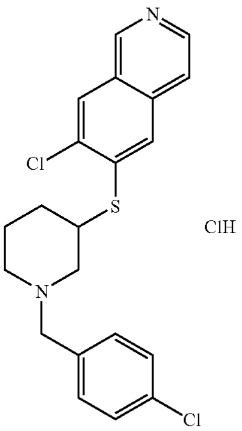 [SMILES: Clc1ccc(CN2CCCC(Sc3cc4ccncc4cc3Cl)C2)cc1 ; Cl] |
| 379 | 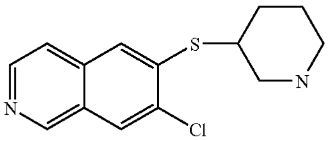 [SMILES: Clc1cc2cnccc2cc1SC1CCCNC1] | 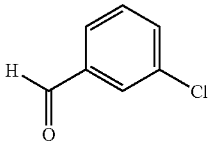 | 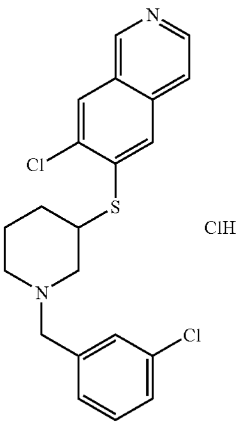 [SMILES: Clc1cccc(CN2CCCC(Sc3cc4ccncc4cc3Cl)C2)c1 ; Cl] |
| 380 | 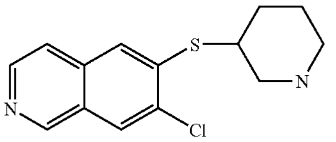 [SMILES: Clc1cc2cnccc2cc1SC1CCCNC1] | 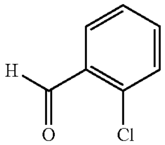 | 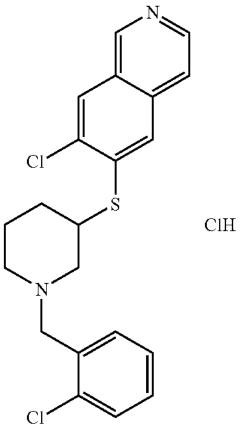 [SMILES: Clc1ccccc1CN1CCCC(Sc2cc3ccncc3cc2Cl)C1 ; Cl] |

TABLE 7-continued
| | | | |
|---|---|---|---|
| 381 | 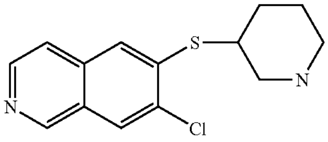 [SMILES: Clc1cc2cnccc2cc1SC1CCCNC1] | 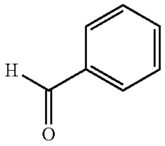 | 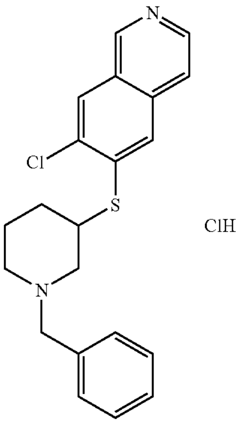 [SMILES: Clc1cc2cnccc2cc1SC1CCCN(Cc2ccccc2)C1 ; Cl] |
| 382 | 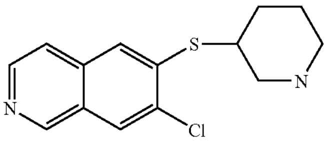 [SMILES: Clc1cc2cnccc2cc1SC1CCCNC1] | 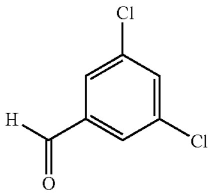 | 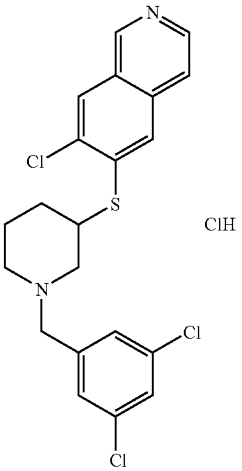 [SMILES: Clc1cc(Cl)cc(CN2CCCC(Sc3cc4ccncc4cc3Cl)C2)c1 ; Cl] |
| 383 | 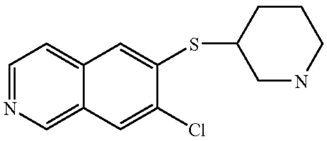 [SMILES: Clc1cc2cnccc2cc1SC1CCCNC1] | 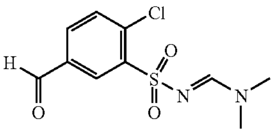 [SMILES: CN(C)/C=N/S(=O)(=O)c1cc(C=O)ccc1Cl] | 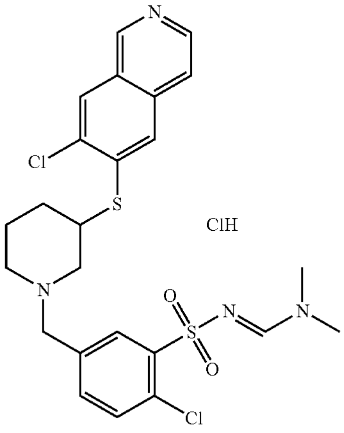 [SMILES: CN(C)/C=N/S(=O)(=O)c1cc(CN2CCCC(Sc3cc4ccncc4cc3Cl)C2)ccc1Cl ; Cl] |

TABLE 7-continued
| | | | |
|---|---|---|---|
| 384 | 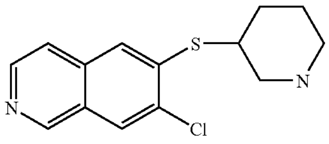 [SMILES: Clc1cc2cnccc2cc1SC1CCCNC1] | 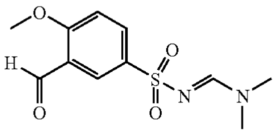 [SMILES: COc1ccc(S(=O)(=O)/N=C/N(C)C)cc1C=O] | 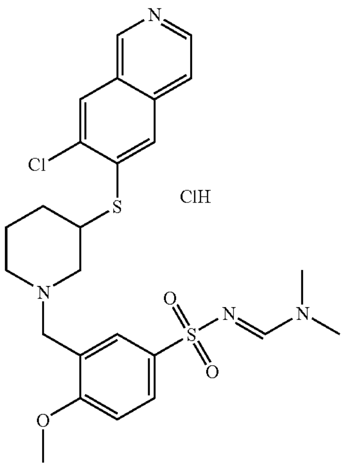 [SMILES: COc1ccc(S(=O)(=O)/N=C/N(C)C)cc1CN1CCCC(Sc2cc3ccncc3cc2Cl)C1 ; Cl] |
| 385 | 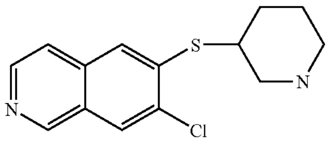 [SMILES: Clc1cc2cnccc2cc1SC1CCCNC1] | 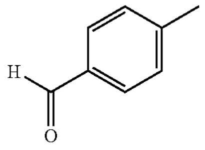 | 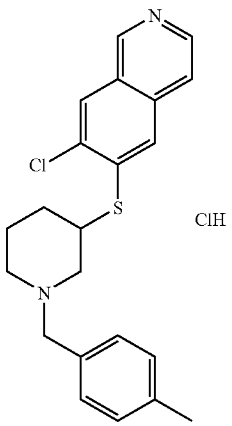 [SMILES: Cc1ccc(CN2CCCC(Sc3cc4ccncc4cc3Cl)C2)cc1 ; Cl] |
| 386 | 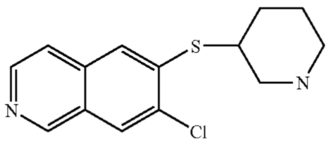 [SMILES: Clc1cc2cnccc2cc1SC1CCCNC1] | 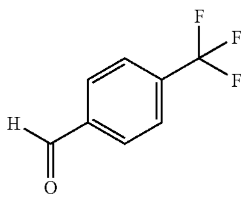 [SMILES: O=Cc1ccc(C(F)(F)F)cc1] | 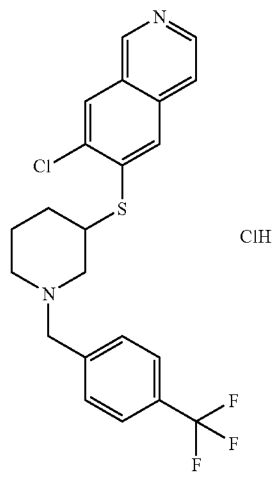 [SMILES: FC(F)(F)c1ccc(CN2CCCC(Sc3cc4ccncc4cc3Cl)C2)cc1 ; Cl] |

TABLE 7-continued

| | | | |
|---|---|---|---|
| 387 | 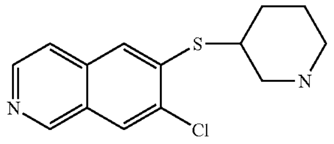 [SMILES: Clc1cc2cnccc2cc1SC1CCCNC1] | 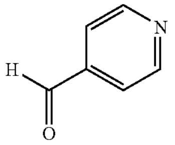 | 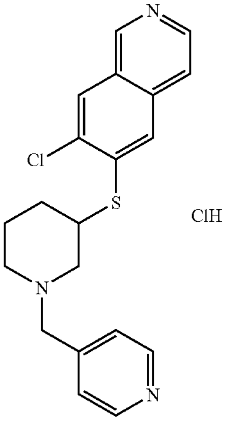 [SMILES: Clc1cc2cnccc2cc1SC1CCCN(Cc2ccncc2)C1 ; Cl] |
| 388 | 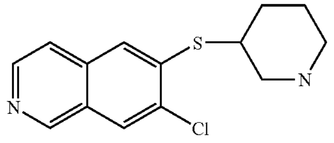 [SMILES: Clc1cc2cnccc2cc1SC1CCCNC1] | 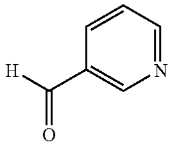 | 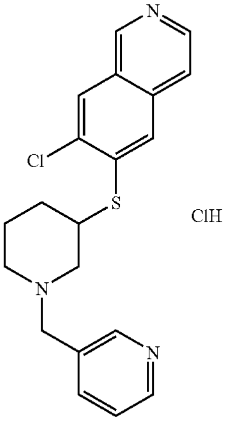 [SMILES: Clc1cc2cnccc2cc1SC1CCCN(Cc2cccnc2)C1 ; Cl] |

| Example. | $R_t$ [min] | Mass [M + H$^+$] | LCMS Method | Chemical name |
|---|---|---|---|---|
| 292 | 0.80 | 307.1/309.1 | B | 7-Chloro-6-((S)-1-propyl-pyrrolidin-3-ylsulfanyl)-isoquinoline |
| 293 | 0.95 | 321.1.2/323.1 | B | 6-((S)-1-Butyl-pyrrolidin-3-ylsulfanyl)-7-chloro-isoquinoline |
| 294 | 0.82 | 307.1/309.1 | B | 7-Chloro-6-((S)-1-isopropyl-pyrrolidin-3-ylsulfanyl)-isoquinoline |
| 295 | 0.89 | 321.1.2/323.1 | B | 7-Chloro-6-((S)-1-isobutyl-pyrrolidin-3-ylsulfanyl)-isoquinoline |
| 296 | 0.81 | 319.1/321.1 | B | 7-Chloro-8-((S)-1-cyclopropyl-methyl-pyrrolidin-3-ylsulfanyl)-isoquinoline |
| 298 | 1.01 | 335.1/337.1 | B | 7-Chloro-6-[(S)-1-(3-methyl-butyl)-pyrrolidin-3-ylsulfanyl]-isoquinoline |
| 299 | 0.92 | 361.0 | B | 7-Chloro-6-[(S)-1-(3,3,3-trifluoro-propyl)-pyrrolidin-3-ylsulfanyl]-isoquinoline |
| 300 | 1.07 | 361.2/363.2 | B | 7-Chloro-6-((S)-1-cyclohexylmethyl-pyrrolidin-3-ylsulfanyl)-isoquinoline |
| 301 | 0.95 | 347.1/349.1 | B | 7-Chloro-6-((S)-1-cyclohexyl-pyrrolidin-3-ylsulfanyl)-isoquinoline |

TABLE 7-continued

| | | | | |
|---|---|---|---|---|
| 302 | 1.12 | 389.2/391.2 | B | 7-Chloro-6-[(S)-1-(4-chloro-benzyl)-pyrrolidin-3-ylsulfanyl]-isoquinoline |
| 303 | 1.15 | 389.0 | B | 7-Chloro-6-[(S)-1-(3-chloro-benzyl)-pyrrolidin-3-ylsulfanyl]-isoquinoline |
| 304 | 1.06 | 389.1 | B | 7-Chloro-6-[(S)-1-(2-chloro-benzyl)-pyrrolidin-3-ylsulfanyl]-isoquinoline |
| 305 | 1.15 | 423.0 | B | 7-Chloro-6-[(S)-1-(2,4-dichloro-benzyl)-pyrrolidin-3-ylsulfanyl]-isoquinoline |
| 306 | 1.01 | 355.1/357.1 | B | 6-((S)-1-Benzyl-pyrrolidin-3-ylsulfanyl)-7-chloro-isoquinoline |
| 307 | 1.15 | 423.1/427.1 | B | 7-Chloro-6-[(S)-1-(3,5-dichloro-benzyl)-pyrrolidin-3-ylsulfanyl]-isoquinoline |
| 308 | 0.99 | 523.1/525.1 | B | 2-Chloro-5-[(S)-3-(7-chloro-isoquinolin-6-ylsulfanyl)-pyrrolidin-1-ylmethyl]-N-[1-dimethylamino-meth-(E)-ylidene]-benzenesulfonamide |
| 309 | 0.95 | 519.1/512.2 | B | 2-[(S)-3-(7-Chloro-isoquinolin-6-ylsulfanyl)-pyrrolidin-1-ylmethyl]-N-[1-dimethylamino-meth-(E)-ylidene]-4-methoxy-benzenesulfonamide |
| 310 | 1.06 | 369.1/371.1 | B | 7-Chloro-6-[(S)-1-(4-methyl-benzyl)-pyrrolidin-3-ylsulfanyl]-isoquinoline |
| 311 | 1.13 | 423.1/425.1 | B | 7-Chloro-6-[(S)-1-(4-trifluoromethyl-benzyl)-pyrrolidin-3-ylsulfanyl]-isoquinoline |
| 312 | 0.72 | 356.1/358.1 | B | 7-Chloro-6-((S)-1-pyridin-4-ylmethyl-pyrrolidin-3-ylsulfanyl)-isoquinoline |
| 313 | 0.75 | 356.1/358.1 | B | 7-Chloro-6-((S)-1-pyridin-3-ylmethyl-pyrrolidin-3-ylsulfanyl)-isoquinoline |
| 314 | 0.82 | 356.1/358.1 | B | 7-Chloro-6-((S)-1-pyridin-2-ylmethyl-pyrrolidin-3-ylsulfanyl)-isoquinoline |
| 315 | 0.87 | 433.1/435.1 | B | 7-Chloro-6-[(S)-1-(4-methanesulfonyl-benzyl)-pyrrolidin-3-ylsulfanyl]-isoquinoline |
| 316 | 0.95 | 451.1/453.1 | B | 7-Chloro-6-[(S)-1-(5-fluoro-2-methanesulfonyl-benzyl)-pyrrolidin-3-ylsulfanyl]-isoquinoline |
| 317 | 1.16 | 487.1/489.1 | B | 7-Chloro-6-[(S)-1-(4-trifluoromethanesulfonyl-benzyl)-pyrrolidin-3-ylsulfanyl]-isoquinoline |
| 317 | 1.14 | 405.1/407.1 | BB | 7-Chloro-6-((S)-1-naphthalen-2-ylmethyl-pyrrolidin-3-ylsulfanyl)-isoquinoline |

TABLE 7-continued

| | | | | |
|---|---|---|---|---|
| 318 | 0.77 | 307.1/309.1 | B | 7-Chloro-6-(1-ethyl-piperidin-4-ylsulfanyl)-isoquinoline |
| 319 | 0.85 | 321.1/323.1 | | 7-Chloro-6-(1-propyl-piperidin-4-ylsulfanyl)-isoquinoline |
| 320 | 0.92 | 335.1/337.1 | B | 6-(1-Butyl-piperidin-4-ylsulfanyl)-7-chloro-isoquinoline |
| 321 | 1.10 | 321.1/323.1 | B | 7-Chloro-6-(1-isopropyl-piperidin-4-ylsulfanyl)-isoquinoline |
| 322 | 0.92 | 335.1/337.1 | B | 7-Chloro-6-(1-isobutyl-piperidin-4-ylsulfanyl)-isoquinoline |
| 323 | 0.93 | 333.1/335.1 | B | 7-Chloro-6-(1-cyclopropylmethyl-piperidin-4-ylsulfanyl)-isoquinoline |
| 324 | 1.07 | 349.1/351.2 | B | 7-Chloro-6-[1-(3-methyl-butyl)-piperidin-4-ylsulfanyl]-isoquinoline |
| 325 | 0.90 | 375.1/377.1 | B | 7-Chloro-6-[1-(3,3,3-trifluoro-propyl)-piperidin-4-ylsulfanyl]-isoquinoline |
| 326 | 1.08 | 375.2/377.2 | B | 7-Chloro-6-(1-cyclohexylmethyl-piperidin-4-ylsulfanyl)-isoquinoline |
| 327 | 0.97 | 361.1/363.2 | B | 7-Chloro-6-(1-cyclohexyl-piperidin-4-ylsulfanyl)-isoquinoline |
| 328 | 1.10 | 403.1/405.1 | B | 7-Chloro-6-[1-(4-chloro-benzyl)-piperidin-3-ylsulfanyl]-isoquinoline |
| 329 | 1.09 | 403.1/405.1 | B | 7-Chloro-6-[1-(3-chloro-benzyl)-piperidin-3-ylsulfanyl]-isoquinoline |
| 330 | 1.05 | 403.1/405.1 | B | 7-Chloro-6-[1-(2-chloro-benzyl)-piperidin-3-ylsulfanyl]-isoquinoline |
| 331 | 1.15 | 437.1 | B | 7-Chloro-6-[1-(2,4-dichloro-benzyl)-piperidin-3-ylsulfanyl]-isoquinoline |
| 332 | 1.09 | 369.1/371.1 | B | 6-(1-Benzyl-piperidin-3-ylsulfanyl)-7-chloro-isoquinoline |
| 333 | 1.20 | 437.1 | B | 7-Chloro-6-[1-(3,5-dichloro-benzyl)-piperidin-3-ylsulfanyl]-isoquinoline |
| 334 | 1.05 | 537.1/539.1 | B | 2-Chloro-5-[3-(7-chloro-isoquinolin-6-ylsulfanyl)-piperidin-1-ylmethyl]-N-[1-dimethylamino-meth-(E)-ylidene]-benzenesulfonamide |
| 335 | 1.00 | 533.2/535.1 | B | 3-[3-(7-Chloro-isoquinolin-6-ylsulfanyl)-piperidin-1-ylmethyl]-N-[1-dimethylamino-meth-(E)-ylidene]-4-methoxy-benzenesulfonamide |
| 336 | 1.07 | 383.1/385.2 | B | 7-Chloro-6-[1-(4-methyl-benzyl)-piperidin-3-ylsulfanyl]-isoquinoline |

TABLE 7-continued

| | | | | |
|---|---|---|---|---|
| 337 | 1.19 | 437.1/439.1 | B | 7-Chloro-6-[1-(4-trifluoromethyl-benzyl)-piperidin-3-ylsulfanyl]-isoquinoline |
| 338 | 0.76 | 370.1 | B | 7-Chloro-6-(1-pyridin-4-ylmethyl-piperidin-3-ylsulfanyl)-isoquinoline |
| 339 | 0.75 | 370.1/372.1 | B | 7-Chloro-6-(1-pyridin-3-ylmethyl-piperidin-3-ylsulfanyl)-isoquinoline |
| 340 | 0.95 | 370.1/372.1 | B | 7-Chloro-6-(1-pyridin-2-ylmethyl-piperidin-3-ylsulfanyl)-isoquinoline |
| 341 | 0.93 | 447.1/449.1 | B | 6-Chloro-7-(pyrrolidin-2-ylmethyl-sulfanyl)-isoquinoline |
| 342 | 0.81 | 351.1 | B | 7-Bromo-6-(1-ethyl-piperidin-4-ylsulfanyl)-isoquinoline |
| 343 | 0.87 | 365.1 | B | 7-Bromo-6-(1-propyl-piperidin-4-ylsulfanyl)-isoquinoline |
| 344 | 0.95 | 379.1/381.1 | B | 7-Bromo-6-(1-butyl-piperidin-4-ylsulfanyl)-isoquinoline |
| 345 | 0.85 | 365.1/367.1 | B | 7-Bromo-6-(1-isopropyl-piperidin-4-ylsulfanyl)-isoquinoline |
| 346 | 1.00 | 379.1/381.1 | B | 7-Bromo-6-(1-isobutyl-piperidin-4-ylsulfanyl)-isoquinoline |
| 347 | 0.95 | 377.1/379.1 | B | 7-Bromo-6-(1-cyclopropylmethyl-piperidin-4-ylsulfanyl)-isoquinoline |
| 348 | 1.02 | 393.1 | B | 7-Bromo-6-[1-(3-methyl-butyl)-piperidin-4-ylsulfanyl]-isoquinoline |
| 349 | 0.90 | 419.0 | B | 7-Bromo-6-[1-(3,3,3-trifluoro-propyl)-piperidin-4-ylsulfanyl]-isoquinoline |
| 350 | 1.10 | 419.1 | B | 7-Bromo-6-(1-cyclohexylmethyl-piperidin-4-ylsulfanyl)-isoquinoline |
| 351 | 0.99 | 405.1 | B | 7-Bromo-6-(1-cyclohexyl-piperidin-4-ylsulfanyl)-isoquinoline |
| 352 | 1.13 | 449.1 | B | 7-Bromo-6-[1-(4-chloro-benzyl)-piperidin-4-ylsulfanyl]-isoquinoline |
| 353 | 1.10 | 449.0 | B | 7-Bromo-6-[1-(3-chloro-benzyl)-piperidin-4-ylsulfanyl]-isoquinoline |
| 354 | 1.06 | 449.0 | B | 7-Bromo-6-[1-(2-chloro-benzyl)-piperidin-4-ylsulfanyl]-isoquinoline |
| 355 | 1.16 | 481.1/483.1/485.1 | B | 7-Bromo-6-[1-(2,4-dichloro-benzyl)-piperidin-4-ylsulfanyl]-isoquinoline |
| 356 | 1.05 | 413.1 | B | 7-Bromo-6-[1-benzyl-piperidin-4-ylsulfanyl]-isoquinoline |
| 357 | 1.20 | 483.0/485.0 | B | 7-Bromo-6-[1-(3,5-dichloro-benzyl)-piperidin-4-ylsulfanyl]-isoquinoline |

TABLE 7-continued

| | | | | |
|---|---|---|---|---|
| 358 | 1.03 | 581.1/583.1 | B | 2-Chloro-5-[4-(7-bromo-isoquinolin-6-ylsulfanyl)-piperidin-1-ylmethyl]-N-[1-dimethylaminometh-(E)-ylidene]-benzene-sulfonamide |
| 359 | 1.05 | 579.1 | B | 3-[4-(7-Bromo-isoquinolin-6-ylsulfanyl)-piperidin-1-ylmethyl]-N-dimethylamino-meth(E)-ylidene-4-methoxy benzene-sulfonamide |
| 360 | 1.18 | 481.0 | B | 7-Bromo-6-[1-(4-trifluoromethyl-benzyl)-piperidin-4-ylsulfanyl]-isoquinoline |
| 361 | 0.89 | 414.1 | B | 7-Bromo-6-(1-pyridin-2-ylmethyl-piperidin-4-ylsulfanyl)-isoquinoline |
| 362 | 1.00 | 509.1 | B | 7-Bromo-6-[1-(5-fluoro-2-methanesulfonyl-benzyl)-piperidin-4-ylsulfanyl]-isoquinoline |
| 363 | 1.22 | 545.0 | B | 7-Bromo-6-[1-(4-trifluoromethanesulfonyl-benzyl)-piperidin-4-ylsulfanyl]-isoquinoline |
| 364 | 1.18 | 463.1/465.1 | B | 7-Bromo-6-(1-naphthalen-2-ylmethyl-piperidin-4-ylsulfanyl)-isoquinoline |
| 365 | 1.16 | 463.1 | B | 7-Bromo-6-(1-naphthalen-1-ylmethyl-piperidin-4-ylsulfanyl)-isoquinoline |
| 366 | 1.00 | 416.1 | B | 7-Bromo-6-[1-(1-methyl-1H-pyrrol-3-ylmethyl)-piperidin-4-ylsulfanyl]-isoquinoline |
| 367 | 0.86 | 417.1 | B | 7-Bromo-6-[1-(1-methyl-1H-pyrazol-4-ylmethyl)-piperidin-4-ylsulfanyl]-isoquinoline |
| 368 | 0.95 | 307.1/309.1 | B | 7-Chloro-6-(1-ethyl-piperidin-3-ylsulfanyl)-isoquinoline |
| 369 | 0.99 | 321.1/323.1 | B | 7-Chloro-6-(1-propyl-piperidin-3-ylsulfanyl)-isoquinoline |
| 370 | 0.96 | 335.1/337.2 | B | 6-(1-Butyl-piperidin-3-ylsulfanyl)-7-chloro-isoquinoline |
| 371 | 0.84 | 321.1/323.1 | B | 7-Chloro-6-(1-isopropyl-piperidin-3-ylsulfanyl)-isoquinoline |
| 372 | 0.90 | 335.1 | B | 7-Chloro-6-(1-isobutyl-piperidin-3-ylsulfanyl)-isoquinoline |
| 373 | 0.90 | 333.1/335.2 | B | 7-Chloro-6-(1-cyclopropylmethyl-piperidin-3-ylsulfanyl)-isoquinoline |
| 374 | 1.02 | 349.1 | B | 7-Chloro-6-[1-(3-methyl-butyl)-piperidin-3-ylsulfanyl]-isoquinoline |
| 375 | 1.10 | 375.4/377.4 | B | 7-Chloro-6-[1-(3,3,3-trifluoro-propyl)-piperidin-3-ylsulfanyl]-isoquinoline |
| 376 | 1.26 | 375.5/377.5 | B | 7-Chloro-6-(1-cyclohexylmethyl-piperidin-3-ylsulfanyl)-isoquinoline |

TABLE 7-continued

| | | | | |
|---|---|---|---|---|
| 377 | 1.04 | 361.1/363.1 | B | 7-Chloro-6-(1-cyclohexyl-piperidin-3-ylsulfanyl)-isoquinoline |
| 378 | 1.17 | 403.0 | B | 7-Chloro-6-[1-(4-chloro-benzyl)-piperidin-3-ylsulfanyl]-isoquinoline |
| 379 | 1.09 | 403.0 | B | 7-Chloro-6-[1-(3-chloro-benzyl)-piperidin-3-ylsulfanyl]-isoquinoline |
| 380 | 1.12 | 403.1 | B | 7-Chloro-6-[1-(2-chloro-benzyl)-piperidin-3-ylsulfanyl]-isoquinoline |
| 381 | 1.07 | 369.1/371.1 | B | 6-(1-Benzyl-piperidin-3-ylsulfanyl)-7-chloro-isoquinoline |
| 382 | 1.21 | 437.1 | B | 7-Chloro-6-[1-(3,5-dichloro-benzyl)-piperidin-3-ylsulfanyl]-isoquinoline |
| 383 | 1.07 | 537.1/539.2 | B | 2-Chloro-5-[3-(7-chloro-isoquinolin-6-ylsulfanyl)-piperidin-1-ylmethyl]-N-[1-dimethylamino-meth-(E)-ylidene]-benzenesulfonamide |
| 384 | 1.00 | 533.2 | B | 3-[3-(7-Chloro-isoquinolin-6-ylsulfanyl)-piperidin-1-ylmethyl]-N-[1-dimethylamino-meth-(E)-ylidene]-4-methoxy-benzenesulfonamide |
| 385 | 1.07 | 383.1/385.2 | B | 7-Chloro-6-[1-(4-methyl-benzyl)-piperidin-3-ylsulfanyl]-isoquinoline |
| 386 | 1.16 | 437.1/439.2 | B | 7-Chloro-6-[1-(4-trifluoromethyl-benzyl)-piperidin-3-ylsulfanyl]-isoquinoline |
| 387 | 0.85 | 370.1/372.2 | B | 7-Chloro-6-(1-pyridin-4-ylmethyl-piperidin-3-ylsulfanyl)-isoquinoline |
| 388 | 0.83 | 370.1/372.2 | B | 7-Chloro-6-(1-pyridin-3-ylmethyl-piperidin-3-ylsulfanyl)-isoquinoline |

Determination of Rho Kinase Inhibition

To measure Rho-kinase inhibition, $IC_{50}$ values were determined according to the following protocol:

Active human recombinant ROCK II (N-terminal His6-tagged recombinant human ROCK-II residues 11-552) was purchased from Upstate Ltd., Dundee, UK. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-Hydroxyethyl)piperazine-1-ethanesulfonic acid (Hepes), Brij-35 and dithiothreitol (DTT) were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM $MgCl_2$, 2 mM DTT, 0.02% (w/v) BSA and 3% DMSO). The ROCK II enzyme was diluted to a concentration of 100 ng/ml in buffer 2 (25 mM Tris-HCl, pH 7.4, 5 mM $MgCl_2$, 2 mM DTT and 0.02% (w/v) BSA). The peptide substrate and ATP were diluted to concentrations of 3 μM and 120 μM, respectively, in the buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 9(5), 409-416, 2004). Separation conditions were as follows: Pressure −1.3 psi, upstream voltage −1562 V, downstream voltage −500 V, sample sip time 200 ms. Positive controls (buffer 1 instead of compound) and negative controls (buffer 1 instead of compound and buffer 2 instead of ROCK II) were run in parallel on each plate. The following products/compounds were tested in said assay by using the respective form (salt or free base) obtained as in the examples described above and the following activities were measured.

| Compound No. | pIC50 |
|---|---|
| 99 | ++++ |
| 166 | ++++ |
| 169 | ++++ |
| 195 | ++++ |
| 196 | +++++ |
| 199 | +++++ |
| 207 | +++++ |
| 213 | ++++ |
| 215 | ++++ |
| 218 | +++++ |
| 220 | +++++ |
| 226 | +++++ |
| 234 | ++++ |
| 236 | +++++ |
| 243 | +++++ |
| 246 | ++++ |
| 248 | ++++ |
| 249 | +++++ |
| 251 | ++++ |
| 253 | ++++ |
| 259 | +++++ |
| 269 | +++++ |
| 271 | +++++ |
| 277 | +++++ |
| 279 | ++++ |
| 286 | +++++ |
| 288 | +++++ |
| 290 | ++++ |

The given activity is denoted as the negative decadal logarithm of the $IC_{50}$ ($pIC_{50}$) as follows:
+: pIC50 ≤ 3.0
++: 3.0 ≤ $pIC_{50}$ < 4.0
+++ 4.0 ≤ $pIC_{50}$ < 5.0
++++: 5.0 ≤ $pIC_{50}$ < 6.0
+++++: 6.0 ≤ $pIC_{50}$

The invention claimed is:

1. A compound of the formula (I)

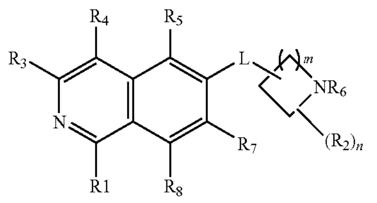

(I)

wherein $R_1$ is H;

$R_2$ is H, halogen or $(C_1-C_6)$alkyl;

$R_3$ is
H,
halogen,
$(C_1-C_6)$alkyl,
OH,
O—R",
$NH_2$,
NHR",
NR"R" or
NH—C(O)—R";

$R_4$ is
H,
halogen,
hydroxy,
CN,
$(C_1-C_6)$alkyl, $R_5$ is
H,
halogen,
CN,
$NO_2$,
$(C_1-C_6)$alkyl,
$(C_2-C_6)$alkenyl,
CH(OH)—$(C_1-C_6)$alkyl,
$NH_2$,
NH—$SO_2$H,
NH—$SO_2$—$(C_1-C_6)$alkyl,
NH—C(O)—$(C_1-C_6)$alkyl,
C(O)N[$(C_1-C_6)$alkyl]$_2$,
C(O)OH, or
C(O)O—$(C_1-C_6)$alkyl;

$R_6$ is
H,
R',
$(C_1-C_8)$alkyl,
$(C_1-C_6)$alkylene-R',
$(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)$NH_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)O—$(C_1-C_6)$alkyl,
C(O)OR',
C(O)$(C_1-C_6)$alkyl,
C(O)R',
C(O)NH—$(C_1-C_6)$alkyl,
C(O)NHR',
C(O)N[$(C_1-C_6)$alkyl]R'
C(O)N[$(C_1-C_6)$alkyl]$_2$,
C(O)—$(C_1-C_6)$alkylene-R',
C(O)O$(C_1-C_6)$alkylene-R';

$R_7$ is
H,
halogen,
CN,
$NO_2$,
$(C_1-C_6)$alkyl,
O—$(C_1-C_6)$alkyl,
$(C_2-C_6)$alkenyl,
CH(OH)—$(C_1-C_6)$alkyl,
$NH_2$,
NH—$SO_2$H,
NH—$SO_2$—$(C_1-C_6)$alkyl,
$SO_2$—$NH_2$,
NH—C(O)—$(C_1-C_6)$alkyl,
C(O)N[$(C_1-C_6)$alkyl]$_2$,
C(O)OH, or
C(O)O—$(C_1-C_6)$alkyl;

$R_8$ is H, halogen or $(C_1-C_6)$alkyl;

n is 1, 2, 3 or 4;

m is 3; and

L is S$(CH_2)$p, S(O)$(CH_2)$p, $SO_2(CH_2)$p, NH$(CH_2)$p, N$(C_1-C_6)$alkyl-$(CH_2)$p, N$(C_3-C_6)$cycloalkyl $(CH_2)$p, N[CO$(C_1-C_6)$alkyl]-$(CH_2)$p or N[$(C_1-C_3)$alkylene-R']—$(CH_2)$p;

p is 0, 1, 2, 3, or 4;

R' is $(C_3-C_8)$cycloalkyl, $(C_5-C_{10})$heterocyclyl, $(C_6-C_{10})$aryl;

R" is $(C_1-C_6)$alkylene-O—$(C_1-C_6)$alkyl, or $(C_1-C_6)$alkylene-$NR_xR_y$; and $R_x$ and $R_y$ are independently of each other $(C_1-C_6)$alkyl, $(C_1-C_4)$alkylene-NH$(C_1-C_6)$alkyl, or $(C_1-C_4)$alkylene-N$[(C_1-C_6)alkyl]_2$, wherein in residues $R_4$, $R_5$, $R_6$, $R_7$ and $R_8$ as alkyl, alkylene or cycloalkyl can optionally be substituted one or more times by OH, $OCH_3$, COOH, $COOCH_3$, $NH_2$, $NHCH_3$, $N(CH_3)_2$, $CONH_2$, $CONHCH_3$ or $CON(CH_3)_2$;

wherein in residues $R_2$ to $R_8$ as alkyl or alkylene can optionally be substituted one or more times by halogen;

wherein in residues $R_6$ as $(C_6-C_{10})$aryl and $(C_5-C_{10})$heterocyclyl are unsubstituted or substituted one or more times by a suitable group independently selected from halogen, OH, $NO_2$, $N_3$, CN, C(O)—$(C_1-C_6)$alkyl, C(O)—$(C_6-C_{10})$aryl, COOH, COO$(C_1-C_6)$alkyl, $CONH_2$, CONH$(C_1-C_6)$alkyl, CONR$[(C_1-C_6)alkyl]_2$, $(C_3-C_8)$cycloalkyl, $(C_1-C_6)$alkyl, $(C_1-C_6)$alkylene-OH, $(C_1-C_6)$alkylene-$NH_2$, $(C_1-C_6)$alkylene-NH$(C_1-C_6)$alkyl, $(C_1-C_6)$alkylene-N$[(C_1-C_6)alkyl]_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2NH(C_1-C_6)$alkyl, $SO_2N[(C_1-C_6)alkyl]_2$, S—$(C_1-C_6)$alkyl; SO—$(C_1-C_6)$alkyl, $SO_2$—$(C_1-C_6)$alkyl, $SO_2$—N═CH—N$[(C_1-C_6)alkyl]_2$, C(NH)$(NH_2)$, $NH_2$, NH—$(C_1-C_6)$alkyl, N$[(C_1-C_6)alkyl]_2$, NH—C(O)—$(C_1-C_6)$alkyl, NH—C(O)O—$(C_1-C_6)$alkyl, NH—$SO_2$—$(C_1-C_6)$alkyl, NH—$SO_2$—$(C_6-C_{10})$aryl, NH—$SO_2$—$(C_5-C_{10})$heterocyclyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heterocyclyl, $(C_1-C_6)$alkylene-$(C_5-C_{10})$heterocyclyl, and O—$(C_1-C_6)$alkylene-$(C_5-C_{10})$heterocyclyl, wherein the $(C_6-C_{10})$aryl or $(C_5-C_{10})$heterocyclyl in the substituent may be substituted one to three times by a group independently selected from halogen, OH, $NO_2$, CN, O—$(C_1-C_6)$alkyl, $(C_1-C_6)$alkyl, $NH_2$, NH$(C_1-C_6)$alkyl, N$[(C_1-C_6)alkyl]_2$, $SO_2CH_3$, COOH, C(O)O—$(C_1-C_6)$alkyl, $CONH_2$, $(C_1-C_6)$alkylene-O—$(C_1-C_6)$alkyl, $(C_1-C_6)$alkylene-O—$(C_6-C_{10})$aryl, and O—$(C_1-C_6)$alkylene-$(C_6-C_{10})$aryl; or wherein $(C_6-C_{10})$aryl is vicinally substituted by a O—$(C_1-C_4)$alkylene-O group whereby a 5-8-membered ring is formed together with the carbon atoms the oxygen atoms are attached to; and wherein aryl or heterocyclyl substituent of $(C_6-C_{10})$aryl and $(C_5-C_{10})$heterocyclyl substituent groups may not be further substituted by an aryl or heterocyclyl containing group; or stereoisomeric form thereof and/or tautomeric form thereof and/or pharmaceutically acceptable salt thereof.

2. The compound according to claim 1, having the formula (II)

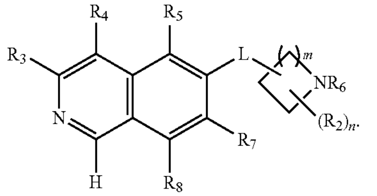

(II)

3. The compound according to claim 1, wherein $R_3$ is H, halogen, O—R" or NHR".

4. The compound according to claim 3, wherein $R_3$ is H or NHR".

5. The compound according to claim 4, wherein $R_3$ is H.

6. The compound according to claim 5, wherein $R_3$ is H.

7. The compound according to claim 1, wherein $R_8$ is H, halogen or $(C_1-C_4)$alkyl.

8. The compound according to claim 7, wherein $R_8$ is H, Cl, F, methyl or ethyl.

9. The compound according to claim 8, wherein $R_8$ is H.

10. The compound according to claim 1, wherein $R_4$ is H, halogen or $(C_1-C_6)$alkyl.

11. The compound according to claim 10, wherein $R_4$ is H, halogen or $(C_1-C_4)$alkyl.

12. The compound according to claim 11, wherein $R_4$ is H.

13. The compound according to claim 1, wherein $R_5$ is H, halogen, CN, $(C_1-C_6)$alkyl, $(C_2-C_6)$alkenyl.

14. The compound according to claim 13, wherein $R_5$ is H, halogen, $(C_1-C_6)$alkyl, $(C_2-C_6)$alkenyl.

15. The compound according to claim 14, wherein $R_5$ is H, halogen, methyl, ethyl, or vinyl.

16. The compound according to claim 15, wherein $R_5$ is H, halogen, methyl, or ethyl.

17. The compound according to claim 16, wherein $R_5$ is H.

18. The compound according to claim 1, wherein $R_7$ is H, halogen, CN, $(C_1-C_6)$alkyl, O—$(C_1-C_6)$alkyl, or $(C_2-C_6)$alkenyl.

19. The compound according to claim 18, wherein $R_7$ is H, halogen, CN, $(C_1-C_4)$alkyl, O—$(C_1-C_4)$alkyl, or $(C_2-C_4)$alkenyl.

20. The compound according to claim 19, wherein $R_7$ is H, fluoro, chloro, bromo, methyl, ethyl, methoxy, phenyl, CN, or vinyl.

21. The compound according to claim 20, wherein $R_7$ is H, fluoro, chloro, bromo, methyl or methoxy.

22. The compound according to claim 21, wherein $R_7$ is H.

23. The compound according to claim 1, wherein $R_2$ is H, halogen, or $(C_1-C_4)$alkyl.

24. The compound according to claim 23, wherein $R_2$ is H or $(C_1-C_2)$alkyl.

25. The compound according to claim 24, wherein $R_2$ is H, methyl or ethyl.

26. The compound according to claim 1, wherein n is 1, 2 or 3.

27. The compound according to claim 26, wherein n is 1 or 2.

28. The compound according to claim 27, wherein n is 1.

29. The compound according to claim 1, wherein
$R_6$ is
H,
$(C_1-C_6)$alkyl,
R',
$(C_1-C_4)$alkylene-$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_6)$alkylene-O—$(C_1-C_6)$alkyl,
$(C_1-C_4)$alkylene-C(O)—$(C_5-C_{10})$heterocyclyl,
$(C_1-C_4)$alkylene-C(O)—$(C_6-C_{10})$aryl,
$(C_1-C_6)$alkylene-C(O)N[$(C_1-C_6)$alkyl$]_2$,
$(C_1-C_6)$alkylene-C(O)NH—$(C_1-C_6)$alkyl,
$(C_1-C_6)$alkylene-C(O)O—$(C_1-C_6)$alkyl,
C(O)O—$(C_1-C_6)$alkyl,
C(O)$(C_1-C_6)$alkyl,
C(O)R',
C(O)NH—$(C_1-C_6)$alkyl,
C(O)N[$(C_1-C_6)$alkyl$]_2$, or
C(O)$(C_1-C_6)$alkylene-R'.

30. The compound according to claim 29, wherein $R_6$ is
H,
$(C_1-C_6)$alkyl,
$(C_5-C_{10})$heterocyclyl,
$(C_3-C_8)$cycloalkyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_6)$alkylene-C(O)N[$(C_1-C_6)$alkyl$]_2$,
$(C_1-C_6)$alkylene-C(O)NH—$(C_1-C_6)$alkyl,
$(C_1-C_6)$alkylene-C(O)O—$(C_1-C_6)$alkyl,
C(O)O—$(C_1-C_6)$alkyl,
C(O)$(C_1-C_6)$alkyl,
C(O)$(C_5-C_{10})$heterocyclyl,
C(O)$(C_3-C_8)$cycloalkyl
C(O)NH—$(C_1-C_6)$alkyl,
C(O)N[$(C_1-C_6)$alkyl$]_2$,
C(O)$(C_1-C_6)$alkylene-$(C_3-C_8)$cycloalkyl,
C(O)$(C_1-C_6)$alkylene-$C_5-C_{10}$)heterocyclyl, or
C(O)$(C_1-C_6)$alkylene-$(C_6-C_{10})$aryl.

31. The compound according to claim 30, wherein
$R_6$ is
H,
$(C_1-C_6)$alkyl,
$(C_3-C_8)$cycloalkyl,
$(C_5-C_{10})$heterocyclyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_6)$alkylene-C(O)NH—$(C_1-C_6)$alkyl,
$(C_1-C_6)$alkylene-C(O)N[$(C_1-C_6)$alkyl$]_2$,
C(O)O—$(C_1-C_6)$alkyl,
C(O)$(C_1-C_6)$alkyl,
C(O)$(C_3-C_8)$cycloalkyl,
C(O)—$(C_5-C_{10})$heterocyclyl,
C(O)NH—$(C_1-C_6)$alkyl,
C(O)N[$(C_1-C_6)$alkyl$]_2$,
C(O)$(C_1-C_6)$alkylene-$(C_3-C_8)$cycloalkyl,
C(O)$(C_1-C_6)$alkylene-$(C_5-C_{10})$heterocyclyl, or
C(O)$(C_1-C_6)$alkylene-$(C_6-C_{10})$aryl.

32. The compound according to claim 31, wherein
$R_6$ is
H,
$(C_1-C_6)$alkyl,
$(C_3-C_8)$cycloalkyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_4)$alkylene-O—$(C_1-C_4)$alkyl,
C(O)$(C_1-C_6)$alkyl,
C(O)$(C_3-C_8)$cycloalkyl,
C(O)—$(C_5-C_{10})$heterocyclyl,
C(O)$(C_1-C_4)$alkylene-$(C_5-C_{10})$heterocyclyl, or
C(O)$(C_1-C_4)$alkylene-$(C_6-C_{10})$aryl.

33. The compound according to claim 32, wherein
$R_6$ is
H;
$(C_1-C_6)$alkyl;
$(C_3-C_8)$cycloalkyl;
$(C_1-C_4)$alkylene-$(C_3-C_8)$cycloalkyl;
$(C_1-C_4)$alkylene-$(C_5-C_{10})$heterocyclyl wherein heterocyclyl is unsubstituted or substituted one or more times by $(C_1-C_4)$alkyl;
$(C_1-C_4)$alkylene-$(C_6-C_{10})$aryl wherein aryl is unsubstituted or substituted one or more times by halogen, $(C_1-C_4)$alkyl, O—$(C_1-C_4)$alkyl, $SO_2$—$(C_1-C_4)$alkyl or $SO_2$—N[$(C_1-C_6)$alkyl$]_2$.

34. The compound according to claim 33, wherein $R_6$ is H, $(C_1-C_6)$alkyl or $(C_3-C_8)$cycloalkyl.

35. The compound according to claim 34, wherein $R_6$ is H, unsubstituted $(C_1-C_6)$alkyl or unsubstituted $(C_3-C_8)$cycloalkyl.

36. The compound according to claim 35, wherein $R_6$ is H.

37. The compound according to claim 1, wherein m is 3 and L is attached to the 3-position or to the 4-position of the piperidine ring.

38. The compound according to claim 1, wherein m is 3 and L is attached to the 4-position of the piperidine ring.

39. The compound according to claim 1, wherein L is $S(CH_2)p$, $S(O)(CH_2)p$ or $SO_2(CH_2)p$.

40. The compound according to claim 1, wherein L is $NH(CH_2)p$ or N$(C_1-C_6)$alkyl-$(CH_2)p$.

41. The compound according to claim 1, wherein p is 0.

42. The compound according to claim 1, wherein
$R_1$ is H;
$R_3$ is H, halogen, O—R" or NHR";
$R_4$ is H, halogen or $(C_1-C_6)$alkyl;
$R_5$ is H, $(C_1-C_6)$alkyl, halogen, CN, $(C_2-C_6)$alkenyl;
$R_6$ is H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R'$]_2$, $(C_1-C_6)$alkylene-C(O)$NH_2$, $(C_1-C_6)$alkylene-C(O)NH—R', $(C_1-C_6)$alkylene-C(O)N[$(C_1-C_4)$alkyl$]_2$, $(C_1-C_6)$alkylene-C(O)N[R'$]_2$; C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N[$(C_1-C_6)$alkyl$]_2$, C(O)$(C_1-C_6)$alkylene-$C_3-C_8$)cycloalkyl, C(O)$(C_1-C_6)$alkylene-$C_5-C_{10}$)heterocyclyl, or C(O)$(C_1-C_6)$alkylene-$(C_6-C_{10})$aryl;
$R_7$ is H, halogen, CN, $(C_1-C_6)$alkyl, O—$(C_1-C_6)$alkyl, $(C_2-C_6)$alkenyl;
m is 3,
n is 1, 2 or 3,
L is $S(CH_2)p$, $NH(CH_2)p$ or N$(C_1-C_6)$alkyl-$(CH_2)p$, and
p is 0, 1 or 2.

43. The compound according to claim 1, wherein $R_1$ is H;

$R_2$ is H or $(C_1-C_4)$alkyl;

$R_3$ is H, halogen or NHR";

$R_4$ is H, halogen or $(C_1-C_4)$alkyl;

$R_5$ is H, $(C_1-C_6)$alkyl, halogen, or $(C_2-C_4)$alkenyl;

$R_6$ is H, $(C_3-C_8)$cycloalkyl, $(C_1-C_8)$alkyl, $(C_1-C_3)$alkylene-R', C(O)O—$(C_1-C_6)$alkyl, C(O)$(C_1-C_6)$alkyl, C(O)$(C_3-C_8)$cycloalkyl, C(O)—$(C_5-C_{10})$heterocyclyl, C(O)NH—$(C_1-C_6)$alkyl, C(O)N[$(C_1-C_6)$alkyl]$_2$, C(O)$(C_1-C_6)$alkylene-$(C_3-C_8)$cycloalkyl, C(O)$(C_1-C_6)$alkylene-$(C_5-C_{10})$heterocyclyl, or C(O)$(C_1-C_6)$alkylene-$(C_6-C_{10})$aryl;

$R_7$ is H, halogen, CN, $(C_1-C_6)$alkyl, O$(C_1-C_6)$alkyl, or $(C_2-C_6)$alkenyl;

m is 3;

n is 1, 2 or 3;

L is is S$(CH_2)$p or NH$(CH_2)$p, and p is 0 or 1.

44. The compound according to claim 1, wherein $R_1$ is H;

$R_2$ is H, $(C_1-C_4)$alkyl;

$R_3$ is H;

$R_4$ is H, halogen or $(C_1-C_4)$alkyl;

$R_5$ is H, $(C_1-C_4)$alkyl, halogen, or $(C_2-C_4)$alkenyl;

$R_6$ is H, $(C_3-C_8)$cycloalkyl, $(C_1-C_8)$alkyl, $(C_1-C_3)$alkylene-R'; C(O)$(C_1-C_6)$alkyl, C(O)$(C_3-C_8)$cycloalkyl, C(O)-$(C_5-C_{10})$heterocyclyl, C(O)$(C_1-C_3)$alkylene-$(C_5-C_{10})$heterocyclyl or C(O)$(C_1-C_3)$alkylene-$(C_6-C_{10})$aryl;

$R_7$ is H, halogen, CN, $(C_1-C_4)$alkyl, O—$(C_1-C_4)$alkyl, or $(C_2-C_4)$alkenyl;

$R_8$ is H, halogen or $(C_1-C_4)$alkyl;

m is 3;

n is 1; and

L is NH or S.

45. A pharmaceutical composition comprising a pharmaceutically effective amount of at least one compound according to claim 1 and/or a pharmacologically acceptable salt thereof, and physiologically tolerated excipient or carriers, and optionally one or more additives and/or one or more other active compounds.

* * * * *